US009181242B2

(12) United States Patent
Alcaraz et al.

(10) Patent No.: US 9,181,242 B2
(45) Date of Patent: *Nov. 10, 2015

(54) KINASE INHIBITORS

(71) Applicant: CHIESI FARMACEUTICI S.p.A., Parma (IT)

(72) Inventors: Lilian Alcaraz, Harlow (GB); Christopher Hurley, Harlow (GB); Andrew Peter Cridland, Harlow (GB); Andrew Stephen Robert Jennings, Harlow (GB)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/296,794

(22) Filed: Jun. 5, 2014

(65) Prior Publication Data

US 2014/0364412 A1    Dec. 11, 2014

(30) Foreign Application Priority Data

Jun. 6, 2013  (EP) .................................... 13170937

(51) Int. Cl.
*C07D 211/40* (2006.01)
*C07D 471/04* (2006.01)
*C07C 53/06* (2006.01)
*C07D 519/00* (2006.01)

(52) U.S. Cl.
CPC ............. *C07D 471/04* (2013.01); *C07C 53/06* (2013.01); *C07D 519/00* (2013.01)

(58) Field of Classification Search
CPC .................................................. C07D 519/00
USPC .......................................................... 546/119
See application file for complete search history.

(56) References Cited

U.S. PATENT DOCUMENTS

| 8,835,431 B2 * | 9/2014 | Van Niel et al. ........... 514/233.2 |
| 2013/0143914 A1 | 6/2013 | Woo et al. |
| 2013/0150343 A1 | 6/2013 | Van Niel et al. |
| 2013/0150361 A1 | 6/2013 | Van Niel et al. |

FOREIGN PATENT DOCUMENTS

| WO | 2010/094956 | 8/2010 |
| WO | 2011/154738 | 12/2011 |

OTHER PUBLICATIONS

Venkatesh et al., J. Pharm. Sci. 89, 145-54 (2000) (p. 146, left column).*
Dorwald F. A. Side Reactions in Organic Synthesis, 2005, Wiley: VCH, Weinheim p. IX of Preface p. 1-15.*
U.S. Appl. No. 14/296,730, filed Jun. 5, 2014, Woo, et al.
U.S. Appl. No. 14/330,145, filed Jul. 14, 2014, Van Niel, et al.
U.S. Appl. No. 14/363,556, filed Jun. 6, 2014, Finch, et al.
U.S. Appl. No. 14/451,600, filed Aug. 5, 2014, Van Niel, et al.
European Search Report in Application No. 13170937.0, issued Dec. 13, 2013.
U.S. Appl. No. 14/513,663, filed Oct. 14, 2014, Van Niel, et al.

* cited by examiner

*Primary Examiner* — Nizal Chandrakumar
(74) *Attorney, Agent, or Firm* — Oblon, McClelland, Maier & Neustadt, L.L.P.

(57) ABSTRACT

This invention relates to compounds and compositions that are p38 MAPK inhibitors, useful as anti-inflammatory agents in the treatment of, inter alia, diseases of the respiratory tract.

9 Claims, No Drawings

KINASE INHIBITORS

CROSS REFERENCES TO RELATED APPLICATIONS

This application claims priority to European Patent Application No. 13170937.0 filed on Jun. 6, 2013, which is incorporated herein by reference in its entirety.

BACKGROUND OF THE INVENTION

1. Field of the Invention

The present invention relates to compounds and compositions that are p38 MAPK inhibitors and which are useful as anti-inflammatory agents in the treatment of, inter alia, diseases of the respiratory tract.

2. Discussion of the Background

Mitogen activated protein kinases (MAPK) constitute a family of proline-directed serine/threonine kinases that activate their substrates by dual phosphorylation. There are four known human isoforms of p38 MAP kinase, p38α, p38β, p38γ, and p38δ. The p38 kinases, which are also known as cytokine suppressive anti-inflammatory drug binding proteins (CSBP), stress activated protein kinases (SAPK) and RK, are responsible for phosphorylating (Stein et al., Ann. Rep. Med Chem., 1996, 31, 289-298, which is incorporated herein by reference in its entirety) and activating transcription factors (such as ATF-2, MAX, CHOP and C/ERPb) as well as other kinases (such as MAPKAP-K2/3 or MK2/3), and are themselves activated by physical and chemical stress (e.g. UV, osmotic stress), pro-inflammatory cytokines and bacterial lipopolysaccharide (LPS) (Herlaar E. & Brown Z., Molecular Medicine Today, 1999, 5, 439-447, which is incorporated herein by reference in its entirety). The products of p38 phosphorylation have been shown to mediate the production of inflammatory cytokines, including tumor necrosis factor alpha (TNF α) and interleukin-(IL-)-1, and cyclooxygenase-2 (COX-2). IL-1 and TNFα are also known to stimulate the production of other proinflammatory cytokines such as IL-6 and IL-8.

IL-1 and TNFα are biological substances produced by a variety of cells, such as monocytes or macrophages. IL-1 has been demonstrated to mediate a variety of biological activities thought to be important in immunoregulation and other physiological conditions such as inflammation (e.g. Dinarello et al., Rev. Infect. Disease, 1984, 6, 51, which is incorporated herein by reference in its entirety). Excessive or unregulated TNF production (particularly TNFα) has been implicated in mediating or exacerbating a number of diseases, and it is believed that TNF can cause or contribute to the effects of inflammation in general. IL-8 is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes and basophils. Increase in IL-8 production is also responsible for chemotaxis of neutrophils into the inflammatory site in vivo.

Inhibition of signal transduction via p38, which in addition to IL-1, TNF and IL-8 described above is also required for the synthesis and/or action of several additional pro-inflammatory proteins (e.g., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for p38 kinase inhibitors (Badger et al., J. Pharm. Exp. Thera., 1996, 279, 1453-1461; Griswold et al, Pharmacol. Comm., 1996, 7, 323-229, which are incorporated herein by reference in their entireties). In particular, p38 kinase inhibitors have been described as potential agents for treating rheumatoid arthritis. In addition to the links between p38 activation and chronic inflammation and arthritis, there is also data implicating a role for p38 in the pathogenesis of airway diseases in particular COPD and asthma. Stress stimuli (including tobacco smoke, infections or oxidative products) can cause inflammation within the lung environment. Inhibitors of p38 have been shown to inhibit LPS and ovalbumin induced airway TNF-α IL-1β, IL-6, IL-4, IL-5 and IL-13 (Haddad et al, Br. J. Pharmacol., 2001, 132 (8), 1715-1724; Underwood et al, Am. J. Physiol. Lung Cell. Mol. 2000, 279, 895-902; Duan et al., 2005 Am. J. Respir. Crit. Care Med., 171, 571-578; Escott et al Br. J. Pharmacol., 2000, 131, 173-176; Underwood et al., J. Pharmacol. Exp. Ther. 2000, 293, 281-288, which are incorporated herein by reference in their entireties). Furthermore, they significantly inhibit neutrophilia and the release of MMP-9 in LPS, ozone or cigarette smoke animal models. There is also a significant body of preclinical data highlighting the potential benefits of inhibition of the p38 kinase that could be relevant in the lung (Lee et al., Immunopharmacology, 2000, 47, 185-200, which is incorporated herein by reference in its entirety). Thus, therapeutic inhibition of p38 activation may be important in the regulation of airway inflammation.

The implication of the p38MAPK pathway in various diseases has been reviewed by P. Chopra et al. (Expert Opinion on Investigational Drugs, 2008, 17(10), 1411-1425, which is incorporated herein by reference in its entirety). It is believed that the compounds of the present invention can be used to treat p38 mediated diseases such as: chronic obstructive pulmonary disease (COPD), asthma, chronic or acute bronchoconstriction, bronchitis, acute lung injury and bronchiectasis, pulmonary artery hypertension, tuberculosis, lung cancer, inflammation generally (e.g. inflammatory bowel disease), arthritis, neuroinflammation, pain, fever, fibrotic diseases, pulmonary disorders and diseases (e.g., hyperoxic alveolar injury), cardiovascular diseases, post-ischemic reperfusion injury and congestive heart failure, cardiomyopathy, stroke, ischemia, reperfusion injury, renal reperfusion injury, brain edema, neurotrauma and brain trauma, neurodegenerative disorders, central nervous system disorders, liver disease and nephritis, gastrointestinal conditions, ulcerative diseases, Crohn's disease, ophthalmic diseases, ophthalmological conditions, glaucoma, acute injury to the eye tissue and ocular traumas, diabetes, diabetic nephropathy, skin-related conditions, myalgias due to infection, influenza, endotoxic shock, toxic shock syndrome, autoimmune disease, graft rejection, bone resorption diseases, multiple sclerosis, psoriasis, eczema, disorders of the female reproductive system, pathological (but non-malignant) conditions, such as hemangiomas, angiofibroma of the nasopharynx, and avascular necrosis of bone, benign and malignant tumors/neoplasia including cancer, leukaemia, lymphoma, systemic lupus erythematosus (SLE), angiogenesis including neoplasia, haemorrhage, coagulation, radiation damage, and/or metastasis. Chronic release of active TNF can cause cachexia and anorexia, and TNF can be lethal. TNF has also been implicated in infectious diseases. These include, for example, malaria, mycobacterial infection and meningitis. These also include viral infections, such as HIV, influenza virus, and herpes virus, including herpes simplex virus type-1 (HSV-1), herpes simplex virus type-2 (HSV-2), cytomegalovirus (CMV), varicella-zoster virus (VZV), Epstein-Barr virus, human herpes virus-6

(HHV-6), human herpesvirus-7 (HHV7), human herpesvirus-8 (HHV-8), pseudorabies and rhinotracheitis, among others.

Known P38 kinase inhibitors have been reviewed by G. J. Hanson (Expert Opinions on Therapeutic Patents, 1997, 7, 729-733) J Hynes et al. (Current Topics in Medicinal Chemistry, 2005, 5, 967-985), C. Dominguez et al (Expert Opinions on Therapeutics Patents, 2005, 15, 801-816) and L. H. Pettus & R. P. Wurtz (Current Topics in Medicinal Chemistry, 2008, 8, 1452-1467), which are incorporated herein by reference in their entireties. P38 kinase inhibitors containing a triazolopyridine motif are known in the art, for example WO 07/091, 152, WO 04/072072, and WO 06/018727, which are incorporated herein by reference in their entireties.

WO 2010/094956, which is incorporated herein by reference in its entirety, discloses triazolopyridine derivatives of formula (I) as being p38 MAP Kinase inhibitors:

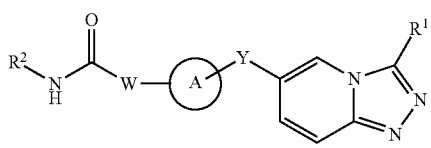

(I)

In such compounds, A represents an optionally substituted divalent arylene radical, an heteroarylene radical, a ($C_5$-$C_6$) divalent cycloalkylene radical having 5 or 6 ring atoms or a pyperidinylene radical.

Other p38 MAP Kinase inhibitors are described in the co-pending applications PCT/EP2011/072375, PCT/EP2012/074446 and PCT/EP2012/074450, which are incorporated herein by reference in their entireties.

The compounds are said to be useful in as anti-inflammatory agents in the treatment of diseases of the respiratory tract.

However, there remains a need for improved p38 mitogen activated protein kinase inhibitors.

SUMMARY OF THE INVENTION

Accordingly, it is one object of the present invention to provide novel p38 mitogen activated protein kinase inhibitors which are useful in the treatment of inflammatory and obstructive diseases of the respiratory tract.

It is another object of the present invention, to provide novel p38 mitogen activated protein kinase inhibitors which show an appropriate developability profile on inhalatory administration to effectively treat respiratory obstructive or inflammatory diseases. It is to be understood that such profile may be achieved in a number of different ways by modulation of specific properties; by way of example, it could be achieved by administration of a low effective dose of the drug thus limiting side effects or via a long duration of action in the lungs which may reduce the frequency of administration.

It is another object of the present invention to provide novel methods of treating certain diseases and/or conditions by administering such a p38 mitogen activated protein kinase inhibitor.

These and other objects, which will become apparent during the following detailed description, have been achieved by the inventors' discovery of the compounds of formula (I) described below.

The compounds of the present invention are inhibitors of p38 mitogen activated protein kinase ("p38 MAPK", "p38 kinase" or "p38"), including p38α kinase, and are inhibitors of cytokine and chemokine production including TNFα and IL-8 production. They have a number of therapeutic applications, in the treatment of inflammatory diseases, particularly allergic and non-allergic airways diseases, more particularly obstructive or inflammatory airways diseases such as chronic obstructive pulmonary disease ("COPD") and asthma. They are therefore particularly suited for pulmonary delivery, by inhalation by nose or mouth.

DETAILED DESCRIPTION OF THE PREFERRED EMBODIMENTS

According to the invention there is provided a compound of formula (I), or a pharmaceutically acceptable salt thereof:

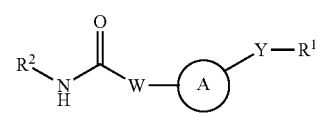

(I)

wherein:

W is a heteroatom selected from N or O, wherein N is substituted with —H, $C_1$-$C_6$ alkyl or $C_3$-$C_5$ cycloalkyl;

Y is selected in the group consisting of: a group —S(O)$_p$— wherein p is 0, 1 or 2; a group —O($CR^3R^4$)$_n$—; a group —($CR^5R^6$)$_n$—; a group —$NR^7$—; a group —OC(O)—; a group —OC(O)NH—; and a group —OC(O)O—;

$R^3$, $R^4$, $R^5$ and $R^6$ are each independently —H, —F or $C_1$-$C_6$ alkyl, or, respectively, $R^3$ and $R^4$, or $R^5$ and $R^6$ may form together with the carbon atom to which they are attached a saturated 3-6 membered carbocyclic monocyclic ring optionally substituted by a group $C_1$-$C_6$ alkyl, hydroxyl or halo;

n is 0, 1, 2 or 3;

$R^7$ is —H, $C_1$-$C_6$ alkyl, or $C_3$-$C_7$ cycloalkyl wherein such $C_1$-$C_6$ alkyl or $C_3$-$C_7$ cycloalkyl are optionally substituted by a group $C_1$-$C_3$ alkyl, $C_3$-$C_6$ cycloalkyl, hydroxyl, —CN or halo;

$R^1$ is a group selected from (IIa)-(IIc):

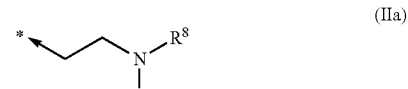

(IIa)

(IIb)

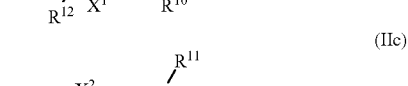

(IIc)

$R^8$ and $R^9$ are each independently —H or $C_1$-$C_6$ alkyl, or $R^8$ and $R^9$ may form together with the nitrogen atom to which they are attached a 4-11-membered saturated monocyclic or a fused or spiro bicyclic ring system optionally containing a further heteroatom which is oxygen or nitrogen, said nitrogen atom being optionally substituted by $C_1$-$C_6$ alkyl; wherein such $C_1$-$C_6$ alkyl groups may be optionally substituted by a group $C_1$-$C_6$ alkyl, $C_3$-$C_6$ cycloalkyl, hydroxyl or halo;

$X^1$, $X^2$, $X^3$, $X^4$ and $X^5$ are each independently a carbon atom, a nitrogen atom, a group —(CH)— or a group —NH—; such that each combination thereof forms an aromatic ring system;

$R^{10}$ is selected from a group consisting of: —H, —CN, —$NR^A R^B$, —N($R^C$)($C_2$-$C_6$alkylene)-$NR^A R^B$, —N($R^C$)($C_3$-$C_7$cycloalkylene)-$NR^A R^B$, —($C_1$-$C_6$alkylene)-$NR^A R^B$, —($C_3$-$C_7$cycloalkylene)-$NR^A R^B$, —O—($C_2$-$C_6$alkylene)-$NR^A R^B$, —O—($C_3$-$C_7$cycloalkylene)-$NR^A R^B$, —S—($C_2$-$C_6$alkylene)-$NR^A R^B$, —S—($C_3$-$C_7$cycloalkylene)-$NR^A R^B$, —N($R^C$)C(O)—($C_1$-$C_6$alkylene)-$NR^A R^B$, —N($R^C$)C(O)—($C_3$-$C_7$cycloalkylene)-$NR^A R^B$, —C(O)N($R^C$)—($C_2$-$C_6$alkylene)-$NR^A R^B$, —C(O)N($R^C$)—($C_3$-$C_7$cycloalkylene)-$NR^A R^B$, —C(O)N($R^C$)—($C_2$-$C_6$alkylene)-$OR^D$, —C(O)N($R^C$)—($C_3$-$C_7$cycloalkylene)-$OR^D$, —N($R^C$)C(O)$NR^A R^B$, —C(O)$NR^A R^B$, —N($R^C$)C(O)N($R^C$)—($C_2$-$C_6$alkylene)-$NR^A R^B$, —N($R^C$)C(O)N($R^C$)—($C_3$-$C_7$cycloalkylene)-$NR^A R^B$, —($C_2$-$C_6$alkylene)-$OR^D$, —($C_3$-$C_7$cycloalkylene)-$OR^D$, —O—($C_2$-$C_6$alkylene)-$OR^D$, —O—($C_3$-$C_7$cycloalkylene)-$OR^D$, —S—($C_2$-$C_6$alkylene)-$OR^D$, —S—($C_3$-$C_7$cycloalkylene)-$OR^D$, —N($R^C$)S(O)$_2$—($C_1$-$C_6$alkylene)-$NR^A R^B$, —N($R^C$)S(O)$_2$—($C_3$-$C_7$cycloalkylene)-$NR^A R^B$, —S(O)$_2$N($R^C$)—($C_2$-$C_6$alkylene)-$NR^A R^B$, —S(O)$_2$N($R^C$)—($C_3$-$C_7$cycloalkylene)-$NR^A R^B$, —S(O)$_2$N($R^C$)—($C_2$-$C_6$alkylene)-$OR^D$, —S(O)$_2$N($R^C$)—($C_3$-$C_7$cycloalkylene)-$OR^D$, —N($R^C$)S(O)$_2$—($C_2$-$C_6$alkylene)-$OR^D$, —N($R^C$)S(O)$_2$—($C_3$-$C_7$cycloalkylene)-$OR^D$, —S(O)$_2$N($R^A R^B$), —N($R^C$)S(O)$_2 R^D$, —N($R^C$)C(O)$R^C$, —$OR^C$, —$SR^C$, —($C_3$-$C_7$heterocycloalkyl), ($C_5$-$C_7$heterocycloalkyl)-($C_1$-$C_6$alkyl), ($C_5$-$C_7$heterocycloalkyl)($C_3$-$C_6$cycloalkyl)-, and $C_3$-$C_7$ heterocycloalkylcarbonyl; wherein any of such $C_1$-$C_6$alkyl, $C_3$-$C_6$cycloalkyl, —($C_1$-$C_6$alkylene)-($C_2$-$C_6$alkylene)-, —($C_3$-$C_7$cycloalkylene)-, —($C_3$-$C_7$heterocycloalkyl), ($C_5$-$C_7$heterocycloalkyl)-($C_1$-$C_6$ alkyl), ($C_5$-$C_7$ heterocycloalkyl)-($C_3$-$C_6$ cycloalkyl) and ($C_3$-$C_7$heterocycloalkyl) carbonyl portion in the above listed groups may be optionally substituted by a group $C_1$-$C_6$ alkyl, $C_3$-$C_7$ cycloalkyl, hydroxyl or halo;

$R^{11}$ is linked to $X^4$ and is selected from a group consisting of:
—H; —CN; $C_1$-$C_6$ alkyl which is substituted by a group selected from —CN, —$OR^C$, —$SR^C$, halo; $C_3$-$C_6$cycloalkyl which is substituted by a group selected from $C_1$-$C_4$ alkyl, —CN, —$OR^C$, —$SR^D$, halo; —$NR^A R^B$, —N($R^C$)($C_2$-$C_6$alkylene)-$NR^A R^B$, —N($R^C$)($C_3$-$C_7$cycloalkylene)-$NR^A R^B$, —($C_1$-$C_6$alkylene)-$NR^A R^B$, —($C_3$-$C_7$cycloalkylene)-$NR^A R^B$, —O—($C_2$-$C_6$alkylene)-$NR^A R^B$, —O—($C_3$-$C_7$cycloalkylene)-$NR^A R^B$, —S—($C_2$-$C_6$alkylene)-$NR^A R^B$, —S—($C_3$-$C_7$cycloalkylene)-$NR^A R^B$, —N($R^C$)C(O)—($C_1$-$C_6$alkylene)-$NR^A R^B$, —N($R^C$)C(O)—($C_3$-$C_7$cycloalkylene)-$NR^A R^B$, —C(O)N($R^C$)—($C_2$-$C_6$alkylene)-$NR^A R^B$, —C(O)N($R^C$)—($C_3$-$C_7$cycloalkylene)-$NR^A R^B$, —C(O)N($R^C$)—($C_2$-$C_6$alkylene)-$OR^D$, —C(O)N($R^C$)—($C_3$-$C_7$cycloalkylene)-$OR^D$, —N($R^C$)C(O)N($R^A R^B$), —C(O)N($R^A R^B$), —N($R^C$)C(O)N($R^C$)—($C_2$-$C_6$alkylene)-$NR^A R^B$, —N($R^C$)C(O)N($R^C$)—($C_3$-$C_7$cycloalkylene)-$NR^A R^B$, —O—($C_2$-$C_6$alkylene)-$OR^D$, —O—($C_3$-$C_7$cycloalkylene)-$OR^D$, —S—($C_2$-$C_6$alkylene)-$OR^D$, —S—($C_3$-$C_7$cycloalkylene)-$OR^D$, —N($R^C$)S(O)$_2$—($C_1$-$C_6$alkylene)-$NR^A R^B$, —N($R^C$)S(O)$_2$—($C_3$-$C_7$cycloalkylene)-$NR^A R^B$, —S(O)$_2$N($R^C$)—($C_2$-$C_6$alkylene)-$NR^A R^B$, —S(O)$_2$N($R^C$)—($C_3$-$C_7$cycloalkylene)-$NR^A R^B$, —S(O)$_2$N($R^C$)—($C_2$-$C_6$alkylene)-$OR^D$, —S(O)$_2$N($R^C$)—($C_3$-$C_7$cycloalkylene)-$OR^D$, —N($R^C$)S(O)$_2$—($C_2$-$C_6$alkylene)-$OR^D$, —N($R^C$)S(O)$_2$—($C_3$-$C_7$cycloalkylene)-$OR^D$, —S(O)$_2$N($R^A R^B$), —N($R^C$)S(O)$_2 R^D$, —N($R^C$)C(O)$R^C$, $OR^C$, $SR^C$, —($C_3$-$C_7$heterocycloalkyl), ($C_5$-$C_7$heterocycloalkyl)-($C_1$-$C_6$alkyl), ($C_5$-$C_7$heterocycloalkyl)($C_3$-$C_6$cycloalkyl) and ($C_3$-$C_7$ heterocycloalkyl)carbonyl, wherein any of such $C_1$-$C_6$alkyl, $C_3$-$C_6$cycloalkyl, —($C_1$-$C_6$alkylene)-($C_2$-$C_6$alkylene)-, —($C_3$-$C_7$cycloalkylene)-, —($C_3$-$C_7$heterocycloalkyl), ($C_5$-$C_7$heterocycloalkyl)-($C_1$-$C_6$ alkyl), ($C_5$-$C_7$ heterocycloalkyl)-($C_3$-$C_6$ cycloalkyl) and ($C_3$-$C_7$heterocycloalkyl) carbonyl portion in the above listed groups may be optionally substituted by one, two or three groups $R^{25}$ which are independently selected in the list consisting of: $C_1$-$C_6$ alkyl, ($C_1$-$C_3$)haloalkyl, ($C_1$-$C_4$)hydroxyalkyl, $C_3$-$C_7$ cycloalkyl, hydroxyl, —CN, $OR^D$ and halo; or $R^{11}$ is linked to $X^4$ and is phenyl or 5- or 6-membered monocyclic heteroaryl, wherein such phenyl or 5- or 6-membered monocyclic heteroaryl is substituted by a group selected in the list consisting of: $C_1$-$C_6$ alkyl which is substituted by a group —CN; $C_3$-$C_6$ cycloalkyl which is substituted by a group selected from: —CN, —$OR^C$, —$SR^C$ or halo; —N($R^C$)($C_2$-$C_6$alkylene)-$NR^A R^B$, —N($R^C$)($C_3$-$C_7$cycloalkylene)-$NR^A R^B$, —($C_1$-$C_6$alkylene)-$NR^A R^B$, —($C_3$-$C_7$cycloalkylene)-$NR^A R^B$, —O—($C_3$-$C_7$cycloalkylene)-$NR^A R^B$, —S—($C_2$-$C_6$alkylene)-$NR^A R^B$, —S—($C_3$-$C_7$cycloalkylene)-$NR^A R^B$, —N($R^C$)C(O)—($C_1$-$C_6$alkylene)-$NR^A R^B$, —N($R^C$)C(O)—($C_3$-$C_7$cycloalkylene)-$NR^A R^B$, —C(O)N($R^C$)—($C_2$-$C_6$alkylene)-$NR^A R^B$, C(O)N($R^C$)—($C_3$-$C_7$cycloalkylene)-$NR^A R^B$, —C(O)N($R^C$)—($C_2$-$C_6$alkylene)-$OR^D$, —C(O)N($R^C$)—($C_3$-$C_7$cycloalkylene)-$OR^D$, —N($R^C$)C(O)N($R^C$)—($C_2$-$C_6$alkylene)-$NR^A R^B$, —N($R^C$)C(O)N($R^C$)—($C_3$-$C_7$cycloalkylene)-$NR^A R^B$, —O—($C_3$-$C_7$cycloalkylene)-$OR^D$, —S—($C_3$-$C_7$cycloalkylene)-$OR^D$, —N($R^C$)S(O)$_2$—($C_1$-$C_6$alkylene)-$NR^A R^B$, —N($R^C$)S(O)$_2$—($C_3$-$C_7$cycloalkylene)-$NR^A R^B$, —S(O)$_2$N($R^C$)—($C_2$-$C_6$alkylene)-$NR^A R^B$, —S(O)$_2$N($R^C$)—($C_3$-$C_7$cycloalkylene)-$NR^A R^B$, —S(O)$_2$N($R^C$)—($C_2$-$C_6$alkylene)-$OR^D$, —S(O)$_2$N($R^C$)—($C_3$-$C_7$cycloalkylene)-$OR^D$, —N($R^C$)S(O)$_2$—($C_2$-$C_6$alkylene)-$OR^D$, —N($R^C$)S(O)$_2$—($C_3$-$C_7$cycloalkylene)-$OR^D$, —N($R^C$)S(O)$_2 R^D$, —($C_3$-$C_7$heterocycloalkyl), ($C_5$-$C_7$heterocycloalkyl)-($C_1$-$C_6$alkyl), ($C_5$-$C_7$heterocycloalkyl)($C_3$-$C_6$cycloalkyl) and ($C_3$-$C_7$heterocycloalkyl)carbonyl, wherein any of such $C_1$-$C_6$alkyl, $C_3$-$C_6$cycloalkyl, —($C_1$-$C_6$alkylene)-($C_2$-$C_6$alkylene)-, —($C_3$-$C_7$cycloalkylene)-, —($C_3$-$C_7$heterocycloalkyl), ($C_5$-$C_7$heterocycloalkyl)-($C_1$-$C_6$ alkyl), ($C_5$-$C_7$ heterocycloalkyl)-($C_3$-$C_6$ cycloalkyl) and ($C_3$-$C_7$heterocycloalkyl)carbonyl portion in the above listed groups may be optionally substituted by one, two or three groups $R^{25}$ which are independently selected in the group consisting of: $C_1$-$C_6$alkyl, ($C_1$-$C_3$) haloalkyl, ($C_1$-$C_4$)hydroxyalkyl, $C_3$-$C_7$cycloalkyl, hydroxyl, —CN, $OR^D$ and halo;

$R^A$ and $R^B$ are at each occurrence independently —H, $C_1$-$C_6$ alkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —$OR^D$, —CN or halo; alternatively, $R^A$ and $R^B$, may form together with the nitrogen atom to which they are attached an azetidine or a 4-11-membered saturated heterocyclic monocyclic or bicyclic ring system which is optionally substituted by one or more group —$OR^D$, —CN, halo, $C_1$-$C_6$ alkyl, ($C_1$-$C_6$)hydroxyalkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —$OR^D$, —CN or halo; and which 6-11-membered saturated heterocyclic monocyclic or bicyclic ring optionally contains a further heteroatom which is oxygen or nitrogen, said nitrogen atom optionally substituted by $C_1$-$C_6$ alkyl or $C_3$-$C_6$ cycloalkyl, wherein any of such $C_1$-$C_6$ alkyl or $C_3$-$C_6$ cycloalkyl may be optionally substituted by a group $C_1$-$C_6$ alkyl, $C_3$-$C_7$ cycloalkyl, —$OR^D$, —CN, or halo; or $R^A$ and $R^B$ may be linked to one carbon atom of the —($C_1$-$C_6$alkylene)-, —($C_2$-$C_6$alkylene)- or —($C_3$-$C_7$cycloalkylene)-portion of the group linked to the nitrogen to which they are connected to form a saturated cycle of up to 6 ring atoms;

$R^C$ is at each occurrence independently —H, $C_1$-$C_6$ alkyl, ($C_1$-$C_4$)hydroxyalkyl or $C_3$-$C_6$ cycloalkyl, such $C_1$-$C_6$ alkyl and $C_3$-$C_6$ cycloalkyl being optionally substituted by a group $C_1$-$C_3$ alkyl, —$OR^D$, —CN or halo;

alternatively $R^C$ may be linked to one carbon atom of the —($C_2$-$C_6$alkylene)- or —($C_3$-$C_7$cycloalkylene)-portion of the group linked to the nitrogen to which they are connected to form a saturated cycle of up to 6 ring atoms $R^D$ is at each occurrence independently —H, —$CH_3$ or —$C_2H_5$;

$R^{12}$ and $R^{13}$ are independently —H, $C_1$-$C_6$ alkyl, or halogen;

A is a divalent cycloalkylene radical having 5, 6 or 7 ring atoms; said cycloalkylene ring being attached to W and Y and fused to a phenyl ring or to a monocyclic heteroaryl ring having 5 or 6 ring atoms, such phenyl or heteroaryl ring being optionally substituted by one or two groups $R^{24}$;

$R^{24}$ is at each occurrence independently selected from the group consisting of $C_1$-$C_6$ alkyl, halogen and —CN;

$R^2$ is a radical of formula (IIIb):

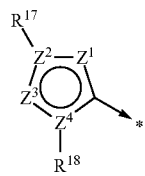

(IIIb)

wherein $R^{17}$ is selected from the group consisting of lone electron pair, —H, —$CF_3$, —$NR^ER^F$, —($C_3$-$C_7$cycloalkyl), —($C_3$-$C_7$heterocycloalkyl), aryl or heteroaryl wherein any of such —($C_3$-$C_7$cycloalkyl), —($C_3$-$C_7$heterocycloalkyl), aryl or heteroaryl may be optionally substituted by a group $C_1$-$C_6$ alkyl, $C_3$-$C_7$ cycloalkyl or halo; or $R^{17}$ is a group of general formula (IV)

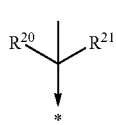

(IV)

wherein $R^{20}$ is selected in the group consisting of —F, —$CH_3$, —$C_2H_5$, —$CH_2OH$, —$CH_2OMe$, —$CF_2CF_3$, —$CH_2SCH_3$, —$SCH_3$ and —$SC_2H_5$;

$R^{21}$ is —$CH_3$ or —$C_2H_5$;

or $R^{20}$ and $R^{21}$ as defined above may form together with the carbon atom to which they are attached a saturated 3-7-membered monocyclic ring;

$R^E$ and $R^F$ are each independently $C_1$-$C_6$ alkyl, optionally substituted by a group $C_1$-$C_3$ alkyl, —$OR^G$, —CN or halo; alternatively $R^E$ and $R^F$ may form together with the nitrogen atom to which they are attached a 5-11-membered saturated monocyclic or bicyclic heterocyclic ring system which is optionally substituted by one or more groups —$OR^G$, —CN, halo, $C_1$-$C_6$ alkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —$OR^G$, —CN or halo; and which 5-11-membered saturated monocyclic or bicyclic heterocyclic ring optionally contains a further heteroatom which is oxygen or nitrogen, said nitrogen atom optionally substituted by $C_1$-$C_6$ alkyl or $C_3$-$C_6$ cycloalkyl, wherein any of such $C_1$-$C_6$ alkyl or $C_3$-$C_6$ cycloalkyl may be optionally substituted by a group $C_1$-$C_6$ alkyl or $C_3$-$C_7$ cycloalkyl;

$R^G$ is —H, —$CH_3$ or —$C_2H_5$;

$R^{18}$ is selected in the group consisting of aryl, heterocycloalkyl and heteroaryl, wherein any of such aryl, heterocycloalkyl or heteroaryl is substituted by two or more groups independently selected from —CN, —OH, =O, halo, —CO-$OR^M$, $C_1$-$C_6$ alkyl, $C_3$-$C_6$cycloalkyl, —O—($C_1$-$C_6$alkyl), —($C_1$-$C_6$)hydroxyalkyl, —O—($C_3$-$C_6$cycloalkyl), —S—($C_1$-$C_6$alkyl), —S—($C_3$-$C_6$cycloalkyl), —$NR^HR^J$, —N($R^L$)($C_2$-$C_6$alkylene)-$NR^HR^J$, —N($R^L$)($C_3$-$C_7$cycloalkylene)-$NR^HR^J$, —($C_1$-$C_6$alkylene)-$NR^HR^J$, —($C_3$-$C_7$cycloalkylene)-$NR^HR^J$, —O—($C_2$-$C_6$alkylene)-$NR^HR^J$, —O—($C_3$-$C_7$cycloalkylene)-$NR^HR^J$, —S—($C_2$-$C_6$alkylene)-$NR^HR^J$, —S—($C_3$-$C_7$cycloalkylene)-$NR^HR^J$, —N($R^L$)C(O)—($C_1$-$C_6$alkylene)-$NR^HR^J$, —N($R^L$)C(O)—($C_3$-$C_7$cycloalkylene)-$NR^HR^J$, —C(O)N($R^L$)—($C_2$-$C_6$alkylene)-$NR^HR^J$, —C(O)N($R^L$)—($C_3$-$C_7$cycloalkylene)-$NR^HR^J$, —C(O)N($R^L$)—($C_2$-$C_6$alkylene)-$OR^M$, —C(O)N($R^L$)—($C_3$-$C_7$cycloalkylene)-$OR^M$, —N($R^L$)C(O)N($R^HR^J$), —C(O)N($R^HR^J$), —N($R^L$)C(O)N($R^L$)—($C_2$-$C_6$alkylene)-$NR^HR^J$, —N($R^L$)C(O)N($R^L$)—($C_3$-$C_7$cycloalkylene)-$NR^HR^J$, —O—($C_2$-$C_6$alkylene)-$OR^M$, —O—($C_3$-$C_7$cycloalkylene)-$OR^M$, —S—($C_2$-$C_6$alkylene)-$OR^M$, —S—($C_3$-$C_7$cycloalkylene)-$OR^M$, —N($R^L$)S(O)$_2$—($C_1$-$C_6$alkylene)-$NR^HR^J$, —N($R^L$)S(O)$_2$—($C_3$-$C_7$cycloalkylene)-$NR^HR^J$, —S(O)$_2$N($R^L$)—($C_2$-$C_6$alkylene)-$NR^HR^J$, —S(O)$_2$N($R^L$)—($C_3$-$C_7$cycloalkylene)-$NR^HR^J$, —S(O)$_2$N($R^L$)—($C_2$-$C_6$alkylene)-$OR^M$, —S(O)$_2$N($R^L$)—($C_3$-$C_7$cycloalkylene)-$OR^M$, —N($R^L$)S(O)$_2$—($C_2$-$C_6$alkylene)-$OR^M$, —N($R^L$)S(O)$_2$—($C_3$-$C_7$cycloalkylene)-$OR^M$, —S(O)$_2$N($R^HR^J$), —N($R^L$)S(O)$_2R^L$, —N($R^L$)C(O)$R^L$, $OR^L$, $SR^L$, —($C_3$-$C_7$heterocycloalkyl), ($C_5$-$C_7$heterocycloalkyl)-($C_1$-$C_6$ alkyl) and ($C_5$-$C_7$ heterocycloalkyl)-($C_3$-$C_6$ cycloalkyl), wherein any of such $C_1$-$C_6$alkyl, $C_3$-$C_6$cycloalkyl, —($C_1$-$C_6$alkylene)-, —($C_2$-$C_6$alkylene)-, —($C_3$-$C_7$cycloalkylene)-, —($C_3$-$C_7$heterocycloalkyl), ($C_5$-$C_7$heterocycloalkyl)-($C_1$-$C_6$ alkyl) and ($C_5$-$C_7$ heterocycloalkyl)-($C_3$-$C_6$ cycloalkyl) portion in the above listed groups may be optionally substituted by a group $C_1$-$C_6$ alkyl, $C_3$-$C_7$ cycloalkyl, —$OR^L$ or halo;

$R^H$ and $R^J$ are at each occurrence independently —H, $C_1$-$C_6$ alkyl or $C_3$-$C_6$ cycloalkyl, such $C_1$-$C_6$ alkyl or $C_3$-$C_6$ cycloalkyl being optionally substituted by a group $C_1$-$C_3$ alkyl, —$OR^M$, CN or halo; alternatively, $R^H$ and $R^J$ may also form together with the nitrogen atom to which they are attached a 4-11 membered saturated monocyclic or bicyclic heterocyclic ring system which is optionally substituted by one or more groups —$OR^M$, —CN, halo, $NR^OR^P$, $C_1$-$C_6$ alkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —$OR^M$, CN or halo; and which 6-11-membered saturated monocyclic or bicyclic heterocyclic ring optionally contains a further heteroatom which is oxygen or nitrogen, said nitrogen atom optionally substituted by $C_1$-$C_6$ alkyl or $C_3$-$C_6$ cycloalkyl, wherein any of such $C_1$-$C_6$ alkyl or $C_3$-$C_6$ cycloalkyl may be optionally substituted by a group $C_1$-$C_6$ alkyl, $C_3$-$C_7$ cycloalkyl, —$OR^M$, CN, or halo; or $R^H$ and $R^J$ may be linked to one carbon atom of the —($C_1$-$C_6$alkylene)-, —($C_2$-$C_6$alkylene)- or —($C_3$-$C_7$cycloalkylene)-portion of the group linked to the nitrogen to which they are connected to form a saturated cycle of up to 6 ring atoms;

$R^L$ is at each occurrence independently —H, $C_1$-$C_6$ alkyl or $C_3$-$C_6$ cycloalkyl, such $C_1$-$C_6$ alkyl or $C_3$-$C_6$ cycloalkyl being optionally substituted by a group $C_1$-$C_3$ alkyl, —$OR^M$, —CN or halo;

$R^M$ is at each occurrence independently —H, $C_1$-$C_6$ alkyl or $C_3$-$C_6$ cycloalkyl, such $C_1$-$C_6$ alkyl or $C_3$-$C_6$ cycloalkyl being optionally substituted by a group hydroxyl, —CN or halo;

$R^O$ and $R^P$ are each independently $C_1$-$C_6$ alkyl or $C_1$-$C_6$ cycloalkyl, optionally substituted by a group $C_1$-$C_3$ alkyl, —$OR^Q$, —CN or halo; alternatively, $R^O$ and $R^P$ may form together with the nitrogen atom to which they are attached a 4-8-membered saturated monocyclic heterocyclic ring system which is optionally substituted by one or more groups —$OR^Q$, —CN, halo, $C_1$-$C_6$ alkyl or $C_3$-$C_7$ cycloalkyl, and which 4-8-membered saturated monocyclic heterocyclic ring optionally contains a further heteroatom which is oxygen or nitrogen, said nitrogen atom optionally substituted by $C_1$-$C_6$ alkyl or $C_3$-$C_6$ cycloalkyl;

$R^Q$ is —H, —$CH_3$ or —$C_2H_5$;

$z^1$, $z^2$, $z^3$, and $z^4$ are independently selected in the group consisting of C, N, S, O, a group —CH— and a group —NH—, in such a combination that the resulting ring formed is an aromatic system;

with the proviso that when Y is a group —O($CR^3R^4$)$_n$—, n is 1 and $R^{10}$ is —$NR^AR^B$, —$N(R^C)C(O)$—($C_1$-$C_6$alkylene)-$NR^AR^B$, —$N(R^C)C(O)$—($C_3$-$C_7$cycloalkylene)-$NR^AR^B$, —$N(R^C)C(O)N(R^AR^B)$, —$N(R^C)C(O)N(R^C)$—($C_2$-$C_6$alkylene)-$NR^AR^B$, —$N(R^C)C(O)N(R^C)$—($C_3$-$C_7$cycloalkylene)-$NR^AR^B$ or —$N(R^C)C(O)R^C$, then $X_1$ is nitrogen.

In one embodiment there is provided a compound of formula (IP), or a pharmaceutically acceptable salt thereof

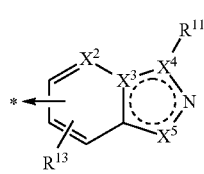

(IP)

wherein

W is N substituted with —H, $C_1$-$C_6$ alkyl or $C_3$-$C_5$ cycloalkyl;

Y is —O($CR^3R^4$)$_n$—;

$R^3$ and $R^4$ are each independently —H, —F or $C_1$-$C_6$ alkyl;

n is 0, 1, 2 or 3;

$R^1$ is a group (IIc)

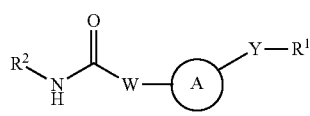

(IIc)

$X^2$, $X^3$, $X^4$ and $X^5$ are each independently a carbon atom, a nitrogen atom, a group —(CH)— or a group —NH—; such that each combination thereof forms an aromatic ring system;

$R^{11}$ is linked to $X^4$ and is selected from a group consisting of: —$NR^AR^B$, —$N(R^C)(C_2$-$C_6$alkylene)-$NR^AR^B$, —$N(R^C)(C_3$-$C_7$cycloalkylene)-$NR^AR^B$, —($C_1$-$C_6$alkylene)-$NR^AR^B$, —($C_3$-$C_7$cycloalkylene)-$NR^AR^B$ wherein any of such —($C_2$-$C_6$alkylene)- and —($C_3$-$C_7$cycloalkylene)-portion in the above listed groups may be optionally substituted by one, two or three groups $R^{25}$ which are independently selected in the list consisting of $C_1$-$C_6$ alkyl, ($C_1$-$C_3$) haloalkyl, ($C_1$-$C_4$) hydroxyalkyl, $C_3$-$C_7$ cycloalkyl, hydroxyl, —CN, $OR^D$ and halo;

$R^A$ and $R^B$ may form together with the nitrogen atom to which they are attached an azetidine or a 4-11-membered saturated heterocyclic monocyclic ring system which is optionally substituted by one or more group —$OR^D$, —CN, halo, $C_1$-$C_6$ alkyl, ($C_1$-$C_6$)hydroxyalkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —$OR^D$, —CN or halo; and which 6-11-membered saturated heterocyclic monocyclic or bicyclic ring optionally contains a further heteroatom which is oxygen or nitrogen, said nitrogen atom optionally substituted by $C_1$-$C_6$ alkyl or $C_3$-$C_6$ cycloalkyl, wherein any of such $C_1$-$C_6$ alkyl or $C_3$-$C_6$ cycloalkyl may be optionally substituted by a group $C_1$-$C_6$ alkyl, $C_3$-$C_7$ cycloalkyl, —$OR^D$, —CN, or halo; or $R^A$ and $R^B$ may be linked to one carbon atom of the —($C_1$-$C_6$alkylene)-, —($C_2$-$C_6$alkylene)- or —($C_3$-$C_7$cycloalkylene)-portion of the group linked to the nitrogen to which they are connected to form a saturated cycle of up to 6 ring atoms;

$R^C$ is at each occurrence independently —H, $C_1$-$C_6$ alkyl, ($C_1$-$C_4$)hydroxyalkyl or $C_3$-$C_6$ cycloalkyl, such $C_1$-$C_6$ alkyl and $C_3$-$C_6$ cycloalkyl being optionally substituted by a group $C_1$-$C_3$ alkyl, —$OR^D$, —CN or halo; alternatively $R^C$ may be linked to one carbon atom of the —($C_2$-$C_6$alkylene)- or —($C_3$-$C_7$cycloalkylene)-portion of the group linked to the nitrogen to which they are connected to form a saturated cycle of up to 6 ring atoms;

$R^D$ is at each occurrence independently —H, —$CH_3$ or —$C_2H_5$;

$R^{12}$ and $R^{13}$ are independently —H, $C_1$-$C_6$ alkyl or halogen;

A is a divalent cycloalkylene radical having 5, 6 or 7 ring atoms; said cycloalkylene ring being attached to W and Y, and fused to a phenyl ring or to a monocyclic heteroaryl ring having 5 or 6 ring atoms, such phenyl or heteroaryl ring being optionally substituted by one or two groups $R^{24}$;

$R^{24}$ is at each occurrence independently selected from the group consisting of: $C_1$-$C_6$ alkyl, halogen and —CN;

$R^2$ is a radical of formula (IIIb)

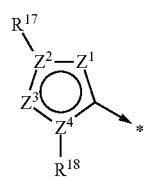

(IIIb)

wherein
R$^{17}$ is a group of general formula (IV)

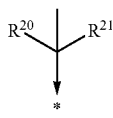

(IV)

wherein
R$^{20}$ is selected in the group consisting of —F, —CH$_3$, —C$_2$H$_5$, —CH$_2$OH, —CH$_2$OMe, —CF$_2$CF$_3$, —CH$_2$SCH$_3$, —SCH$_3$ and —SC$_2$H$_5$;
R$^{21}$ is —CH$_3$ or —C$_2$H$_5$;
or
R$^{20}$ and R$^{21}$ as defined above may form together with the carbon atom to which they are attached a saturated 3-7-membered monocyclic ring;
R$^{18}$ is selected in the group consisting of aryl, heterocycloalkyl and heteroaryl, wherein any of such aryl, heterocycloalkyl or heteroaryl is substituted by two or more groups independently selected from —CN, —OH, =O, halo, —CO-OR$^M$, C$_1$-C$_6$ alkyl, C$_3$-C$_6$cycloalkyl, —O—(C$_1$-C$_6$alkyl), —(C$_1$-C$_6$)hydroxyalkyl, —O—(C$_3$-C$_6$cycloalkyl), —NR$^H$R$^J$, —N(R$^L$)(C$_2$-C$_6$alkylene)-NR$^H$R$^J$, —N(R$^L$)(C$_3$-C$_7$cycloalkylene)-NR$^H$R$^J$, —(C$_1$-C$_6$alkylene)-NR$^H$R$^J$, —(C$_3$-C$_7$cycloalkylene)-NR$^H$R$^J$, —O—(C$_2$-C$_6$alkylene)-NR$^H$R$^J$, —O—(C$_3$-C$_7$cycloalkylene)-NR$^H$R$^J$, —N(R$^L$)C(O)—(C$_1$-C$_6$alkylene)-NR$^H$R$^J$, —N(R$^L$)C(O)—(C$_3$-C$_7$cycloalkylene)-NR$^H$R$^J$, —N(R$^L$)C(O)N(R$^H$R$^J$, —N(R$^L$)C(O)N(R$^L$)—(C$_2$-C$_6$alkylene)-NR$^H$R$^J$, —N(R$^L$)C(O)N(R$^L$)—(C$_3$-C$_7$cycloalkylene)-NR$^H$R$^J$, —O—(C$_2$-C$_6$alkylene)-OR$^M$, —O—(C$_3$-C$_7$cycloalkylene)-OR$^M$, —N(R$^L$)S(O)$_2$—(C$_1$-C$_6$alkylene)-NR$^H$R$^J$, N(R$^L$)S(O)$_2$—(C$_3$-C$_7$cycloalkylene)-NR$^H$R$^J$, —N(R$^L$)S(O)$_2$—(C$_2$-C$_6$alkylene)-OR$^M$, —(C$_3$-C$_7$cycloalkylene)-OR$^M$, —N(R$^L$)C(O)R$^L$, OR$^L$, —(C$_3$-C$_7$heterocycloalkyl), (C$_5$-C$_7$heterocycloalkyl)-(C$_1$-C$_6$alkyl) and (C$_5$-C$_7$heterocycloalkyl)-(C$_3$-C$_6$ cycloalkyl), wherein any of such C$_1$-C$_6$alkyl, C$_3$-C$_6$cycloalkyl, —(C$_1$-C$_6$alkylene)-, —(C$_2$-C$_6$alkylene)-, —(C$_3$-C$_7$cycloalkylene)-, —(C$_3$-C$_7$heterocycloalkyl), (C$_5$-C$_7$heterocycloalkyl)-(C$_1$-C$_6$alkyl) and (C$_5$-C$_7$ heterocycloalkyl)-(C$_3$-C$_6$ cycloalkyl) portion in the above listed groups may be optionally substituted by a group C$_1$-C$_6$ alkyl, C$_3$-C$_7$ cycloalkyl, —OR$^L$ or halo;
R$^H$ and R$^J$ are at each occurrence independently —H, C$_1$-C$_6$ alkyl or C$_3$-C$_6$ cycloalkyl, such C$_1$-C$_6$ alkyl or C$_3$-C$_6$ cycloalkyl being optionally substituted by a group C$_1$-C$_3$ alkyl, —OR$^M$, CN or halo; alternatively, R$^H$ and R$^J$ may also form together with the nitrogen atom to which they are attached a 4-11 membered saturated monocyclic or bicyclic heterocyclic ring system which is optionally substituted by one or more groups —OR$^M$, —CN, halo, NR$^O$R$^P$, C$_1$-C$_6$ alkyl or C$_3$-C$_7$ cycloalkyl, such C$_1$-C$_6$ alkyl and C$_3$-C$_7$ cycloalkyl being optionally substituted by a group C$_1$-C$_3$ alkyl, C$_3$-C$_7$cycloalkyl, —OR$^M$, CN or halo; and which 6-11-membered saturated monocyclic or bicyclic heterocyclic ring optionally contains a further heteroatom which is oxygen or nitrogen, said nitrogen atom optionally substituted by C$_1$-C$_6$ alkyl or C$_3$-C$_6$ cycloalkyl, wherein any of such C$_1$-C$_6$ alkyl or C$_3$-C$_6$ cycloalkyl may be optionally substituted by a group C$_1$-C$_6$ alkyl, C$_3$-C$_7$ cycloalkyl, —OR$^M$, CN, or halo; or R$^H$ and R$^J$ may be linked to one carbon atom of the —(C$_1$-C$_6$alkylene)-, —(C$_2$-C$_6$alkylene)- or —(C$_3$-C$_7$cycloalkylene)- portion of the group linked to the nitrogen to which they are connected to form a saturated cycle of up to 6 ring atoms;
R$^L$ is at each occurrence independently —H, C$_1$-C$_6$ alkyl or C$_3$-C$_6$ cycloalkyl, such C$_1$-C$_6$ alkyl or C$_3$-C$_6$ cycloalkyl being optionally substituted by a group C$_1$-C$_3$ alkyl, —OR$^M$, —CN or halo;
R$^M$ is at each occurrence independently —H, C$_1$-C$_6$ alkyl or C$_3$-C$_6$ cycloalkyl, such C$_1$-C$_6$alkyl or C$_3$-C$_6$ cycloalkyl being optionally substituted by a group hydroxyl, —CN or halo;
R$^O$ and R$^P$ are each independently C$_1$-C$_6$ alkyl or C$_1$-C$_6$ cycloalkyl, optionally substituted by a group C$_1$-C$_3$ alkyl, —OR$^Q$, —CN or halo; alternatively, R$^O$ and R$^P$ may form together with the nitrogen atom to which they are attached a 4-8-membered saturated monocyclic heterocyclic ring system which is optionally substituted by one or more groups —OR$^Q$, —CN, halo, C$_1$-C$_6$ alkyl or C$_3$-C$_7$ cycloalkyl, and which 4-8-membered saturated monocyclic heterocyclic ring optionally contains a further heteroatom which is oxygen or nitrogen, said nitrogen atom optionally substituted by C$_1$-C$_6$ alkyl or C$_3$-C$_6$ cycloalkyl;
R$^Q$ is —H, —CH$_3$ or —C$_2$H$_5$;
z$^1$, z$^2$, z$^3$, and z$^4$ are independently selected in the group consisting of: C, N, S, O, a group —CH—, and a group —NH—, in such a combination that the resulting ring formed is an aromatic system;
with the proviso that when Y is a group —O(CR$^3$R$^4$)$_n$—, n is 1 and R$^{10}$ is —NR$^A$R$^B$, —N(R$^C$)C(O)—(C$_1$-C$_6$alkylene)-NR$^A$R$^B$, —N(R$^C$)C(O)—(C$_3$-C$_7$cycloalkylene)-NR$^A$R$^B$, —N(R$^C$)C(O)N(R$^A$R$^B$), —N(R$^C$)C(O)N(R$^C$)—(C$_2$-C$_6$alkylene)-NR$^A$R$^B$, —N(R$^C$)C(O)N(R$^C$)—(C$_3$-C$_7$cycloalkylene)-NR$^A$R$^B$ or —N(R$^C$)C(O)R$^C$,
then X$_1$ is nitrogen.

In another aspect, the invention includes pharmaceutical compositions comprising a compound of the invention, together with one or more pharmaceutically acceptable carriers and/or excipients. Particularly preferred are compositions adapted for inhalation for pulmonary administration.

In another aspect, the invention includes the use of a compound of the invention for the treatment of diseases or conditions which benefit from inhibition of p38 MAP kinase activity. The treatment of obstructive or inflammatory airways diseases is a preferred use. All forms of obstructive or inflammatory airways diseases are potentially treatable with the compounds of the present invention, in particular an obstructive or inflammatory airways disease that is a member selected from the group consisting of chronic eosinophilic pneumonia, asthma, COPD, COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, chronic inflammatory diseases including cystic fibrosis, bronchiectasis and pulmonary fibrosis (Idiopathic). Efficacy is anticipated when p38 kinase inhibitors are administered either locally to the lung (for example by inhalation and intranasal delivery) or via systemic routes (for example, oral, intravenous and subcutaneous delivery).

Terminology.

As used herein, the terms "halogen" or "halo" include fluorine, chlorine, bromine and iodine atoms.

As used herein, the term "C$_x$-C$_y$alkyl" wherein x and y are integers, refers to a straight or branched chain alkyl radical having from x to y carbon atoms. Thus when x is 1 and y is 6, for example, the term includes methyl, ethyl, n-propyl, iso-propyl, n-butyl, isobutyl, sec-butyl, t-butyl, n-pentyl and n-hexyl.

As used herein, the term "$C_x$-$C_y$haloalkyl" refers to the above "$C_x$-$C_y$alkyl" group wherein one or more hydrogen atoms are replaced by one or more halogen atoms.

As used herein, the term "$C_x$-$C_y$hydroxyalkyl" refers to the above "$C_x$-$C_y$alkyl" group wherein one hydrogen atom is replaced by one hydroxyl group.

As used herein, the term "$C_x$-$C_y$alkylene" wherein x and y are integers, refers to a $C_x$-$C_y$alkyl radical having in total two unsatisfied valencies, such as a divalent methylene radical.

As used herein, the term "carbocyclic" refers to a mono-, bi- or tricyclic radical having up to 16 ring atoms, all of which are carbon, and includes aryl and cycloalkyl.

As used herein, the term "$C_z$-$C_k$cycloalkyl" wherein z and k are integers refers to a monocyclic saturated carbocyclic radical having from z to k carbon atoms and includes, for example, cyclopropyl, cyclobutyl, cyclopentyl, cyclohexyl, cycloheptyl and cyclooctyl. Comprised within the scope of the term "$C_z$-$C_k$cycloalkyl,", are those radicals having two unsatisfied valencies on the same carbon atom which will link to any $C_x$-$C_y$alkyl, $C_x$-$C_y$alkylene $C_z$-$C_k$cycloalkyl $C_z$-$C_k$cycloalkylene, $C_z$-$C_k$heterocycloalkyl, $C_z$-$C_k$heterocycloalkyl$C_x$-$C_y$alkyl, $C_z$-$C_k$heterocycloalkyl$C_z$-$C_k$cycloalkyl or ($C_z$-$C_k$)heterocycloalkylcarbonyl group by replacement of two hydrogen atoms placed on the same carbon. In such circumstances, this radical forms a gem—disubstituted or spiro system together with the $C_x$-$C_y$alkyl, $C_x$-$C_y$alkylene $C_z$-$C_k$cycloalkyl $C_z$-$C_k$cycloalkylene, $C_z$-$C_k$heterocycloalkyl, $C_z$-$C_k$heterocycloalkyl$C_x$-$C_y$alkyl, $C_z$-$C_k$heterocycloalkyl$C_z$-$C_k$cycloalkyl or ($C_z$-$C_k$)heterocycloalkylcarbonyl group it is linked to.

The term "$C_z$-$C_k$cycloalkylene radical" refers to a $C_z$-$C_k$cycloalkyl radical having two unsatisfied valencies on different cycle carbon atoms as follows:

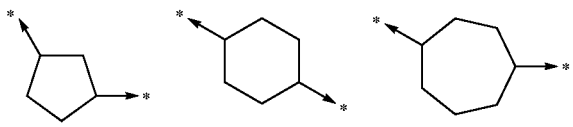

As used herein, the unqualified term "aryl" refers to a mono- or bi-cyclic carbocyclic aromatic radical, and includes radicals having two monocyclic carbocyclic aromatic rings which are directly linked by a covalent bond. Illustrative of such radicals are phenyl, biphenyl and naphthyl.

As used herein, the unqualified term "heteroaryl" refers to a mono- or bi-cyclic aromatic radical containing one or more heteroatoms selected from S, N and O, and includes radicals having two such monocyclic rings, or one such monocyclic ring and one monocyclic aryl ring, which are fused through a common bond. Illustrative examples of 5,6-membered heteroaryl are: are thienyl, furyl, pyrrolyl, imidazolyl, thiazolyl, isothiazolyl, pyrazolyl, oxazolyl, isoxazolyl, isothiazolyl, triazolyl, thiadiazolyl, oxadiazolyl, pyridinyl, pyridazinyl, pyrimidinyl, pyrazinyl, and triazinyl. Illustrative examples of 8,10-membered heteroaryl are: benzothienyl, benzofuryl, benzimidazolyl, benzothiazolyl, benzisothiazolyl, benzoxazolyl, benzisoxazolyl, benzotriazolyl, indolyl and indazolyl.

As used herein, the unqualified term "heterocyclyl" or "heterocyclic" and relates to a saturated mono-, bi- or tricyclic non-aromatic radical containing one or more heteroatoms selected from S, N and O. In the case of bicyclic heterocyclic systems, included within the scope of the term are fused, spiro and bridged bicyclic systems. In particular, the term "$C_z$-$C_k$heterocycloalkyl" refers to monocyclic ($C_z$-$C_k$) cycloalkyl groups, in which at least one ring carbon atom is replaced by a heteroatom (e.g. N, NH, S or O). Examples of ($C_z$-$C_k$)heterocycloalkyl include dihydropyridinyl, pyridonyl, pyrrolidinyl, thiazolidinyl, piperazinyl, piperidinyl, morpholinyl, and thiomorpholinyl.

By analogy, the term "$C_z$-$C_k$heterocycloalkylene", refers to a divalent $C_z$-$C_k$heterocycloalkyl radical, wherein $C_z$-$C_k$heterocycloalkyl is as above defined.

The term "$C_z$-$C_k$heterocycloalkyl$C_x$-$C_y$alkyl" refers to the above "$C_x$-$C_y$alkyl" group wherein one or more hydrogen atoms are replaced by one or more "$C_z$-$C_k$heterocycloalkyl" groups. Comprised within the scope of the term $C_z$-$C_k$heterocycloalkyl$C_x$-$C_y$alkyl" are systems where two hydrogen atoms linked to the same carbon atom in "$C_x$-$C_y$alkyl" group are replaced by one "$C_z$-$C_k$heterocycloalkyl" group. Such radical thus form a gem-disubstituted "$C_z$-$C_k$heterocycloalkyl$C_x$-$C_y$alkyl" system, such as a 1,2-dimethyl-pyrrolidin-2-yl radical.

The term "$C_z$-$C_k$heterocycloalkyl$C_z$-$C_k$cycloalkyl" refers to the above "$C_z$-$C_k$cycloalkyl" group wherein one or more hydrogen atoms are replaced by one or more "$C_z$-$C_k$heterocycloalkyl" groups.

The expression "($C_z$-$C_k$)cycloalkylcarbonyl" refers to ($C_z$-$C_k$)cycloalkyl-CO— groups wherein the group "($C_z$-$C_k$)cycloalkyl" has the meaning above defined.

The expression "($C_z$-$C_k$)heterocycloalkylcarbonyl" refers to ($C_z$-$C_k$)heterocycloalkyl-CO— groups wherein the group "($C_z$-$C_k$)heterocycloalkyl" has the meaning above defined.

Compounds of the invention may exist in one or more geometrical, optical, enantiomeric, diastereomeric and tautomeric forms, including but not limited to cis- and trans-forms, E- and Z-forms, R-, S- and meso-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers may be prepared by the application of adaptation of known methods (e.g. asymmetric synthesis).

Throughout the specification the use of an asterisk "*" in the definition of a structural formula, indicates the point of attachment for the radical group to the rest of the molecule.

As used herein the term "salt" includes base addition, acid addition and ammonium salts. As briefly mentioned above compounds of the invention which are acidic can form salts, including pharmaceutically acceptable salts, with bases such as alkaline metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)aminomethane, L-arginine, L-lysine, N-ethyl piperidine, dibenzylamine and the like. Those compounds of the invention which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, formic, trifluoroacetic, tartaric, succinic, fumaric, maleic, malic, salicylic, citric, methanesulphonic, p-toluenesulphonic, benzoic, benzenesulfonic, glutamic, lactic, and mandelic acids and the like. Those compounds (I) which have a basic nitrogen can also form quaternary ammonium salts with a pharmaceutically acceptable counter-ion such as ammonium, chloride, bromide, acetate, formate, p-toluenesulfonate, succinate, hemi-succinate, naphthalene-bis sulfonate, methanesulfonate, trifluoroacetate, xinafoate, and the like. For a review on salts, see *Handbook of Pharmaceutical Salts: Properties, Selection, and Use* by Stahl and Wermuth (Wiley-VCH, Weinheim, Germany, 2002), which is incorporated herein by reference in its entirety.

It is expected that compounds of the invention may be prepared in the form of hydrates, and solvates. Any reference herein, including the claims herein, to "compounds with which the invention is concerned" or "compounds of the invention" or "the present compounds", and the like, includes reference to salts hydrates, and solvates of such compounds. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Individual compounds of the invention may exist in several polymorphic forms and may be obtained in different crystal or co-crystal habits, and they are intended to be included within the meaning of the term "compounds of the invention".

The compounds may also be administered in the form of prodrugs thereof. Thus certain derivatives of the compounds which may be active in their own right or may have little or no pharmacological activity themselves can, when administered into or onto the body, be converted into compounds of the invention having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and V. J. Stella) and *Bioreversible Carriers in Drug Design*, Pergamon Press, 1987 (ed. E. B. Roche, American Pharmaceutical Association; C. S. Larsen and J. Østergaard, Design and application of prodrugs, In Textbook of Drug Design and Discovery, 3$^{rd}$ Edition, 2002, Taylor and Francis), which are incorporated herein by reference in their entireties.

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985), which is incorporated herein by reference in its entirety. Such examples could be a prodrug of a carboxyl group (such as —CP—O—CH$_2$—O—CO-tBu as used in the pivampicillin prodrug of ampicillin), an amide (—CO—NH—CH$_2$—NAlk$_2$) or an amidine (—C(=N—O—CH$_3$)—NH$_2$).

Embodiments of the Invention.

It is to be understood that all preferred groups or embodiments described herebelow for compounds of formula (I) may be combined among each other and apply as well to compounds of formula (Ia), (Ib), (Ic), (IA), (IB), (IC) and (ID) as below defined mutatis mutandis.

In one embodiment, compounds of formula (Ia) are provided, which are compounds of formula (I) as above defined wherein carbon stereogenic center on the cycloalkylene portion of ring A which is linked to group W and identified with number (1) herebelow, possess the absolute configuration herebelow represented:

(Ia)

In another embodiment, compounds of formula (Ib) are provided, which are compounds of formula (I) as above defined wherein carbon stereogenic center on the cycloalkylene portion of ring A which are linked to group W and Y and identified, respectively, with numbers (1) and (2) herebelow, possess the absolute configuration herebelow represented:

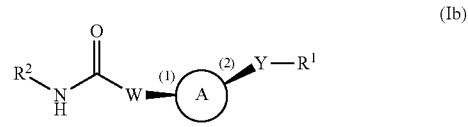

(Ib)

In a further embodiment, compound of formula (Ic) are provided, which are compounds of formula (I) as above defined wherein carbon stereogenic center on the cycloalkylene portion of ring A which are linked to group W and Y and identified, respectively, with numbers (1) and (2) herebelow, possess the absolute configuration herebelow represented:

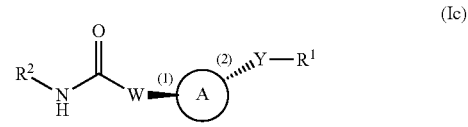

(Ic)

In one embodiment, W is NH or O. In a further embodiment, W is NH.

In one embodiment, Y is a group —S(O)$_p$—, a group —O(CR$^3$R$^4$)$_n$—, a group —(CR$^5$R$^6$)$_n$—, or a group —NR$^7$—; p is zero and n is 0, 1 or 2. In another embodiment, Y is a group —S(O)$_p$— or a group —O(CR$^3$R$^4$)$_n$ or; p is zero and n is 0 or 1.

In a further embodiment, Y is a group —O(CR$^3$R$^4$)$_n$— and n is 0.

In one embodiment, R$^3$, R$^4$, R$^5$ and R$^6$ are each independently —H, —F or C$_1$-C$_6$ alkyl. In another embodiment, R$^3$, R$^4$, R$^5$ and R$^6$ are —H.

In one embodiment, R$^7$ is —H, C$_1$-C$_6$ alkyl, or C$_3$-C$_7$ cycloalkyl.

In one embodiment, R$^7$ is —H.

In one embodiment, A is a divalent cycloalkylene radical having 5 or 6 ring atoms; said cycloalkylene ring being attached to W and Y, and fused to a phenyl ring or to a monocyclic heteroaryl ring having 5 or 6 ring atoms, such phenyl or heteroaryl ring being optionally substituted by one or two groups R$^{24}$.

In a further embodiment, A is group selected in the group consisting of

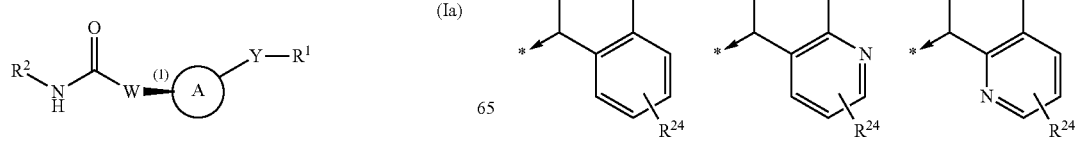

-continued

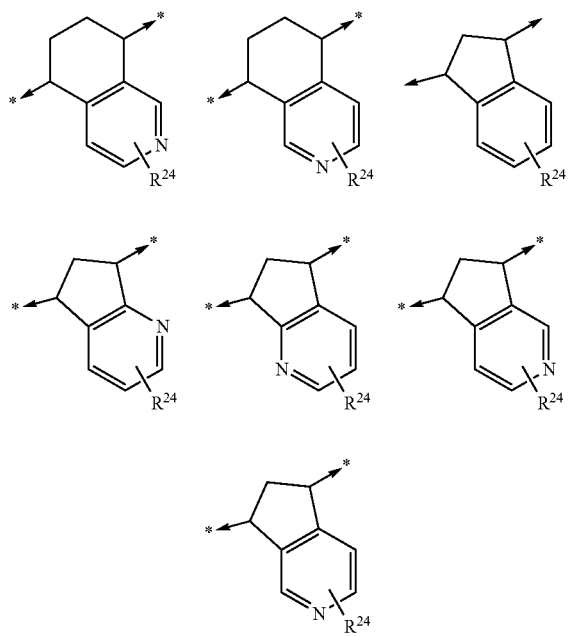

In a still further embodiment, A is group

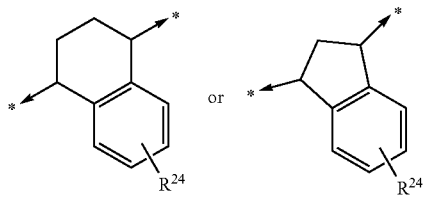

In an additional embodiment A is group

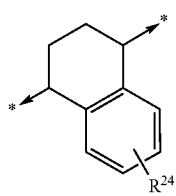

In one embodiment $R^{24}$ is not present or, if present, is at each occurrence independently selected from the group consisting of: $C_1$-$C_2$ alkyl, —F, —Cl and cyano; in a further embodiment, $R^{24}$ is not present or, if present, is at each occurrence independently methyl or —F. In a further embodiment, $R^{24}$ is not present.

In one embodiment, $R^1$ is a group of formula (IIa)

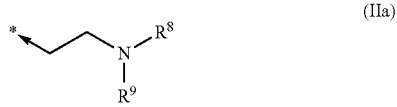

(IIa)

In a further embodiment, $R^1$ is a group of formula (IIa)

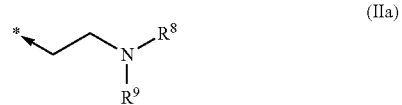

(IIa)

and $R^8$ and $R^9$ form together with the nitrogen atom to which they are attached a 4-11-membered saturated monocyclic or a fused or spiro bicyclic ring system optionally containing a further heteroatom which is oxygen or nitrogen, said nitrogen atom being optionally substituted by $C_1$-$C_6$ alkyl; wherein such $C_1$-$C_6$ alkyl groups may be optionally substituted by a group $C_1$-$C_6$ alkyl, $C_3$-$C_6$ cycloalkyl, hydroxyl or halo.

In an additional embodiment, $R^1$ is a group of formula (IIa)

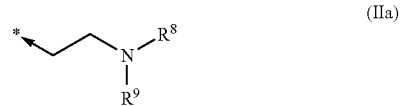

(IIa)

and $R^8$ and $R^9$ form together with the nitrogen atom to which they are attached a 4 to 7-membered saturated monocyclic ring system optionally containing a further heteroatom which is oxygen or nitrogen, said nitrogen atom being optionally substituted by $C_1$-$C_6$ alkyl. In a still further embodiment, such saturated monocyclic ring system is a morpholine ring.

In another embodiment, $R^1$ is a group of formula (IIb)

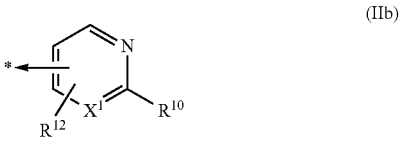

(IIb)

In one embodiment, $X^1$ is a group —(CH)— or a nitrogen atom. In another embodiment, $X^1$ is a group —(CH)—.

In one embodiment, $R^{10}$ is selected from a group consisting of: —CN, —C(O)N($R^A R^B$) and —N($R^C$)C(O)$R^C$.

In one embodiment, $R^{12}$ is —H, $C_1$-$C_6$ alkyl or halogen.

In a further embodiment, $R^1$ is a group of formula (IIb)

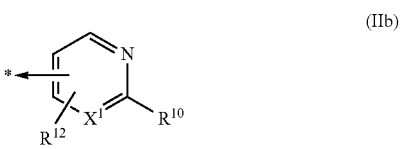

(IIb)

wherein $X^1$ is a group —(CH)—, $R^{10}$ is selected from a group consisting of —CN, —C(O)N($R^A R^B$), and —N($R^C$)C(O)$R^C$; and $R^{12}$ is —H.

In a further embodiment, $R^1$ is a group of formula (IIc)

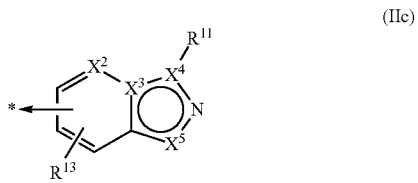

(IIc)

In one embodiment, the group (IIc) is a group of formula (IIca) or (IIcb) which is connected to the group Y through one of the carbons as below indicated

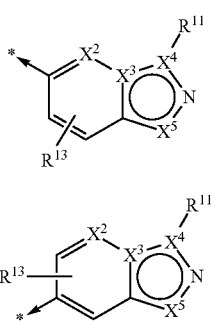
(IIca)

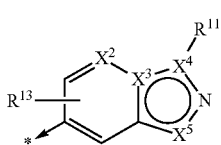
(IIcb)

In another embodiment, the group (IIc) is a group of formula (IIca) as above defined which is connected to the group Y through the carbon adjacent to $X_2$

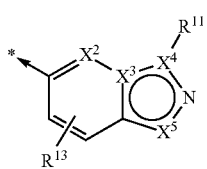
(IIca)

In one embodiment, $X^4$ is a carbon atom.

In one embodiment, $X^5$ is a nitrogen atom.

In another embodiment, $X^4$ is a carbon atom, $X^5$ is a nitrogen atom, $X^3$ is a nitrogen atom and $X^2$ is nitrogen.

In another embodiment, $X^4$ is a carbon atom, $X^5$ is a nitrogen atom, $X^3$ is a nitrogen atom and $X^2$ is group —CH—.

In another embodiment, $X^4$ is a nitrogen atom, $X^5$ is a group —CH— atom, $X^3$ is a carbon atom and $X^2$ is a group —CH—.

In one embodiment, $R^{13}$ is —H, $C_1$-$C_6$ alkyl or halogen.

In a further embodiment, the group (IIc) is a group of formula (IIca) as above defined which is connected to the group Y through the carbon adjacent to $X_2$

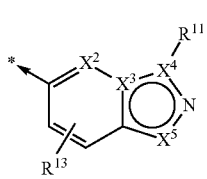
(IIca)

and wherein $X^4$ is a carbon atom, $X^5$ is a nitrogen atom, $X^3$ is a nitrogen atom and $X^2$ is a group —CH—, and $R^{13}$ is —H.

In one embodiment, $R^{11}$ is selected from a group consisting of —$NR^AR^B$, ($C_5$-$C_7$heterocycloalkyl)-($C_1$-$C_6$alkyl), —($C_3$-$C_7$heterocycloalkyl), wherein any of such ($C_5$-$C_7$heterocycloalkyl)-($C_1$-$C_6$alkyl) or —($C_3$-$C_7$heterocycloalkyl) may be optionally substituted by a group $C_1$-$C_6$ alkyl, $C_3$-$C_7$ cycloalkyl, hydroxyl or halo.

In another embodiment, $R^{11}$ is selected from a group consisting of —$NR^AR^B$, —($C_1$-$C_6$alkylene)-$NR^AR^B$, ($C_5$-$C_7$heterocycloalkyl)-($C_1$-$C_6$alkyl), —($C_3$-$C_7$heterocycloalkyl), wherein any of such ($C_5$-$C_7$heterocycloalkyl)-($C_1$-$C_6$alkyl) or —($C_3$-$C_7$heterocycloalkyl) may be optionally substituted by one, two or three groups $R^{25}$ which are independently selected in the list consisting of $C_1$-$C_6$ alkyl, ($C_1$-$C_3$) haloalkyl, ($C_1$-$C_4$) hydroxyalkyl, $C_3$-$C_7$ cycloalkyl, hydroxyl, —CN, $OR^D$ and halo.

In another embodiment, $R^{11}$ is phenyl or 5- or 6-membered monocyclic heteroaryl which is substituted by ($C_5$-$C_7$heterocycloalkyl)-($C_1$-$C_6$alkyl) or —($C_3$-$C_7$heterocycloalkyl), wherein any of such ($C_5$-$C_7$heterocycloalkyl)-($C_1$-$C_6$alkyl) or —($C_3$-$C_7$heterocycloalkyl) may be optionally substituted by a group $C_1$-$C_6$ alkyl, $C_3$-$C_7$ cycloalkyl, hydroxyl or halo.

In another embodiment, $R^{11}$ is phenyl or 5- or 6-membered monocyclic heteroaryl which is substituted by ($C_5$-$C_7$heterocycloalkyl)-($C_1$-$C_6$alkyl) or —($C_3$-$C_7$heterocycloalkyl), wherein any of such ($C_5$-$C_7$heterocycloalkyl)-($C_1$-$C_6$alkyl) or —($C_3$-$C_7$heterocycloalkyl) may be optionally substituted by one, two or three groups $R^{25}$ which are independently selected in the list consisting of $C_1$-$C_6$ alkyl, ($C_1$-$C_3$) haloalkyl, ($C_1$-$C_4$) hydroxyalkyl, $C_3$-$C_7$ cycloalkyl, hydroxyl and halo.

In one embodiment, $R^{25}$ is one, two or three groups independently selected in the list consisting of $C_1$-$C_6$ alkyl, ($C_1$-$C_3$)haloalkyl, ($C_1$-$C_4$)hydroxyalkyl, $C_3$-$C_7$ cycloalkyl, hydroxyl, —CN, $OR^D$ and halo.

In one embodiment, $R^A$ and $R^B$ are at each occurrence independently $C_1$-$C_6$ alkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, $OR^D$, CN or halo.

In another embodiment, $R^A$ and $R^B$ form together with the nitrogen atom to which they are attached an azetidine or a 4-11-membered saturated monocyclic or bicyclic heterocyclic ring system which is optionally substituted by one or more groups —$OR^D$, CN, halo, $C_1$-$C_6$ alkyl, ($C_1$-$C_6$)hydroxyalkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl —$OR^D$, —CN or halo.

In a still further embodiment $R^A$ and $R^B$ form together with the nitrogen atom to which they are attached an azetidine or a 4-11-membered saturated monocyclic or bicyclic heterocyclic ring system which is optionally substituted by one or more groups —$OR^D$, —CN, halo, $C_1$-$C_6$ alkyl, ($C_1$-$C_6$)hydroxyalkyl or $C_3$-$C_7$ cycloalkyl, such $C_1$-$C_6$ alkyl, ($C_1$-$C_6$) hydroxyalkyl and $C_3$-$C_7$ cycloalkyl being optionally substituted by a group $C_1$-$C_3$ alkyl, $C_3$-$C_7$cycloalkyl, —$OR^D$, —CN or halo; and which 6-11-membered saturated monocyclic or bicyclic heterocyclic ring contains a further heteroatom which is oxygen or nitrogen, said nitrogen atom optionally substituted by $C_1$-$C_6$ alkyl or $C_3$-$C_6$ cycloalkyl, wherein any of such $C_1$-$C_6$ alkyl or $C_3$-$C_6$ cycloalkyl may be optionally substituted by a group $C_1$-$C_6$ alkyl, $C_3$-$C_7$ cycloalkyl, $OR^D$, CN or halo.

In one embodiment, $R^{11}$ is a group

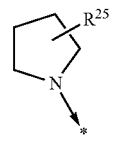

wherein $R^{25}$ is optionally present and represents one, two or three substituents independently selected in the list consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl, —CN, $OR^D$ and halo; and wherein the asterisk represents the point of attachment for group $R^{11}$ to the rest of the molecule via $X^4$.

In one embodiment, $R^{11}$ is a group

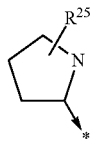

wherein $R^{25}$ is optionally present and represents one, two or three substituents independently selected in the list consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl, —CN, $OR^D$ and halo; and wherein the asterisk represents the point of attachment for group $R^{11}$ to the rest of the molecule via $X^4$.

In further embodiment, $R^{11}$ is a group

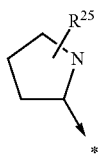

wherein $R^{25}$ represents one or two $C_1$-$C_6$ alkyl substituents and wherein the asterisk represents the point of attachment for group $R^{11}$ to the rest of the molecule via $X^4$.

In one embodiment, $R^{11}$ is a group

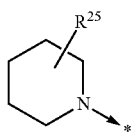

wherein $R^{25}$ is optionally present and represents one, two or three substituents independently selected in the list consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl, —CN, $OR^D$ and halo; and wherein the asterisk represents the point of attachment for group $R^{11}$ to the rest of the molecule via $X^4$.

In a further embodiment, $R^{11}$ is a group

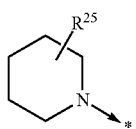

wherein $R^{25}$ represents one, two or three substituents independently selected in the list consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl, —CN, $OR^D$ and halo and wherein the asterisk represents the point of attachment for group $R^{11}$ to the rest of the molecule via $X^4$.

In a still further embodiment, $R^{11}$ is a group

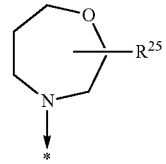

wherein $R^{25}$ represents one, two or three substituents independently selected in the list consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl, —CN, $OR^D$ and halo and wherein the asterisk represents the point of attachment for group $R^{11}$ to the rest of the molecule via $X^4$.

In a further embodiment, $R^{11}$ is a group

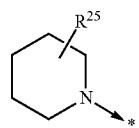

wherein $R^{25}$ represents independently one or two $C_1$-$C_6$ alkyl substituents and wherein the asterisk represents the point of attachment for group $R^{11}$ to the rest of the molecule via $X^4$.

In a further embodiment, $R^{11}$ is a group

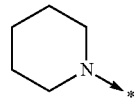

wherein the asterisk represents the point of attachment for group $R^{11}$ to the rest of the molecule via $X^4$.

In a further embodiment, $R^{11}$ is a group

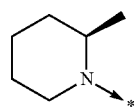

wherein the asterisk represents the point of attachment for group $R^{11}$ to the rest of the molecule via $X^4$.

In a still further embodiment, $R^{11}$ is a group

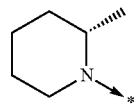

wherein the asterisk represents the point of attachment for group $R^{11}$ to the rest of the molecule via $X^4$.

In a still further embodiment, $R^{11}$ is a group

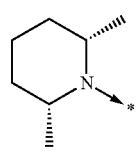

wherein the asterisk represents the point of attachment for group $R^{11}$ to the rest of the molecule via $X^4$.

In a still further embodiment, $R^{11}$ is a group

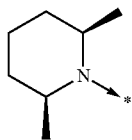

wherein the asterisk represents the point of attachment for group $R^{11}$ to the rest of the molecule via $X^4$.

In a still further embodiment, $R^{11}$ is a group

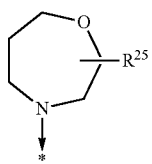

wherein the asterisk represents the point of attachment for group $R^{11}$ to the rest of the molecule via $X^4$.

In another embodiment, $R^2$ is a radical of formula (IIIb)

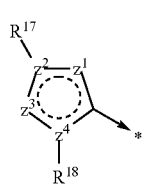

(IIIB)

In one embodiment $R^{17}$ is selected from the group consisting of lone electron pair, —H, —CF$_3$, —NR$^E$R$^F$, —(C$_3$-C$_6$cycloalkyl), —(C$_4$-C$_6$heterocycloalkyl), aryl or heteroaryl wherein any of such —(C$_3$-C$_6$cycloalkyl), —(C$_4$-C$_6$heterocycloalkyl), aryl or heteroaryl may be optionally substituted by a group methyl, isopropyl or halo. In another embodiment, $R^{17}$ is selected from the group consisting of lone electron pair, —H, —CF$_3$, morpholine, cyclohexyl, phenyl or pyridyl.

In another embodiment, $R^{17}$ is a group of general formula (IV)

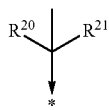

(IV)

In one embodiment, $R^{20}$ is selected in the group consisting of F, —CH$_3$; —CH$_2$OH, —CH$_2$OMe, —CH$_2$SCH$_3$; in another embodiment, $R^{20}$ is selected in the group consisting of —CH$_3$; —CH$_2$OH, —CH$_2$OMe. In another embodiment, $R^{20}$ is —CH$_3$.

In one embodiment, $R^{21}$ is —CH$_3$.

In another embodiment $R^{20}$ and $R^{21}$ are —CH$_3$.

In another embodiment, $R^{20}$ and $R^{21}$ as defined above may form together with the carbon atom to which they are attached a cyclohexane or cyclopropyl ring; in a further embodiment, $R^{20}$ and $R^{21}$ as defined above may form together with the carbon atom to which they are attached a cyclopropyl ring.

In one embodiment $R^{18}$ is phenyl, heterocycloalkyl or heteroaryl wherein any of such phenyl, heterocycloalkyl or heteroaryl is substituted by two or more groups independently selected from —CN, —OH, =O, halo, —COOR$^M$, C$_1$-C$_6$alkyl, C$_3$-C$_6$cycloalkyl, —O—(C$_1$-C$_6$alkyl), —O—(C$_3$-C$_6$cycloalkyl), —S—(C$_1$-C$_6$alkyl), —S—(C$_3$-C$_6$cycloalkyl), —NR$^H$R$^J$, —N(R$^L$)(C$_2$-C$_6$alkylene)-NR$^H$R$^J$, —N(R$^L$)(C$_3$-C$_7$cycloalkylene)-NR$^H$R$^J$, —(C$_1$-C$_6$alkylene)-NR$^H$R$^J$, —(C$_3$-C$_7$cycloalkylene)-NR$^H$R$^J$, —O—(C$_2$-C$_6$alkylene)-NR$^H$R$^J$, —O—(C$_3$-C$_7$cycloalkylene)-NR$^H$R$^J$, —S—(C$_2$-C$_6$alkylene)-NR$^H$R$^J$, —S—(C$_3$-C$_7$cycloalkylene)-NR$^H$R$^J$, —N(R$^L$)C(O)—(C$_1$-C$_6$alkylene)-NR$^H$R$^J$, —N(R$^L$)C(O)—(C$_3$-C$_7$cycloalkylene)-NR$^H$R$^J$, —C(O)N(R$^L$)—(C$_2$-C$_6$alkylene)-NR$^H$R$^J$, —C(O)N(R$^L$)—(C$_3$-C$_7$cycloalkylene)-NR$^H$R$^J$, —C(O)N(R$^L$)—(C$_2$-C$_6$alkylene)-OR$^M$, —C(O)N(R$^L$)—(C$_3$-C$_7$cycloalkylene)-OR$^M$, —N(R$^L$)C(O)N(R$^H$R$^J$), —C(O)N(R$^H$R$^J$), —N(R$^L$)C(O)N(R$^L$)—(C$_2$-C$_6$alkylene)-NR$^H$R$^J$, —N(R$^L$)C(O)N(R$^L$)—(C$_3$-C$_7$cycloalkylene)-NR$^H$R$^J$, —O—(C$_2$-C$_6$alkylene)-OR$^M$, —O—(C$_3$-C$_7$cycloalkylene)-OR$^M$, —S—(C$_2$-C$_6$alkylene)-OR$^M$, —S—(C$_3$-C$_7$cycloalkylene)-OR$^M$, —N(R$^L$)S(O)$_2$—(C$_1$-C$_6$alkylene)-NR$^H$R$^J$, —N(R$^L$)S(O)$_2$—(C$_3$-C$_7$cycloalkylene)-NR$^H$R$^J$, —S(O)$_2$N(R$^L$)—(C$_2$-C$_6$alkylene)-NR$^H$R$^J$, —S(O)$_2$N(R$^L$)—(C$_3$-C$_7$cycloalkylene)-NR$^H$R$^J$, —S(O)$_2$N(R$^L$)—(C$_2$-C$_6$alkylene)-OR$^M$, —S(O)$_2$N(R$^L$)—(C$_3$-C$_7$cycloalkylene)-OR$^M$, —N(R$^L$)S(O)$_2$—(C$_2$-C$_6$alkylene)-OR$^M$, —N(R$^L$)S(O)$_2$—(C$_3$-C$_7$cycloalkylene)-OR$^M$, —S(O)$_2$N(R$^H$R$^J$), —N(R$^L$)S(O)$_2$R$^L$, —N(R$^L$)C(O)R$^L$, OR$^L$, SR$^L$, —(C$_3$-C$_7$heterocycloalkyl), (C$_5$-C$_7$heterocycloalkyl)-(C$_1$-C$_6$ alkyl) and (C$_5$-C$_7$ heterocycloalkyl)-(C$_3$-C$_6$ cycloalkyl), wherein any of such alkyl, cycloalkyl, alkylene, cycloalkylene, heterocycloalkyl, heterocycloalkyl-(C$_1$-C$_6$ alkyl), heterocycloalkyl)-(C$_3$-C$_6$ cycloalkyl) and heterocycloalkylcarbonyl portion in the above listed groups may be optionally substituted by a group C$_1$-C$_6$ alkyl, C$_3$-C$_7$ cycloalkyl, —OR$^L$ or halo.

In one embodiment R$^H$ and R$^J$ are independently —H, C$_1$-C$_6$ alkyl or C$_3$-C$_6$ cycloalkyl, such C$_1$-C$_6$ alkyl or C$_3$-C$_6$ cycloalkyl being optionally substituted by a group C$_1$-C$_3$ alkyl, —OR$^M$, CN or halo; alternatively, R$^H$ and R$^J$ may also form together with the nitrogen atom to which they are attached a 4-11 membered saturated monocyclic or bicyclic heterocyclic ring system which is optionally substituted by one or more groups —OR$^M$, —CN, halo, NR$^O$R$^P$, C$_1$-C$_6$ alkyl or C$_3$-C$_7$ cycloalkyl, such C$_1$-C$_6$ alkyl and C$_3$-C$_7$ cycloalkyl being optionally substituted by a group C$_1$-C$_3$ alkyl, C$_3$-C$_7$cycloalkyl, —OR$^M$, CN or halo; and which 6-11-membered saturated monocyclic or bicyclic heterocyclic ring optionally contains a further heteroatom which is oxygen or nitrogen, said nitrogen atom optionally substituted by C$_1$-C$_6$ alkyl or C$_3$-C$_6$ cycloalkyl, wherein any of such C$_1$-C$_6$ alkyl or C$_3$-C$_6$ cycloalkyl may be optionally substituted by a group C$_1$-C$_6$ alkyl, C$_3$-C$_7$ cycloalkyl, —OR$^M$, CN or halo; or R$^H$ and R$^J$ may be linked to one carbon atom of the —(C$_1$-C$_6$alkylene)-, —(C$_2$-C$_6$alkylene)- or —(C$_3$-C$_7$cycloalkylene)- portion of the group linked to the nitrogen to which they are connected to form a saturated cycle of up to 6 ring atoms.

In a further embodiment R$^H$ and R$^J$ are independently —H, C$_1$-C$_6$ alkyl or C$_3$-C$_6$ cycloalkyl, such C$_1$-C$_6$ alkyl or C$_3$-C$_6$ cycloalkyl being optionally substituted by a group C$_1$-C$_3$ alkyl, —OR$^M$, CN or halo; alternatively, R$^H$ and R$^J$ may also form together with the nitrogen atom to which they are attached a 4-7 membered saturated monocyclic heterocyclic ring system which is optionally substituted by one or more groups halo, NR$^O$R$^P$ or C$_1$-C$_6$ alkyl, such C$_1$-C$_6$ alkyl being optionally substituted by a group $C_1$-$C_3$ alkyl, $C_3$-$C_7$cycloalkyl, —$OR^M$, CN or halo; and which 6-7-membered saturated monocyclic heterocyclic ring optionally contains a further heteroatom which is oxygen or nitrogen, said nitrogen atom optionally substituted by $C_1$-$C_6$ alkyl or $C_3$-$C_6$ cycloalkyl, wherein any of such $C_1$-$C_6$ alkyl or $C_3$-$C_6$ cycloalkyl may be optionally substituted by a group $C_1$-$C_6$ alkyl, $C_3$-$C_7$ cycloalkyl, —$OR^M$, CN, or halo; or $R^H$ and $R^J$ may be linked to one carbon atom of the —($C_1$-$C_6$alkylene)-, —($C_2$-$C_6$alkylene)- or —($C_3$-$C_7$cycloalkylene)-portion of the group linked to the nitrogen to which they are connected to form a saturated cycle of up to 6 ring atoms.

In another embodiment, $R^L$ is at each occurrence independently —H, $C_1$-$C_6$ alkyl or $C_3$-$C_6$ cycloalkyl, such $C_1$-$C_6$ alkyl or $C_3$-$C_6$ cycloalkyl being optionally substituted by a group $C_1$-$C_3$ alkyl, —$OR^M$, —CN or halo; $R^M$ is at each occurrence independently —H, $C_1$-$C_6$ alkyl or $C_3$-$C_6$ cycloalkyl, such $C_1$-$C_6$ alkyl or $C_3$-$C_6$ cycloalkyl being optionally substituted by a group hydroxyl, —CN or halo; $R^O$ and $R^P$ are each independently $C_1$-$C_6$ alkyl or $C_1$-$C_6$ cycloalkyl, optionally substituted by a group $C_1$-$C_3$ alkyl, —$OR^Q$, —CN or halo; alternatively, $R^O$ and $R^P$ may form together with the nitrogen atom to which they are attached a 4-8-membered saturated monocyclic heterocyclic ring system which is optionally substituted by one or more groups —$OR^Q$, —CN, halo, $C_1$-$C_6$ alkyl or $C_3$-$C_7$ cycloalkyl, and which 4-8-membered saturated monocyclic heterocyclic ring optionally contains a further heteroatom which is oxygen or nitrogen, said nitrogen atom optionally substituted by $C_1$-$C_6$ alkyl or $C_3$-$C_6$ cycloalkyl; $R^Q$ is —H, —$CH_3$ or —$C_2H_5$.

In one embodiment, $z^1$=—CH—, $z^2$=C, $z^3$ and $z^4$ are N; in another embodiment, $z^1$=O, $z^2$=C, $z^3$ and $z^4$ are N; in a further embodiment, $z^1$=—CH—, $z^2$ and $z^3$ are N and $z^4$ is —CH—; in an additional embodiment, $z^1$=N, $z^2$ is C, $z^3$ is N and $z^4$ is O; in a still further embodiment, $z^1$=N, $z^2$ is C, $z^3$ is O and $z^4$ is N.

In a further embodiment, $R^2$ is a radical of formula (IIIb)

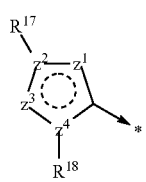

(IIIB)

wherein $z^1$=—CH—, $z^2$=C, $z^3$ and $z^4$ are N and $R^{17}$ is a group of general formula (IV)

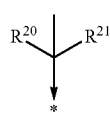

(IV)

wherein $R^{20}$ is —$CH_3$ or —$CH_2OH$, and $R^{21}$ is —$CH_3$.

In another embodiment $R^2$ is a radical of formula (IIIb)

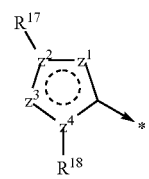

(IIIB)

wherein $z^1$=—CH—, $z^2$=C, $z^3$ and $z^4$ are N and $R^{17}$ is a group of general formula (IV)

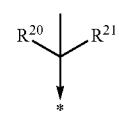

(IV)

wherein $R^{20}$ and $R^{21}$ are —$CH_3$ and wherein $R^{18}$ is phenyl substituted by two or more groups independently selected from —CN, —OH, halo, —$COOR^M$, $C_1$-$C_6$alkyl, —N($R^L$)($C_2$-$C_6$alkylene)-$NR^HR^J$, —($C_1$-$C_6$alkylene)-$NR^HR^J$, —O—($C_2$-$C_6$alkylene)-$NR^HR^J$, —O—($C_2$-$C_6$alkylene)-$OR^M$, —S—($C_2$-$C_6$alkylene)-$OR^M$, ($C_5$-$C_7$heterocycloalkyl)-($C_1$-$C_6$alkyl), and ($C_5$-$C_7$heterocycloalkyl)-($C_3$-$C_6$ cycloalkyl) wherein any of such $C_1$-$C_6$alkyl, —($C_1$-$C_6$alkylene)-, —($C_2$-$C_6$alkylene), ($C_5$-$C_7$heterocycloalkyl)-($C_1$-$C_6$alkyl) and ($C_5$-$C_7$heterocycloalkyl)-($C_3$-$C_6$ cycloalkyl) may be optionally substituted by a group $C_1$-$C_6$ alkyl, $C_3$-$C_7$ cycloalkyl, $OR^L$ or halo; wherein $R^H$ and $R^J$ are independently $C_1$-$C_6$ alkyl or $C_3$-$C_6$ cycloalkyl optionally substituted by a group $C_1$-$C_3$ alkyl, —$OR^M$, CN or halo; alternatively, $R^H$ and $R^J$ may also form together with the nitrogen atom to which they are attached a 4-11 membered saturated monocyclic heterocyclic ring system which is optionally substituted by one or more groups —$OR^M$, —CN, halo, $NR^OR^P$, $C_1$-$C_6$ alkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —$OR^M$, CN or halo; and which 6-11-membered saturated monocyclic or bicyclic heterocyclic ring optionally contains a further heteroatom which is oxygen or nitrogen, said nitrogen atom optionally substituted by $C_1$-$C_6$ alkyl or $C_3$-$C_6$ cycloalkyl, wherein any of such $C_1$-$C_6$ alkyl or $C_3$-$C_6$ cycloalkyl may be optionally substituted by a group $C_1$-$C_6$ alkyl, $C_3$-$C_7$ cycloalkyl, —$OR^M$, CN, or halo; or $R^H$ and $R^J$ may be linked to one carbon atom of the —($C_1$-$C_6$alkylene)-, —($C_2$-$C_6$alkylene)- or —($C_3$-$C_7$cycloalkylene)-portion of the group linked to the nitrogen to which they are connected to form a saturated cycle of up to 6 ring atoms; wherein $R^L$ is at each occurrence independently —H, $C_1$-$C_6$ alkyl or $C_3$-$C_6$ cycloalkyl, such $C_1$-$C_6$ alkyl or $C_3$-$C_6$ cycloalkyl being optionally substituted by a group $C_1$-$C_3$ alkyl, —$OR^M$, —CN or halo; and wherein $R^M$ is at each occurrence independently —H, $C_1$-$C_6$ alkyl or $C_3$-$C_6$ cycloalkyl, such $C_1$-$C_6$ alkyl or $C_3$-$C_6$ cycloalkyl being optionally substituted by a group hydroxyl, —CN or halo.

In an additional embodiment R² is a radical of formula (IIIb)

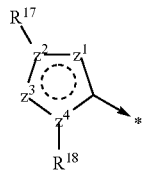

(IIIB)

wherein $z^1$=—CH—, $z^2$=C, $z^3$ and $z^4$ are N and $R^{17}$ is a group of general formula (IV)

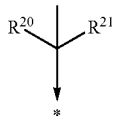

(IV)

wherein $R^{20}$ and $R^{21}$ are —CH₃ and $R^{18}$ is phenyl substituted by two or more groups independently selected from halo, —OH, $C_1$-$C_6$ alkyl, —O—($C_2$-$C_6$alkylene)-NR$^H$R$^J$ and —($C_1$-$C_6$alkylene)-NR$^H$R$^J$.

In another embodiment R² is a radical of formula (IIIb)

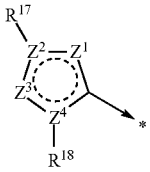

(IIIB)

wherein $z^1$=—CH—, $z^2$=C, $z^3$ and $z^4$ are N and $R^{17}$ is a group of general formula (IV)

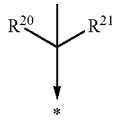

(IV)

wherein $R^{20}$ and $R^{21}$ are —CH₃ and $R^{18}$ is a 5 or 6-membered heteroaryl which is substituted by two or more groups independently selected from $C_1$-$C_6$alkyl, —($C_1$-$C_6$)hydroxyalkyl, —N(R$^L$)($C_2$-$C_6$alkylene)-NR$^H$R$^J$ and —($C_1$-$C_6$alkylene)-NR$^H$R$^J$ wherein any of such $C_1$-$C_6$alkyl, —($C_1$-$C_6$)hydroxyalkyl, —($C_1$-$C_6$alkylene)-, —($C_2$-$C_6$alkylene)-, ($C_5$-$C_7$heterocycloalkyl)-($C_1$-$C_6$alkyl) and ($C_5$-$C_7$ heterocycloalkyl)-($C_3$-$C_6$ cycloalkyl) portion in the above listed groups may be optionally substituted by a group $C_1$-$C_6$ alkyl, $C_3$-$C_7$ cycloalkyl OR$^L$ or halo.

In another embodiment, R² is a radical of formula (IIIb)

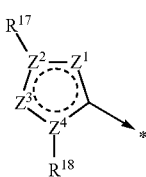

(IIIB)

wherein $z^1$=—CH—, $z^2$=C, $z^3$ and $z^4$ are N and $R^{17}$ is a group of general formula (IV)

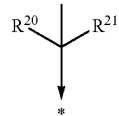

(IV)

wherein $R^{20}$ and $R^{21}$ are —CH₃ and $R^{18}$ is a heterocycloalkyl which is substituted by two or more groups independently selected from =O, $C_1$-$C_6$alkyl, —N(R$^L$)($C_2$-$C_6$alkylene)-NR$^H$R$^J$ and —($C_1$-$C_6$alkylene)-NR$^H$R$^J$ wherein any of such $C_1$-$C_6$alkyl and —($C_1$-$C_6$alkylene)-portion in the above listed groups may be optionally substituted by a group $C_1$-$C_6$ alkyl, $C_3$-$C_7$ cycloalkyl OR$^L$ or halo.

In one embodiment, compounds of formula (IA) are provided wherein W is NH, Y is a group —O(CR³R⁴)$_n$— and n is 0, A is group

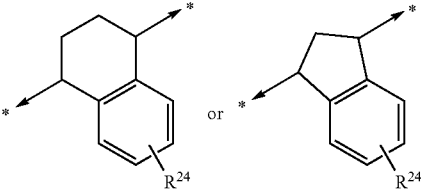

wherein R¹ is a group of formula (IIca) as above defined which is connected to the group Y through the carbon adjacent to X²

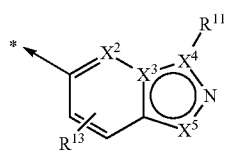

(IIca)

and wherein X⁴ is a carbon atom, X⁵ is a nitrogen atom, X³ is a nitrogen atom and X² is a group —CH—, and R¹³ is —H; wherein R¹¹ is a group:

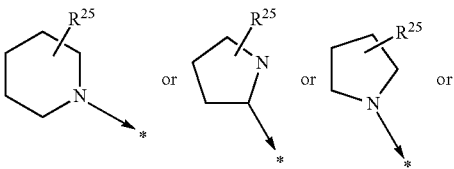

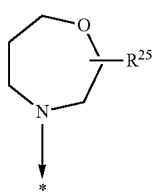

wherein R²⁵ is optionally present and represents one, two or three substituents independently selected in the list consisting of C₁-C₆ alkyl, (C₁-C₃) haloalkyl, (C₁-C₄)hydroxyalkyl, C₃-C₇ cycloalkyl, hydroxyl and halo; and wherein the asterisk represents the point of attachment for group R¹¹ to the rest of the molecule via X⁴; wherein R² is a radical of formula (IIIb)

(IIIB)

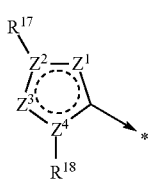

wherein z¹=—CH—, z²=C, z³ and z⁴ are N and R¹⁷ is a group of general formula (IV)

(IV)

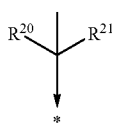

wherein R²⁰ and R²¹ are —CH₃ and wherein R¹⁸ is aryl substituted by two or more groups independently selected from —CN, —OH, halo, —COOR^M, C₁-C₆alkyl, —O—(C₁-C₆alkyl), —(C₁-C₆)hydroxyalkyl, —N(R^L)(C₂-C₆alkylene)-NR^H R^J, —(C₁-C₆alkylene)-NR^H R^J, —O—(C₂-C₆alkylene)-NR^H R^J, —O—(C₂-C₆alkylene)-OR^M, —S—(C₂-C₆alkylene)-OR^M, (C₅-C₇heterocycloalkyl)-(C₁-C₆ alkyl) and (C₅-C₇ heterocycloalkyl)-(C₃-C₆ cycloalkyl) wherein any of such C₁-C₆alkyl, —(C₁-C₆alkylene)-, —(C₂-C₆alkylene)-, (C₅-C₇heterocycloalkyl)-(C₁-C₆alkyl) and (C₅-C₇ heterocycloalkyl)-(C₃-C₆ cycloalkyl) portion may be optionally substituted by a group C₁-C₆ alkyl, C₃-C₇ cycloalkyl, OR^L or halo; wherein R^H and R^J are independently —H, C₁-C₆ alkyl or C₃-C₆ cycloalkyl, such C₁-C₆ alkyl or C₃-C₆ cycloalkyl being optionally substituted by a group C₁-C₃ alkyl, —OR^M, CN or halo; or R^H and R^J may form together with the nitrogen atom to which they are attached a 4-11 membered saturated monocyclic or bicyclic heterocyclic ring system which is optionally substituted by one or more C₁-C₆alkyl and which 4-1-membered saturated monocyclic or bicyclic heterocyclic ring optionally contain a further heteroatom which is oxygen or nitrogen and R^M is —H.

In one embodiment, compounds of formula (IB) are provided wherein W is NH, Y is a group —O(CR³R⁴)ₙ— and n is 0, A is group:

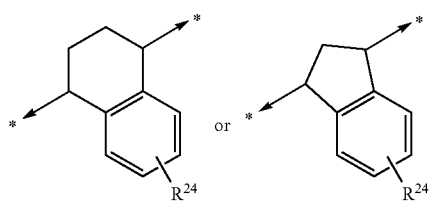

wherein R¹ is a group of formula (IIca) as above defined which is connected to the group Y through the carbon adjacent to X²

(IIca)

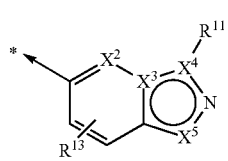

and wherein X⁴ is a carbon atom, X⁵ is a nitrogen atom, X³ is a nitrogen atom and X² is a group —CH—, and R¹³ is —H; R¹¹ is a group

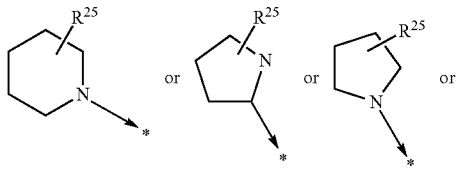

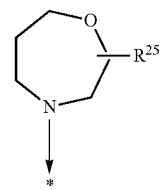

wherein R²⁵ is optionally present and represents one, two or three substituents independently selected in the list consisting of C₁-C₆ alkyl, (C₁-C₃) haloalkyl, (C₁-C₄)hydroxyalkyl, C₃-C₇ cycloalkyl, hydroxyl and halo; and wherein the asterisk represents the point of attachment for group R¹¹ to the rest of the molecule via X⁴; R² is a radical of formula (IIIb):

(IIIB)

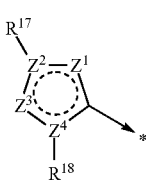

wherein z¹=—CH—, z³ and z⁴ are N and R¹⁷ is a group of general formula (IV)

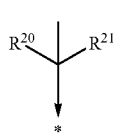
(IV)

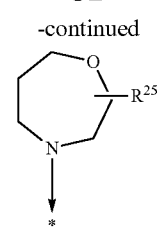

wherein $R^{20}$ and $R^{21}$ are —$CH_3$ and $R^{18}$ is a phenyl substituted by two or more groups independently selected from —OH, halo, $C_1$-$C_6$alkyl, —($C_1$-$C_6$)hydroxyalkyl, —O—($C_2$-$C_6$alkylene)-$NR^HR^J$ or —($C_1$-$C_6$alkylene)-$NR^HR^J$, wherein any of such $C_1$-$C_6$alkyl, —($C_1$-$C_6$alkylene)- and —($C_2$-$C_6$alkylene)- portion may be optionally substituted by a group $C_1$-$C_6$ alkyl, $C_3$-$C_7$ cycloalkyl, $OR^L$ or halo; wherein $R^H$ and $R^J$ are independently —H, $C_1$-$C_6$ alkyl or $C_3$-$C_6$ cycloalkyl, such $C_1$-$C_6$ alkyl or $C_3$-$C_6$ cycloalkyl being optionally substituted by a group $C_1$-$C_3$ alkyl, —$OR^M$, CN or halo; or $R^H$ and $R^J$ may form together with the nitrogen atom to which they are attached a 4-11 membered saturated monocyclic or bicyclic heterocyclic ring system which is optionally substituted by one or more $C_1$-$C_6$alkyl and which 4-11 membered saturated monocyclic or bicyclic heterocyclic ring optionally contain a further heteroatom which is oxygen or nitrogen and $R^M$ is —H.

In one embodiment, compounds of formula (IC) are provided wherein W is NH, Y is a group —$O(CR^3R^4)_n$— and n is 0, A is group

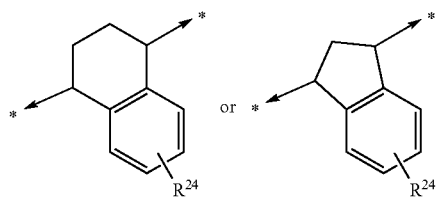

$R^1$ is a group of formula (IIca) as above defined which is connected to the group Y through the carbon adjacent to $X_2$

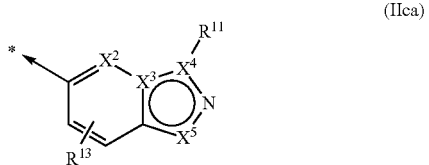

and wherein $X^4$ is a carbon atom, $X^5$ is a nitrogen atom, $X^3$ is a nitrogen atom and $X^2$ is a group —CH—, and $R^{13}$ is —H; wherein $R^{11}$ is a group

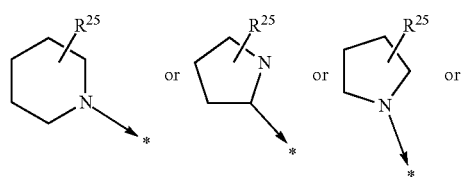

-continued

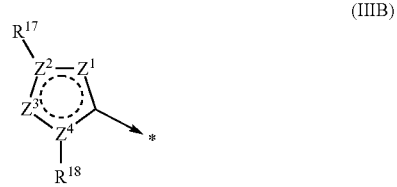

wherein $R^{25}$ is optionally present and represents one two or three substituents independently selected in the list consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$; wherein $R^2$ is a radical of formula (IIIb)

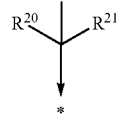

(IIIB)

wherein $z^1$=—CH—, $z^2$=C, $z^3$ and $z^4$ are N and $R^{17}$ is a group of general formula (IV)

(IV)

wherein $R^{20}$ and $R^{21}$ are —$CH_3$ and $R^{18}$ is a 5 or 6-membered heteroaryl which is substituted by two or more groups independently selected from $C_1$-$C_6$alkyl, —($C_1$-$C_6$)hydroxyalkyl, —N($R^L$)($C_2$-$C_6$alkylene)-$NR^HR^J$ and —($C_1$-$C_6$alkylene)-$NR^HR^J$, wherein any of such $C_1$-$C_6$alkyl, —($C_1$-$C_6$alkylene)- and —($C_2$-$C_6$alkylene)- portion in the above listed groups may be optionally substituted by a group $C_1$-$C_6$ alkyl, $C_3$-$C_7$ cycloalkyl $OR^L$ or halo.

In one embodiment, compounds of formula (ID) are provided wherein W is NH, Y is a group —$O(CR^3R^4)_n$— and n is 0, A is group

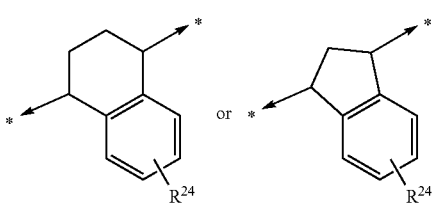

wherein $R^1$ is a group of formula (IIca) as above defined which is connected to the group Y through the carbon adjacent to $X_2$

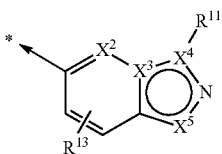
(IIca)

and wherein $X^4$ is a carbon atom, $X^5$ is a nitrogen atom, $X^3$ is a nitrogen atom and $X^2$ is a group —CH—, and $R^{13}$ is —H; wherein $R^{11}$ is a group

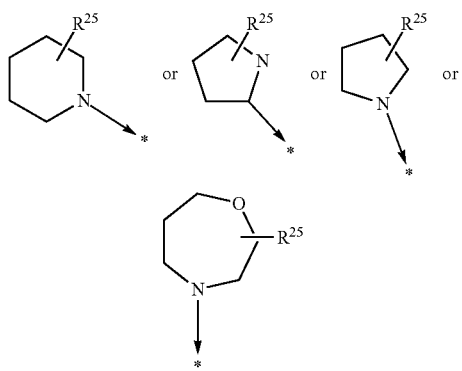

wherein $R^{25}$ is optionally present and represents one two or three substituents independently selected in the list consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$; wherein $R^2$ is a radical of formula (IIIb)

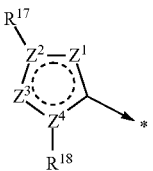
(IIIB)

wherein $z^1$=—CH—, $z^2$=C, $z^3$ and $z^4$ are N and $R^{17}$ is a group of general formula (IV)

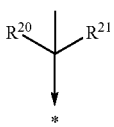
(IV)

wherein $R^{20}$ and $R^{21}$ are —$CH_3$ and $R^{18}$ is a heterocycloalkyl substituted by two or more groups independently selected from =O, $C_1$-$C_6$alkyl, —N($R^L$)($C_2$-$C_6$alkylene)-$NR^H R^J$ or —($C_1$-$C_6$alkylene)-$NR^H R^J$, wherein any of such $C_1$-$C_6$alkyl and —($C_1$-$C_6$alkylene)-portion in the above listed groups may be optionally substituted by a group $C_1$-$C_6$ alkyl, $C_3$-$C_7$ cycloalkyl $OR^L$ or halo.

In one embodiment, a compound of formula (I) is selected from the group consisting of:

1-[5-tert-Butyl-2-(2-fluoro-5-pyrrolidin-1-ylmethyl-phenyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[2-fluoro-5-(4-methyl-piperazin-1-ylmethyl)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}urea;

1-[5-tert-Butyl-2-(2-fluoro-5-pyrrolidin-1-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[2-fluoro-5-(4-methyl-piperazin-1-ylmethyl)-phenyl]-2H-pyrazol-3-yl}-3-(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl urea formate salt;

1-{5-tert-Butyl-2-[5-(2-dimethylamino-ethoxy)-2-fluorophenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[5-(2-dimethylamino-ethoxy)-2-fluorophenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[4-chloro-3-(4-methyl-piperazin-1-ylmethyl)-phenyl]-2H-pyrazol-3-yl}-3-(1S,4R)-4-(3-piperidin-1-yl-[1,2,4]triazolo[4,3-a]pyridin-6-yloxy)-1,2,3,4-tetrahydro-naphthalen-1-yl]-urea;

1-[5-tert-Butyl-2-(4-chloro-3-morpholin-4-ylmethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[4-chloro-3-(2-dimethylamino-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[4-chloro-3-(2-diethylamino-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[4-chloro-3-(2-piperidin-1-yl-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[4-chloro-3-(2-pyrrolidin-1-yl-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[4-methyl-3-(2-morpholin-4-yl-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt;

1-{5-tert-Butyl-2-[3-(2-dimethylamino-ethoxy)-4-fluorophenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[3-chloro-5-(2-dimethylamino-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[4-chloro-3-(2-morpholin-4-yl-ethyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt;

1-{5-tert-Butyl-2-[4-chloro-3-(2-dimethylamino-ethyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt;

1-[5-tert-Butyl-2-(3-chloro-5-piperidin-1-ylmethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[3-chloro-5-(4-methyl-piperazin-1-ylmethyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[2-chloro-5-(2-dimethylamino-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt;

1-[5-tert-Butyl-2-(3-fluoro-5-morpholin-4-ylmethyl-phenyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[3-fluoro-5-(4-methyl-piperazin-1-ylmethyl)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[3-(2-dimethylamino-ethoxy)-5-fluoro-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-[5-tert-Butyl-2-(3-fluoro-5-morpholin-4-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[3-fluoro-5-(4-methyl-piperazin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[3-(2-dimethylamino-ethoxy)-5-fluoro-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[4-cyano-3-(2-dimethylamino-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[4-chloro-3-(2-[1,4]oxazepan-4-yl-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt;

1-(5-tert-Butyl-2-{4-chloro-3-[2-(3-oxa-8-aza-bicyclo[3.2.1]oct-8-yl)-ethoxy]-phenyl}-2H-pyrazol-3-yl)-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt;

1-{5-tert-Butyl-2-[4-chloro-3-(2-dimethylamino-ethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[4-chloro-3-(2-dimethylamino-ethyl)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[4-chloro-3-(2-morpholin-4-yl-ethyl)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-(5-tert-Butyl-2-{4-chloro-3-[2-(4-methyl-piperazin-1-yl)-ethyl]-phenyl}-2H-pyrazol-3-yl)-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-(5-tert-Butyl-2-{4-fluoro-3-[2-(4-methoxy-piperidin-1-yl)-ethyl]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{2-[3-(2-Azetidin-1-yl-ethyl)-4-fluoro-phenyl]-5-tert-butyl-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-(5-tert-Butyl-2-{3-[2-(3-dimethylamino-azetidin-1-yl)-ethyl]-4-fluoro-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[3-(2-dimethylamino-ethyl)-4-fluoro-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[4-chloro-3-(2-dimethylamino-ethoxy)-phenyl]-2H-pyrazol-3-yl}-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea formate salt;

1-{5-tert-Butyl-2-[4-chloro-3-(2-morpholin-4-yl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[5-tert-Butyl-2-(4-chloro-3-pyrrolidin-1-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[5-tert-Butyl-2-(4-chloro-3-morpholin-4-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[4-chloro-3-(4-methyl-piperazin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[5-tert-Butyl-2-(4-chloro-3-morpholin-4-ylmethyl-phenyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[4-chloro-3-(4-methyl-piperazin-1-ylmethyl)-phenyl]-2H-pyrazol-3-yl}-3-{(1S,4R)-4-[3-((2S, 6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-[5-tert-Butyl-2-(4-fluoro-3-pyrrolidin-1-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[4-fluoro-3-(4-methyl-piperazin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[5-tert-Butyl-2-(4-fluoro-3-morpholin-4-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[5-tert-Butyl-2-(4-chloro-3-hydroxy-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[5-tert-Butyl-2-(3-chloro-4-hydroxy-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[5-tert-Butyl-2-(3-chloro-4-hydroxy-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-[5-tert-Butyl-2-(4-chloro-3-hydroxy-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-[5-tert-Butyl-2-(3-chloro-4-hydroxy-phenyl)-2H-pyrazol-3-yl]-3-{(1S,4R)-4-[3-(4-hydroxymethyl-piperidin-1-yl)-[1,2,4]triazolo[4,3-a]pyridin-6-yloxy]-1,2,3,4-tetrahydronaphthalen-1-yl}-urea;

1-{5-tert-Butyl-2-[4-chloro-3-(2-hydroxy-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[5-tert-Butyl-2-(3-hydroxy-5-methyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[3-(2-dimethylamino-ethoxy)-4-hydroxymethyl-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[5-tert-Butyl-2-[4-hydroxymethyl-3-(2-pyrrolidin-1-yl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-(5-tert-Butyl-2-{4-hydroxymethyl-3-[2-(4-methyl-piperazin-1-yl)-ethoxy]-phenyl}-2H-pyrazol-3-yl)-3-(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[3-(2-dimethylamino-ethoxy)-4-hydroxymethyl-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[4-hydroxymethyl-3-(2-pyrrolidin-1-yl-ethoxy)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl]-urea formate salt;

1-(5-tert-Butyl-2-{4-hydroxymethyl-3-[2-(4-methyl-piperazin-1-yl)-ethoxy]-phenyl}-2H-pyrazol-3-yl)-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

-{5-tert-Butyl-2-[4-hydroxy-3-(4-methyl-piperazin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[5-tert-Butyl-2-(3-chloro-5-hydroxy-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-[5-tert-Butyl-2-(3-chloro-5-hydroxy-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[5-tert-Butyl-2-(4-chloro-3-hydroxy-phenyl)-2H-pyrazol-3-yl]-3-[(1S,4R)-4-(3-[1,4]oxazepan-4-yl-[1,2,4]triazolo[4,3-a]pyridin-6-yloxy)-1,2,3,4-tetrahydro-naphthalen-1-yl]-urea;

1-[5-tert-Butyl-2-(4-chloro-3-piperidin-1-ylmethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[5-tert-Butyl-2-(4-chloro-3-pyrrolidin-1-ylmethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[1-(2-dimethylamino-ethyl)-2-oxo-1,2-dihydro-pyridin-4-yl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}urea formate salt;

1-{5-tert-Butyl-2-[4-chloro-3-(piperidin-4-yloxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[4-chloro-3-(1-methyl-piperidin-4-yloxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[4-chloro-3-((R)-piperidin-3-yloxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[4-chloro-3-((S)-piperidin-3-yloxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[4-chloro-3-((R)-1-methyl-piperidin-3-yloxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[4-chloro-3-((S)-1-methyl-piperidin-3-yloxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[3-tert-Butyl-1'-(2-dimethylamino-ethyl)-3'-hydroxymethyl-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[4-chloro-3-(2-hydroxy-propoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[4-chloro-3-(3-morpholin-4-yl-propoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[4-chloro-3-(3-morpholin-4-yl-propoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[4-chloro-3-(2-dimethylamino-ethoxy)-phenyl]-2H-pyrazol-3-yl}-3-{1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[4-chloro-3-(2-dimethylamino-ethoxy)-phenyl]-2H-pyrazol-3-yl}-3-{1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[4-chloro-3-(2-dimethylamino-ethoxy)-phenyl]-2H-pyrazol-3-yl}-3-{(1S,4R)-4-[3-((S)-2-methyl-pyrrolidin-1-yl)-[1,2,4]triazolo yloxy]-1,2,3,4-tetrahydro-naphthalen-1-yl}-urea formate salt;

1-{5-tert-Butyl-2-[4-chloro-3-(2-dimethylamino-ethoxy)-phenyl]-2H-pyrazol-3-yl}-3-{(1S,4R)-4-[3-((R)-2-methyl-pyrrolidin-1-yl)-[1,2,4]triazolo[4,3-a]pyridin-6-yloxy]-1,2,3,4-tetrahydro-naphthalen-1-yl}-urea formate salt;

1-[5-tert-Butyl-2-(3,4-dimethyl-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-[5-tert-Butyl-2-(2,5-dimethyl-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-[5-tert-Butyl-2-(4-chloro-3-hydroxymethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[5-tert-Butyl-2-(2,4-dimethyl-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-{5-tert-Butyl-2-[4-chloro-3-(2-morpholin-4-yl-ethoxy)-phenyl]-2H-pyrazol-3-yl}-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-{5-tert-Butyl-2-[4-chloro-3-(2-morpholin-4-yl-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[4-methyl-3-(2-morpholin-4-yl-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[5-tert-Butyl-2-(3-chloro-5-hydroxymethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[3-tert-Butyl-1'-(2-dimethylamino-ethyl)-4'-hydroxymethyl-1'H-[1,3']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-[5-tert-Butyl-2-(3,5-dimethyl-isoxazol-4-yl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea and pharmaceutically acceptable salts thereof.

Utility.

As mentioned above the compounds of the invention are p38MAPK inhibitors, and thus may have utility for the treatment of diseases or conditions which benefit from inhibition of the p38 enzyme. Such diseases and conditions are known from the literature and several have been mentioned above. However, the compounds are generally of use as anti-inflammatory agents, particularly for use in the treatment of respiratory disease In particular, the compounds may be used in the treatment of chronic obstructive pulmonary disease (COPD), chronic bronchitis, lung fibrosis, pneumonia, acute respiratory distress syndrome (ARDS), pulmonary emphysema, or smoking-induced emphysema, intrinsic (non-allergic asthma and extrinsic (allergic) asthma, mild asthma, moderate asthma, severe asthma, steroid resistant asthma, neutrophilic asthma, bronchitic asthma, exercise induced asthma, occupational asthma and asthma induced following bacterial infection, cystic fibrosis, pulmonary fibrosis and bronchiectasis.

The present invention provides the use of the compounds of the invention for the prevention and/or treatment of any disease or condition which benefit from inhibition of the p38 enzyme.

In a further aspect the present invention provides the use of compounds of the invention for the preparation of a medicament for the prevention and/or treatment of any disease or condition which benefit from inhibition of the p38 enzyme.

Moreover the present invention provides a method for prevention and/or treatment of any disease which benefit from inhibition of the p38 enzyme, said method comprises administering to a patient in need of such treatment a therapeutically effective amount of a compound of the invention.

Compositions.

As mentioned above, the compounds with which the invention is concerned are p38 kinase inhibitors, and are useful in the treatment of several diseases for example inflammatory diseases of the respiratory tract. Examples of such diseases are referred to above, and include asthma, rhinitis, allergic airway syndrome, bronchitis and chronic obstructive pulmonary disease.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range for oral administration will lie within the range of from about 0.001 mg to about 100 mg per kg body weight of a human, often 0.01 mg to about 50 mg per kg, for example 0.1 to 10 mg per kg, in single or divided doses. In general, the daily dose range for inhaled administration will lie within the range of from about 0.1 µg to about 1 mg per kg body weight of a human, preferably 0.1 µg to 50 µg per kg, in single or divided doses. On the other hand, it may be necessary to use dosages outside these limits in some cases. For the purpose of the invention, inhaled administration is preferred.

The compounds with which the invention is concerned may be prepared for administration by any route consistent with their pharmacokinetic properties. Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or coloring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

However, for treatment of an inflammatory disease of the respiratory tract, compounds of the invention may also be formulated for inhalation, for example as a nasal spray, or dry powder or aerosol inhalers. For delivery by inhalation, the active compound is preferably in the form of microparticles. They may be prepared by a variety of techniques, including spray-drying, freeze-drying and micronisation. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

By way of example, a composition of the invention may be prepared as a suspension for delivery from a nebuliser or as an aerosol in a liquid propellant, for example for use in a pressurised metered dose inhaler (PMDI). Propellants suitable for use in a PMDI are known to the skilled person, and include CFC-12, HFA-134a, HFA-227, HCFC-22 ($CCl_2F_2$) and HFA-152 ($CH_4F_2$ and isobutane).

In a preferred embodiment of the invention, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 µm.

In the case of an aerosol-based formulation, an example is:

| | |
|---|---|
| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321, which is incorporated herein by reference in its entirety). Additionally, compounds of the invention may be delivered in multi-chamber devices thus allowing for delivery of combination agents.

Combinations.

Other compounds may be combined with compounds with which the invention is concerned for the prevention and treatment of inflammatory diseases, in particular respiratory diseases. Thus the present invention is also concerned with pharmaceutical compositions comprising a therapeutically effective amount of a compound of the invention and one or more other therapeutic agents. Suitable therapeutic agents for a combination therapy with compounds of the invention include, but are not limited to: (1) corticosteroids, such as fluticasone propionate, fluticasone furoate, mometasone furoate, beclometasone dipropionate, ciclesonide, budesonide, GSK 685698, GSK 870086, QAE 397, QMF 149, TPI-1020; (2) β2-adrenoreceptor agonists such as salbutamol, albuterol, terbutaline, fenoterol, and long acting β2-adrenoreceptor agonists such as salmeterol, indacaterol, formoterol (including formoterol fumarate), arformoterol, carmoterol, GSK 642444, GSK 159797, GSK 159802, GSK 597501, GSK 678007, AZD3199, vilanterol, olodaterol and abediterol; (3) corticosteroid/long acting β2 agonist combination products such as salmeterol/fluticasone propionate (Advair/Seretide), formoterol/budesonide (Symbicort), formoterol/fluticasone propionate (Flutiform), formoterol/ciclesonide, formoterol/mometasone furoate, formoterol/beclometasone dipropionate, indacaterol/mometasone furoate, Indacaterol/QAE 397, GSK 159797/GSK 685698, GSK 159802/GSK 685698, GSK 642444/GSK 685698, GSK 159797/GSK 870086, GSK 159802/GSK 870086, GSK 642444/GSK 870086, arformoterol/ciclesonide; (4) anticholinergic agents, for example muscarinic-3 (M3) receptor antagonists such as ipratropium bromide, tiotropium bromide, Aclidinium (LAS-34273), NVA-237, GSK 233705, Darotropium, GSK 573719, GSK 961081, QAT 370, QAX 028, EP-101; (5) dual pharmacology M3-anticholinergic/β2-adrenoreceptor agonists such as GSK961081, AZD2115 and LAS190792; (6) leukotriene modulators, for example leukotriene antagonists such as montelukast, zafirulast or pranlukast or leukotriene biosynthesis inhibitors such as Zileuton or BAY-1005, or LTB4 antagonists such as Amelubant, or FLAP inhibitors such as GSK 2190914, AM-103; (7) phosphodiesterase-IV (PDE-IV) inhibitors (oral or inhaled), such as roflumilast, cilomilast, Oglemilast, ONO-6126, Tetomilast, Tofimilast, UK 500,001, GSK 256066; (8) antihistamines, for example selective histamine-1 (H1) receptor antagonists, such as fexofenadine, citirizine, loratidine or astemizole or dual H1/H3 receptor antagonists such as GSK 835726, GSK 1004723, or selective histamine-4 (H4) receptor antagonists, such as ZPL3893787; (9) antitussive agents, such as codeine or dextramorphan; (10) a mucolytic, for example N acetyl cysteine or fudostein; (11) a expectorant/mucokinetic modulator, for example ambroxol, hypertonic solutions (e.g. saline or mannitol) or surfactant; (12) a peptide mucolytic, for example recombinant human deoxyribonuclease I (dornase-alfa and rhDNase) or helicidin; (13) antibiotics, for example azithromycin, tobramycin and aztreonam; (14) non-selective COX-1/COX-2 inhibitors, such as ibuprofen or ketoprofen; (15) COX-2 inhibitors, such as celecoxib and rofecoxib; (16) VLA-4 antagonists, such as those described in WO97/03094 and WO97/02289, which are incorporated herein by reference in their entireties; (17) TACE inhibitors and TNF-α inhibitors, for example anti-TNF monoclonal antibodies, such as Remicade and CDP-870 and TNF receptor immunoglobulin molecules, such as Enbrel; (18) inhibitors of matrix metalloprotease, for example MMP-12; (19) human neutrophil elastase inhibitors, such as ONO-6818 or those described in WO2005/026124, WO2003/053930 and WO06/082412, which are incorporated herein by reference in their entireties; (20) A2b antagonists such as those described in WO2002/42298, which is incorporated herein by reference in its entirety; (21) modulators of chemokine receptor function, for example antagonists of CCR3 and CCR8; (22) compounds which modulate the action of other prostanoid receptors, for example a thromboxane $A_2$ antagonist; DP1 antagonists such as MK-0524, CRTH2 antagonists such as ODC9101 and OC000459 and AZD1981 and mixed DP1/CRTH2 antagonists such as AMG 009 and AMG853; (23) PPAR agonists including PPAR alpha agonists (such as fenofibrate), PPAR delta agonists, PPAR gamma agonists such as Pioglitazone, Rosiglitazone and Balaglitazone; (24) methylxanthines such as theophylline or aminophylline and methylxanthine/corticosteroid combinations such as theophylline/budesonide, theophylline/fluticasone propionate, theophylline/ciclesonide, theophylline/mometasone furoate and theophylline/beclometasone dipropionate; (25) A2a agonists such as those described in EP1052264 and EP1241176, which are incorporated herein by reference in their entireties; (26) CXCR2 or IL-8 antagonists such as SCH 527123 or GSK 656933; (27) IL-R signalling modulators such as kineret and ACZ 885; (28) MCP-1 antagonists such as ABN-912.

The invention is also directed to a kit comprising the pharmaceutical compositions of compounds of the invention alone or in combination with or in admixture with one or more pharmaceutically acceptable carriers and/or excipients and a device which may be a single- or multi-dose dry powder inhaler, a metered dose inhaler or a nebulizer.

Methods of Synthesis.

In one aspect of the present invention, a process for the preparation of compounds of the invention is provided, according to general synthetic routes described in this section. In the following reaction schemes, unless otherwise indicated, the groups mentioned assume the same meaning as those reported for compounds of formula (I).

The skilled person may introduce, where appropriate, suitable variations to the conditions specifically described in the experimentals in order to adapt the synthetic routes to the provision of further compounds of the invention. Such variations may include, but are not limited to, use of appropriate starting materials to generate different compounds, changes in the solvent and temperature of reactions, replacements of reactives with analogous chemical role, introduction or removal of protection/deprotection stages of functional groups sensitive to reaction conditions and reagents, as well as introduction or removal of specific synthetic steps oriented to further functionalisation of the chemical scaffold.

Processes which can be used and are described and reported in Examples and Schemes, should not be viewed as limiting the scope of the synthetic methods available for the preparation of the compounds of the invention.

The process described is particularly advantageous as it is susceptible of being properly modulated, through any proper variant known to the skilled person, so as to obtained any of the desired compounds of the invention. Such variants are comprised within the scope of the present invention.

From all of the above, it should be clear to the skilled person that any of the described groups may be present as such or in any properly protected form.

In particular, functional groups present in the intermediate and compounds and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known to those skilled in the art [see, for a general reference, T. W. Green; Protective Groups in Organic Synthesis (Wiley, N.Y. 1981), which is incorporated herein by reference in its entirety].

Likewise, selective protection and deprotection of any of the said groups, for instance including carbonyl, hydroxyl or amino groups, may be accomplished according to very well-known methods commonly employed in organic synthetic chemistry.

Optional salification of the compounds of formula (I) or N-oxides on the pyridine ring thereof may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

For example compounds of the invention of formula (I) may be prepared according to the route illustrated in Scheme 1.

Scheme 1

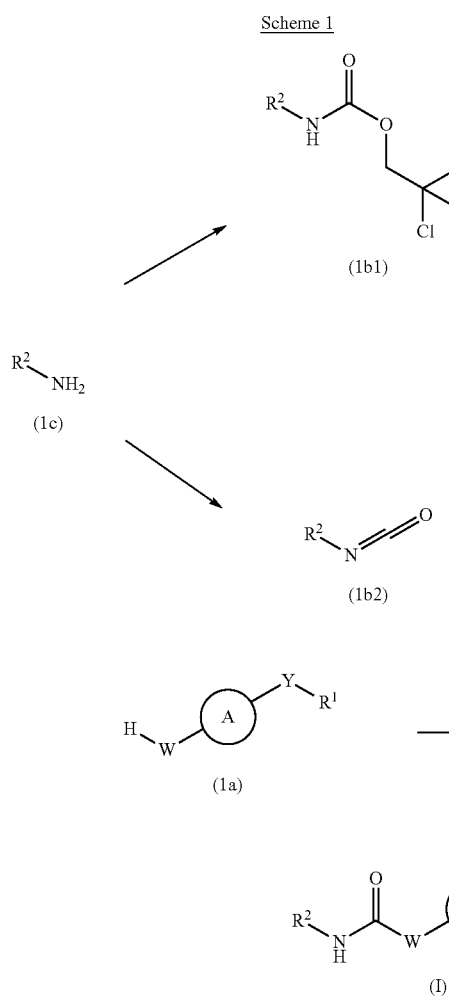

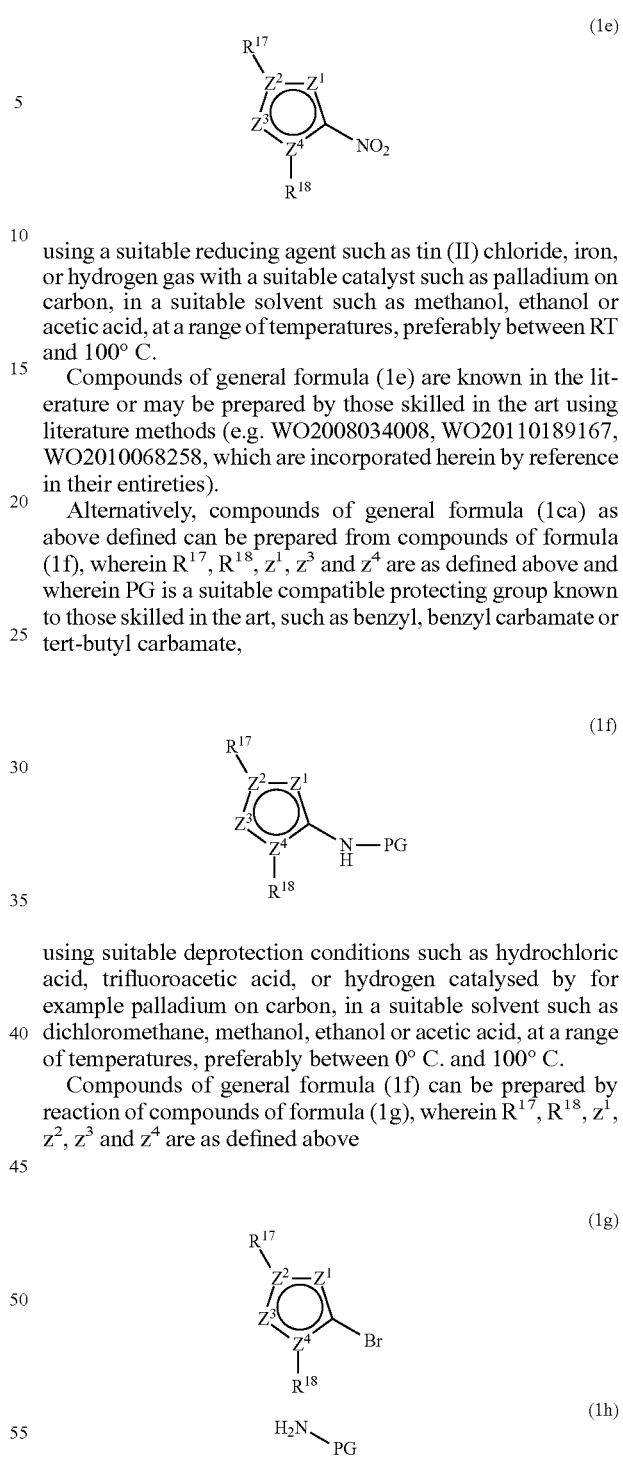

Compounds of general formula (I) may be prepared from compounds of general formula (1a) by reaction with a compound of general formula (1b1) or (1b2) wherein $R^2$ is as defined in general formula (I), in a suitable solvent such as dimethyl sulfoxide, 1,4-dioxane, N,N-dimethylformamide or acetonitrile, in the presence of a base such as diisopropylethylamine at a range of temperatures, preferably between RT and 100° C.

Compounds of general formula (1b1) and (1b2) are either known in the literature or may be prepared from amines of general formula (1c) according to known literature procedures (e.g. see for reference WO2006009741, EP1609789, which are incorporated herein by reference in their entireties).

Compounds of general formula (1c) are either known in the literature or may be synthesised by one skilled in the art by adapting appropriate literature methods (e.g. WO2010077836, WO2006009741, WO2008125014, J. Med Chem., 2007, 50, 4016, Bulletin des Societes Chimiques Belges, 1987, 96, 675-709, Organic & Biomolecular Chemistry, 2006, 4, 4158-4164, which are incorporated herein by reference in their entireties).

Compounds of general formula (1ca), i.e. compounds of formula (1c) wherein $R^2$ is a group of formula (IIIb) and $R^{17}$, $R^{18}$, $z^1$, $z^2$, $z^3$ and $z^4$ are as defined above can be prepared from compounds of formula (1e), using a suitable reducing agent such as tin (II) chloride, iron, or hydrogen gas with a suitable catalyst such as palladium on carbon, in a suitable solvent such as methanol, ethanol or acetic acid, at a range of temperatures, preferably between RT and 100° C.

Compounds of general formula (1e) are known in the literature or may be prepared by those skilled in the art using literature methods (e.g. WO2008034008, WO20110189167, WO2010068258, which are incorporated herein by reference in their entireties).

Alternatively, compounds of general formula (1ca) as above defined can be prepared from compounds of formula (1f), wherein $R^{17}$, $R^{18}$, $z^1$, $z^3$ and $z^4$ are as defined above and wherein PG is a suitable compatible protecting group known to those skilled in the art, such as benzyl, benzyl carbamate or tert-butyl carbamate, using suitable deprotection conditions such as hydrochloric acid, trifluoroacetic acid, or hydrogen catalysed by for example palladium on carbon, in a suitable solvent such as dichloromethane, methanol, ethanol or acetic acid, at a range of temperatures, preferably between 0° C. and 100° C.

Compounds of general formula (1f) can be prepared by reaction of compounds of formula (1g), wherein $R^{17}$, $R^{18}$, $z^1$, $z^2$, $z^3$ and $z^4$ are as defined above with compounds of formula (1h) as above reported wherein PG is a suitable protecting group known to those skilled in the art, such as benzyl, benzyl carbamate or tert-butyl carbamate, using suitable conditions such as in the presence of a base such as potassium carbonate or diisopropylethyl amine or under Buchwald conditions (with a catalyst such as $Pd(OAc)_2$, a ligand such as 2,2'-bis(diphenylphosphino)-1,1'-binaphthyl and base such as sodium tert-butoxide), in a suitable solvent such as toluene or tetrahydrofuran, at a range of temperatures, preferably between RT and 150° C.

Compounds of general formula (1g) and (1 h) are known in the literature or may be prepared by those skilled in the art by adapting appropriate literature methods (e.g. WO2011042389, Chemistry-A European Journal, 2011, 17, 6606-6609, S6606/1-S6606/38, which are incorporated herein by reference in their entireties).

Compounds of general formula (1a) may be prepared according to the route illustrated in Scheme 2.

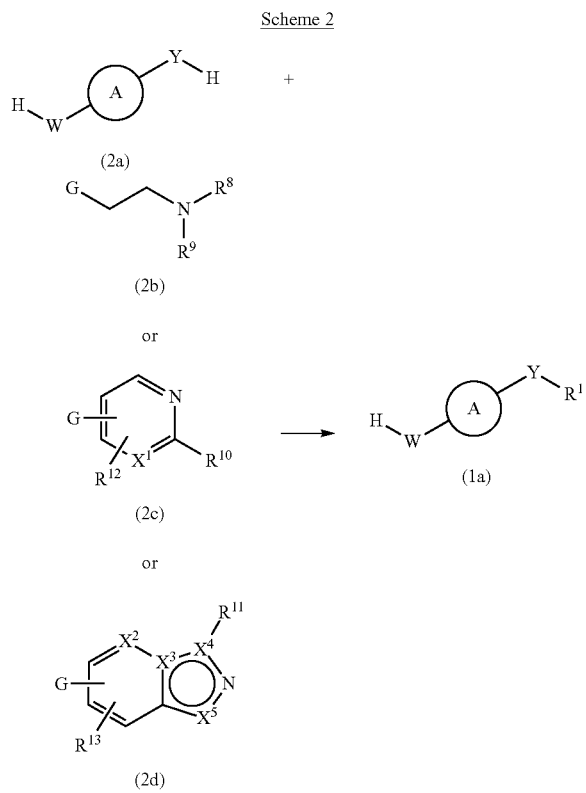

Compounds of general formula (1a) may be prepared from compounds of general formula (2a) by reaction with a compound of general formula (2b), (2c) or (2d), wherein G is a suitable chemical group known to those skilled in the art selected such that it can facilitate a suitable coupling reaction such as nucleophilic displacement or metal catalysed cross coupling. For example in cases such that when Y is —O—, —S— or —NR$^7$—, examples of G may include halogen or a suitable leaving group such as mesylate or triflate either directly linked or attached via a group —(CR$^3$R$^4$)$_n$—. Examples of the coupling conditions used may include using a base such as sodium hydride or potassium tert-butoxide and 1,3-dimethyl-3,4,5,6-tetrahydro-2(1H)-pyrimidinone in a suitable solvent such as N,N-dimethylformamide, toluene, 1,4-dioxane or acetonitrile at a range of temperatures, preferably between RT and 150° C. For example in cases such that when Y is —O— and G is —OH or —SH a method to perform this coupling may involve Mitsunobu conditions (diethylazodicarboxylate/triphenylphosphine) in a suitable solvent such as tetrahydrofuran or 1,4-dioxane at a range of temperatures preferably between −10° C. and 100° C. For example in cases such as when Y is —O—, —S— or —NR$^7$— and G is a group such as halogen, triflate or boronic acid/ester a method to perform this coupling may be under metal (for example palladium or copper) catalysed coupling conditions in the presence of a suitable ligand such as Xantphos or 1,10-phenanthroline in the presence of a base such as caesium carbonate in a suitable solvent such as tetrahydrofuran, 1,4-dioxane or N,N-dimethylformamide at a range of temperatures preferably between −10° C. and 150° C. For example in cases such as when Y is —O— and G is a group such as —COOMe, —COOH, isocyanate, —OCOCl or —NHCOOCH$_2$CCl$_3$ examples of conditions to perform this coupling may involve the use of a base such as sodium hydride or triethylamine or a coupling reagent such as HATU in a suitable solvent such as dichloromethane, tetrahydrofuran, 1,4-dioxane or N,N-dimethylformamide at a range of temperatures preferably between −10° C. and 150° C.

Compounds of formula (2b) are commercial available, are known in the literature or may be synthesised from compounds of formula (2e), wherein R$^8$ and R$^9$ are as defined for compounds of formula (I), by adapting appropriate literature methods (e.g. WO 2006/133006, which is incorporated herein by reference in its entirety) or using methods known to those skilled in the art such as by reacting (2e) with a suitable alkylating agent such as dibromoethane or bromoethanol in the presence of a suitable base such as sodium hydride or potassium carbonate in a suitable solvent such as tetrahydrofuran, 1,4-dioxane or N,N-dimethylformamide at a range of temperatures preferably between −10° C. and 150° C., or by reacting (2e) with a suitable aldehyde in the presence of a reducing agent such as sodium triacetoxyborohydride in a suitable solvent such as dichloroethane or tetrahydrofuran at a range of temperatures preferably between −10° C. and 100° C.

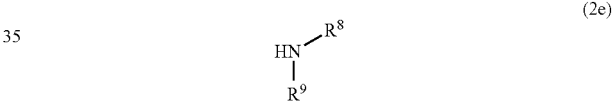

Compounds of formula (2e) are commercially available, are known in the literature or may be synthesised by those skilled in the art using literature methods.

Compounds of formula (2c) may be synthesised from compounds of formula (20:

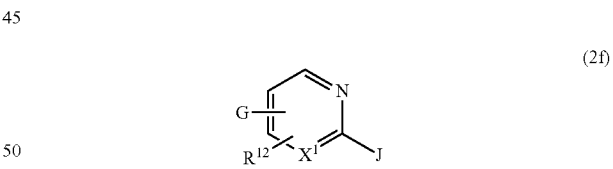

wherein X$_1$ and R$^{12}$ are defined as for compounds of formula (I), G is a group such as halogen, —O-PG or —S-PG wherein PG represents a protecting group such as triisopropylsilyl or tert-butyldimethylsilyl (methods for whose introduction and removal are well known by those skilled in the art) and J may represent groups such as halogen, —NH$_2$, —OH, —SH, —COOH, —SO$_2$Cl which can be modified using literature methods to introduce an appropriate group R$^{10}$ by those skilled in the art. For example in cases such as when J is halogen, a method such as nucleophilic substitution with a suitable alcohol, amine or thiol may be used in the presence of a suitable base such as sodium hydride, triethylamine or potassium carbonate in a suitable solvent such as tetrahydrofuran, 1,4-dioxane or N,N-dimethylformamide at a range of temperatures preferably between −10° C. and 150° C. For example in cases such as when J is —NH$_2$, —OH or —SH, a method such as alkylation may be used with a suitable alkylating agent such as an alkyl halide in the presence of a suitable base such as sodium hydride or potassium carbonate in a suitable solvent such as tetrahydrofuran, 1,4-dioxane or N,N-dimethylformamide at a range of temperatures preferably between −10° C. and 150° C. For example in cases such as where J is —COOH or —SO$_2$Cl a method such as reaction with a suitable amine in the presence of a suitable base such as triethylamine or a coupling reagent such as HATU in a suitable solvent such as tetrahydrofuran, 1,4-dioxane or N,N-dimethylformamide at a range of temperatures preferably between −10° C. and 150° C.

Compounds of formula (2da), i.e. compounds of formula (2a) wherein $X^4$=C may be prepared according to the routes described in Scheme 3 herebelow:

Compounds of formula (3c) are commercially available, known in the literature or may be prepared using literature methods by those skilled in the art.

Alternatively, compounds of formula (2da) may be prepared from compounds of formula (3d) using a suitable dehydrating agent such as Burgess' reagent, triphenyl phosphine and hexachloroethane, phosphorus oxychloride, acetic acid or Mitsunobu conditions (diethylazodicarboxylate/triphenylphosphine/trimethylsilylazide), in the absence or presence of a suitable solvent such as tetrahydrofuran, toluene or NMP, at a range of temperatures, preferably between RT and 150° C.

Compounds of formula (3d) may be prepared from compounds of formula (3a) by reaction with a compound of general formula (3b1) using a suitable acylating/dehydrating agent such as triphenylphosphine/trichloroacetonitrile in the presence of a base such as diisopropylethylamine, in a suit-

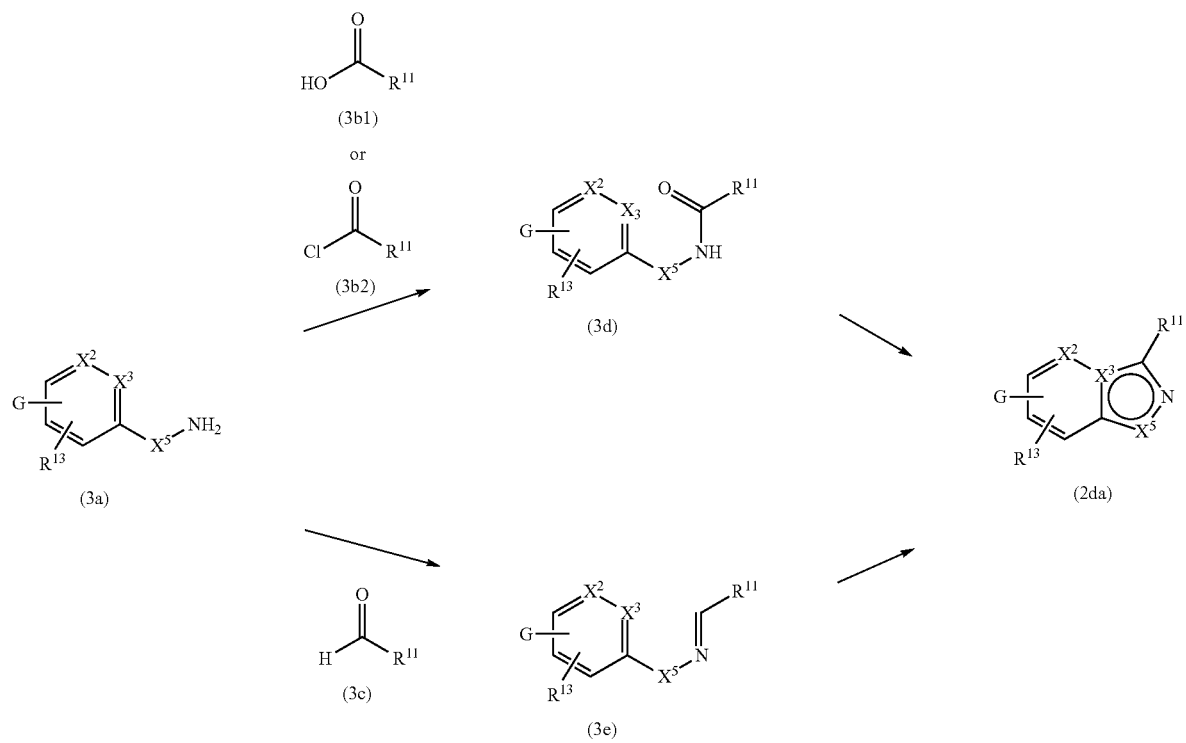

Scheme 3

Compounds of general formula (2da) as above defined may be prepared from compounds of general formula (3e) using a suitable oxidant such as chloramine T, lead tetracetate or phenyl iodine(III) diacetate, in a suitable solvent such as dichloromethane or ethanol at a range of temperatures, preferably between RT and 100° C.

Compounds of general formula (3e) may be prepared from compounds of general formula (3a) by reaction with an aldehyde of general formula (3c) above reported. in a suitable solvent such as ethanol or tetrahydrofuran at a range of temperatures, preferably between RT and 80° C.

able solvent such as dichloromethane or acetonitrile, at a range of temperatures, preferably between RT and 150° C.

Or by reaction with a compound of general formula (3b2) in the presence of a base such as diisopropylethylamine, in a suitable solvent such as dichloromethane or THF at a range of temperatures preferably between −10° C. and the boiling point of the solvent.

Compounds of formulae (3b1) and (3b2) are commercially available, known in the literature or may be prepared by literature methods by those skilled in the art.

Alternatively, compounds of formula (2da) as above defined may be prepared according to the route in Scheme 4:

Scheme 4

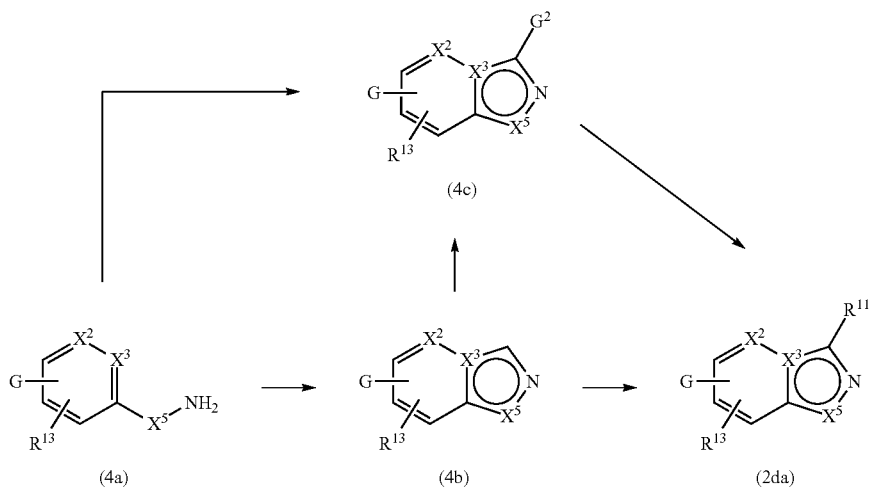

Compounds of general formula (2da) may be prepared from compounds of general formula (4c), wherein $G^2$ may represent groups such as halogen, —CHO, —COOH, —COOEt and $SO_2Cl$.

For example, compounds of general formula (2da) may be prepared from compounds of general formula (4c), wherein $G^2$ represents halogen, using methods such as a metal (for example palladium) catalysed coupling with a suitable $R^{11}G^5$ derivative wherein $G^5$ is a group such as boronate acid/ester or stannane in a suitable solvent such as tetrahydrofuran or 1,4-dioxane at a range of temperatures preferably between RT and 150° C. An alternative method may involve displacement of said halogen with a suitable group $R^{11}H$ (such as that containing an —NH, —OH or —SH group) in the presence of a base such as sodium hydride, potassium tert-butoxide or N,N-diethylisopropylamine in a suitable solvent such as N,N-Dimethylformamide, toluene, 1,4-dioxane or acetonitrile at a range of temperatures, preferably between RT and 150° C.

The group $G^2$ may be also transformed from groups such as halogen to groups such as —CHO, —COOH, —COOEt and $SO_2Cl$ by means of metal insertion methods known to those skilled in the art such as palladium catalysis, Grignard formation or lithium halogen exchange.

Compounds of general formula (2da) wherein $R^{11}$ is a group such as —$CH_2$—$NR^AR^B$, —C(O)N($R^C$)—($C_2$-$C_6$alkylene)-$NR^AR^B$, —C(O)N($R^C$)—($C_3$-$C_7$cycloalkylene)-$NR^AR^B$, —C(O)N($R^C$)—($C_2$-$C_6$alkylene)-$OR^D$, —C(O)N($R^C$)—($C_3$-$C_7$cycloalkylene)-$OR^D$, —C(O)N($R^AR^B$), —S(O)$_2$N($R^C$)—($C_2$-$C_6$alkylene)-$NR^AR^B$, —S(O)$_2$N($R^C$)—($C_3$-$C_7$cycloalkylene)-$NR^AR^B$, —S(O)$_2$N($R^C$)—($C_2$-$C_6$alkylene)-$OR^D$ or —S(O)$_2$N($R^C$)—($C_3$-$C_7$cycloalkylene)-$OR^D$ may be prepared from compounds of general formula (4c), wherein $G^2$ represents —CHO, —COOH, —COOEt and —$SO_2Cl$, by reaction with a suitable amine such as $HNR^AR^B$ etc using methods such as reductive amination (using a reagent such as sodium triacetoxyborohydride) or amide/sulphonamide formation in the presence of suitable reagents such as HATU with a base such as N,N-diethylisopropylamine or trimethylaluminium in a suitable solvent such as dichloromethane, N,N-dimethylformamide, toluene, 1,4-dioxane or acetonitrile at a range of temperatures, preferably between RT and 150° C.

Compounds of general formula (4c) wherein $G^2$ is a group such as —COOEt, may be synthesised from compounds of general formula (4a) by reaction with a compound such as diethyloxalate in the presence of an acid such as acetic acid at a range of temperatures, preferably between RT and 120° C.

Compounds of general formula (4c) wherein $G^2$ is a group such as bromine or chlorine, may be synthesised from compounds of general formula (4b) by reaction with a compound such as N-chlorosuccinimide or N-bromosuccinimide in a solvent such as chloroform at a range of temperatures, preferably between −10° C. and RT.

Compounds of general formula (4b) may be synthesised from compounds of general formula (4a) by reaction with a compound such as diethoxymethylacetate at a range of temperatures, preferably between RT and 100° C.

Compounds of general formula (2db), i.e. compounds of formula (2d) wherein $X_4$ is nitrogen, may be prepared from compounds of general formula (4b) wherein $X^4$=NH, by reaction with a suitable alkylating agent $R^{11}$ in the presence of a base such as caesium carbonate in a suitable solvent such as N,N-dimethylformamide at a range of temperatures, preferably between RT and 150° C.

Alternatively, compounds of general formula (1aa), i.e. compounds of formula (1a) wherein $X^4$ is CH may be prepared according to the route illustrated in Scheme 5.

Scheme 5

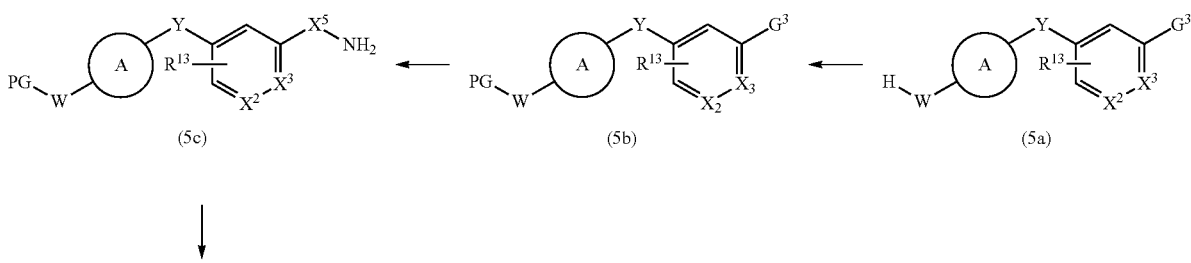

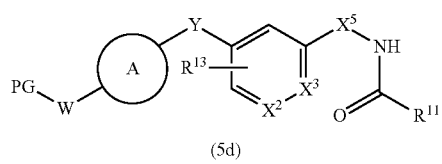
(5d)

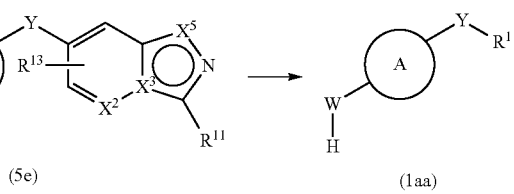
(5e) → (1aa)

Compounds of general formula (1aa) may be prepared from compounds of general formula (5e) wherein PG is a suitable protecting group known in the art such as Boc by using the appropriate deprotection conditions such as trifluoroacetic acid in a solvent such as dichloromethane at a range of temperatures, preferably between −10° C. and RT.

Compounds of general formula (5e) may be prepared from compounds of general formula (5d) using a suitable dehydrating agent such as Burgess' reagent, triphenyl phosphine and hexachloroethane, phosphorus oxychloride, acetic acid or Mitsunobu conditions (diethylazodicarboxylate/triphable protecting group reagent known in the art such as Boc anhydride in the presence of a base such as triethylamine in a suitable solvent such as dichloromethane or tetrahydrofuran at a range of temperatures preferably between RT and 100° C.

Compounds of general formula (5a) can be synthesized by the methods described above for the synthesis of (1a).

Compounds of general formula (2aa), i.e. compounds of formula (2a) wherein Y=O, W=NH and PG is a suitable protective group such as trifluoroacetate may be prepared according to the route illustrated in scheme 6:

Scheme 6

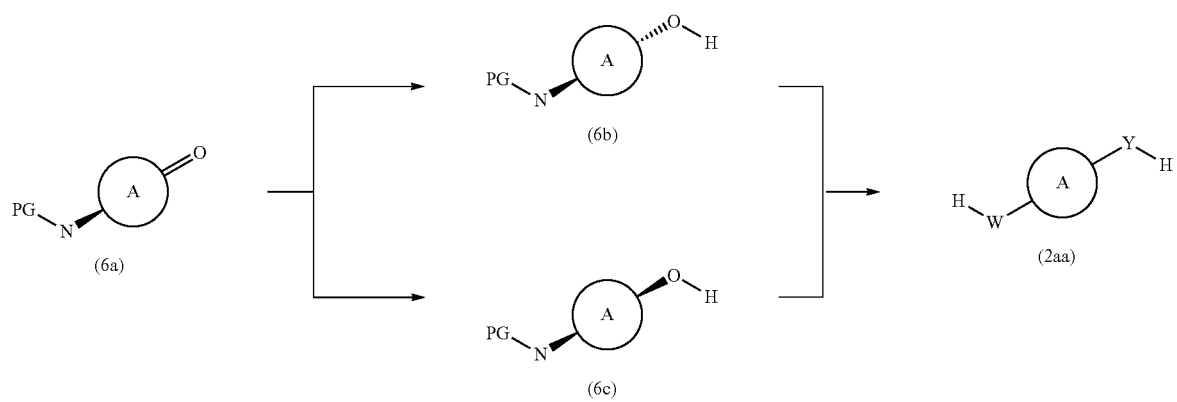

enylphosphine/trimethylsilylazide), in the absence or presence of a suitable solvent such as tetrahydrofuran, toluene or NMP, at a range of temperatures, preferably between RT and 120° C.

Compounds of general formula (5d) may be prepared from compounds of general formula (5c) by reaction with a compound of general formula (3b1) as above defined using a suitable acylating/dehydrating agent such as triphenylphosphine/trichloroacetonitrile in the presence of a base such as diisopropylethylamine, in a suitable solvent such as dichloromethane or acetonitrile, at a range of temperatures, preferably between RT and 150° C., or by reaction with a compound of general formula (3b2) as above defined in the presence of a base such as diisopropylethylamine, in a suitable solvent such as dichloromethane or THF at a range of temperatures preferably between −10° C. and the boiling point of the solvent.

Compounds of general formula (5c) may be prepared from compounds of general formula (5b) wherein $G^3$ is a suitable leaving group such as halogen, by reaction with a reagent such as hydrazine monohydrate in a suitable solvent such as ethanol at a range of temperatures preferably between RT and 100° C.

Compounds of general formula (5b) may be prepared from compounds of general formula (5a) by reaction with a suit- Compounds of general formula (2aa) may be prepared from compounds of general formula (6b) and (6c) by removal of the protecting group PG using methods known in the art such as aqueous sodium hydroxide in a solvent such as methanol at a range of temperatures preferably between RT and 100° C.

Compounds of general formula (6b), wherein PG is a protecting group, preferably trifluoroacetamide, and the group —OH is placed on the cycloalkylene portion of ring A may be prepared from compounds of general formula (6a) by using a chiral reductive method such as using formic acid and RuCl[S,S-Tsdpen(p-cymene)] in the presence of a base such as triethylamine in a solvent such as N,N-dimethylformamide at a range of temperatures preferably between RT and 150° C. It will be recognised that compounds of formula (6a) may be homochiral as illustrated or be the opposite enantiomer or racemic. It will be realised by those skilled in the art that any combination of stereocentres in (2aa) can be prepared using both enantiomers of (6a) and using RuCl[R,R-Tsdpen(p-cymene)] or RuCl[S,S-Tsdpen(p-cymene)]. Compound (2a) is drawn with no defined stereocentres but any combination can be obtained as illustrated in Scheme 2.

Compounds of formula (6a) can be prepared from compounds of formula (6d)

(6d)

using a suitable oxidant such as potassium permanganate and magnesium sulfate in a suitable solvent methanol/water at a range of temperatures preferably between RT and the boiling point of the solvent. It will be recognised that compounds of formula (6d) may be homochiral as illustrated or be the opposite enantiomer or racemic.

Compounds of formula (6d) can be prepared from compounds of formula (6e) where PG is a suitable protecting group such as trifluoroacetate or tert-butyl carbonate:

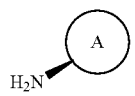

(6e)

using ethyl trifluoroacetate or di-tert-butyl dicarbonate in the presence of base such as triethylamine or diisopropylethylamine in a solvent such as methanol or dichloromethane at a range of temperatures preferably between 0° C. and the boiling point of the solvent. It will be recognised that compounds of formula (6e) may be homochiral as illustrated or be the opposite enantiomer or racemic.

Compounds of formula (6e) are known in the literature and may be prepared by those skilled in the art by adapting literature methods (e.g. for S-(+)-1-amino-1,2,3,4-tetrahydronaphthalene, see Journal of the Chemical Society, Perkin Transactions 1: 1985, 2039-44; for (S)-(+)-8-amino-5,6,7,8-tetrahydroquinoline, see Journal of Organic Chemistry, 2007, 72, 669-671; and for 1-aminoindan see Tetrahedron Letters, 2011, 52, 1310-1312), which are incorporated herein by reference in their entireties.

Compounds of general formula (2ab), i.e. compounds of formula (2a) wherein $Y=NR^7$ and $W=NH$, may be prepared according to the route illustrated in scheme 7:

Compounds of general formula (2ab) may be prepared from compounds of general formula (7a) by removal of the protecting group PG using methods known in the art such as aqueous sodium hydroxide in a solvent such as methanol or trifluoroacetic acid in dichloromethane at a range of temperatures preferably between RT and 100° C.

Compounds of formula (7a) may be prepared from compounds of general formula (6a) and amines (7b) by reaction under reductive amination conditions, using a reducing agent such as sodium triacetoxyborohydride and a solvent such as 1,2-dichloroethane at a range of temperatures preferably between RT and 100° C.

Compounds for formula (7b) are known and may be prepared using known procedures. Compounds of formula (6a) can be prepared as described above.

Alternatively, compounds of formula (7a) may be prepared from compounds of general formula (7c) wherein $G^4$ is a suitable chemical group known to those skilled in the art selected such that it can facilitate a reaction such as a nucleophilic substitution. For example G is a suitable leaving group such as halogen or mesylate which can react with a suitable amine (7b) in the presence of a suitable base such as sodium hydride or potassium tert-butoxide and 1,3-dimethyl-3,4,5,6-tetrahydro-2(1H)-pyrimidinone in a suitable solvent such as N,N-dimethylformamide, toluene, 1,4-dioxane or acetonitrile at a range of temperatures, preferably between RT and 150° C.

Compounds of formula (7c) can be prepared from compounds of formulae (6b) or (6c) using halogenating conditions such as carbon tetrabromide and triphenylphosphine in dichloromethane or activation conditions such as methane sulfonyl chloride in dichloromethane in the presence of base such as diisopropylamine.

Alternatively, compounds of general formula (Id), i.e. compounds of formula (I) wherein $Y=S$ and $W=NH$ may be prepared according to the route illustrated in scheme 8:

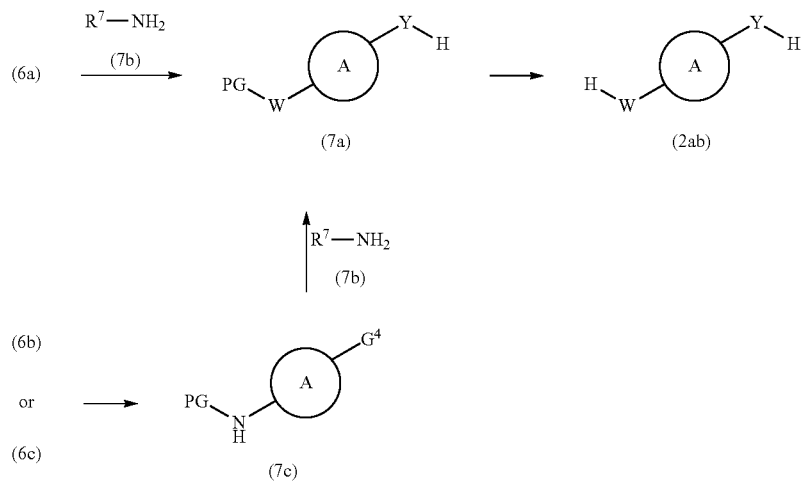

Scheme 7

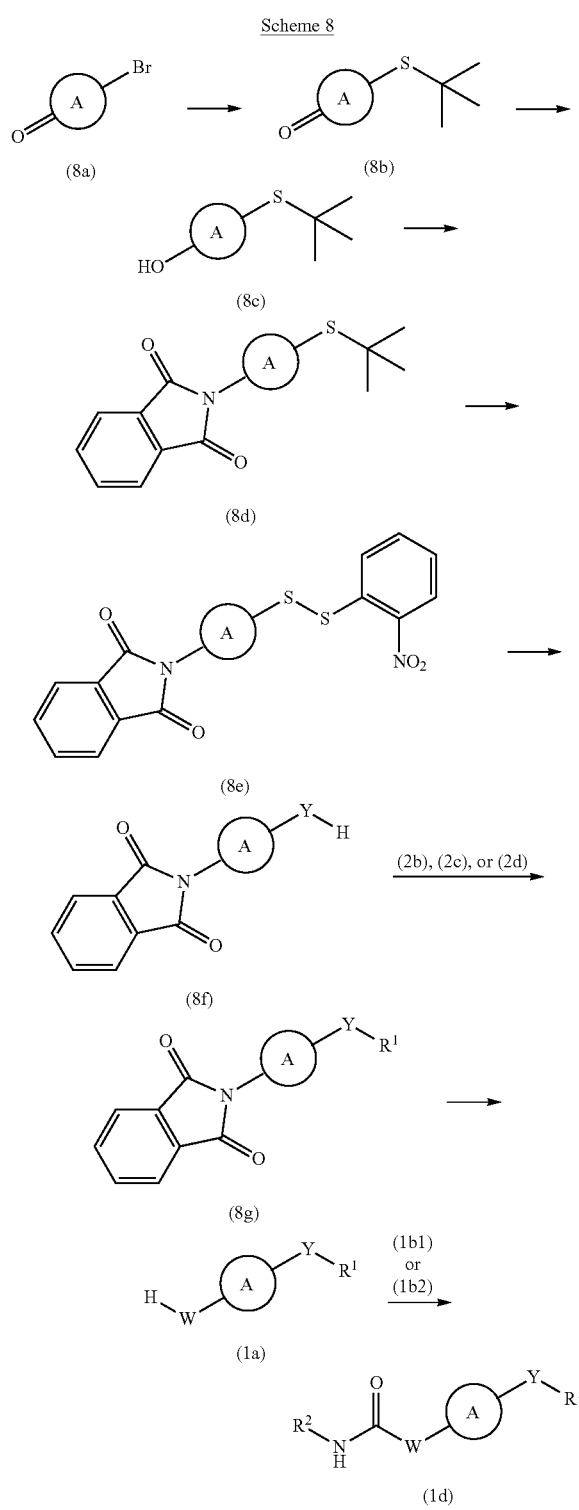

Scheme 8

Compounds of general formula (1d) may be prepared from compounds of general formula (1ab), i.e. compounds of formula (1a) wherein Y=S and W=NH: using compounds of formula (1b1) or (1b2) in a suitable solvent such as dimethyl sulfoxide, 1,4-dioxane, N,N-dimethylformamide or acetonitrile, in the presence of a base such as diisopropylethylamine at a range of temperatures, preferably between RT and 100° C.

Compounds of formula (1ab) as above defined may be prepared from compounds of formula (8g) using deprotection conditions such as hydrazine in methanol at a range of temperatures preferably between RT and the boiling point of the solvent.

Compounds of formula (8g) wherein Y=S, can be prepared from compounds of formula (8f) by reaction with compounds of formulae (2b), (2c) or (2d). Examples of the coupling conditions used may include using a base such as sodium hydride or potassium tert-butoxide and 1,3-dimethyl-3,4,5,6-tetrahydro-2(1H)-pyrimidinone in a suitable solvent such as N,N-dimethylformamide, toluene, 1,4-dioxane or acetonitrile at a range of temperatures, preferably between RT and 150° C. Alternative methods to perform this coupling may involve Mitsunobu conditions (diethylazodicarboxylate/triphenylphosphine) or metal (for example palladium) catalysed coupling conditions in a suitable solvent such as tetrahydrofuran or 1,4-dioxane at a range of temperatures preferably between −10° C. and 150° C. and starting from the appropriate derivative of formula (2b), (2c), or (2d).

Compounds of formula (8f) can be prepared from compounds of formula (8e) using dithiothreitol, monopotassium phosphate, potassium carbonate in a solvent such as methanol in the presence of acetic acid at a range of temperatures preferably between RT and the boiling point of the solvent.

Compounds of formula (8e) can be prepared from compounds of formula (8d) using 2-nitrobenzenesulfenyl chloride in acetic acid at a range of temperatures preferably between RT and 100° C.

Compounds of formula (8d) can be prepared from compounds of formula (8c) using phthalimide, triphenylphosphine and diisopropyl azodicarboxylate in a solvent such as tetrahydrofuran at a range of temperature preferably between 0° C. and the boiling point of the solvent.

Compounds of formula (8c) can be prepared from compounds of formula (8b) using a reducing agent such as sodium borohydride in a solvent such as methanol at a range of temperatures preferably between 0° C. and the boiling point of the solvent.

Compounds of formula (8b) can be prepared from compounds of formula (8a) using tert-butanethiol in the presence of a base such as diisopropylethylamine in a solvent such as tetrahydrofuran at a range of temperatures preferably between 0° C. and the boiling point of the solvent.

Compounds of formula (8a) are known and can be prepared using known methods (e.g. 3-bromo-indan-1-one see WO 2010/108058, which is incorporated herein by reference in its entirety).

Alternatively, compounds of general formula (1 ab), i.e. compounds of formula (1a) wherein Y=CH$_2$, W=NH and PG is a suitable protective group such as trifluoroacetate may be prepared according to the route illustrated in scheme 9:

Scheme 9

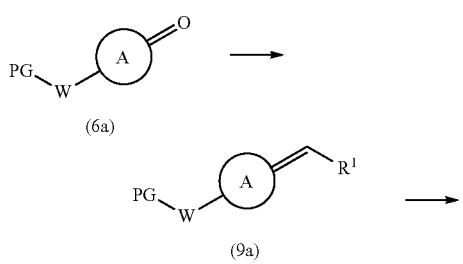

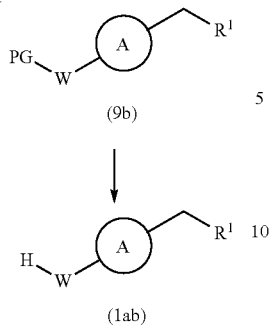

(9b)

↓

(1ab)

Compounds of general formula (1ab) may be prepared from compounds of general formula (9b) by removal of the protecting group PG using methods known in the art such as aqueous sodium hydroxide in a solvent such as methanol at a range of temperatures preferably between RT and 100° C.

Compounds of formula (9b) may be prepared from compounds of general formula (9a) by reaction with a suitable reduction agent for example hydrogen gas in the presence of a suitable catalyst such as palladium on activated charcoal in a suitable solvent such as ethanol at a range of temperatures between RT and 70° C. and pressures between atmospheric and 4 Barr.

Compounds of formula (9a) may be prepared from compounds of general formula (6a) by means of a reaction such as a Wittig (or one of the closely related variants such as the Horner-Wadsworth-Emmons) with a suitable substrate such as $R^1$—$CH_2$—P(O)(OMe)$_2$ in the presence of a suitable base such as sodium hydride in a suitable solvent such as tetrahydrofuran at a range of temperatures preferably between −10° C. and 100° C.

Compounds such as $R^1$—$CH_2$—P(O)(OMe)$_2$ may be synthesised from compounds of the general formula $R^1$—$CH_2$-Hal wherein Hal represents a halogen such as —Br or —Cl by reaction with a compound such as trimethylphosphite at a range of temperatures preferably between 0° C. and 100° C.

Compounds such as $R^1$—$CH_2$-Hal may be synthesised from compounds of formula $R^1$—$CH_3$ by means of a reaction such as a radical halogenation using a reagent such as N-bromosuccinimide in the presence of a catalyst such as AIBN in a suitable solvent such as carbon tetrachloride at a range of temperatures preferably between 0° C. and 80° C. Compounds such as $R^1$—$CH_2$-Hal may also be synthesized from compounds formula $R^1$—$CH_2$—OH by means of using halogenating conditions such as carbon tetrabromide and triphenylphosphine in dichloromethane or activation conditions such as methane sulfonyl chloride in dichloromethane in the presence of base such as diisopropylamine.

Compounds such as $R^1$—$CH_3$ and $R^1$—$CH_2$—OH may be prepared by methods outlined above for compounds (2b), (2c) and (2d).

Compounds of the invention of formula (1ac), i.e. compounds of formula (1a) where Y=(CR$^5$R$^6$)$_n$ and W=NH, may be prepared according to the route illustrated in Scheme 10.

Scheme 10

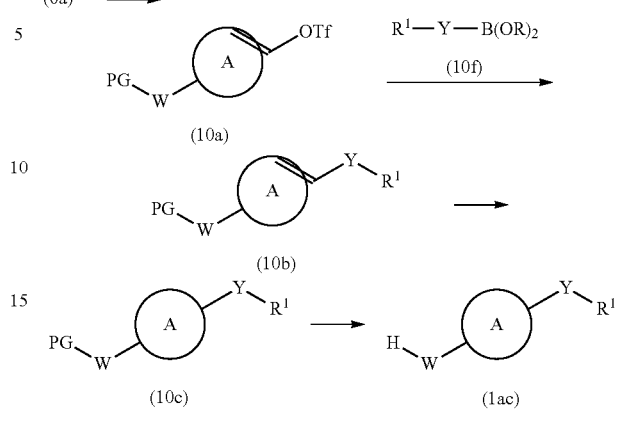

Compounds of formula (1ac) may be prepared from compounds of formula (10c) wherein PG is a suitable protecting group known to those skilled in the art, such as trifluoroacetamide, tert-butyl carbamate and benzyl carbamate by using suitable de-protection conditions such as, sodium hydroxide in methanol, trifluoroacetic acid in dichloromethane or hydrogen gas catalysed by for example palladium on carbon in ethanol, at a range of temperatures, preferably between 0° C. and 100° C.

Compounds of formula (10c) may be prepared from compounds of formula (10b) wherein PG is a suitable known protecting group, such as trifluoroacetamide, tert-butyl carbamate and benzyl carbamate by using hydrogen gas in the presence of a catalyst such as palladium on carbon, in a suitable solvent such as methanol or ethanol, in the presence or absence of an acid such as HCl, at a range of temperatures, preferably between 0° C. and 100° C.

Compounds of formula (10b) may be prepared from compounds of formula (10a) and (10f) by a reaction such as a cross-coupling using a suitable catalyst such as tetrakis(triphenylphosphine)palladium (0) or palladium acetate, and a base such as diisopropylethylamine, sodium tert-butoxide or caesium carbonate in a suitable solvent such as NMP, toluene or DMF, at a range of temperatures, preferably between 0° C. and 100° C. Alternatively (10b) may be prepared by adapting known procedures (e.g. those reported in WO2009/022633, which is incorporated herein by reference in its entirety).

Compounds of formula (10f) are known in the literature or may be prepared by those skilled in the art by adapting literature procedures (e.g. WO2008/063287, which is incorporated herein by reference in its entirety).

Compounds of formula (10a) may be prepared from compounds of formula (6a) using a triflating agent such as triflic anhydride, in the presence of a suitable base such as pyridine or 2,6-bis(tert-butyl)-4-methylpyridine, in a solvent such as dichloromethane or chloroform at a range of temperatures, preferably between 0° C. and boiling point of the solvent. Alternatively (10a) may be prepared by adapting literature procedures (e.g. those described in WO2009/022633, which is incorporated herein by reference in its entirety).

Other features of the invention will become apparent in the course of the following descriptions of exemplary embodiments which are given for illustration of the invention and are not intended to be limiting thereof.

EXAMPLES

Abbreviations used in the experimental section:
AcOH=acetic acid;
$CDCl_3$=deuterated chloroform;
DCM=dichloromethane;
DEAD=Diethyl azodicarboxylate;
DIAD=Diisopropyl azodicarboxylate;
DIPEA=diisopropylethylamine;
DMAP=N,N-dimethylaminopyridine;
DMF=N,N-dimethylformamide;
$d_4$-MeOD=deuterated methanol;
$d_6$-DMSO=deuterated dimethyl sulfoxide;
EDC=1-ethyl-3-(3'-dimethylaminopropyl)carbodiimide Hydrochloride;
EtOAc=ethyl acetate;
EtOH=ethanol;
$Et_2O$=diethyl ether;
$Et_3N$=triethylamine;
$EtNiPr_2$=diisopropylethylamine;
FCC=flash column chromatography;
H=hour;
HATU=2-(7-aza-1H-benzotriazole-1-yl)-1,1,3,3-tetramethyluronium hexafluorophosphate;
HOBt=1-hydroxy-benzotriazole;
HPLC=high performance liquid chromatography;
IMS=Industrial Methylated Spirits;
LCMS=liquid chromatography mass spectrometry;
NaOH=sodium hydroxide;
MeCN=acetonitrile;
MeOH=Methanol;
min=minutes;
$NH_3$=ammonia;
NIS=N-iodosuccinimide;
NMR=nuclear magnetic resonance;
RT=room temperature;
Rt=retention time;
sat.=saturated;
SCX-2=strong cation exchange chromatography;
TBAF=tetrabutylammonium fluoride;
TFA=trifluoroacetic acid;
THF=Tetrahydrofuran;
$H_2O$=water;
Xantphos=4,5-Bis(diphenylphosphino)-9,9-dimethylxanthene;
X-Select=Waters X-select HPLC column;
IPA=propan-2-ol;
LDA=lithium diisopropylamide;
MDAP=mass-directed auto-purification;
$Ph_3P$=triphenylphosphine;
TBAF=tetrabutylammonium fluoride.

In the procedures that follow, after each starting material, reference to an Intermediate/Example number is usually provided. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

The nomenclature of structures was assigned using Autonom 2000 Name software from MDL Inc. When the nomenclature of structures could not be assigned using Autonom, ACD/Name software utility part of the ACD/Labs Release 12.00 Product Version 12.5 (Build 45133, 16 Dec. 2010) was used. Stereochemical assignments of compounds are based on comparisons with data reported in WO2008/043019, which is incorporated herein by reference in its entirety, for key intermediates. All reactions were carried out under anhydrous conditions and an atmosphere of nitrogen or argon unless specified otherwise. Unless otherwise stated all transformations were carried at RT.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane ($\delta$=0 ppm). J values are given in Hz through-out. NMR spectra were assigned using DataChord Spectrum Analyst Version 4.0.b21 or SpinWorks version 3.

Where products were purified by flash column chromatography (FCC), 'flash silica' refers to silica gel for chromatography, 0.035 to 0.070 mm (220 to 440 mesh) (e.g. Fluka silica gel 60), and an applied pressure of nitrogen up to 10 p.s.i accelerated column elution or use of the CombiFlash® Companion purification system or use of the Biotage SP1 purification system. All solvents and commercial reagents were used as received.

Compounds purified by preparative HPLC were purified using a C18-reverse-phase column (100×22.5 mm i.d Genesis column with 7 μm particle size), or a Phenyl-Hexyl column (250×21.2 mm i.d. Gemini column with 5 μm particle size), UV detection between 220-254 nm, flow 5-20 mL/min), eluting with gradients from 100-0 to 0-100% water/acetonitrile (containing 0.1% TFA or 0.1% formic acid) or water/MeOH (containing 0.1% TFA or 0.1% formic acid), or a C18-reverse-phase column (19×250 mm, XBridge OBD, with 5 μm particle size), eluting with gradients from 100-0 to 0-100% water/acetonitrile (containing 0.1% $NH_4OH$); or a ChiralPak IC column (10×250 mm i.d., with 5 μM particle size), unless otherwise indicated. Fractions containing the required product (identified by LCMS analysis) were pooled, the organic solvent removed by evaporation, and the remaining aqueous residue lyophilised, to give the final product. Products purified by preparative HPLC were isolated as free base, formate or TFA salts, unless otherwise stated.

The Liquid Chromatography Mass Spectroscopy (LCMS) and HPLC systems used are:

Method 1.

Waters Platform LC Quadrupole mass spectrometer with a C18-reverse-phase column (30 × 4.6 mm Phenomenex Luna 3 μm particle size), elution with A: water + 0.1% formic acid; B: acetonitrile + 0.1% formic acid. Gradient:

| Gradient - Time | flow mL/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection - MS, ELS, UV (200 μL split to MS with in-line HP1100 DAD detector).
MS ionization method - Electrospray (positive and negative ion).

Method 2.

| Waters ZMD quadrupole mass spectrometer with a C18-reverse-phase column (30 × 4.6 mm Phenomenex Luna 3 μm particle size), elution with A: water + 0.1% formic acid; B: acetonitrile + 0.1% formic acid. Gradient: | | | |
|---|---|---|---|
| Gradient - Time | flow mL/min | % A | % B |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection - MS, ELS, UV (200 μL split to MS with in-line Waters 996 DAD detector).
MS ionization method - Electrospray (positive and negative ion).

Method 3.

| Waters ZMD quadrupole mass spectrometer with a C18-reverse-phase column (30 × 4.6 mm Phenomenex Luna 3 μm particle size), elution with A: water + 0.1% formic acid; B: acetonitrile + 0.1% formic acid. Gradient: | | | |
|---|---|---|---|
| Gradient - Time | flow mL/min | % A | % B |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection - MS, ELS, UV (200 μL split to MS with in-line HP1100 DAD detector).
MS ionization method - Electrospray (positive and negative ion).

Method 4.

| VG Platform II quadrupole spectrometer with a C18-reverse-phase column (30 × 4.6 mm Phenomenex Luna 3 μm particle size, elution with A: water + 0.1% formic acid; B: acetonitrile + 0.1% formic acid. Gradient: | | | |
|---|---|---|---|
| Gradient - Time | flow mL/min | % A | % B |
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection - MS, ELS, UV (200 μl/min split to the ESI source with inline HP1050 DAD detector).
MS ionization method - Electrospray (positive and negative ion).

Method 5.

| Waters micromass ZQ2000 quadrupole mass spectrometer with an Acquity BEH C18 1.7 um 100 × 2.1 mm, Acquity BEH Shield RP18 1.7 um 100 × 2.1 mm or Acquity HSST3 1.8 um 100 × 2.1 mm, maintained at 40° C. Elution with A: water + 0.1% formic acid; B: acetonitrile + 0.1% formic acid. Gradient: | | | |
|---|---|---|---|
| Gradient - Time | flow mL/min | % A | % B |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection - MS, UV PDA.
MS ionization method - Electrospray (positive and negative ion).

Method 6.
Phenomenex Gemini C18-reverse-phase column (250×21.20 mm 5 μm particle size), elution with A: water+ 0.1% formic acid; B: $CH_3CN$+0.1% formic acid. Gradient– 90% A/10% B to 2% A/98% B over 20 min—flow rate 18 mL/min. Detection—In-line UV detector set at 254 nM wavelength.

Method 7.
Agilent 1260 infinity purification system. Column: XSELECT CSH Prep C18 OBD, particle size 5 μm, 30×150 mm, RT. Elution with A: water+0.1% formic acid; B: $CH_3CN$+ 0.1% formic acid. Gradient–90% A/10% B to 2% A/95% B over 22 min—flow rate 60 mL/min. Detection—In-line Agilent 6100 series single Quadrupole LC/MS.

Method 8.
Agilent 1260 infinity purification system. Column: XBridge Prep C18 OBD, particle size 5 μm, 30×150 mm, RT. Elution with A: water+0.1% ammonia; B: $CH_3CN$+0.1% ammonia. Gradient—90% A/10% B to 2% A/95% B over 22 min—flow rate 60 mL/min. Detection—In-line Agilent 6100 series single Quadrupole LC/MS.

Method 9.

| Waters ZQ quadrupole mass spectrometer with a C18-reverse-phase column (30 × 4.6 mm Phenomenex Luna 3 μm particle size), elution with A: water + 0.1% formic acid; B: acetonitrile + 0.1% formic acid. Gradient: | | | |
|---|---|---|---|
| Gradient - Time | flow mL/min | % A | % B |
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.8 | 2.0 | 95 | 5 |
| 6.00 | 2.0 | 95 | 5 |

Detection - MS, ELS, UV (200 μL split to MS with in-line HP1100 DAD detector).
MS ionization method - Electrospray (positive and negative ion).

Intermediate A (1R,4S)-4-Amino-1,2,3,4-tetrahydro-naphthalen-1-ol

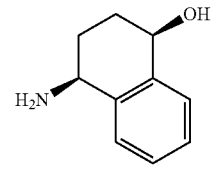 [SMILES: N[C@H]1CC[C@@H](O)c2ccccc21]

a. 2,2,2-Trifluoro-N—(S)-1,2,3,4-tetrahydro-naphthalen-1-yl-acetamide (Intermediate Aa)

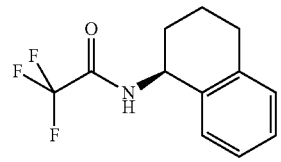 [SMILES: O=C(N[C@H]1CCCc2ccccc21)C(F)(F)F]

To a mechanically stirred solution of (S)-(+)-(1,2,3,4-tetrahydro-naphthalen-1-yl)amine (CAS: 23357-52-0, 175 g, 1.19 mol) and triethylamine (250 mL, 1.79 mol) in MeOH (1.75 L), ethyl trifluoroacetate (170 mL, 1.43 mol) was added dropwise at a rate to maintain the internal temperature below 30° C. (ca. over 20 min). The resulting solution was stirred at RT overnight. The mixture was concentrated in vacuo to give a solid. This was partitioned between DCM (1 L) and water (1 L). The layers were separated and the aqueous layer was extracted with DCM (2×600 mL). The combined organic layers were washed with brine, dried ($Na_2SO_4$), filtered and concentrated in vacuo to yield Intermediate Aa (289.4 g, 100%). $^1$H NMR (400 MHz, $CDCl_3$): 1.80-1.95 (3H, m), 2.05-2.15 (1H, m), 2.75-2.90 (2H, m), 5.18-5.25 (1H, q, J=5.0 Hz), 6.38-6.48 (1H, br s), 7.12-7.16 (1H, m), 7.20-7.26 (3H, m).

b. 2,2,2-Trifluoro-N—((S)-4-oxo-1,2,3,4-tetrahydro-naphthalen-1-yl)-acetamide (Intermediate Ab)

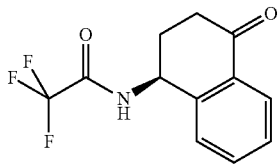 [SMILES: O=C1CC[C@H](NC(=O)C(F)(F)F)c2ccccc21]

A 20 L flask was charged with Intermediate Aa (288 g, 1.19 mol) and acetone (7 L). Magnesium sulfate monohydrate (328 g, 2.37 mol) in water (3 L) was added and the mixture stirred mechanically, and cooled to internal temperature ~1.5° C. Potassium permanganate (562.1 g, 3.56 mol) was then added in 7 equal portions (i.e. 80.3 g) every 15 min for 105 min. Water (0.5 L) was added and the resulting mixture was stirred at RT for 17 h. The mixture was cooled to 15° C. and a solution of sodium thiosulfate pentahydrate (883 g, 3.56 mol) in water (3 L) was added dropwise over 1 h, whilst maintaining internal temperature below 18° C. The resulting slurry was stirred for 1 h and the mixture left to stand at RT overnight. A solid had settled at the bottom of the flask and the solution was decanted and then concentrated to leave a residue. The remaining solid was treated with ethyl acetate (7 L) and water (2 L) and the mixture was filtered through Celite. The filtrate was combined with the residue isolated above. The mixture was separated and the aqueous layer extracted with ethyl acetate (2×1 L). The organics were combined and drying agent ($Na_2SO_4$) and decolourising charcoal were added. The mixture was filtered through Celite and concentrated to dryness in vacuo to yield Intermediate Ab (260 g, 85%). 1H NMR (400 MHz, $CDCl_3$): 2.20-2.30 (1H, dddd, J=13.3, 10.0, 8.8, 4.5 Hz), 2.43-2.52 (1H, dddd, J=13.3, 7.2, 4.6, 4.6 Hz), 2.67-2.77 (1H, ddd, J=17.4, 10.1, 4.6 Hz), 2.78-2.88 (1H, ddd, J=17.4, 7.1, 4.6 Hz), 5.39-5.47 (1H, td, J=8.5, 4.5 Hz), 7.32-7.37 (1H, d, J=7.7 Hz), 7.44-7.49 (1H, t, J=7.6 Hz), 7.59-7.64 (1H, td, J=7.6, 1.4 Hz), 8.03-8.07 (1H, dd, J=7.7, 1.4 Hz).

c. 2,2,2-Trifluoro-N-((1S,4R)-4-hydroxy-1,2,3,4-tetrahydro-naphthalen-1-yl)-acetamide (Intermediate Ac)

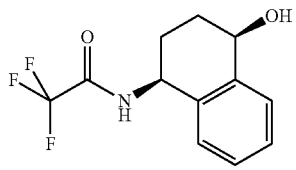 [SMILES: O=C(N[C@H]1CC[C@@H](O)c2ccccc21)C(F)(F)F]

A solution of Intermediate Ab (161 g, 624 mmol) in DMF (2 L) was vacuum degassed with Argon. [N-[(1R,2R)-2-(Amino-κN)-1,2-diphenylethyl]-4-methylbenzenesulfonamidato-κN]chloro[(1,2,3,4,5,6-η)-1-methyl-4-(1-methylethyl)benzene]-ruthenium (CAS: 192139-92-7, 9.95 g, 15.6 mmol) was then added. Formic acid (57.5 g, 1.25 mol) was added slowly to ice cold triethylamine (126 g, 1.25 mol) with stirring, this was then added to the DMF solution. The resulting reaction mixture was heated to 50° C. (internal temperature) for 41 h with stirring. LCMS analysis of the reaction indicated it was incomplete, therefore a solution of formic acid (14.4 g, 313 mmol) was added slowly to ice cold triethylamine (31.6 g, 312 mmol), this was then added to the reaction mixture. Heating was continued for an additional 22 h. After cooling, the mixture was concentrated in vacuo to give an orange residue. The residue was diluted with ethyl acetate (1.5 L) and the solution washed with brine (2×0.5 L). The organics were dried ($Na_2SO_4$), filtered and concentrated in vacuo. Purification by column chromatography (Silica, 3 Kg, 0-50% ethyl acetate in cyclohexane) gave Intermediate Ac (118 g, 73%). 97.5 d.e. % determination by LCMS (Method 4): Rt 3.37 min, M-H=258 (93.7%, desired); Rt 3.25 min, M-H=258 (1.2%, trans isomer). $^1$H NMR (400 MHz, $CDCl_3$): 1.88-1.92 (1H, d, J=4.8 Hz), 1.98-2.18 (4H, m), 4.80-4.88 (1H, m), 5.165-5.24 (1H, m), 6.70-6.80 (1H, br s), 7.25-7.30 (1H, m), 7.30-7.40 (2H, m), 7.45-7.50 (1H, m).

d. (1R,4S)-4-Amino-1,2,3,4-tetrahydro-naphthalen-1-ol (Intermediate A)

To a stirred solution of Intermediate Ac (117 g, 451 mmol) in methanol (0.7 L), 6N sodium hydroxide solution (190 mL, 1.14 mol) was added and stirred at RT for 20 h. The mixture was concentrated in vacuo and the residue was diluted with ethyl acetate (1 L) and water (0.5 L). Concentrated HCl solution (95 mL, 1.14 mol) was added slowly with stirring. Additional HCl was used to adjust the pH of the aqueous layer to pH=2. The mixture was then separated and the organic layer was extracted with HCl solution (2M aqueous, 3×500 mL). The combined aqueous layers were basified to pH ~12, by addition of concentrated $NH_4OH$ solution, and then extracted in to ethyl acetate (5×750 mL). The combined organic extracts were washed with brine (200 mL), dried ($Na_2SO_4$), filtered and concentrated in vacuo (50.8 g). This material was recrystallized (cyclohexane/ethyl acetate [2:1], 350 mL) to provide Intermediate A (44.4 g, 60%). $^1$H NMR (400 MHz, $d_6$-DMSO): 1.66-1.90 (4H, m), 3.71-3.77 (1H, t, J=5.4 Hz), 4.46-4.54 (1H, t, J=5.4 Hz), 7.14-7.22 (2H, m), 7.32-7.38 (1H, m), 7.40-7.46 (1H, m).

Intermediate B (1S,4R)-4-[3-((S)-2-Methyl-piperidin-1-yl)-[1,2,4]triazolo[4,3-a]pyridin-6-yloxy]-1,2,3,4-tetrahydro-naphthalen-1-ylamine

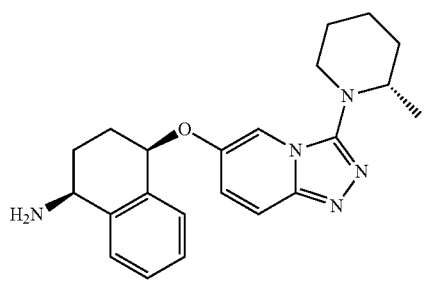 [SMILES: C[C@H]1CCCCN1c1nnc2ccc(O[C@@H]3CC[C@H](N)c4ccccc43)cn12]

a. (R)-Hydroxy-phenyl-acetate(S)-2-methyl-piperidinium (Intermediate Ba)

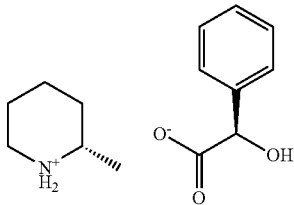

2-Methylpiperidine (CAS: 109-05-7; 99.7 g, 1.00 mol) was dissolved in MeOH (100 mL) in a 2 L Florentine flask and cooled in an ice bath. (R)-(−)-Mandelic acid (CAS: 611-71-2; 152.9 g, 1.00 mol) was then added and the reagents stirred with gentle heating until a homogenous solution resulted. The solution was left to cool, and Et$_2$O (900 mL) was added. The flask walls were scratched to aid crystallisation, and then stored in a fridge for 18 h. The resulting crystals were then filtered off, and washed with cold Et$_2$O. The product was recrystallized again from MeOH (100 mL) and Et$_2$O (500 mL) and left in a fridge for 48 h. The crystals were filtered off, washed with Et$_2$O and dried in a vacuum oven at 50° C. overnight to afford Intermediate Ba (67.0 g, 53%) as colorless crystals. $^1$H NMR (300 MHz, d$_6$-DMSO): 1.12 (3H, d, J=6.5 Hz), 1.20-1.57 (3H, m), 1.58-1.74 (3H, m), 2.72 (1H, dt, J=3.2, 12.4 Hz), 2.88-3.02 (1H, m), 3.06-3.18 (1H, m), 4.51 (1H, s), 7.11-7.19 (1H, m), 7.19-7.29 (2H, m), 7.33-7.42 (2H, m).

Diastereomeric purity was determined using Marfey's method; Intermediate Ba (1 mg, 3.68 µmol) was dissolved in EtOAc (1 mL) and H$_2$O (1 mL) and Marfeys reagent was added (N$_α$-(2,4-Dinitro-5-fluorophenyl)-L-alaninamide, FDAA [CAS 95713-52-3], 1 mg, 3.68 µmol) followed by saturated NaHCO$_3$ solution (50 µL) and heated to 50° C. for 1 h. The mixture was then diluted with H$_2$O (1 mL) and subjected to analytical HPLC (Waters X-Select C18, 2.5 µm, 4.6×50 mm, 32-34% CH$_3$CN/H$_2$O (+0.1% formic acid), 16 min gradient, 1 mL/min, 340 nm). Rt 10.82 min, >99% d.e.

Racemic 2-methylpiperidine was also subjected to Marfey's method; HPLC: Rt 10.75 min (50%), 11.58 min (50%).

b. (S)-2-Methyl-piperidine-1-carbonyl chloride (Intermediate Bb)

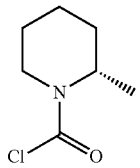

Intermediate Ba (12.0 g, 47.8 mmol) was treated with aqueous NaOH solution (1N; 96 mL, 96.0 mmol) and extracted into DCM (2×75 mL). This solution containing (S)-2-methyl piperidine was transferred to a 3-necked RB flask, stirred under an inert atmosphere and cooled in an ice-bath before pyridine (11.6 mL, 144 mmol) was added followed by triphosgene (14.2 g, 47.8 mmol) during 30 min at <10° C. The cooling bath was removed after 30 min and the mixture stirred at RT for a further 3.5 h. Reaction was quenched by very careful addition of aqueous HCl (1N, 300 mL) at 0-5° C. After 30 min the phases were separated and the aqueous layer extracted with DCM (2×100 mL). Combined DCM extracts were washed with brine, dried (MgSO$_4$), passed through a phase separation cartridge and concentrated in vacuo to give Intermediate Bb (8.6 g, >100%). $^1$H NMR (300 MHz, CDCl$_3$): 1.25 (3H, d, J=6.8 Hz), 1.40-1.80 (6H, m), 3.0 (1H, br), 4.12-4.21 (1H, m), 4.56-4.67 (1H, m).

c. (S)-2-Methyl-piperidine-1-carboxylic acid N'-(5-fluoro-pyridin-2-yl)-hydrazide (Intermediate Bc)

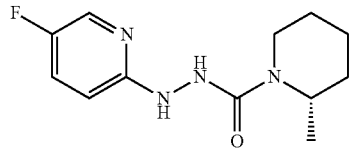 [SMILES: C[C@H]1CCCCN1C(=O)NNc1ccc(F)cn1]

A stirred solution of Intermediate Bb (17.2 g, assumed to be 95.5 mmol) and (5-fluoro-pyridin-2-yl)-hydrazine (12.1 g, 95.5 mmol) in DCM (300 mL) at RT was treated with DIPEA (34.0 mL, 195 mmol) during 5 min. This mixture was continued to be stirred at RT for 4 days before being added to water (500 mL) and phases separated. The aqueous layer was further extracted into DCM (4×100 mL), combined extracts washed with brine, dried (MgSO$_4$), passed through a phase separation cartridge and concentrated in vacuo to give a solid.

This product was treated with Et$_2$O-pentane and the resultant solids filtered off and dried to give Intermediate Bc (18.7 g, 77%). LCMS: Rt 2.26 min, m/z 253 [MH$^+$]. $^1$H NMR (300 MHz, CDCl$_3$): 1.23 (3H, d, J=6.9 Hz), 1.40-1.74 (6H, m), 2.97 (1H, td, J=13.1, 3.0 Hz), 3.82-3.91 (1H, m), 4.27-4.38 (1H, m), 6.54 (1H, s), 6.78 (1H, ddd, J=9.1, 3.7, 0.6 Hz), 7.30 (1H, ddd, J=9.1, 7.8, 2.9 Hz), 8.00 (1H, d, J=2.6 Hz).

d. 6-Fluoro-3-((S)-2-methyl-piperidin-1-yl)-[1,2,4]triazolo[4,3-a]pyridine (Intermediate Bd)

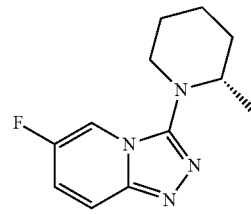

To a stirred solution of Intermediate Bc (14.7 g, 58.3 mmol), Ph$_3$P (30.6 g, 116.5 mmol) and Et$_3$N (33.0 mL, 236.8 mmol) in THF (300 mL) at RT was added hexachloroethane (27.6 g, 116.6 mmol) during 10 min before then heating at 60° C. overnight. The cooled mixture was filtered and concentrated in vacuo to give a residual oil which was dissolved in DCM (200 mL) and extracted into dilute HCl (2M) until most product had been removed from the DCM phase by LCMS. These aqueous extracts were treated with solid NaOH (with cooling) to achieve ~pH9 and extracted into DCM. Combined DCM extracts were washed with brine, dried (MgSO$_4$), passed through a phase separation cartridge and concentrated in vacuo to give Intermediate Bd (11.3 g, 82%). LCMS: Rt 2.99 min, m/z 235 [MH⁺]. ¹H NMR (300 MHz, d₆-DMSO): 0.89 (3H, d, J=6.3 Hz), 1.40-1.88 (6H, m), 2.85-2.96 (1H, m), 3.18 (1H, dt, J=12.0, 4.5 Hz), 3.28-3.35 (1H, m), 7.42 (1H, ddd, J=10.0, 8.0, 2.3 Hz), 7.76 (1H, ddd, J=10.0, 4.9, 0.9 Hz), 8.31-8.35 (1H, m).

e. (1S,4R)-4-[3-((S)-2-Methyl-piperidin-1-yl)-[1,2,4]triazolo[4,3-a]pyridin-6-yloxy]-1,2,3,4-tetrahydro-naphthalen-1-ylamine (Intermediate B)

Sodium hydride (60% dispersion in oil, 12.0 g, 300 mmol) was suspended in DMF (800 mL) and cooled to 0° C. using an ice bath. Intermediate A (24.5 g, 150 mmol) was then added in small portions under N₂ and the resulting suspension was stirred at RT for 45 min (CARE: gas evolution). A solution of Intermediate Bd (35.1 g, 150 mmol) in dry DMF (200 mL) was added and the solution stirred at RT for 18 h. The solution was concentrated in vacuo, the residue was poured into a mixture of brine/1N aqueous NaOH/H₂O (1:1:1; 200 mL); the product was extracted using mixture of EtOAc and Me-THF (300 mL×5). The organic extracts were combined, washed with a small amount of brine, dried over MgSO₄ and concentrated under reduced pressure. The product was purified by FCC, eluting with 0-20% [2M NH₃ in MeOH] in DCM, to provide the title compound (27.1 g, 48%). LCMS (Method 3): Rt 2.29 min, m/z 378 [MH⁺].

Intermediate C (1S,4R)-4-[3-((2S,6R)-2,6-Dimethyl-piperidin-1-yl)-[1,2,4]triazolo[4,3-a]pyridin-6-yloxy]-1,2,3,4-tetrahydro-naphthalen-1-ylamine

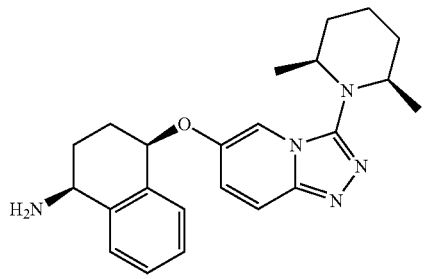 [SMILES: C[C@@H]1CCC[C@H](C)N1c1nnc2ccc(O[C@@H]3CC[C@H](N)c4ccccc43)cn12]

a. (2S,6R)-2,6-Dimethyl-piperidine-1-carbonyl chloride (Intermediate Ca)

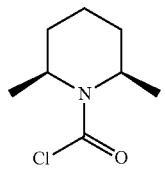

To a solution of triphosgene (20.8 g, 70.0 mmol) in DCM (400 mL) at 5° C. was added pyridine (16.2 mL, 200 mmol) dropwise over 10 min, maintaining the temperature below 10° C. The solution was stirred between 5-10° C. for 1 h, then cis-2,6-dimethyl piperidine (CAS: 766-17-6; 27.0 mL, 200 mmol) was added dropwise over 10 min and the resulting red solution stirred at RT for 4 days. The solution was cooled to 3° C., then a pre-cooled (3° C.) aq. HCl solution (1M, 400 mL) was added and the mixture stirred at 5° C. for 30 min. The aqueous layer was extracted with DCM (200 mL), then the combined organics passed through a hydrophobic fit and concentrated under vacuum affording Intermediate Ca as a red oil (31.5 g, 90%). ¹H NMR (300 MHz, CDCl₃): 1.30 (6H, d, J=7.09 Hz), 1.49-1.87 (6H, m), 4.46-4.56 (2H, m).

b. (2S,6R)-2,6-Dimethyl-piperidine-1-carboxylic acid N-(5-fluoro-pyridin-2-yl)-hydrazide (Intermediate Cb)

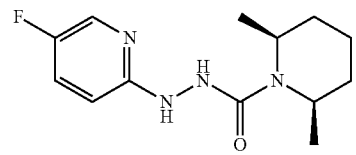 [SMILES: C[C@@H]1CCC[C@H](C)N1C(=O)NNc1ccc(F)cn1]

A dark red solution of (5-fluoro-pyridine-2-yl)-hydrazine (21.7 g, 171 mmol), Intermediate Ca (31.5 g, 180 mmol) and DIPEA (44.7 mmol, 256 mmol) in DCM (350 mL) was stirred at RT for 4 days. Water (350 mL) was added, then the aqueous extracted with DCM (100 mL). The combined organics were passed through a hydrophobic frit and concentrated under vacuum to leave a solid. Trituration with diethyl ether/pentane (1:4, 150 mL), and drying under vacuum at 50° C. left Intermediate Cb (31.7 g, 70%, ~90% purity). LCMS: Rt 2.58 min, m/z 289 [MH⁺]. ¹H NMR (300 MHz, CDCl₃): 1.29 (6H, d, J=7.0 Hz), 1.45-1.89 (6H, m), 4.26 (2H, apparent quin, J=6.5 Hz), 6.53 (1H, s), 6.65 (1H, br s), 6.77 (1H, dd, J=9.0, 3.6 Hz), 7.29-7.28 (1H, ddd, J=9.0, 8.0, 3.0 Hz), 8.02 (1H, d, J=2.9 Hz).

c. 3-((2S,6R)-2,6-Dimethyl-piperidin-1-yl)-6-fluoro-[1,2,4]triazolo[4,3-a]pyridine (Intermediate Cc)

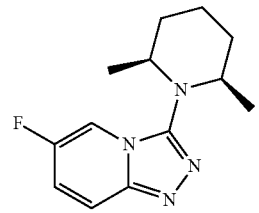 [SMILES: C[C@@H]1CCC[C@H](C)N1c1nnc2ccc(F)cn12]

To a dark red suspension of Intermediate Cb (27.4 g, 103 mmol) and pyridine (25.0 mL, 309 mmol) in toluene (250 mL) at 50° C. was added POCl₃ (11.0 mL, 118 mmol) in 3 portions at 30 s intervals (CARE: exotherm to 70° C.). The suspension was stirred at 50° C. for 1 h, then cooled to RT. Water (100 mL) and sat. aq. NaHCO₃ solution (100 mL) were added (CARE: gas evolution) and the mixture stirred at RT for 30 min. The aqueous was extracted with EtOAc (2×250 mL), then the combined organics washed with brine (250 mL), dried (Na₂SO₄), filtered and concentrated in vacuo to leave a oil (26.3 g). The oil was redissolved in MeOH (150 mL) then charcoal (6 g) was added and the mixture swirled for 30 min. The suspension was filtered through Celite and the filtercake washed with MeOH (25 mL). The combined organics were concentrated in vacuo to leave a red oil. The residue was azeotroped with pentane (25 mL) affording a solid (24.0 g). The solid was slurried in diethyl ether-pentane (1:1, 40 mL), filtered and dried in vacuo to leave Intermediate Cc (20.65 g, 81%). The mother liquor was concentrated in vacuo, the residue dissolved in hot cyclohexane (50° C., 30 mL), then cooled to RT and allowed to stand for over the weekend. The mixture was filtered, the solid washed with cyclohexane (5 mL) then dried in vacuo at 45° C. to leave additional Intermediate Cc (1.8 g, 6%). LCMS: Rt 3.30 min, m/z 249 [MH+].
$^1$H NMR (300 MHz, CDCl$_3$): 0.68 (6H, d, J=6.2 Hz), 1.36-1.49 (2H, m), 1.52-1.68 (1H, m), 1.75-1.90 (3H, m), 3.29-3.40 (2H, m), 7.16 (1H, ddd, J=10.0, 7.6, 2.3 Hz), 7.67 (1H, dd, J=10.0, 4.7 Hz), 8.03 (1H, t, J=2.7 Hz).

d. (1S,4R)-4-[3-((2S,6R)-2,6-Dimethyl-piperidin-1-yl)-[1,2,4]triazolo[4,3-a]pyridin-6-yloxy]-1,2,3,4-tetrahydro-naphthalen-1-ylamine (Intermediate C)

To a solution of Intermediate A (6.59 g, 40.4 mmol) in dry DMF (80 mL) under N$_2$ was added sodium hydride (60% dispersion in oil, 3.20 g, 80.0 mmol) and the resulting solution was stirred at RT for 45 min (CARE: gas evolution). A solution of Intermediate Cc (9.93 g, 40.0 mmol) in dry DMF (20 mL) was added and the solution stirred at RT under N$_2$ for 24 h. The reaction was quenched carefully with saturated aqueous NH$_4$Cl solution (CARE: gas evolution) and H$_2$O. The mixture was stirred for 30 min. Concentration in vacuo gave a gum, which was dissolved in MeOH (125 mL), charcoal was added to the solution and the mixture was stirred at RT for 1 h. The mixture was filtered through Celite and the solution was evaporated under reduced pressure to afford a residue. The residue was suspended in H$_2$O (100 mL), extracted with EtOAc 3×100 mL); the combined organics was washed with brine (75 mL), dried over Na$_2$SO$_4$, filtered and concentrated in vacuo to leave a foam (14.6 g). The foam was triturated with pentane (2×75 mL) using sonication and stirring, the solution was decanted and the solid was left to dry under vacuum and at RT affording Intermediate C (14.21 g, 90%). LCMS (Method 3): Rt 2.32 min, m/z 392 [MH+].

Intermediate D (1S,4R)-4-(3-Piperidin 1-yl-[1,2,4]triazolo[4,3-a]pyridin-6-yloxy)-cis-1,2,3,4-tetrahydro-naphthalen-1-ylamine

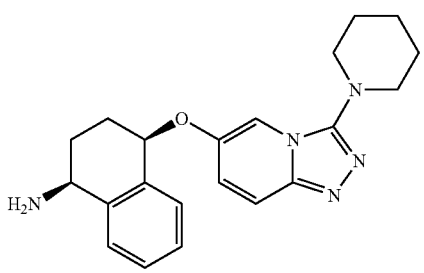 [SMILES: N[C@H]1CC[C@@H](Oc2ccc3nnc(N4CCCCC4)n3c2)c2ccccc21]

a. Piperidine-1-carboxylic acid N'-(5-fluoro-pyridin-2-yl)-hydrazide (Intermediate Da)

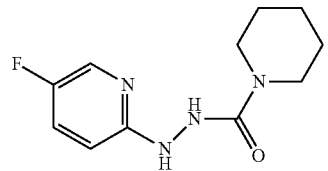 [SMILES: O=C(NNc1ccc(F)cn1)N1CCCCC1]

1-Piperidine carbonyl chloride (348 mg, 0.30 mL, 2.36 mmol) was added dropwise to a solution of 5-fluoro-2-hydrazinyl-pyridine (see for reference WO2010/022076, which is incorporated herein by reference; 0.30 g, 2.36 mmol) and DIPEA (1.20 mL, 7.08 mmol) in DCM (10 mL) at RT under nitrogen and the mixture stirred for 2 h. The solution was washed with water (2×15 mL) and dried (Na$_2$SO$_4$). The solvent was evaporated and the residue triturated (diethyl ether) to afford Intermediate Da (475 mg, 84%). LCMS (Method 1): Rt 1.82 min, m/z 239 [MH+].

b. 6-Fluoro-3-piperidin-1-yl-[1,2,4]triazolo[4,3-a]pyridine (Intermediate Db)

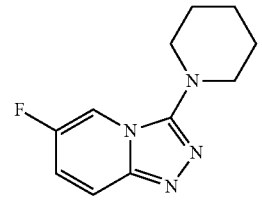 [SMILES: Fc1ccc2nnc(N3CCCCC3)n2c1]

Hexachloroethane (826 mg, 3.92 mmol) was added portionwise to a solution of Intermediate Da (466 mg, 1.95 mmol), triphenylphosphine (1.03 g, 3.92 mmol) and triethylamine (1.10 mL, 7.83 mmol) in dry THF (30 mL) at RT, and the mixture stirred for 2 h. The resulting precipitate was filtered off and the filtrate evaporated. The residue was purified by SCX-2, eluting with MeOH followed by 2M NH$_3$ in MeOH, to give Intermediate Db as a pale orange coloured gum (206 mg, 48%). LCMS (Method 1): Rt 2.44 min, m/z 221 [MH+].

c. (1S,4R)-4-(3-Piperidin 1-yl-[1,2,4]triazolo[4,3-a]pyridin-6-yloxy)-cis-1,2,3,4-tetrahydro-naphthalen-1-ylamine (Intermediate D)

Intermediate A (100 mg, 0.61 mmol) was added portionwise to a suspension of sodium hydride (60% in mineral oil, 73.0 mg, 1.84 mmol) in dry DMF (2 mL) at RT, and the mixture stirred for 15 min. Intermediate Db (135 mg, 0.61 mmol) was then added in one portion and the mixture heated at 60° C. for 1 h. After cooling, saturated NH$_4$Cl (ca. 0.2 mL) was added. The mixture was then partitioned between water (15 mL) and ethyl acetate (3×15 mL) and the combined organic extracts washed with brine (2×15 mL) and dried (Na$_2$SO$_4$). The solvent was evaporated and the residue purified by SCX-2, eluting with MeOH followed by NH$_3$ in MeOH, to give Intermediate D (133 mg, 60%). LCMS (Method 1): Rt 1.95 min, m/z 364 [MH+].

Intermediate E (1S,4R)-4-[3-((S)-1-Methyl-pyrrolidin-2-yl)-[1,2,4]triazolo[4,3-a]pyridin-6-yloxy]-1,2,3,4-tetrahydro-naphthalen-1-ylamine

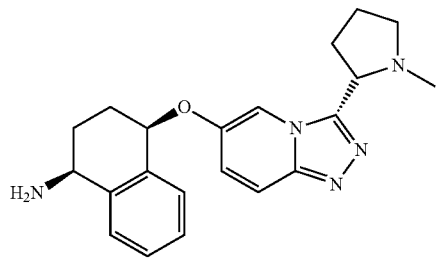

a. (S)-1-Methyl-pyrrolidine-2-carboxylic acid [N'-(5-fluoro-pyridin-2-yl)-hydrazide (Intermediate Ea)

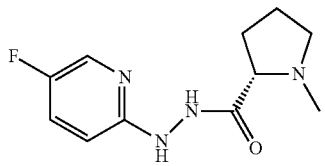 [SMILES: CN1CCC[C@H]1C(=O)NNc1ccc(F)cn1]

EDC (271 mg, 1.41 mmol) was added portionwise to a solution of 5-fluoro-2-hydrazinyl-pyridine (for reference procedure see WO2010/02207, which is incorporated herein by reference 6; 0.15 g, 1.18 mmol), N-methyl-L-proline monohydrate (0.20 g, 1.36 mmol) and HOBt (16 mg, 0.12 mmol) in dry DCM (5 mL) at RT and stirred for 16 h. The solution was diluted with DCM (15 mL), washed with water (150 mL), dried (Na₂SO₄) and evaporated to give Intermediate Ea (189 mg, 67%). LCMS (Method 1): Rt 0.31 min, m/z 239 [MH+].

b. 6-Fluoro-3-((S)-1-methyl-pyrrolidin-2-yl)-[1,2,4]triazolo[4,3-a]pyridine (Intermediate Eb)

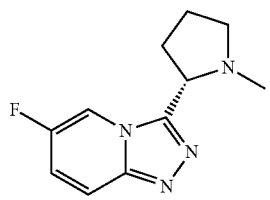 [SMILES: CN1CCC[C@H]1c1nnc2ccc(F)cn12]

Hexachloroethane (375 mg, 1.59 mmol) was added portionwise to a solution of Intermediate Ea (189 mg, 0.79 mmol), triphenylphosphine (416 mg, 1.59 mmol) and triethylamine (0.44 mL, 3.17 mmol) in dry THF (10 mL) at RT and stirred for 4 h. The resulting precipitate was filtered off and the filtrate evaporated. The residue was purified by SCX-2, eluting with MeOH followed by 2M NH₃ in MeOH gave Intermediate Eb (136 mg, 78%). LCMS (Method 1): Rt 0.45 min, m/z 221 [MH+].

c. (1S,4R)-4-[3-((S)-1-Methyl-pyrrolidin-2-yl)-[1,2,4]triazolo[4,3-a]pyridin-6-yloxy]-1,2,3,4-tetrahydro-naphthalen-1-ylamine. (Intermediate E)

Intermediate A (128 mg, 0.77 mmol) was added portionwise to a suspension of sodium hydride (60% in mineral oil, 92 mg, 2.30 mmol) in dry DMF (3 mL) at RT and stirred for 15 min Intermediate Eb (169 mg, 0.77 mmol) was then added in one portion and the mixture heated at 60° C. for 4 h. After cooling, saturated aqueous NH₄Cl (ca. 0.2 mL) was added. The mixture was partitioned between water (10 mL) and ethyl acetate (3×10 mL). The aqueous phase was concentrated in vacuo and the residue purified by SCX-2, eluting with MeOH followed by 2M NH₃ in MeOH, to give Intermediate E (103 mg, 36%). LCMS (Method 1): Rt 1.34 min, m/z 364 [MH+].

Intermediate F (1S,4R)-4-(3-[1,4]Oxazepan-4-yl-[1,2,4]triazolo[4,3-a]pyridin-6-yloxy)-1,2,3,4-tetrahydro-naphthalen-1-ylamine

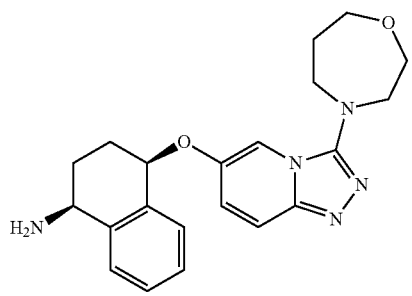 [SMILES: N[C@H]1CC[C@@H](Oc2ccc3nnc(N4CCCOCC4)n3c2)c2ccccc21]

a. 6-Fluoro-[1,2,4]triazolo[4,3-a]pyridine (Intermediate Fa)

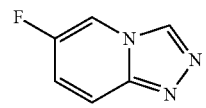

(5-Fluoro-pyridin-2-yl)-hydrazine (500 mg, 3.93 mmol) in diethoxymethyl acetate (5 mL) was stirred at RT for 2 h. The resulting precipitate was diluted with cyclohexane (5 mL) and filtered to give Intermediate Fa (379 mg, 70%). NMR (400 MHz, CDCl₃): 7.25 (1H, m), 7.84 (1H, m), 8.09 (1H, t, J=2.5 Hz), 8.84 (1H, s).

b. 3-Chloro-6-fluoro-[1,2,4]triazolo[4,3-a]pyridine (Intermediate Fb)

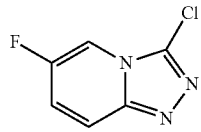 [SMILES: Fc1ccc2nnc(Cl)n2c1]

A solution of Intermediate Fa (789 mg, 5.98 mmol) and N-chlorosuccinimide (878 mg, 6.57 mmol) in chloroform (15 mL) was heated at 65° C. overnight. The cooled mixture was washed with sat. aqueous NaHCO₃ solution (2×15 mL) and dried (Na₂SO₄). The solvent was evaporated, then the residue suspended in diethyl ether (10 mL) and filtered to give Intermediate Fb (730 mg, 76%). LCMS (Method 1): Rt 1.83 min, m/z 172 [MH⁺].

c. 6-Fluoro-3-[1,4]oxazepan-4-yl-[1,2,4]triazolo[4,3-a]pyridine (Intermediate Fc)

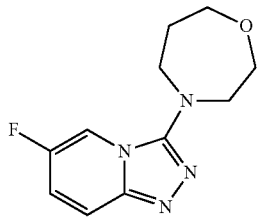 [SMILES: Fc1ccc2nnc(N3CCCOCC3)n2c1]

A solution of Intermediate Fb (429 mg, 2.50 mmol) and homomorpholine (939 mg, 9.30 mmol) in NMP (10 mL) was heated in the microwave at 170° C. for 10 h. The cooled mixture was applied to an SCX-2 cartridge (70 g), washing with methanol then eluting basic components with 0.4-2M NH₃ in MeOH. The product containing fractions were combined and concentrated in vacuo. The residue was purified by FCC, using 0-12% [2M NH₃ in MeOH] in DCM, to give impure product. Further purified by FCC, using 0-12% MeOH in EtOAc gave Intermediate Fc (147 mg, 25%). LCMS (Method 3): Rt 2.11 min, m/z 237 [MH⁺].

d. (1S,4R)-4-(3-[1,4]Oxazepan-4-yl-[1,2,4]triazolo[4,3-a]pyridin-6-yloxy)-1,2,3,4-tetrahydro-naphthalen-1-ylamine (Intermediate F)

To a solution of Intermediate A (145 mg, 0.61 mmol) in DMF (3 mL) was added sodium hydride (60% dispersion in oil, 74 mg, 1.84 mmol). The mixture was stirred at RT for 15 min, then a solution of Intermediate Fc (100 mg, 0.614 mmol) in DMF (3 mL) was added and the mixture stirred at 60° C. for 2.25 h. The cooled mixture was diluted with water and extracted with DCM (4×25 mL). The combined organics were dried and concentrated in vacuo. The residue was purified by FCC, using 0-12% [2M NH₃ in MeOH] in DCM, to give Intermediate F (93 mg, 40%). LCMS (Method 3): Rt 0.43 min, m/z 380 [MH⁺].

Intermediate G

(1S,4R)-4-[3-(4-Triisopropylsilanyloxymethyl-piperidin-1-yl)-[1,2,4]triazolo[4,3-a]pyridin-6-yloxy]-1,2,3,4-tetrahydro-naphthalen-1-ylamine

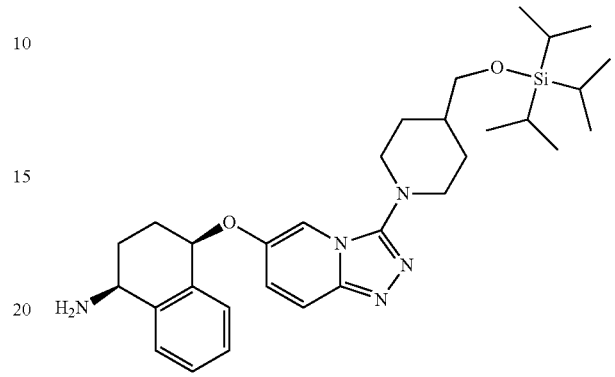

a. [1-(6-Fluoro-[1,2,4]triazolo[4,3-a]pyridin-3-yl)-piperidin-4-yl]-methanol (Intermediate Ga)

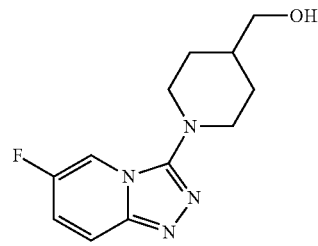 [SMILES: OCC1CCN(c2nnc3ccc(F)cn23)CC1]

A solution of Intermediate Fb (593 mg, 3.45 mmol) and 4-piperidinemethanol (1.59 g, 13.8 mmol) in NMP (10 mL) was heated in the microwave at 170° C. for 3 h. The cooled mixture was applied to an SCX-2 cartridge (70 g), washing with methanol then eluting basic components with 0.4-2 M NH₃ in MeOH. Product containing fractions were combined and concentrated in vacuo. The residue was purified by FCC, using 0-15% MeOH in EtOAc, to give Intermediate Ga (481 mg, 56%). LCMS (Method 3): Rt 2.12 min, m/z 251 [MH⁺].

b. 6-Fluoro-3-(4-triisopropylsilanyloxymethyl-piperidin-1-yl)-[1,2,4]triazolo[4,3-a]pyridine (Intermediate Gb)

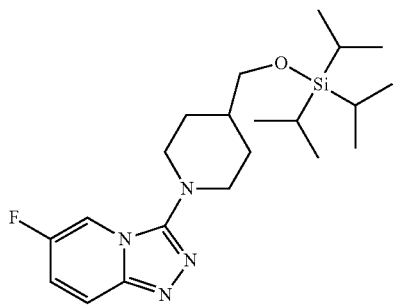 [SMILES: CC(C)[Si](OCC1CCN(c2nnc3ccc(F)cn23)CC1)(C(C)C)C(C)C]

To a solution of Intermediate Ga (470 mg, 1.88 mmol) and Et₃N (390 μL, 2.82 mmol) in DCM (5 mL) was added triisopropylsilyltrifluoromethane sulfonate (607 μL, 2.26 mmol) and the mixture stirred at RT for 0.5 h. The mixture was washed with sat. aqueous $NaHCO_3$ solution, dried and concentrated in vacuo. The residue was purified by FCC, using 0-100% EtOAc in cyclohexane, then 10% MeOH in EtOAc, to give Intermediate Gb (565 mg, 74%). LCMS (Method 3): Rt 5.21 min, m/z 407 [MH$^+$].

c. (1S,4R)-4-[3-(4-Triisopropylsilanyloxymethyl-piperidin-1-yl)-[1,2,4]triazolo[4,3-a]pyridin-6-yloxy]-1,2,3,4-tetrahydro-naphthalen-1-ylamine (Intermediate G)

To a solution of Intermediate A (223 mg, 1.37 mmol) in DMF (3 mL) was added sodium hydride (60% dispersion in oil, 168 mg, 4.20 mmol) and the mixture stirred at RT for 15 min. A solution of Intermediate Gb (555 mg, 1.37 mmol) in DMF (3 mL) was added and the mixture stirred at 60° C. for 1.75 h. The cooled mixture was diluted with water and extracted with DCM (5×20 mL). The combined organics were dried and concentrated in vacuo. The residue was purified by FCC, using 0-14% [2M $NH_3$ in MeOH] in DCM, to give Intermediate G (344 mg, 46%). LCMS (Method 3): Rt 3.29 min, m/z 550 [MH$^+$].

Intermediate Hd

[5-tert-Butyl-2-(2-fluoro-5-hydroxymethyl-phenyl)-2H-pyrazol-3-yl]-carbamic acid 2,2,2-trichloro-ethyl ester

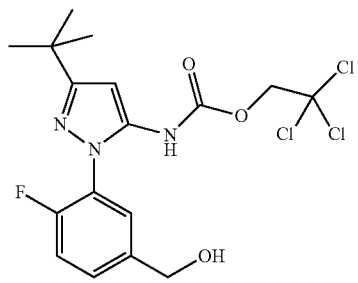 [SMILES: CC(C)(C)c1cc(NC(=O)OCC(Cl)(Cl)Cl)n(-c2cc(CO)ccc2F)n1]

a. (3-Amino-4-fluoro-phenyl)-methanol (Intermediate Ha)

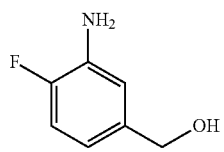

4-Fluoro-3-nitrobenzyl alcohol (3.17 g, 18.5 mmol) was suspended in EtOH, and a slurry of palladium on carbon (10 wt %, 317 mg) in EtOH was added. The flask was sealed with a septum, evacuated, and a $H_2$ filled balloon was introduced via syringe and the reaction was stirred at RT overnight. The reaction mixture was then filtered through a pad of Celite, washed with EtOH and the filtrates concentrated in vacuo to afford a oil which upon scratching crystallised to give the title compound (2.56 g, 98%). $^1$H NMR (300 MHz, CDCl$_3$): 4.57 (2H, s), 6.63-6.71 (1H, m), 6.77-6.84 (1H, m), 6.90-7.00 (1H, dd, J=8.2, 11.0 Hz). No OH or NH signals observed.

b. (4-Fluoro-3-hydrazino-phenyl)-methanol (Intermediate Hb)

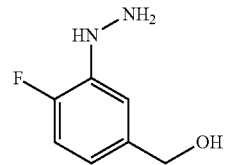

A solution of Intermediate Ha (1.00 g, 7.10 mmol) in concentrated HCl (10 mL) was cooled to −5° C. in an acetone/dry ice bath, and while stirring, a solution of $NaNO_2$ (513 mg, 7.40 mmol) in $H_2O$ (2 mL) was added dropwise over 5 min. The reaction was stirred for 5 min, then a solution of $SnCl_2$ (2.96 g, 15.6 mmol) in concentrated HCl (4 mL) was added dropwise, ensuring the internal temperature did not exceed 0° C. After stirring for 40 min, 4N NaOH solution was added to adjust the pH to 14 (~75 mL). The reaction mixture was then extracted three times with EtOAc, and the organic extracts combined, dried over MgSO$_4$, and concentrated in vacuo to afford the title compound (866 mg, 78%). $^1$H NMR (300 MHz, d$_6$-DMSO): 4.77 (2H, bs), 5.18 (2H, d, J=5.4 Hz), 5.85 (1H, t, J=5.6 Hz), 7.27-7.34 (2H, m), 7.68 (1H, dd, J=8.3, 12.1 Hz), 7.90 (1H, dd, J=2.0, 8.6 Hz).

c. [3-(5-Amino-3-tert-butyl-pyrazol-1-yl)-4-fluoro-phenyl]-methanol (Intermediate Hc)

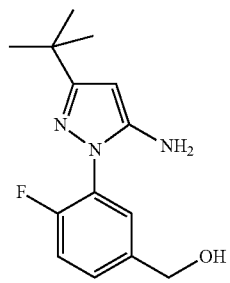 [SMILES: CC(C)(C)c1cc(N)n(-c2cc(CO)ccc2F)n1]

4,4-Dimethyl-3-oxopentanenitrile (694 mg, 5.55 mmol) and Intermediate Hb (866 mg, 5.55 mmol) were suspended in EtOH (25 mL) and refluxed for 72 h. The reaction was cooled, concentrated in vacuo and partitioned between $H_2O$ and EtOAc. The organic layer was separated, and the aqueous extracted with EtOAc. The combined organic extracts were dried over MgSO$_4$, concentrated in vacuo and subjected to FCC, eluting with 0-30% EtOAc/DCM, to afford the title compound (857 mg, 59%). LCMS (Method 3): Rt 2.35 min, m/z 264.3 [MH$^+$]. $^1$H NMR (300 MHz, CDCl$_3$): 1.31 (9H, s), 1.87 (2H, bs), 3.67 (1H, bs), 4.67 (2H, s), 5.55 (1H, s), 7.18 (1H, dd, J=8.5, 10.3 Hz), 7.3-7.37 (1H, m), 7.52 (1H, dd, J=2.3, 7.4 Hz)

d. [5-tert-Butyl-2-(2-fluoro-5-hydroxymethyl-phenyl)-2H-pyrazol-3-yl]-carbamic acid 2,2,2-trichloro-ethyl ester (Intermediate Hd)

To an ice cooled solution of Intermediate Hc (737 mg, 2.80 mmol) in EtOAc (7 mL) and 1N NaOH solution (7 mL) was added 2,2,2-trichloroethyl chloroformate (652 mg, 424 μL, 3.08 mmol) dropwise, and the ice bath removed and the reaction allowed to warm to RT. After 90 min, the reaction was partitioned between H₂O and EtOAc; the organic layer was separated, and the aqueous layer extracted with EtOAc. The combined organic extracts were dried over MgSO₄ and concentrated in vacuo to afford an orange oil, which crystallised on scratching to give the title compound (1.2 g, 98%). LCMS (Method 3): Rt 3.95 min, m/z 438.2 [MH⁺]. ¹H NMR (300 MHz, CDCl₃): 1.35 (9H, s), 4.71 (2H, s), 4.77 (2H, s), 6.42 (1H, s), 7.20-7.28 (1H, m), 7.38-7.45 (1H, m), 7.53-7.58 (1H, m).

Intermediate Ie

{5-tert-Butyl-2-[2-fluoro-5-(2-hydroxyethoxy)-phenyl]-2H-pyrazol-3-yl}-carbamic acid 2,2,2 trichloroethyl ester

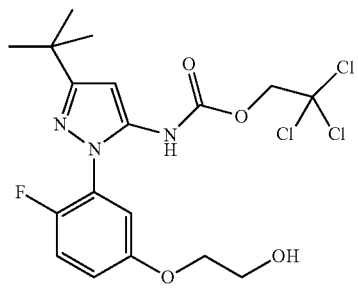 [SMILES: CC(C)(C)c1cc(NC(=O)OCC(Cl)(Cl)Cl)n(-c2cc(OCCO)ccc2F)n1]

a. 4-Fluoro-3-hydrazino-phenol (Intermediate Ia)

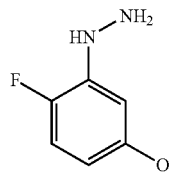

The title compound was prepared in an analogous manner to the procedure described for Intermediate Hb starting from 3-amino-4-fluorophenol (2.00 g, 15.7 mmol) to afford a solid (1.38 g, 62%). ¹H NMR (300 MHz, d₆-DMSO): 3.93 (2H, br s), 5.9 (1H, dt, J=3.2, 8.8 Hz), 6.41 (1H, s), 6.57 (1H, dd, J=3.0, 7.6 Hz), 6.72 (1H, dd, J=8.6, 11.9 Hz), 8.9 (1H, s).

b. 3-(5-Amino-3-tert-butyl-pyrazol-1-yl)-4-fluoro-phenol (Intermediate Ib)

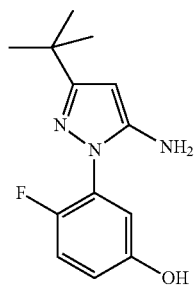 [SMILES: CC(C)(C)c1cc(N)n(-c2cc(O)ccc2F)n1]

The title compound was prepared in an analogous manner to the procedure described for Intermediate Hc starting from Intermediate Ia (1.38 g 9.70 mmol) (737 mg, 30%). ¹H NMR (300 MHz, CDCl₃): 1.33 (9H, s), 3.77 (2H, bs), 5.54 (1H, s), 6.61-6.69 (1H, m), 6.93 (1H, t, J=9.6 Hz), 7.02 (1H, dd, J=3.0, 6.3 Hz).

c. 5-tert-Butyl-2-{2-fluoro-5-[2-(tetrahydro-pyran-2-yloxy)-ethoxy]-phenyl}-2H-pyrazol-3-ylamine (Intermediate Ic)

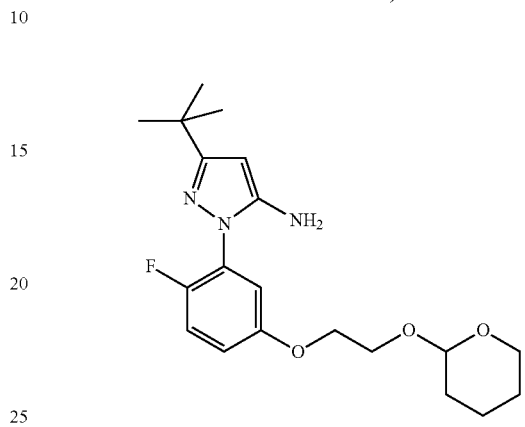

To an ice cooled solution of Intermediate Ib (737 mg, 2.96 mmol), 2-(tetrahydro-2H-pyran-2-yloxy)ethanol (648 mg, 602 μL, 4.43 mmol) and triphenylphosphine (1.55 g, 5.91 mmol) in anhydrous THF (250 mL) was added dropwise diisopropyl azodicarboxylate (1.20 g, 1.16 mL, 5.91 mmol), and the reaction allowed to warm to RT and stirred for 18 h. The reaction mixture was concentrated in vacuo, and subjected to FCC, eluting with 0-10% EtOAc/cyclohexane, and the product fractions combined, concentrated in vacuo and subjected again to FCC, eluting with 0-10% Et₂O/DCM, to afford the title compound (1.74 g). LCMS (Method 3): Rt 3.31 min, m/z 378.3 [MH⁺].

d. 2-[3-(5-Amino-3-tert-butyl-pyrazol-1-yl)-4-fluoro-phenoxy]-ethanol (Intermediate Id)

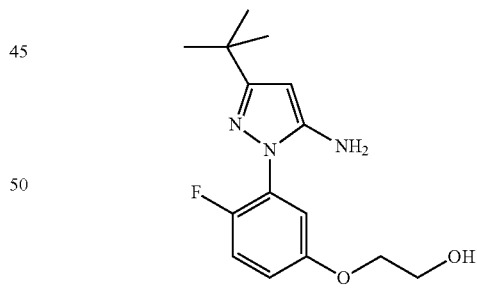

Intermediate Ic was suspended in MeOH (5 mL) and applied to a 10 g SCX-2 SPE cartridge and washed with MeOH. The product was eluted with 2M NH₃ in MeOH and the basic eluent concentrated in vacuo to afford the title compound (411 mg, 37%). LCMS (Method 3): Rt 2.47 min, m/z 294.3 [MH⁺].

e. {5-tert-Butyl-2-[2-fluoro-5-(2-hydroxyethoxy)-phenyl]-2H-pyrazol-3-yl}-carbamic acid 2,2,2 trichloro-ethyl ester (Intermediate Ie)

To an ice cooled solution of Intermediate Id (411 mg, 1.40 mmol) in EtOAc (3.5 mL) and 1N NaOH solution (3.5 mL)

was added 2,2,2-trichloroethyl chloroformate (327 mg, 212 µL, 1.54 mmol) dropwise, and the ice bath removed and the reaction allowed to warm to RT. After 2 h, a further 0.5 eq of 2,2,2-trichloroethyl chloroformate was added and the reaction continued for a further 1 h. The reaction was partitioned between H$_2$O and EtOAc. The organic layer was separated, and the aqueous extracted with EtOAc. The combined organic extracts were dried over MgSO$_4$, concentrated in vacuo and subjected to FCC, eluting with 0-50% EtOAc/cyclohexane, to afford the title compound (246 mg, 37%). LCMS (Method 3): Rt 3.97 min, m/z 468.2 [MH$^+$]. $^1$H NMR (300 MHz, CDCl$_3$): 1.35 (9H, s), 3.92-4.00 (2H, m), 4.06-4.12 (2H, m), 4.78 (2H, s), 6.40 (1H, s), 6.75 (1H, br s), 6.95 (1H, dt, J=3.5, 9.0 Hz), 7.08 (1H, dd, J=3.0, 6.0 Hz), 7.17 (1H, t, J=9.4 Hz).

Intermediate Jb

[5-tert-Butyl-2-(3,4-dimethyl-phenyl)-2H-pyrazol-3-yl]-carbamic acid 2,2,2-trichloro-ethyl ester

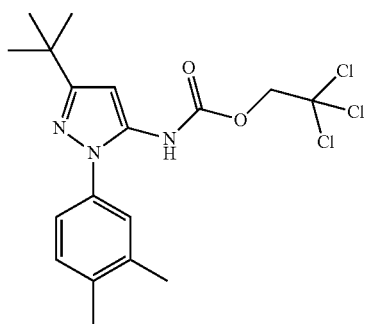 [SMILES: Cc1ccc(-n2nc(C(C)(C)C)cc2NC(=O)OCC(Cl)(Cl)Cl)cc1C]

a. 5-tert-Butyl-2-(3,4-dimethyl-phenyl)-2H-pyrazol-3-ylamine (Intermediate Ja)

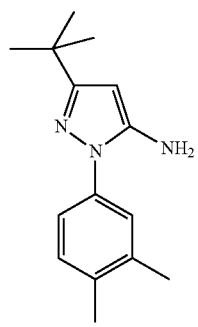 [SMILES: Cc1ccc(-n2nc(C(C)(C)C)cc2N)cc1C]

A black solution of 3,4-dimethylphenyl hydrazine hydrochloride (Apollo, 1.73 g, 10.0 mmol) and 4,4-dimethyl-3-oxopentanenitrile (1.38 g, 11.0 mmol) in EtOH (20 mL) was stirred at reflux for 5 h. The cooled solution was concentrated in vacuo, redissolved in diethyl ether (20 mL) and washed with aqueous NaOH solution (1M, 20 mL). The aqueous was extracted with diethyl ether (2×20 mL), then the combined organics washed with brine (20 mL), dried (Na$_2$SO$_4$), filtered and concentrated in vacuo to leave the title compound (2.18 g, 90%). LCMS (Method 3): Rt 2.75 min, m/z 244 [MH$^+$].

b. [5-tert-Butyl-2-(3,4-dimethyl-phenyl)-2H-pyrazol-3-yl]-carbamic acid 2,2,2-trichloro-ethyl ester (Intermediate Jb)

To a solution of Intermediate Ja (487 mg, 2.00 mmol) in EtOAc (5 mL) and aqueous NaOH solution (1M, 5.0 mL, 5.0 mmol) at RT was added 2,2,2-trichloroethyl chloroformate (0.303 mL, 2.20 mmol) and the resulting mixture stirred for 90 min. The aqueous layer was extracted with EtOAc (10 mL), then the combined organics washed with brine (10 mL), dried (Na$_2$SO$_4$), filtered and concentrated in vacuo. Trituration with pentane/diethyl ether (2:1, 30 mL), and drying in vacuo afforded the title compound (446 mg, 53%). LCMS (Method 3): Rt 4.70 min, m/z 418, 420 [MH$^+$].

Intermediate K

[5-tert-Butyl-2-(2,5-dimethyl-phenyl)-2H-pyrazol-3-yl]-carbamic acid 2,2,2-trichloro-ethyl ester

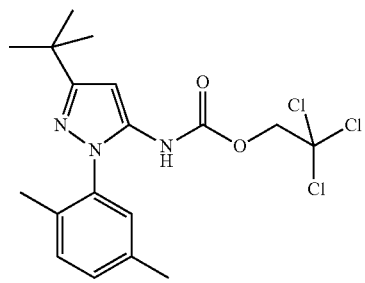 [SMILES: Cc1ccc(C)c(-n2nc(C(C)(C)C)cc2NC(=O)OCC(Cl)(Cl)Cl)c1]

The title compound was prepared starting from 2,5-dimethylphenyl hydrazine hydrochloride using analogous procedures to those described for Intermediate Jb. LCMS (Method 3): Rt 4.68 min, m/z 418, 420 [MH$^+$].

Intermediate L

[5-tert-Butyl-2-(2,4-dimethyl-phenyl)-2H-pyrazol-3-yl]-carbamic acid 2,2,2-trichloro-ethyl ester

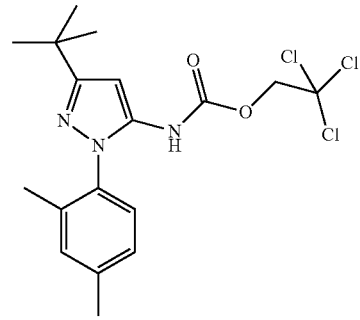 [SMILES: Cc1ccc(-n2nc(C(C)(C)C)cc2NC(=O)OCC(Cl)(Cl)Cl)c(C)c1]

The title compound was prepared starting from 2,4-dimethylphenyl hydrazine using analogous procedures to those described for Intermediate Jb. LCMS (Method 3): Rt 4.00 min, m/z 418, 420 [MH+].

Intermediate Md

[5-tert-Butyl-2-(4-chloro-3-hydroxymethyl-phenyl)-2H-pyrazol-3-yl]-carbamic acid 2,2,2-trichloro-ethyl ester

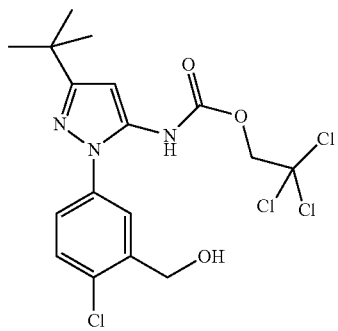 [SMILES: CC(C)(C)c1cc(NC(=O)OCC(Cl)(Cl)Cl)n(-c2ccc(Cl)c(CO)c2)n1]

a. (5-Amino-2-chloro-phenyl)-methanol (Intermediate Ma)

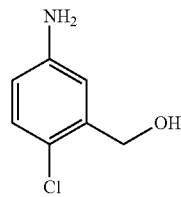

To a solution of (2-chloro-5-nitrophenyl)methanol (5.00 g, 26.7 mmol) in EtOAc (100 mL) was added water (2.41 mL, 134 mmol) followed by tin(II) chloride (12.7 g, 67.0 mmol). The solution was stirred at RT for 21 h, then additional tin(II) chloride (5.06 g, 26.7 mmol) was added, and the mixture heated at 50° C. for 2 h, and then at 70° C. for 3 h. The cooled mixture was slowly basified with 1N sodium hydroxide solution (~300 mL). The suspension was filtered through Celite, washing with EtOAc. The aqueous layer was extracted with EtOAc (3×100 mL), then the combined organics washed with brine, dried over MgSO4, and concentrated in vacuo to give the title compound (3.92 g, 93%). LCMS (Method 3): Rt 0.98 min, m/z 158 [MH+].

b. (2-Chloro-5-hydrazino-phenyl)-methanol (Intermediate Mb)

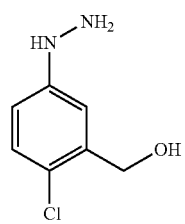 [SMILES: NNc1ccc(Cl)c(CO)c1]

To a suspension of Intermediate Ma (3.90 g, 24.8 mmol) in concentrated hydrochloric acid (30 mL) at 0° C. was added, slowly, a solution of sodium nitrite (2.07 g, 30.0 mmol) in water (10 mL). The mixture was stirred at 0° C. for 1.25 h, then a solution of tin(II) chloride (11.8 g, 62.0 mmol) in water (5 mL) and concentrated hydrochloric acid (20 mL) was added slowly. The mixture was stirred at 0° C. for 1.5 h, then was diluted with water and basified with NaOH (~25 g). EtOAc was added, then the mixture filtered through Celite, and the filter-cake washed with EtOAc. The aqueous layer was extracted with EtOAc (3×100 mL), then the combined organics were dried, and concentrated in vacuo to give the title compound (3.57 g, 84%). LCMS (Method 3): Rt 1.38 min, no mass data. $^1$H NMR (300 MHz, d$_6$-DMSO): 3.96 (2H, s), 4.45 (2H, d, J=5.5 Hz), 5.21 (1H, t, J=5.5 Hz), 6.66 (1H, dd, J=8.6, 2.8 Hz), 6.82 (1H, s), 6.98 (1H, d, J=2.8 Hz), 7.06 (1H, d, J=8.6 Hz).

c. [5-(5-Amino-3-tert-butyl-pyrazol-1-yl)-2-chloro-phenyl]-methanol hydrochloride (Intermediate Mc)

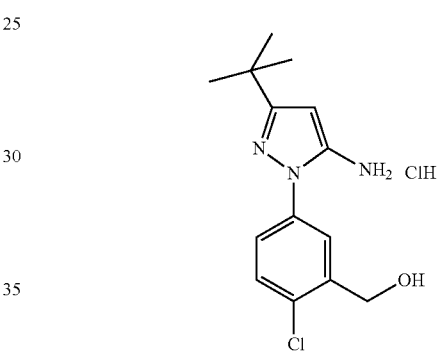

A mixture of Intermediate Mb (3.55 g, 20.6 mmol), 4,4-dimethyl-3-oxopentanenitrile (2.57 g, 20.6 mmol) and concentrated hydrochloric acid (1.72 mL, 20.6 mmol) in ethanol (55 mL) was stirred at reflux for 3.5 h then cooled to RT and concentrated in vacuo. The residue was triturated with cyclohexane (3×100 mL), then suspended in cyclohexane (150 ml) and filtered. The solid was washed with diethyl ether (2×25 mL), air dried, then dried in vacuo at 45° C. to give the title compound as a pale orange powder (6.30 g, 97%). LCMS (Method 3): Rt 2.68 min, m/z 280 [MH+].

d. [5-tert-Butyl-2-(4-chloro-3-hydroxymethyl-phenyl)-2H-pyrazol-3-yl]-carbamic acid 2,2,2-trichloro-ethyl ester (Intermediate Md)

To a mixture of Intermediate Mc (3.16 g, 10.0 mmol) in EtOAc (60 mL) and 1N NaOH solution (28.0 ml, 28.0 mmol) at 0° C. was added 2,2,2-trichloroethyl chloroformate (1.92 mL, 14.0 mmol) and the mixture stirred for 2 h. Solid NaOH (0.40 g, 10.0 mmol) and 2,2,2-trichloroethyl chloroformate (0.69 mL, 5.00 mmol) were added sequentially, and the mixture stirred at 0° C. for 1.5 h. The organic layer was washed with brine, dried and concentrated in vacuo. The residue was suspended with cyclohexane, the solid filtered, washed with cyclohexane, air dried, then dried in vacuo at 50° C. to give the title compound (2.74 g, 60%). LCMS (Method 3): Rt 4.13 min, m/z 454, 456, 458 [MH+].

Intermediate Nc

{5-tert-Butyl-2-[4-fluoro-3-(2-hydroxy-ethoxy)-phenyl]-2H-pyrazol-3-yl}-carbamic acid 2,2,2-trichloro-ethyl ester

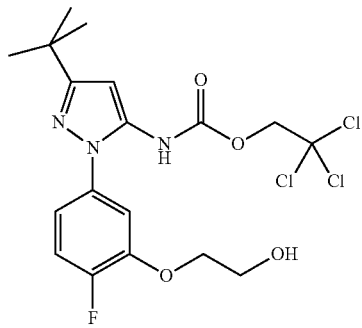 [SMILES: CC(C)(C)c1cc(NC(=O)OCC(Cl)(Cl)Cl)n(-c2ccc(F)c(OCCO)c2)n1]

a. 5-(5-Amino-3-tert-butyl-pyrazol-1-yl)-2-fluoro-phenol (Intermediate Na)

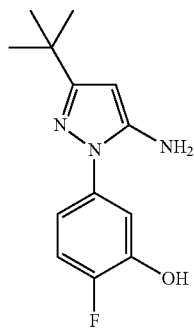 [SMILES: CC(C)(C)c1cc(N)n(-c2ccc(F)c(O)c2)n1]

To a solution of 3-(tert-butyl)-1H-pyrazol-5-amine (1.00 g, 7.20 mmol) in toluene (13 mL) was added 5-bromo-2-fluorophenol (1.51 g, 7.90 mmol), potassium carbonate (2.08 g, 15.1 mmol), (1S,2S)—N,N'-bis-methyl-1,2-cyclohexane-diamine (0.20 g, 1.40 mmol) then copper (I) iodide (0.07 g, 0.36 mmol). The mixture was degassed then heated at 150° C. for 1 h using microwave irradiation. Another portion of copper (I) iodide (0.07 g, 0.36 mmol) was added and the reaction mixture heated at 150° C. for a further 1 h using microwave irradiation. The mixture was diluted with EtOAc and water and the phases separated. The aqueous layer was then extracted with EtOAc (2×). The combined organic layers were washed with brine, dried (Na2SO4), filtered and evaporated in vacuo to give an impure solid. The residue was partitioned between DCM and water and the phases separated. The organic layer was evaporated in vacuo and the residue was purified by FCC, using 0-5% MeOH in DCM. Further purification by FCC, using 0-25% EtOAc in DCM, gave the title compound as an orange gum (1.25 g, 70%). LCMS (Method 3): Rt 2.33 min, m/z 250.3 [MH+].

b. 5-Tert-butyl-2-{4-fluoro-3-[2-(tetrahydro-pyran-2-yloxy-ethoxy]-phenyl}-2H-pyrazol-3-ylamine (Intermediate Nb)

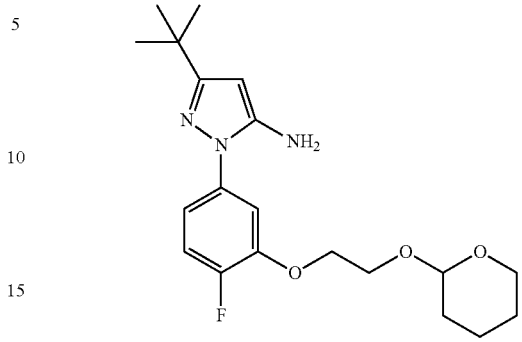

A solution of Intermediate Na (1.25 g, 5.00 mmol) in dry THF (35 mL) was treated with 2-(tetrahydro-2H-pyran-2-yloxy)ethanol (1.02 mL, 7.50 mmol) and triphenylphosphine (2.63 g, 10.0 mmol) then cooled to 0° C. Diisopropyl azodicarboxylate (1.97 mL, 10.0 mmol) was added dropwise then the mixture was stirred at RT for 2.75 h. The mixture was treated with water (0.45 mL) then evaporated in vacuo. The residue was purified by FCC, using 0-10% EtOAc in DCM. Further purification by FCC, using 0-40% EtOAc in cyclohexane gave the title compound as pale orange viscous oil (1.44 g, 76%). LCMS (Method 3): Rt 3.32 min, m/z 378.4 [MH+].

c. {5-tert-Butyl-2-[4-fluoro-3-(2-hydroxy-ethoxy)-phenyl]-2H-pyrazol-3-yl}-carbamic acid 2,2,2-trichloro-ethyl ester (Intermediate Nc)

To a solution of Intermediate Nb (1.44 g, 3.80 mmol) in EtOAc (20 mL) was added 1N aqueous NaOH solution (6.80 mL, 6.80 mmol) followed by 2,2,2-trichloroethylchloroformate (0.58 mL, 4.20 mmol). The reaction was stirred for 2.5 h then diluted with EtOAc and water. The aqueous layer was then extracted with EtOAc (2×). The combined organic layers were washed with brine, dried (Na2SO4), filtered and evaporated in vacuo. The residue was purified by FCC, using 0-40% EtOAc in cyclohexane, to give the title compound as a colorless oil (0.51 g, 28%). LCMS (Method 3): Rt 4.06, m/z 468, 470 [MH+].

Intermediate Ob

{5-tert-Butyl-2-[4-chloro-3-(2-morpholin-4-yl-ethoxy)-phenyl]-2H-pyrazol-3-yl}-carbamic acid 2,2,2-trichloro-ethyl ester

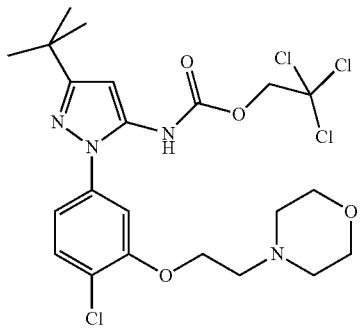 [SMILES: CC(C)(C)c1cc(NC(=O)OCC(Cl)(Cl)Cl)n(-c2ccc(Cl)c(OCCN3CCOCC3)c2)n1]

a. 5-tert-Butyl-2-[4-chloro-3-(2-morpholin-4-yl-ethoxy)-phenyl]-2H-pyrazol-3-ylamine (Intermediate Oa)

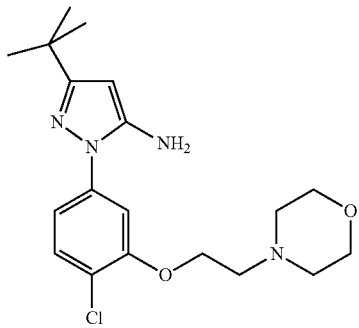 [SMILES: CC(C)(C)c1cc(N)n(-c2ccc(Cl)c(OCCN3CCOCC3)c2)n1]

To a stirred solution of 5-(5-amino-3-tert-butyl-pyrazol-1-yl)-2-chloro-phenol (WO2007/091152, which is incorporated herein by reference; 200 mg, 0.75 mmol), 2-N morpholino ethanol (137 µL, 1.13 mmol) and Ph$_3$P (394 mg, 1.50 mmol) in THF (7.5 mL) at 0° C. was added DEAD (236 µL, 1.50 mmol). After 1 h, the reaction mixture was diluted with water and extracted with DCM. The combined organics were dried and concentrated in vacuo. The residue was purified by FCC, using 0-5% [2M NH$_3$ in MeOH] in DCM, to give the title compound (228 mg, 80%). LCMS (Method 3): Rt 2.28 min, m/z 379 [MH$^+$].

b. {5-tert-Butyl-2-[4-chloro-3-(2-morpholin-4-yl-ethoxy)-phenyl]-2H-pyrazol-3-yl}-carbamic acid 2,2,2-trichloro-ethyl ester (Intermediate Ob)

To a solution of Intermediate Oa (228 mg, 0.60 mmol) and DIPEA (236 µL, 1.35 mmol) in THF (7.5 mL) at 0° C. was added 2,2,2-trichloroethyl chloroformate (124 µL, 0.90 mmol) and the mixture stirred for 1.25 h. The reaction mixture was diluted with water and extracted with DCM. The combined organics were washed with brine, dried and concentrated in vacuo. The residue was purified by FCC, using 0-5% [2M NH$_3$ in MeOH] in DCM, to give the title compound (330 mg, 99%). LCMS (Method 3): Rt 3.15 min, m/z 553, 555, 557 [MH$^+$].

Intermediate Pd

{5-tert-Butyl-2-[4-methyl-3-(2-morpholin-4-yl-ethoxy)-phenyl]-2H-pyrazol-3-yl}-carbamic acid 2,2,2-trichloro-ethyl ester

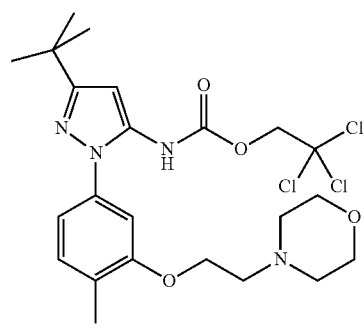 [SMILES: Cc1ccc(-n2nc(C(C)(C)C)cc2NC(=O)OCC(Cl)(Cl)Cl)cc1OCCN1CCOCC1]

a. 5-Hydrazino-2-methyl-phenol hydrochloride salt (Intermediate Pa)

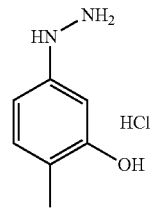

To an ice cold slurry of 4-amino-2-hydroxytoluene (6.22 g, 50.0 mmol), ice (10.0 g) and hydrochloric acid (37% aqueous, 15.0 mL) was added an ice-cold solution of sodium nitrite (3.49 g, 50.0 mmol) in water (10.0 mL) over 30 min. The resultant slurry was added over 30 min to an ice-cold slurry of tin (II) chloride (25.3 g, 133 mmol) in water (30.0 mL) and hydrochloric acid (37% aqueous, 30.0 mL) and the reaction stirred overnight. The mixture was cooled in an ice/water bath and the solid collected by filtration, washing with ice-cold cyclohexane. The residue was dried in vacuo at 50° C. to give the title compound (water retained, 11.1 g). 1H NMR (300 MHz, d$_4$-MeOD): 2.12 (3H, s), 6.38 (1H, dd, J=2.3, 8.0 Hz), 6.44 (1H, d, J=2.3 Hz), 7.02 (1H, d, J=8.1 Hz). No NH, OH or HCl signals.

b. 5-(5-Amino-3-tert-butyl-pyrazol-1-yl)-2-methyl-phenol (Intermediate Pb)

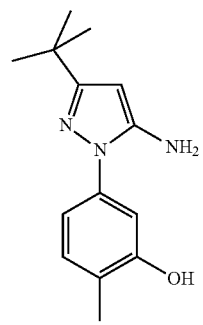 [SMILES: Cc1ccc(-n2nc(C(C)(C)C)cc2N)cc1O]

4,4-Dimethyloxo-pentanenitrile (7.50 g, 60.0 mmol) was added to a solution of Intermediate Pa (wet 11.1 g) in MeOH (200 mL) and the reaction stirred overnight. The reaction was then heated to 60° C. overnight, then cooled, and evaporated in vacuo. The residue was suspended in EtOAc and stirred for 15 min, then the solid collected by filtration. The filtrate was evaporated in vacuo then purified by FCC, using 0-10% [2M NH$_3$ in MeOH] in DCM, and combined with the filtered solid to give the title compound (5.78 g, 47%). LCMS (Method 4): Rt 2.07, m/z 240.6 [MH$^+$].

c. 5-tert-Butyl-2-[4-methyl-3-(2-morpholin-4-yl-ethoxy)-phenyl]-2H-pyrazol-3-ylamine (Intermediate Pc)

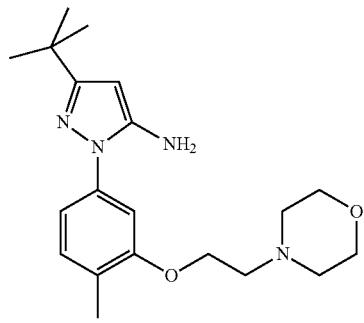 [SMILES: Cc1ccc(-n2nc(C(C)(C)C)cc2N)cc1OCCN1CCOCC1]

DIAD (788 µL, 4.02 mmol) was added to a solution of Intermediate Pb (500 mg, 2.01 mmol), 4-(2-hydroxyethyl-morpholine) (367 µL, 3.02 mmol) and Ph$_3$P (1.05 g, 4.02 mmol) in THF/DMF (2:1, 12.0 mL). The reaction was heated to 60° C. overnight then cooled and partitioned between EtOAc and water. The aqueous layer was then extracted with EtOAc (3×). The combined organic layers were washed with brine, dried (MgSO$_4$), filtered and evaporated in vacuo. The residue was purified by FCC, using 0-5% [2M NH$_3$ in MeOH] in DCM, to give the title compound (400 mg, 56%). LCMS (Method 1): Rt 1.81, m/z 359.1 [MH$^+$].

d. {5-tert-Butyl-2-[4-methyl-3-(2-morpholin-4-yl-ethoxy)-phenyl]-2H-pyrazol-3-yl}-carbamic acid 2,2,2-trichloro-ethyl ester (Intermediate Pd)

To an ice-cold solution of Intermediate Pc (148 mg, 0.41 mmol) in THF (4.0 mL) was added DIPEA (287 µL, 1.65 mmol) followed by 2,2,2-trichloroethylchloroformate (114 µL, 0.83 mmol). The reaction was stirred overnight, then partitioned between EtOAc and water. The aqueous layer was then extracted with EtOAc (3×). The combined organic layers were washed with brine, dried (MgSO$_4$), filtered and evaporated in vacuo. The residue was taken up in DCM/EtOAc (1:1, 20.0 mL) and NH$_2$-silica (11.0 g) added. The mixture was stirred for 2 h then filtered and the filtrate evaporated in vacuo. The residue was purified by FCC, using 0-5% [2M NH$_3$ in MeOH] in DCM, to give the title compound (163 mg, 74%). LCMS (Method 1): Rt 2.88, m/z 533, 535 [MH$^+$].

Intermediate Qc

{5-tert-Butyl-2-[3-chloro-5-(2-hydroxy-ethoxy)-phenyl]-2H-pyrazol-3-yl}-carbamic acid 2,2,2-trichloro-ethyl ester

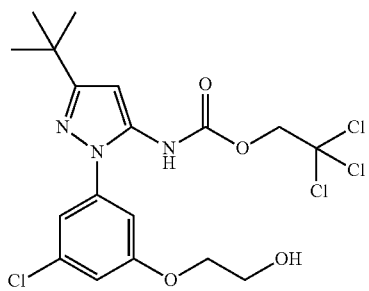 [SMILES: CC(C)(C)c1cc(NC(=O)OCC(Cl)(Cl)Cl)n(-c2cc(Cl)cc(OCCO)c2)n1]

a. 5-tert-Butyl-2-{3-chloro-5-[2-(tetrahydro-pyran-2-yloxy)-ethoxy]-phenyl}-2H-pyrazol-3-ylamine (Intermediate Qa)

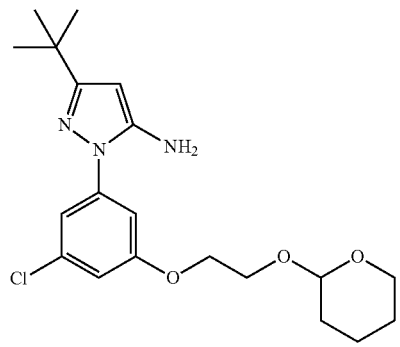 [SMILES: CC(C)(C)c1cc(N)n(-c2cc(Cl)cc(OCCOC3CCCCO3)c2)n1]

To a solution of Intermediate 62b (550 mg, 2.07 mmol), Ph$_3$P (1.09 g, 4.14 mmol) and 2-(tetrahydro-2H-pyran-2-yloxy)ethanol (0.42 mL, 3.10 mmol) in THF (10 mL) was added DEAD (0.65 mL, 4.10 mmol) and the solution stirred at RT for 10 min. Water (0.1 mL) was added, then the mixture concentrated in vacuo to ~3 mL volume. FCC, using 5-35% EtOAc in cyclohexane, gave the title compound (733 mg, 90%). LCMS (Method 3): Rt 4.05 min, m/z 394 [MH$^+$].

b. (5-tert-Butyl-2-{3-chloro-5-[2-(tetrahydro-pyran-2-yloxy)-ethoxy]-phenyl}-2H-pyrazol-3-yl)-carbamic acid 2,2,2-trichloro-ethyl ester (Intermediate Qb)

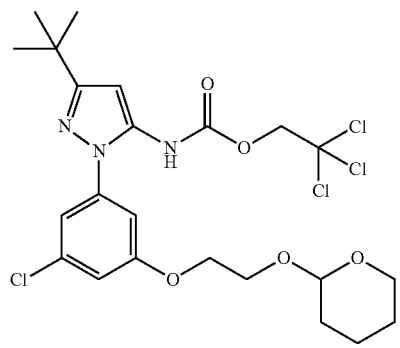 [SMILES: CC(C)(C)c1cc(NC(=O)OCC(Cl)(Cl)Cl)n(-c2cc(Cl)cc(OCCOC3CCCCO3)c2)n1]

To a solution of Intermediate Qa (732 mg, 1.86 mmol) in aq. NaOH solution (1M, 2.8 mL) and EtOAc (5 mL) at RT was added 2,2,2-trichloroethyl chloroformate (0.28 mL, 2.00 mmol) and the mixture stirred at RT for 2 h. The aqueous layer was extracted with EtOAc (10 mL), then the combined organics washed with brine (5 mL), dried (Na$_2$SO$_4$), filtered and concentrated in vacuo to leave a oil (1.04 g). FCC, using 5-25% EtOAc in cyclohexane, gave the title compound (714 mg, 67%). LCMS (Method 3): Rt 4.99 min, m/z 568, 570 [MH$^+$].

c. {5-tert-Butyl-2-[3-chloro-5-(2-hydroxy-ethoxy)-phenyl]-2H-pyrazol-3-yl}-carbamic acid 2,2,2-trichloro-ethyl ester (Intermediate Qc)

A solution of Intermediate Qb (518 mg, 0.910 mmol) and PPTS (686 mg, 2.73 mmol) in MeOH (15 mL) was stirred at 40° C. for 2 h. The cooled solution was concentrated in vacuo, suspended in water (5 mL) and sat. aq. NaHCO₃ solution (5 mL), and then extracted with DCM (10 mL). The organics were passed through a hydrophobic frit and concentrated in vacuo to leave a solid. Residual pyridine was removed with toluene azeotropes (2×20 mL) to leave the title compound (428 mg, 97%). LCMS (Method 3): Rt 4.30 min, m/z 484, 486 [MH$^+$].

Intermediate Rd

{5-tert-Butyl-2-[4-chloro-3-(2-hydroxy-ethyl)-phenyl]-2H-pyrazol-3-yl}-carbamic acid 2,2,2-trichloro-ethyl ester

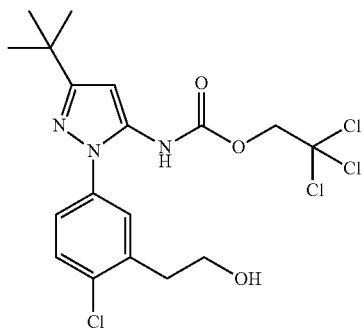 [SMILES: CC(C)(C)c1cc(NC(=O)OCC(Cl)(Cl)Cl)n(-c2ccc(Cl)c(CCO)c2)n1]

a. (2-Chloro-5-iodo-phenyl)-acetic acid methyl ester (Intermediate Ra)

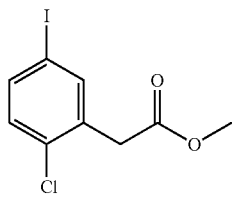

A dark red solution of (2-chlorophenyl)acetic acid methyl ester (TCI, 1.53 mL, 10.0 mmol), NIS (2.36 g, 10.5 mmol) and AuCl₃ (152 mg, 0.50 mmol) in DCE (25 mL) was stirred at reflux under Ar for 18 h. The solution was cooled to RT, NIS (563 mg, 2.50 mmol) added and the purple solution stirred at reflux for 2 h. The solution was cooled to RT, filtered through Celite and the filtercake washed with DCM. The combined organics were concentrated in vacuo to leave a solid that was dissolved in diethyl ether (50 mL), washed with water (2×50 mL), brine (50 mL), dried (Na₂SO₄), filtered and concentrated in vacuo to leave a purple oil (3.0 g). FCC, using 2-7% EtOAc in cyclohexane, gave the title compound as a clear oil (1.07 g, 34%) and a clear oil (mixed fractions, 814 mg, 26%). LCMS (Method 3): Rt 4.09 min, m/z 311 [MH$^+$].

b. 2-(2-Chloro-5-iodo-phenyl)-ethanol (Intermediate Rb)

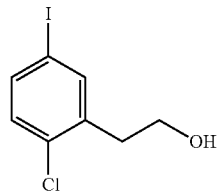 [SMILES: OCCc1cc(I)ccc1Cl]

To a solution of Intermediate Ra (810 mg, 2.61 mmol) in dry THF (10 mL) at 0° C. under N₂ was added LiAlH₄ (198 mg, 5.22 mmol) and the grey suspension stirred at RT for 90 min. Water (0.2 mL), 15% aqueous NaOH solution (0.2 mL) and water (0.6 mL) were added sequentially (CARE: gas evolution and exotherm) and the mixture stirred at RT for 1 h. The suspension was diluted with THF (25 mL), filtered through Celite and the filtercake washed with diethyl ether (50 mL). Water (50 mL) was added to the combined organics and the mixture shaken. The aqueous was extracted with diethyl ether (50 mL), then the combined organics washed with brine (50 mL), dried (Na₂SO₄), filtered and concentrated in vacuo to leave a clear oil (499 mg). FCC, using 10-30% EtOAc in cyclohexane, gave the title compound as a clear oil (236 mg, 32%). LCMS (Method 3): Rt 3.61 min, m/z 265 [M-H₂O+H$^+$].

c. 2-[5-(5-Amino-3-tert-butyl-pyrazol-1-yl)-2-chloro-phenyl]-ethanol (Intermediate Rc)

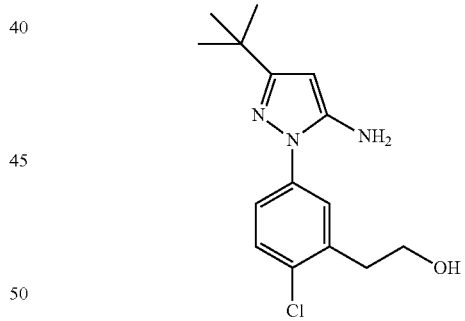

A suspension of Intermediate Rb (236 mg, 0.835 mmol), 3-tert-butyl-1H-pyrazole-5-amine (Fluorochem, 122 mg, 0.88 mmol), copper(I) iodide (8.00 mg, 0.04 mmol), trans-N,N'-dimethylcyclohexane-1,2-diamine (23.8 mg, 0.17 mmol) and K₂CO₃ (242 mg, 1.75 mmol) in degassed toluene (1 mL) was stirred at 100° C. under Ar for 3 h, and then heated to 150° C. for 5 h using microwave irradiation. The cooled solution was partitioned between EtOAc (10 mL), water (5 mL) and concentrated aqueous ammonia (5 mL). The aqueous layer was extracted with EtOAc (10 mL), then the combined organics washed with water (10 mL), brine (10 mL), dried (Na₂SO₄), filtered and concentrated in vacuo to leave a oil (305 mg). FCC, using 20-45% EtOAc in cyclohexane, gave the title compound as an opaque sticky gum (129 mg, 53%). LCMS (Method 3): Rt 2.80 min, m/z 294 [MH$^+$].

d. {5-tert-Butyl-2-[4-chloro-3-(2-hydroxy-ethyl)-phenyl]-2H-pyrazol-3-yl}-carbamic acid 2,2,2-trichloro-ethyl ester (Intermediate Rd)

A biphasic mixture of Intermediate Rc (129 mg, 0.44 mmol) and 2,2,2-trichloroethyl chloroformate (66.5 µL, 0.48 mmol) in EtOAc (1 mL) and aqueous NaOH solution (1M, 0.66 mL, 0.66 mmol) was stirred at RT for 1 h. The mixture was diluted with EtOAc (20 mL), then the organics washed with brine (10 mL), dried ($Na_2SO_4$), filtered and concentrated in vacuo to leave a oil. FCC, using 10-35% EtOAc in cyclohexane, gave the title compound (143 mg, 69%). LCMS (Method 3): Rt 4.26 min, m/z 468, 470, 472 [$MH^+$].

Intermediate Sb

[5-tert-Butyl-2-(3-chloro-5-hydroxymethyl-phenyl)-2H-pyrazol-3-yl]-carbamic acid 2,2,2-trichloro-ethyl ester

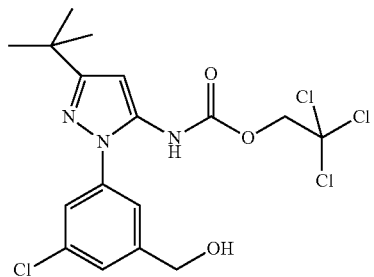 [SMILES: CC(C)(C)c1cc(NC(=O)OCC(Cl)(Cl)Cl)n(-c2cc(Cl)cc(CO)c2)n1]

a. 3-(5-Amino-3-tert-butyl-pyrazol-1-yl)-5-chloro-benzoic acid ethyl ester (Intermediate Sa)

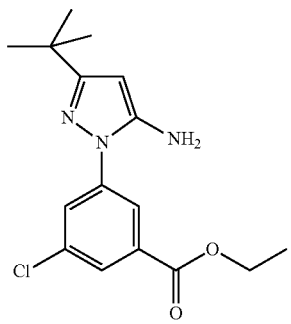 [SMILES: CCOC(=O)c1cc(Cl)cc(-n2nc(C(C)(C)C)cc2N)c1]

3-(Tert-butyl)-1H-pyrazol-5-amine (1.10 g, 7.90 mmol), potassium carbonate (2.29 g, 16.6 mmol), and copper (I) iodide (75.0 mg, 1.58 mmol) were weighed into a microwave vial and purged with argon. 3-Bromo-5-chloro-benzoic acid ethyl ester (2.50 g, 9.49 mmol) was then added, followed by trans-N,N'-dimethylcyclohexane-diamine (225 mg, 1.58 mmol) and the reaction vessel purged with argon. The reagents were then solvated with toluene (8 mL), and then degassed with argon, sealed and subjected to microwave irradiation (135° C., 6 h). The reaction mixture was filtered through Celite, concentrated in vacuo and purified by FCC, eluting with 0-10% EtOAc/cyclohexane, to afford the title compound (489 mg, 19%). LCMS (Method 3) Rt 4.26 min, 322.1 [$MH^+$].

b. [5-tert-Butyl-2-(3-chloro-5-hydroxymethyl-phenyl)-2H-pyrazol-3-yl]-carbamic acid 2,2,2-trichloro-ethyl ester (Intermediate Sb)

Intermediate Sa (489 mg, 1.52 mmol) was suspended in IMS (15 mL) and sodium borohydride (143 mg, 3.80 mmol) was added portionwise and the reaction stirred at RT. After 18 h, a further 1.0 eq of sodium borohydride was added and the mixture heated to 50° C. After 6 h, the reaction was cooled, partitioned between $H_2O$ and DCM and passed through a phase separator, and the organics concentrated in vacuo. The resultant product (413 mg, 1.48 mmol) was then suspended in an EtOAc/$H_2O$ mixture (3:1, 15 mL), and sodium hydroxide (159 mg, 3.99 mmol) added. While stirring at RT, 2,2,2-trichlorethyl chloroformate (244 µL, 1.77 mmol) was added dropwise. After 45 min, the reaction was partitioned between $H_2O$ and DCM. The organic layer was separated, dried over $MgSO_4$, concentrated in vacuo and purified by FCC, eluting with 0-50% EtOAc/cyclohexane, to afford the title compound (656 mg, 97%). LCMS (Method 3) Rt 4.29 min, 455.9, 457.9 [$MH^+$].

Intermediate Td (5-tert-Butyl-2-{2-chloro-5-[2-(tetrahydro-pyran-2-yloxy)-ethoxy]-phenyl}-2H-pyrazol-3-yl)-carbamic acid 2,2,2-trichloro-ethyl ester

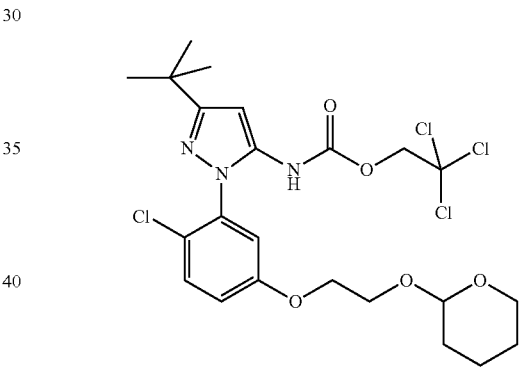

a. 4-Chloro-3-hydrazino-phenol hydrochloride salt (Intermediate Ta)

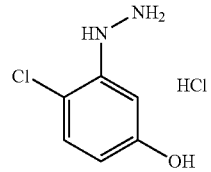

A solution of sodium nitrite (2.07 g, 30.0 mmol) in water (6.0 mL) was added dropwise to an ice cold slurry of 3-amino-4-chlorophenol (4.30 g, 30.0 mmol) and hydrochloric acid (37% aqueous, 9.0 mL) and the mixture stirred for 45 min. Tin (II) chloride (15.4 g, 81.0 mmol) in water (18.0 mL) and hydrochloric acid (37% aqueous, 18.0 mL) was added dropwise and the reaction stirred overnight. The mixture was cooled in an ice/water bath, diluted with water and neutralised by addition of NaOH (1M aq). The aqueous layer was then extracted with EtOAc (3×). The combined organic layers were washed with brine, dried (MgSO$_4$), filtered and evaporated in vacuo. The residue was passed through an acidic ion-exchange cartridge (SCX-2), washing with methanol and eluting with 2M ammonia in methanol. The basic fraction was evaporated in vacuo then purified by FCC, using 3-10% [2M NH$_3$ in MeOH] in DCM, to give the title compound (1.30 g, 27%). $^1$H NMR (300 MHz, d$_6$-DMSO): 4.12 (2H, br s), 6.03 (1H, dd, J=8.5, 2.9 Hz), 6.26 (1H, s), 6.63 (1H, d, J=2.7 Hz), 6.93 (1H, d, J=8.5 Hz), 9.22 (1H, s).

b 3-(5-Amino-3-tert-butyl-pyrazol-1-yl)-4-chlorophenol (Intermediate Tb)

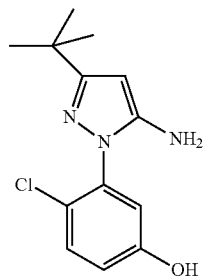 [SMILES: CC(C)(C)c1cc(N)n(-c2cc(O)ccc2Cl)n1]

4,4-Dimethyloxo-pentanenitrile (1.15 g, 9.23 mmol) was added to a solution of Intermediate Ta (1.20 g, 7.69 mmol) in MeOH (20 mL) and hydrochloric acid (37% aqueous, 0.2 mL) and the reaction was heated to 65° C. overnight, then cooled and evaporated in vacuo. The residue was taken up in EtOAc and water and the aqueous layer was then extracted with EtOAc (3×). The combined organic layers were washed with brine, dried (MgSO$_4$), filtered and evaporated in vacuo. The residue was purified by FCC, using 0-100% EtOAc in cyclohexane, to give the title compound (1.35 g, 66%). LCMS (Method 4): Rt 2.21 min, m/z 266 [MH$^+$].

c. 5-tert-Butyl-2-{2-chloro-5-[2-(tetrahydro-pyran-2-yloxy)-ethoxy]-phenyl}-2H-pyrazol-3-ylamine (Intermediate Tc)

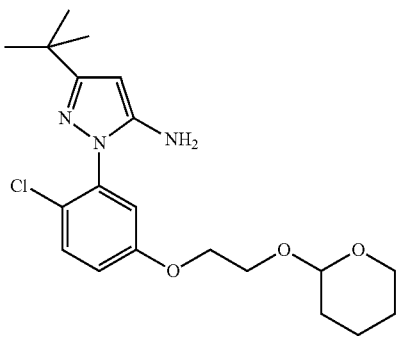 [SMILES: CC(C)(C)c1cc(N)n(-c2cc(OCCOC3CCCCO3)ccc2Cl)n1]

DEAD (799 µL, 5.09 mmol) was added dropwise to a solution of Intermediate Tb (675 mg, 2.55 mmol), 2-(tetrahydro-2H-pyran-2-yloxy)ethanol (518 µL, 3.83 mmol) and Ph$_3$P (1.33 g, 5.09 mmol) in THF (11.0 mL). The reaction was stirred over the weekend and then partitioned between EtOAc and water. The aqueous layer was then extracted with EtOAc (3×). The combined organic layers were washed with brine, dried (MgSO$_4$), filtered and evaporated in vacuo. The residue was purified by FCC, using 0-70% EtOAc in cyclohexane, to give an inseparable mixture of title compound and Intermediate Tb. This was resubmitted to the same reaction and purification conditions to give the title compound (150 mg, 35%). LCMS (Method 4): Rt 2.94 min, m/z 394 [MH$^+$].

d. (5-tert-Butyl-2-{2-chloro-5-[2-(tetrahydro-pyran-2-yloxy)-ethoxy]-phenyl}-2H-pyrazol-3-yl)-carbamic acid 2,2,2-trichloro-ethyl ester (Intermediate Td)

To an ice-cold solution of Intermediate Tc (350 mg, 0.89 mmol) in EtOAc/water (2:1, 4.5 mL) was added sodium hydroxide (71.0 mg, 1.78 mmol) followed by 2,2,2-trichloroethylchloroformate (147 µL, 1.07 mmol). The reaction was stirred for 90 min and then partitioned between EtOAc and water. The aqueous layer was then extracted with EtOAc (3×). The combined organic layers were washed with brine, dried (MgSO$_4$), filtered and evaporated in vacuo. The residue was purified by FCC, using 0-70% EtOAc in cyclohexane, to give the title compound (396 mg, 78%). LCMS (Method 4): Rt 4.44 min, m/z 568, 570 [MH$^+$].

Intermediate TeD

1-{(5-tert-Butyl-2-[2-chloro-5-(2-hydroxy-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea

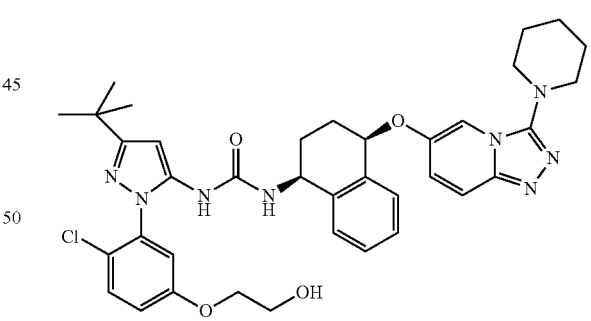

Pyridinium para-toluene sulfonate (76.0 mg, 0.31 mmol) was added to a solution of Intermediate (TdD) (118 mg, 0.15 mmol) in MeOH (2.0 mL). The reaction was heated to 55° C. for 90 min then cooled and partitioned between EtOAc and water. The aqueous layer was then extracted with EtOAc (3×). The combined organic layers were washed with brine, dried (MgSO$_4$), filtered and evaporated in vacuo to give the title compound (83.0 mg, 77%). LCMS (Method 4): Rt 3.21 min, m/z 699 [MH$^+$].

Intermediate Ub

[5-tert-Butyl-2-(3-fluoro-5-hydroxymethyl-phenyl)-2H-pyrazol-3-yl]-carbamic acid 2,2,2-trichloro-ethyl ester

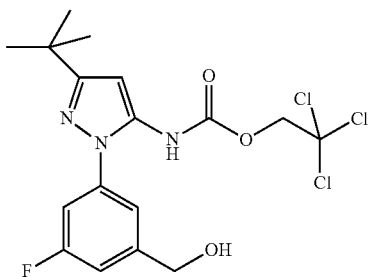 [SMILES: CC(C)(C)c1cc(NC(=O)OCC(Cl)(Cl)Cl)n(-c2cc(F)cc(CO)c2)n1]

a. [3-(5-Amino-3-tert-butyl-pyrazol-1-yl)-5-fluoro-phenyl]-methanol (Intermediate Ua)

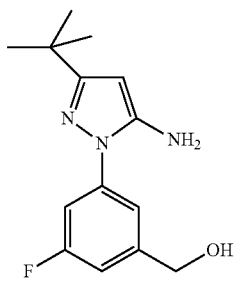 [SMILES: CC(C)(C)c1cc(N)n(-c2cc(F)cc(CO)c2)n1]

Degassed toluene (sparged with argon for 25 mins, 10.0 mL) was added to a mixture of 3-bromo-5-fluorobenzylalcohol (1.00 g, 4.88 mmol), 3-tert-butyl-1H-pyrazole-5-amine (678 mg, 4.88 mmol), copper (I) iodide (46.0 mg, 0.24 mmol) and potassium carbonate (1.41 g, 10.2 mmol). Trans-N,N'-dimethylcyclohexanediamine (154 µL, 0.98 mmol) was added and the reaction heated to 150° C. for 18 h using microwave irradiation. The mixture was partitioned between EtOAc and water. The aqueous layer was then extracted with EtOAc (3×). The combined organic layers were washed with brine, dried (MgSO$_4$), filtered and evaporated in vacuo. The residue was purified by FCC, using 0-100% EtOAc in cyclohexane, to give the title compound (307 mg, 24%). LCMS (Method 4): Rt 2.34 min, m/z 264 [MH$^+$].

b [5-tert-Butyl-2-(3-fluoro-5-hydroxymethyl-phenyl)-2H-pyrazol-3-yl]-carbamic acid 2,2,2-trichloro-ethyl ester (Intermediate Ub)

To a solution of Intermediate Ua (307 mg, 1.17 mmol) in EtOAc/water (2:1, 6.0 mL) was added sodium hydroxide (93.0 mg, 2.33 mmol) followed by 2,2,2-trichloroethylchloroformate (193 µL, 1.40 mmol). The reaction was stirred for 3 h then partitioned between EtOAc and water. The aqueous layer was then extracted with EtOAc (3×). The combined organic layers were washed with brine, dried (MgSO$_4$), filtered and evaporated in vacuo to give the title compound (486 mg, 94%). LCMS (Method 4): Rt 3.78 min, m/z 438, 440 [MH$^+$].

Intermediate Ve

4-{5-[3-tert-Butyl-5-(2,2,2-trichloro-ethoxycarbonylamino)-pyrazol-1-yl]-2-chloro-phenoxy}-piperidine-1-carboxylic acid 2-trimethylsilanyl-ethyl ester

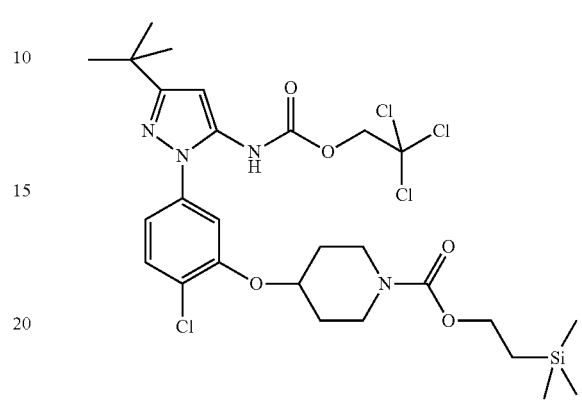

a. 4-(2-Chloro-5-iodo-phenoxy)-piperidine-1-carboxylic acid tert-butyl ester (Intermediate Va)

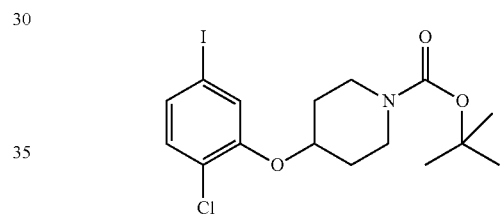

2-Chloro-5-iodophenol (2.50 g, 9.83 mmol), tert-butyl 4-hydroxy-1-piperidinecarboxylate (2.97 g, 14.7 mmol) and triphenylphosphine (5.15 g, 19.6 mmol), were suspended in THF (50 mL) and cooled to 0° C. Diethyl azodicarboxylate (3.08 mL, 19.6 mmol) was then added dropwise, the reaction was stirred under a N$_2$ atmosphere for 18 h. The reaction was then partitioned between H$_2$O and EtOAc. The organic layer was separated, washed with saturated brine, dried over MgSO$_4$, concentrated in vacuo and subjected to FCC, eluting with 0-50% EtOAc/cyclohexane, to afford the title compound (3.43 g, 80%). (Method 3): Rt 4.98 min, m/z 337.9 [M–BOC$^+$].

b. 4-(2-Chloro-5-iodo-phenoxy)-piperidine (Intermediate Vb)

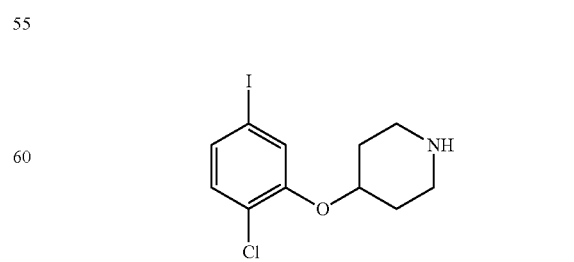

Trifluoroacetic acid (10 mL) was added to a solution of Intermediate Va (3.43 g, 7.84 mmol) in DCM (30 mL). After c. 4-(2-Chloro-5-iodo-phenoxy)-piperidine-1-carboxylic acid 2-trimethylsilanyl-ethyl ester (Intermediate Vc)

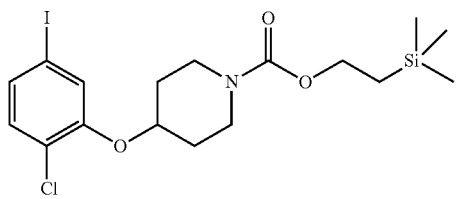 [SMILES: C[Si](C)(C)CCOC(=O)N1CCC(Oc2cc(I)ccc2Cl)CC1]

To a stirred solution of Intermediate Vb (3.02 g, 8.94 mmol) and triethylamine (2.49 mL, 17.9 mmol) in THF (45 mL) was added 1-[2-(trimethylsilyl)ethoxy-carbonyloxy]pyrrolidin-2,5-dione (2.78 g, 10.7 mmol) and heated to reflux under a N₂ atmosphere. After 1 h, the reaction was cooled, partitioned between H₂O and DCM, and the organic layer separated, dried over MgSO₄, concentrated in vacuo and subjected to FCC, eluting with 0-50% EtOAc/cyclohexane, to afford the title compound (4.26 g, 99%). LCMS (Method 3) Rt 5.34 min.

d. 4-[5-(5-Amino-3-tert-butyl-pyrazol-1-yl)-2-chloro-phenoxy]-piperidine-1-carboxylic acid 2-trimethylsilanyl-ethyl ester (Intermediate Vd)

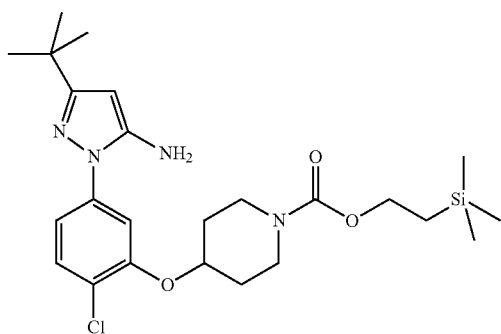 [SMILES: CC(C)(C)c1cc(N)n(-c2ccc(Cl)c(OC3CCN(C(=O)OCC[Si](C)(C)C)CC3)c2)n1]

A microwave vial was charged with 3-tert butyl-1H-pyrazole-5-amine (1.03 g, 7.39 mmol), copper (I) iodide (70.3 mg, 0.37 mmol) and potassium carbonate (2.14 g, 15.5 mmol) and the vial sealed with a septum, evacuated and purged with argon. Trans-N,N'-dimethylcyclohexane-1,2-diamine (210 mg, 1.48 mmol) was then added, then a solution of Intermediate Vc (4.26 g, 8.86 mmol) in toluene (7.5 mL, degassed with argon) was added, and the reaction was subjected to microwave irradiation (150° C. for 1 h). The reaction mixture was then filtered through Celite, and the filtrate concentrated in vacuo. Purification by FCC, eluting with 0-60% EtOAc/cyclohexane, to afford the title compound (2.41 g, 66%). LCMS (Method 3) Rt 4.68 min, m/z 493, 495 [MH⁺].

e. 4-{5-[3-tert-Butyl-5-(2,2,2-trichloro-ethoxycarbonylamino)-pyrazol-1-yl]-2-chloro-phenoxy}-piperidine-1-carboxylic acid 2-trimethylsilanyl-ethyl ester (Intermediate Ve)

2,2,2-Trichloroethyl chloroformate (760 µL, 5.58 mmol) was added to a stirred solution of Intermediate Vd (2.29 g, 4.65 mmol) and NaOH (602 mg, 15.1 mmol) in EtOAc (4.5 mL) and H₂O (11.5 mL) at RT. After 1 h, a further 0.2 eq. of 2,2,2-trichloroethyl chloroformate was added. After a further 15 min, the reaction was partitioned between H₂O and EtOAc. The organic layer was separated, dried over MgSO₄ and concentrated in vacuo to afford the title compound (3.56 g, 100%). LCMS (Method 3) Rt 5.39 min, m/z 666, 668 [MH⁺].

Intermediate Wc (5-tert-Butyl-2-{3-fluoro-5-[2-(tetrahydro-pyran-2-yloxy)-ethoxy]-phenyl}-2H-pyrazol-3-yl)-carbamic acid 2,2,2-trichloro-ethyl ester

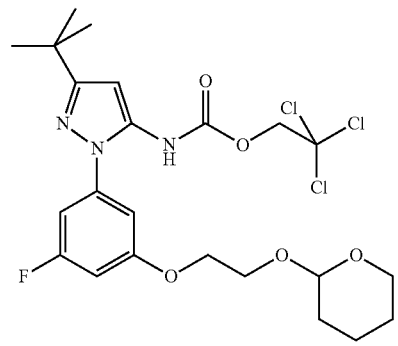 [SMILES: CC(C)(C)c1cc(NC(=O)OCC(Cl)(Cl)Cl)n(-c2cc(F)cc(OCCOC3CCCCO3)c2)n1]

a. 3-(5-Amino-3-tert-butyl-pyrazol-1-yl)-5-fluorophenol (Intermediate Wa)

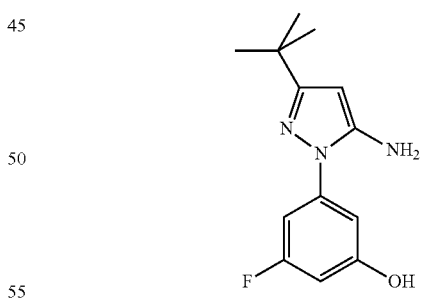

Degassed toluene (sparged with argon for 25 mins, 10.0 mL) was added to a mixture of 3-bromo-5-fluorophenol (1.00 g, 5.23 mmol), 3-tert-butyl-1H-pyrazole-5-amine (728 mg, 5.23 mmol), copper (I) iodide (50.0 mg, 0.26 mmol) and potassium carbonate (1.52 g, 11.0 mmol). Trans-N,N'-dimethylcyclohexanediamine (165 µL, 1.05 mmol) was added and the reaction heated to 150° C. for 3.5 h using microwave irradiation. The mixture was partitioned between EtOAc and water. The aqueous layer was then extracted with EtOAc (3×). The combined organic layers were washed with brine, dried (MgSO₄), filtered and evaporated in vacuo. The residue was purified by FCC, using 0-75% EtOAc in cyclohexane, to give the title compound (488 mg, 37%). LCMS (Method 4): Rt 2.49 min, m/z 250 [MH$^+$].

b 5-tert-Butyl-2-{3-fluoro-5-[2-(tetrahydro-pyran-2-yloxy)-ethoxy]-phenyl}-2H-pyrazol-3-ylamine (Intermediate Wb)

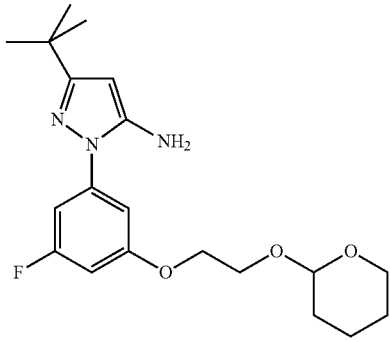 [SMILES: CC(C)(C)c1cc(N)n(-c2cc(F)cc(OCCOC3CCCCO3)c2)n1]

DEAD (614 µL, 3.92 mmol) was added dropwise to a solution of Intermediate Wa (488 mg, 1.96 mmol), 2-(tetrahydro-2H-pyran-2-yloxy)ethanol (397 µL, 2.94 mmol) and Ph$_3$P (1.03 g, 3.92 mmol) in THF (10.0 mL). The reaction was then stirred over the weekend, then partitioned between EtOAc and water. The aqueous layer was then extracted with EtOAc (3×). The combined organic layers were washed with brine, dried (MgSO$_4$), filtered and evaporated in vacuo. The residue was purified by FCC, using 0-60% EtOAc in cyclohexane, to give the title compound (635 mg, 86%). LCMS (Method 1): Rt 3.50 min, m/z 378 [MH$^+$].

c (5-tert-Butyl-2-{3-fluoro-5-[2-(tetrahydro-pyran-2-yloxy)-ethoxy]-phenyl}-2H-pyrazol-3-yl)-carbamic acid 2,2,2-trichloro-ethyl ester (Intermediate Wc)

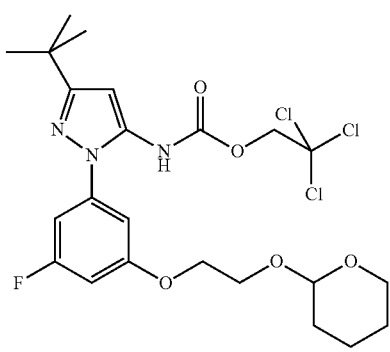 [SMILES: CC(C)(C)c1cc(NC(=O)OCC(Cl)(Cl)Cl)n(-c2cc(F)cc(OCCOC3CCCCO3)c2)n1]

To a solution of Intermediate Wb (488 mg, 1.96 mmol) in EtOAc/water (2:1, 7.5 mL) was added sodium hydroxide (135 mg, 3.37 mmol) followed by 2,2,2-trichloroethylchloroformate (278 µL, 2.02 mmol). The reaction was stirred for 2 h then partitioned between EtOAc and water. The aqueous layer was then extracted with EtOAc (3×). The combined organic layers were washed with brine, dried (MgSO$_4$), filtered and evaporated in vacuo to give the title compound (740 mg, 80%). LCMS (Method 4): Rt 4.56 min, m/z 552, 554 [MH$^+$].

Intermediate WdC

1-{5-tert-Butyl-2-[3-fluoro-5-(2-hydroxy-ethoxy)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea

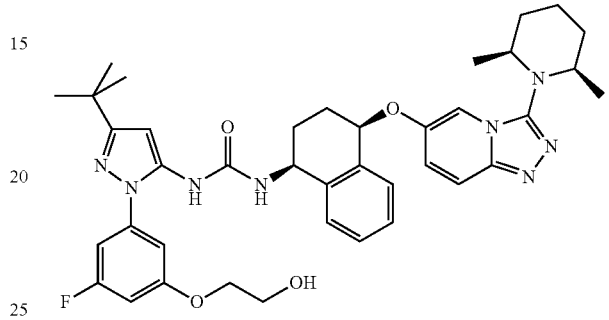

Pyridinium para-toluene sulfonate (199 mg, 0.79 mmol) was added to a solution of Intermediate WcC (315 mg, 0.40 mmol) in MeOH (4.0 mL). The reaction was heated to 55° C. for 2 h then cooled and partitioned between EtOAc and water. The aqueous layer was then extracted with EtOAc (3×). The combined organic layers were washed with brine, dried (MgSO$_4$), filtered and evaporated in vacuo to give the title compound (192 mg, 68%). LCMS (Method 4): Rt 3.63 min, m/z 711 [MH$^+$].

Intermediate WdB

1-{5-tert-Butyl-2-[3-fluoro-5-(2-hydroxy-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea

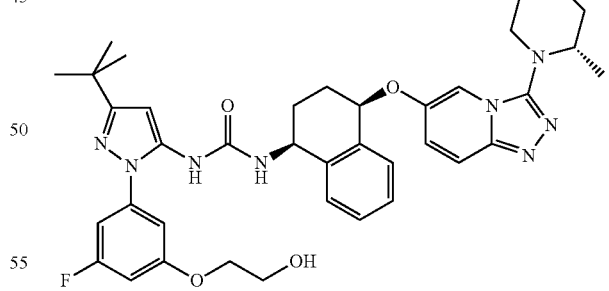

Pyridinium para-toluene sulfonate (163 mg, 0.65 mmol) was added to a solution of Intermediate WcB (253 mg, 0.32 mmol) in MeOH (3.5 mL). The reaction was heated to 55° C. for 3 h then cooled and partitioned between EtOAc and water. The aqueous layer was then extracted with EtOAc (3×). The combined organic layers were washed with brine, dried (MgSO$_4$) and evaporated in vacuo. The residue was purified by FCC, using 3-10% [2M NH$_3$ in MeOH] in DCM, to give the title compound (200 mg, 90%). LCMS (Method 4): Rt 3.44 min, m/z 697 [MH$^+$].

Intermediate Xc

{5-tert-Butyl-2-[4-cyano-3-(2-hydroxy-ethoxy)-phenyl]-2H-pyrazol-3-yl}-carbamic acid 2,2,2-trichloro-ethyl ester

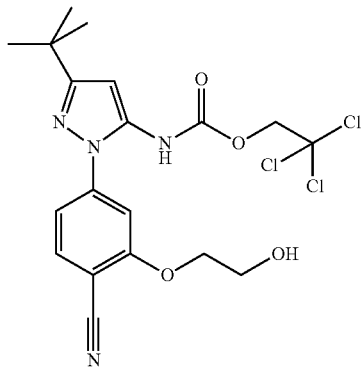 [SMILES: CC(C)(C)c1cc(NC(=O)OCC(Cl)(Cl)Cl)n(-c2ccc(C#N)c(OCCO)c2)n1]

a. 4-Bromo-2-(2-hydroxy-ethoxy)-benzonitrile (Intermediate Xa)

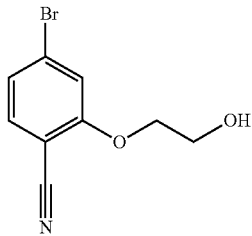 [SMILES: N#Cc1ccc(Br)cc1OCCO]

4-Bromo-2-hydroxybenzonitrile (1.00 g, 5.05 mmol), ethylene carbonate (467 mg, 5.30 mmol) and potassium carbonate (348 mg, 2.52 mmol) were suspended in DMF (2.00 mL) and heated to 125° C. for 4.5 h. The mixture was partitioned between EtOAc and water. The aqueous layer was then extracted with EtOAc (3×). The combined organic layers were washed with brine, dried (MgSO$_4$), filtered and evaporated in vacuo. The residue was purified by FCC, using 0-100% EtOAc in cyclohexane to give the title compound (686 mg, 56%). $^1$H NMR (300 MHz, d$_4$-MeOD): 3.92 (2H, t, J=4.7 Hz), 4.21 (2H, t, J=4.7 Hz), 7.26 (1H, dd, J=8.2, 1.7 Hz), 7.44 (1H, d, J=1.6 Hz), 7.53 (1H, d, J=8.2 Hz).

b. 4-(5-Amino-3-tert-butyl-pyrazol-1-yl)-2-(2-hydroxy-ethoxy)-benzonitrile (Intermediate Xb)

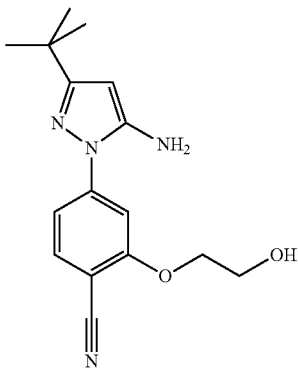 [SMILES: CC(C)(C)c1cc(N)n(-c2ccc(C#N)c(OCCO)c2)n1]

Degassed toluene (sparged with argon for 25 mins, 10.0 mL) was added to a mixture of Intermediate Xa (1.30 g, 5.37 mmol), 3-tert-butyl-1H-pyrazole-5-amine (821 mg, 5.90 mmol), copper (I) iodide (51.0 mg, 0.27 mmol) and potassium carbonate (1.56 g, 11.3 mmol). Trans-N,N'-dimethylcyclohexanediamine (169 µL, 1.07 mmol) was added and the reaction heated to 150° C. for 15 h using microwave irradiation. The mixture was partitioned between EtOAc and water. The aqueous layer was then extracted with EtOAc (3×). The combined organic layers were washed with brine, dried (MgSO$_4$), filtered and evaporated in vacuo. The residue was purified by FCC, using 0-100% EtOAc in cyclohexane, to give the title compound (490 mg, 32%). LCMS (Method 4): Rt 2.72 min, m/z 301 [MH$^+$].

c. {5-tert-Butyl-2-[4-cyano-3-(2-hydroxy-ethoxy)-phenyl]-2H-pyrazol-3-yl}-carbamic acid 2,2,2-trichloro-ethyl ester (Intermediate Xc)

To a solution of Intermediate Xb (490 mg, 1.63 mmol) in EtOAc/water (2:1, 24.0 mL) was added sodium hydroxide (131 mg, 3.27 mmol) followed by 2,2,2-trichloroethylchloroformate (270 µL, 1.96 mmol). The reaction was stirred for 4 h then further sodium hydroxide (90.0 mg, 2.25 mmol) and 2,2,2-trichloroethylchloroformate (135 µL, 0.98 mmol) were added. The reaction was stirred overnight, then partitioned between EtOAc and water. The aqueous layer was then extracted with EtOAc (3×). The combined organic layers were washed with brine, dried (MgSO$_4$), filtered and evaporated in vacuo. The residue was purified by FCC, using 0-60% EtOAc in cyclohexane, to give the title compound (557 mg, 72%). LCMS (Method 4): Rt 3.74 min, m/z 474, 476 [MH$^+$].

Intermediate Yd

{5-tert-Butyl-2-[4-fluoro-3-(2-hydroxy-ethyl)-phenyl]-2H-pyrazol-3-yl}-carbamic acid 2,2,2-trichloro-ethyl ester

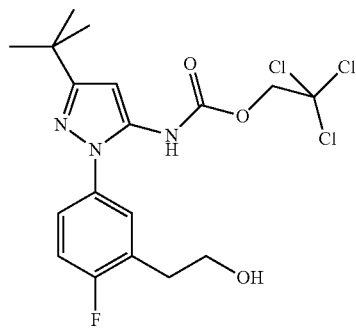 [SMILES: CC(C)(C)c1cc(NC(=O)OCC(Cl)(Cl)Cl)n(-c2ccc(F)c(CCO)c2)n1]

a. 2-(5-Amino-2-fluoro-phenyl)-ethanol (Intermediate Ya)

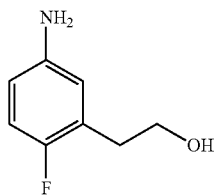 [SMILES: Nc1ccc(F)c(CCO)c1]

Borane-THF complex (1M, 11.8 mL, 11.8 mmol) was added to a solution of (5-amino-2-fluoro-phenyl)-acetic acid (1.00 g, 5.91 mmol) in dry THF (10 mL), under argon, over 20 min. Once the effervescence had ceased, the reaction mixture was heated to 50° C. for 2 h. The mixture was left to cool and then concentrated in vacuo. The residue was re-dissolved in DCM (25 mL) and treated with MeOH (2 mL). The mixture was stirred vigorously and then concentrated in vacuo. The residue was dissolved in MeOH (25 mL) and re-concentrated in vacuo. The residue was purified by FCC, using 0-10% [2M NH$_3$ in MeOH] in DCM, to afford the title compound (0.54 g, 59%). LCMS (Method 3): Rt: 0.41 min, m/z 156 [MH$^+$].

b. 2-(2-Fluoro-5-hydrazino-phenyl)-ethanol (Intermediate Yb)

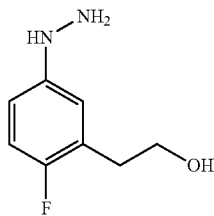 [SMILES: NNc1ccc(F)c(CCO)c1]

Intermediate Ya (0.54 g, 3.48 mmol) was dissolved in concentrated aqueous HCl (5 mL) and cooled to −5° C. To this was added a solution of sodium nitrite (0.25 g, 3.65 mmol), in water (0.75 mL), dropwise. Stirring continued for 5 min, before a solution of tin (II) chloride (1.45 g, 7.66 mmol) in concentrated aqueous HCl (2.2 mL) was added. The reaction mixture was stirred just below 0° C. for 40 min and then basified using aqueous NaOH (4M, 30 mL). The mixture was then stirred at RT for 1.5 h. This was extracted into EtOAc (3×50 mL). The combined organics were washed with brine (2×50 mL), dried (MgSO$_4$), filtered and concentrated in vacuo to afford the title compound (302 mg, 51%). LCMS (Method 3): Rt: 0.42 min, m/z 171 [MH$^+$].

c. 2-[5-(5-Amino-3-tert-butyl-pyrazol-1-yl)-2-fluoro-phenyl]-ethanol (Intermediate Yc)

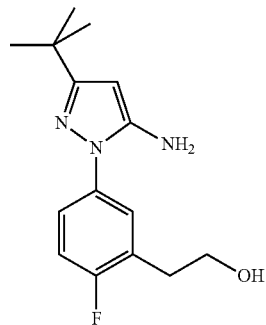 [SMILES: CC(C)(C)c1cc(N)n(-c2ccc(F)c(CCO)c2)n1]

A mixture of 4,4-dimethyl-3-oxo-pentanenitrile (200 mg, 1.60 mmol) and Intermediate Yb (300 mg, 1.76 mmol) and concentrated aqueous HCl (0.02 mL) in IMS (5 mL) was refluxed for 18 h. The reaction mixture was left to cool and concentrated in vacuo. The residue was purified by FCC, using 0-10% [2M NH$_3$ in MeOH] in DCM, to afford the title compound (350 mg, 79%). LCMS (Method 3): Rt: 0.44/2.04/2.26 min, m/z 278 [MH$^+$].

d. {5-tert-Butyl-2-[4-fluoro-3-(2-hydroxy-ethyl)-phenyl]-2H-pyrazol-3-yl}-carbamic acid 2,2,2-trichloro-ethyl ester (Intermediate Yd)

A solution of Intermediate Yc (345 mg, 1.24 mmol) in EtOAc (3.5 mL) was treated with aqueous NaOH (1M, 2.24 mmol), followed by 2,2,2-trichloroethyl chloroformate (205 µL, 1.49 mmol) and the reaction mixture was stirred at RT for 1 h. The mixture was partitioned between EtOAc (10 mL) and water (10 mL). The layers were separated and the aqueous layer was extracted with a further EtOAc (10 mL). The combined organic layers were washed with water (10 mL) and brine (10 mL), dried (MgSO4), filtered and concentrated in vacuo. The residue was purified by FCC, using 0-50% EtOAc in cyclohexane, to afford the title compound (472 mg, 84%). LCMS (Method 3): Rt 4.09 min, m/z 452/454 [MH$^+$].

Intermediate Zb

[5-tert-Butyl-2-(4-fluoro-3-hydroxymethyl-phenyl)-2H-pyrazol-3-yl]-carbamic acid 2,2,2-trichloro-ethyl ester

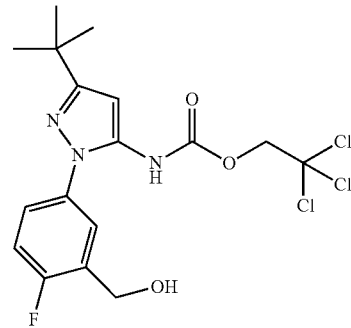 [SMILES: CC(C)(C)c1cc(NC(=O)OCC(Cl)(Cl)Cl)n(-c2ccc(F)c(CO)c2)n1]

a. [5-(5-Amino-3-tert-butyl-pyrazol-1-yl)-2-fluoro-phenyl]-methanol (Intermediate Za)

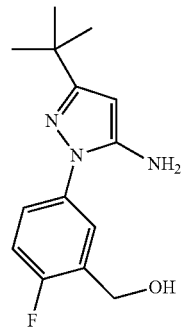 [SMILES: CC(C)(C)c1cc(N)n(-c2ccc(F)c(CO)c2)n1]

A microwave vial (25 mL) was charged with 3-(tert-butyl)-1H-pyrazol-5-amine (1.05 g, 7.54 mmol), 5-bromo-2-fluorobenzyl alcohol (1.70 g, 8.29 mmol) copper (I) iodide (72.0 mg, 5 mol %), trans-N,N'-dimethylcyclohexane-1,2-diamine (0.21 g, 1.47 mmol) and potassium carbonate (2.19 g, 15.8 mmol) under argon. Xylenes (12 mL) was added and the mixture degassed (5×), the vial sealed and then heated to 135° C. overnight. After cooling, the mixture was partitioned between EtOAc (100 mL) and water (100 mL), separated and the aqueous layer extracted with EtOAc (100 mL). The organic extracts were combined and washed (water and brine), then dried (MgSO$_4$) and concentrated. The residue was purified by FCC, eluting with DCM/cyclohexane (1:1) and then 0-5% [2M NH$_3$ in MeOH] in DCM, to give a residue (0.85 g). The product was triturated (DCM/pentane) and air dried to afford the title compound (0.46 g). LCMS (Method 3): Rt 2.23 min, m/z 264 [MH$^+$]. $^1$H NMR (300 MHz, CDCl$_3$): 1.31 (9H, s), 4.77 (2H, br s), 5.52 (1H, s), 7.11 (1H, t, J=9.0 Hz), 7.45 (1H, m), 7.66 (1H, m).

b. [5-tert-Butyl-2-(4-fluoro-3-hydroxymethyl-phenyl)-2H-pyrazol-3-yl]-carbamic acid 2,2,2-trichloroethyl ester (Intermediate Zb)

2,2,2-Trichloroethyl chloroformate (0.26 mL, 1.89 mmol) was added to a stirred mixture of Intermediate Za (0.46 g, 1.75 mmol) and NaOH (aq 1M, 3.2 mL, 3.20 mmol) in EtOAc (4 mL). Stirring was continued at RT for 1 h and the mixture was diluted with water, and then extracted with EtOAc (2×25 mL). The combined extracts were washed (water and brine), then dried (MgSO$_4$) and concentrated to give the title compound. LCMS (Method 3): Rt 4.05 min, m/z 438 [MH$^+$].

Intermediate 53cE

1-{5-tert-Butyl-2-[4-chloro-3-(2-hydroxy-ethoxy)-phenyl]-2H-pyrazol-3-yl}-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea

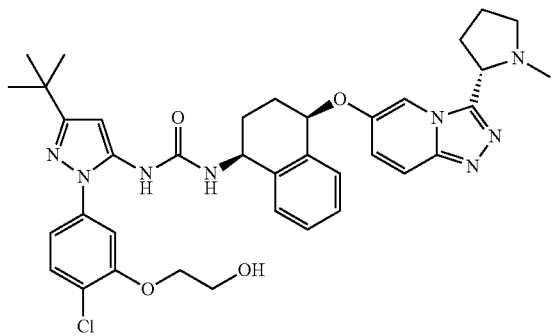 [SMILES: CN1CCC[C@H]1c1nnc2ccc(O[C@@H]3CC[C@H](NC(=O)Nc4cc(C(C)(C)C)nn4-c4ccc(Cl)c(OCCO)c4)c4ccccc43)cn12]

a. 1-(5-tert-Butyl-2-{4-chloro-3-[2-(tetrahydro-pyran-2-yloxy)-ethoxy]-phenyl}-2H-pyrazol-3-yl)-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea (Intermediate 53bE)

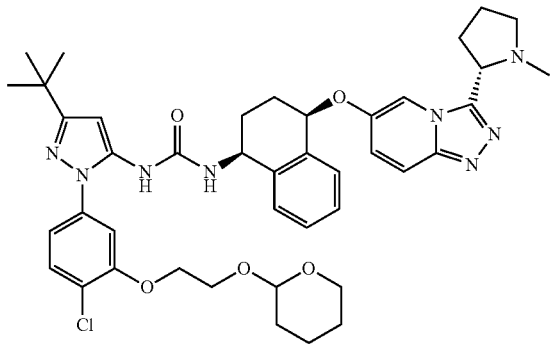 [SMILES: CN1CCC[C@H]1c1nnc2ccc(O[C@@H]3CC[C@H](NC(=O)Nc4cc(C(C)(C)C)nn4-c4ccc(Cl)c(OCCOC5CCCCO5)c4)c4ccccc43)cn12]

A solution of Intermediate 53b (299 mg, 0.525 mmol), Intermediate E (182 mg, 0.50 mmol) and DIPEA (0.11 mL, 0.63 mmol) in dry dioxane (10 mL) was stirred at 75° C. for 18 h. The cooled solution was concentrated in vacuo, suspended in water (10 mL) and extracted with DCM (2×10 mL). The combined organics were passed through a hydrophobic fit and concentrated in vacuo to leave the title compound (451 mg). LCMS (Method 3): Rt 3.22 min, m/z 783 [MH$^+$].

b. 1-{5-tert-Butyl-2-[4-chloro-3-(2-hydroxy-ethoxy)-phenyl]-2H-pyrazol-3-yl}-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea (Intermediate 53cE)

A solution of Intermediate 53bE (assume 0.50 mmol) and pyridinium p-toluenesulfonate (377 mg, 1.50 mmol) in MeOH was stirred at 40° C. for 16 h. The solution was concentrated in vacuo, suspended in water (10 mL) and sat. aq. NaHCO$_3$ solution (10 ml), and then extracted with DCM (2×10 mL). The combined organics were passed through a hydrophobic fit and concentrated in vacuo. FCC, using 2-6% MeOH in DCM, gave the title compound (149 mg, 43%). LCMS (Method 3): Rt 2.85 min, m/z 699 [MH$^+$].

General Procedure for Table 1—Urea Formation.

The compounds synthesized in Table 1 were prepared according to the following general procedure: A mixture of Intermediate LHS (1.0 eq), Intermediate RHS (1.0 eq) and DIPEA (1.2-1.5 eq.) in a suitable solvent (for example 1,4-dioxane, 2-methyltetrahydrofuran or THF) was heated (60-80° C.) for a suitable time until the reaction was complete (e.g. 5-24 h). The reaction mixture was cooled, concentrated in vacuo and subjected to chromatographic purification methods described herein.

TABLE 1

Urea Formation.

| Interm. No. | Interm. used (LHS) | Interm. used (RHS) | Intermediate Structure | NMR (δ) | LCMS |
|---|---|---|---|---|---|
| Intermediate HdC | Hd | C | 1-[l5-tert-Butyl-2-(2-fluoro-5-hydroxymethyl-phenyl)-2H-pyrazol-3-yl]-3-{(lS,4R)-4-[3-((2S,6R)-2,6-dimethyl-piperidin-1-yl)-[1,2,4]triazolo[4,3-a]pyridin-6-yloxy]-1,2,3,4-tetrahydro-naphlhalen-1-yl}-urea | (300 MHz, CDCl$_3$): 0.64 (6H, t, J = 6.8 Hz), 1.34 (9H, s), 1.36-1.63 (3H, m) 1.69-1.97 (3H, m), 1.98-2.27 (4H, m), 3.15-3.32 (2H, m), 4.59 (2H, s), 5.00-5.11 (1H, m), 5.17-5.23 (1H, m), 5.87-5.95 (1H, m), 6.36 (1H, s), 6.94 (1H, dd, J = 2.2, 9.9 Hz), 6.99-7.11 (2H, m), 7.20-7.38 (5H, m), 7.39-7.45 (1H, d, J = 9.9 Hz), 7.48 (1H, dd, J = 2.0, 7.4 Hz), 7.66 (1H, d, J = 1.6 Hz). | (Method 3): Rt 3.85 min, m/z 681.5 [MH$^+$]. |
| Intermediate HdB | Hd | B | 1-[5-tert-Butyl-2-(2-fluoro-5-hydroxymethyl-phenyl)-2H-pyrazol-3-yl]-3-{(lS,4R)-4-[3-((S)-2-methyl-piperidin-1-yl)-[l,2,4]triazolo[4,3-a]pyridin-6-yloxy]-l,2,3,4-tetrahydro-naphlhalen-1-yl}-urea | | (Method 3): 3.61 min, m/z 667.4 [MH$^+$]. |
| Intermediate IeB | Ie | B | 1-{5-tert-Bulyl-2-[2-fluoro-5-(2-hydroxy-ethoxy)-phenyl]-2H-pyrazol-3-yl}-3-{(1S,4R)-4-[3-((S)-2-methyl-piperidin-l-yl)-[l,2,4]triazolo[4,3-a]pyridin-6-yloxy]-l,2,3,4-tetrahydro-naphthalen-1-yl}-urea | | (Method 3): Rt 3.63 min, m/z 697.5 [MH$^+$]. |

TABLE 1-continued

Urea Formation.

| Interm. No. | Interm. used (LHS) | Interm. used (RHS) | Intermediate Structure | NMR (δ) | LCMS |
|---|---|---|---|---|---|
| Intermediate IeC | Ie | C | 1-{5-tert-Butyl-2-[2-fluoro-5-(2-hydroxy-ethoxy)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea | | (Method 3): Rt 3.85 min, m/z 711.3 [MH$^+$]. |
| Intermediate NcB | Nc | B | 1-{5-tert-Butyl-2-[4-fluoro-3-(2-hydroxy-ethoxy)-phenyl]-2H-pyrazol-3-yl}-3-{(1S,4R)-4-(3-((S)-2-methyl-piperidin-1-yl)-[1,2,4]triazolo[4,3-a]pyridin-6-yloxy]-1,2,3,4-tetrahydro-naphthalen-1-yl}-urea | | (Method 3): Rt 3.69 mins, m/z 697 [MH$^+$]. |
| Intermediate NcC | Nc | C | 1-{5-tert-Butyl-2-[4-fluoro-3-(2-hydroxy-ethoxy)-phenyl]-2H-pyrazol-3-yl}-3-{(1S,4R)-4-[3-((2S,6R)-dimethyl-piperidin-1-yl)-[1,2,4]triazolo[4,3-a]pyridin-6-yloxy]-1,2,3,4-tetrahydro-naphthalen-1-yl}-urea | | (Method 3): Rt 3.90 mins, m/z 711 [MH$^+$]. |

TABLE 1-continued

Urea Formation.

| Interm. No. | Interm. used (LHS) | Interm. used (RHS) | Intermediate Structure | NMR (δ) | LCMS |
|---|---|---|---|---|---|
| Intermediate QcB | Qc | B | 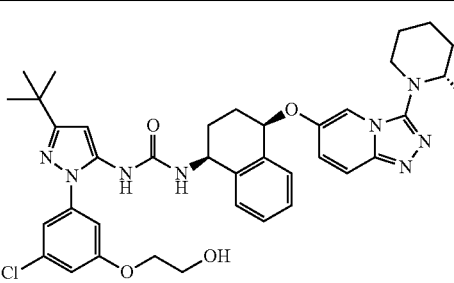<br>1-{5-tert-Butyl-2-[3-chloro-5-(2-hydroxy-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea | (300 MHz, CDCl$_3$): 0.85 (3H, d, J 6.2), 1.33 (9H, s), 1.39-1.48 (2H, m), 1.57-1.67 (2H, m), 1.71-1.8 (2H, m), 1.89-2.13 (3H, m), 2.20-2.30 (1H, m), 2.76-2.84 (1H, m), 2.95-3.02 (1H, m), 3.11-3.20 (1H, m), 3.83 (2H, t, J 4.3), 3.96 (2H, t, J 4.3), 5.08 (1H, td, J 8.4, 5.2), 5.19 (1H, t, J 3.9), 6.40 (1H, s), 6.64 (1H, t, J 2.0), 6.87 (1H, d, J 2.3), 6.90 (1H, d, J 2.3), 7.04 (1H, t, J 2.0), 7.14 (1H, t, J 1.8), 7.20-7.30 (4H, m), 7.38-7.41 (2H, m), 8.11 (1H, br s). OH signal missing. | (Method 3): Rt 3.91 min, m/z 713 [MH$^+$]. |
| Intermediate RdD | Rd | D | 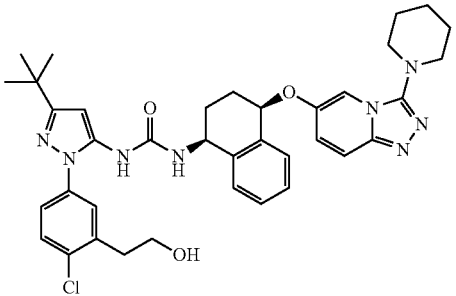<br>1-{5-tert-Butyl-2-[4-chloro-3-(2-hydroxy-ethyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydronaphthalen-1-yl]-urea | (300 MHz, d$_6$-DMSO): 1.28 (9H, s), 1.57-1.67 (2H, m), 1.68-1.77 (3H, s), 1.82-2.00 (3H, s), 2.02-2.18 (2H, m), 2.91 (2H, t, J 6.9), 3.14 (4H, t, J 5.1), 3.65 (2H, apparent q, J 6.4), 4.77 (1H, t, J 5.3), 4.81 (1H, m), 5.55 (1H, t, J 4.2), 6.34 (1H, s), 7.05 (1H, d, J 8.5), 7.16 (1H, dd, J 9.8, 2.1), 7.24-7.40 (5H, m), 7.50 (1H, d, J 2.6), 7.54 (1H, d, J 8.6), 7.59-7.64 (2H, m), 8.13 (1H, s). | (Method 3): Rt 3.69 min, m/z 683 [MH$^+$]. |
| Intermediate TdD | Td | D | 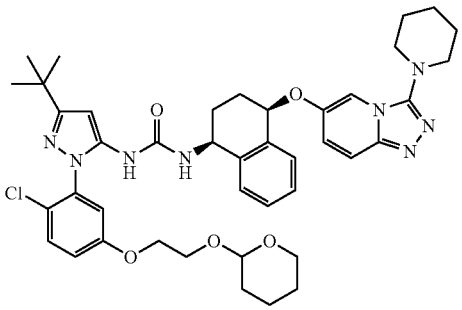<br>1-(5-tert-Butyl-2-{2-chloro-5-[2-(tetrahydro-pyran-2-yloxy)-ethoxy]-phenyl}-2H-pyrazol-3-yl)-3-[(1S,4R)-4-(3-piperidin-1-yl-[1,2,4]triazolo[4,3-a]pyridin-6-yloxy)-1,2,3,4-tetrahydro-naphthalen-1-yl]-urea |  | (Method 4): Rt 3.73 mins, m/z 783 [MH$^+$]. |

TABLE 1-continued

Urea Formation.

| Interm. No. | Interm. used (LHS) | Interm. used (RHS) | Intermediate Structure | NMR (δ) | LCMS |
|---|---|---|---|---|---|
| Intermediate UbC | Ub | C | 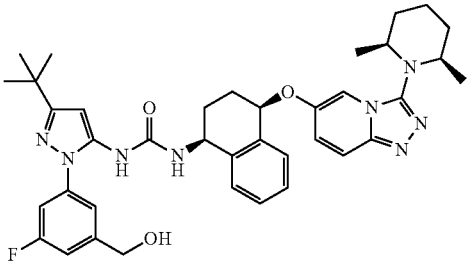<br>1-[5-tert-Butyl-2-(3-fluoro-5-hydroxymethyl-phenyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea | | (Method 4): Rt 3.63 mins, m/z 681 [MH⁺]. |
| Intermediate VeD | Ve | D | 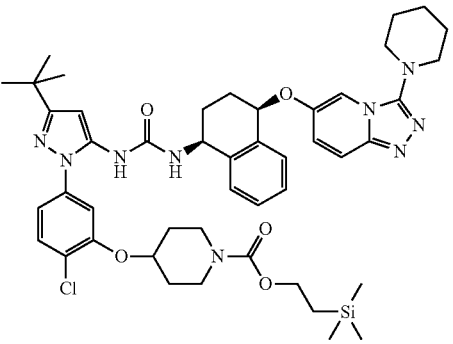<br>4-[5-(3-tert-Butyl-5-{3-[(1S,4R)-4-(3-piperidin-1-yl-[1,2,4]triazolo[4,3-a]pyridin-6-yloxy)-1,2,3,4-tetrahydro-naphthalen-1-yl]-ureido}-pyrazol-1-yl)-2-chloro-phenoxy]-piperidine-1-carboxylic acid 2-trimethylsilanyl-ethyl ester | | (Method 3): Rt 4.92 mins, m/z 882.1 [MH⁺]. |
| Intermediate WcC | Wc | C | 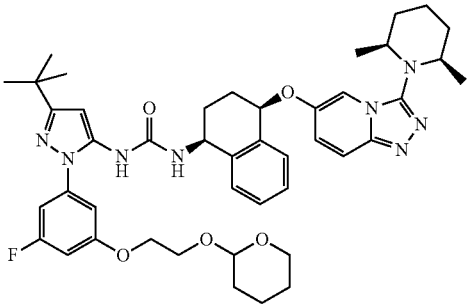<br>1-(5-tert-Butyl-2-{3-fluoro-5-[2-(tetrahydro-pyran-2-yloxy)-ethoxy]-phenyl}-2H-pyrazol-3-yl)-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea | | (Method 4): Rt 4.22 mins, m/z 795 [MH⁺]. |

TABLE 1-continued

Urea Formation.

| Interm. No. | Interm. used (LHS) | Interm. used (RHS) | Intermediate Structure | NMR (δ) | LCMS |
|---|---|---|---|---|---|
| Intermediate UbB | Ub | B | 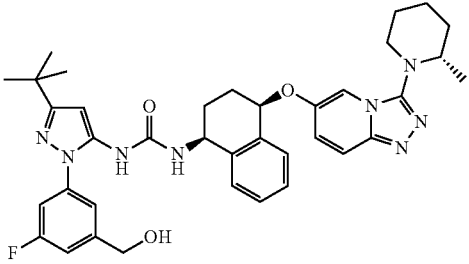<br>1-[5-tert-Butyl-2-(3-fluoro-5-hydroxymethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea | | (Method 4): Rt 3.38 mins, m/z 667 [MH⁺]. |
| Intermediate WcB | Wc | B | 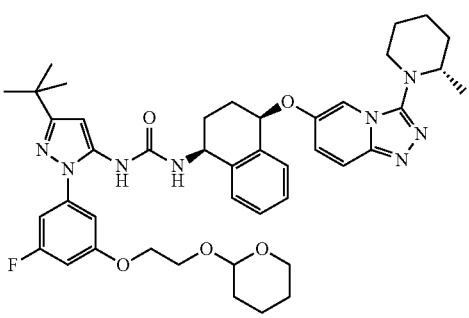<br>1-(5-tert-Butyl-2-{3-fluoro-5-[2-(tetrahydro-pyran-2-yloxy)-ethoxy]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea | | (Method 4): Rt 3.99 mins, m/z 781 [MH⁺]. |
| Intermediate XcB | Xc | B | 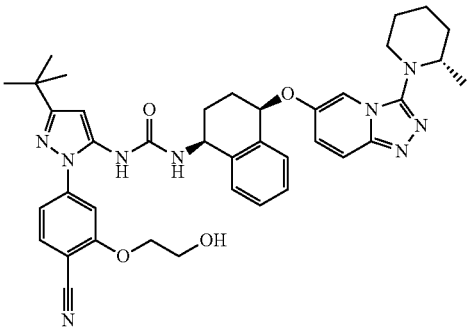<br>1-{5-tert-Butyl-2-[4-cyano-3-(2-hydroxy-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea | | (Method 9): Rt 3.25 mins, m/z 704 [MH⁺]. |

TABLE 1-continued

Urea Formation.

| Interm. No. | Interm. used (LHS) | Interm. used (RHS) | Intermediate Structure | NMR (δ) | LCMS |
|---|---|---|---|---|---|
| Intermediate RdC | Rd | C | 1-{5-tert-Butyl-2-[4-chloro-3-(2-hydroxy-ethyl)-phenyl]-2H-pyrazol-3-yl}-{(1S,4R)4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea | | (Method 3): Rt 4.09 mins, m/z 711/713 |
| Intermediate RdB | Rd | B | 1-{5-tert-Butyl-2-[4-chloro-3-(2-hydroxy-ethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea | | (Method 3): Rt 3.87 mins, m/z 697/699 [MH$^+$]. |
| Intermediate MdB | Md | B | 1-[5-tert-Butyl-2-(4-chloro-3-hydroxymethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea | (300 MHz, d$_6$-DMSO): 0.91 (3H, d, J 6.3), 1.28 (9H, s), 1.51 (2H, m), 1.61-2.18 (8H, m), 2.90 (1H, ddd, J 12.2, 8.5, 4.3), 3.16 (1H, dt, J 12.1, 4.3), 3.25-3.31 (1H, m), 4.61 (2H, d, J 5.5), 4.80 (1H, td, J 8.4, 5.7), 5.50-5.56 (2H, m), 6.34 (1H, s), 7.04 (1H, d, J 8.6), 7.19 (1H, dd, J 9.9, 2.1), 7.25-7.44 (5H, m), 7.52 (1H, d, J 8.5), 7.64 (1H, d, J 9.9), 7.69 (2H, m), 8.14 (1H, s). | (Method 3): Rt 3.83 min, m/z 683 [MH$^+$]. |

TABLE 1-continued

Urea Formation.

| Interm. No. | Interm. used (LHS) | Interm. used (RHS) | Intermediate Structure | NMR (δ) | LCMS |
|---|---|---|---|---|---|
| Intermediate MdC | Md | C | 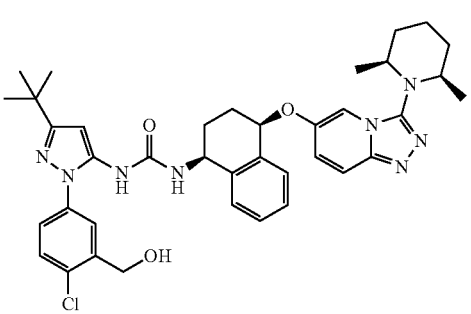<br>1-[5-tert-Butyl-2-(4-chloro-3-hydroxymethyl-phenyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea | (300 MHz, $d_6$-DMSO): 0.60 (3H, d, J 6.0), 0.63 (3H, d, J 6.1), 1.28 (9H, s), 1.37-1.62 (3H, m), 1.66-1.97 (5H, m), 2.00-2.13 (2H, m), 3.17 (2H, m), 4.61 (2H, d, J 5.5), 4.81 (1H, td, J 8.5, 5.6), 5.52 (1H, m), 5.54 (1H, t, J 5.7), 6.33 (1H, s), 7.04 (1H, d, J 8.6), 7.21 (1H, dd, J 9.9, 2.2), 7.25-7.36 (4H, m), 7.42 (1H, dd, J 8.5, 2.6), 7.52 (1H, d, J 8.5), 7.65-7.69 (2H, m), 7.89 (1H, d, J 2.1), 8.15 (1H, s). | (Method 3): Rt 4.05 min, m/z 697 [MH$^+$]. |
| Intermediate YdB | Yd | B | 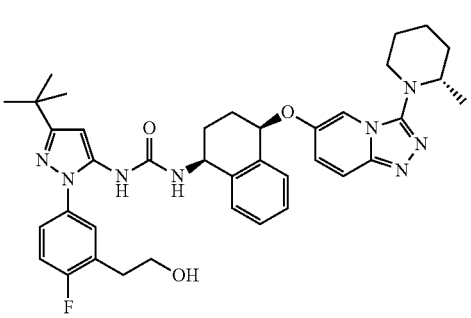<br>1-{5-tert-Butyl-2-[4-fluoro-3-(2-hydroxy-ethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea | (400 MHz, CDCl$_3$): 0.86 (3H, d, J = 6.1 Hz), 1.35 (9H, s), 1.38-1.53 (2H, m), 1.56-1.84 (4H, m), 1.86-1.99 (1H, m), 2.00-2.26 (3H, m), 2.48-2.61 (1H, m), 2.64-2.77 (1H, m), 2.79-2.92 (1H, m), 2.96-3.06 (1H, m), 3.13-3.26 (1H, m,), 3.31-3.45 (1H, m,), 3.52-3.63 (1H, m), 5.04-5.15 (1H, m), 5.15-5.21 (1H, m), 6.49 (1H, s), 6.79-6.97 (2H, m), 7.09-7.34 (5H, m, obscured by solvent), 7.35-7.47 (3H, m). | |
| Intermediate ZbB | Zb | B | 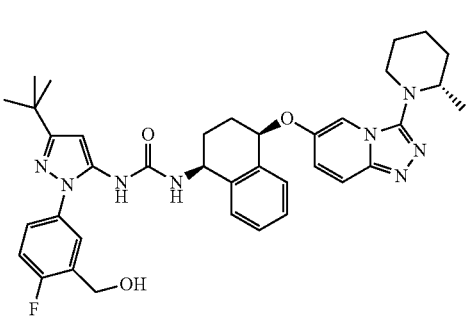<br>1-[5-tert-Butyl-2-(4-fluoro-3-hydroxymethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea | | (Method 3): Rt 3.68 mins, m/z 667 [MH$^+$]. |

123

General Procedure for Table 2. Mesylate Formation.

The compounds synthesised in Table 2 were prepared according to the following general procedure: the intermediate obtained in Table A (1.0 eq.) and DIPEA (3.0 eq.) were suspended in DCM, and methanesulfonyl chloride (1.2 eq.) added and stirred at RT. After 1 h, the reaction mixture was partitioned with H$_2$O and DCM, the organic layer separated, dried, and concentrated in vacuo and used directly in the following step.

TABLE 2

Mesylate Formation.

| Intermediate used | Structure of product | Intermediate No. | LCMS |
|---|---|---|---|
| HdC | 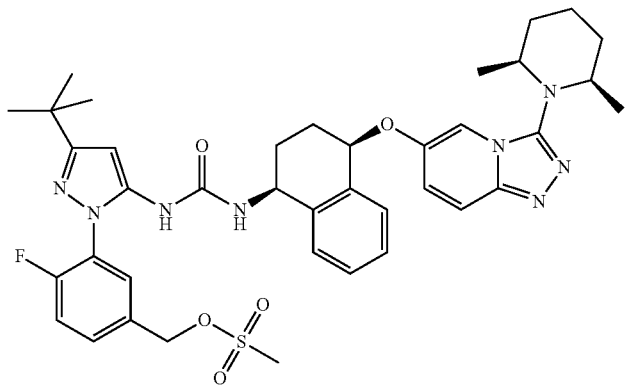<br>Methanesulfonic acid 3-[3-tert-butyl-5-(3-{(1S,4R)-4-[3-((2S,6R)-2,6-dimethyl-piperidin-1-yl)-[1,2,4]triazolo[4,3-a]pyridin-6-yloxy]-1,2,3-tetrahydro-naphthalen-1-yl}-ureido)-pyrazol-1-yl]-4-fluoro-benzyl ester | HeC | (Method 3): Rt 4.09 min, m/z 759.5 [MH$^+$]. |
| HdB | 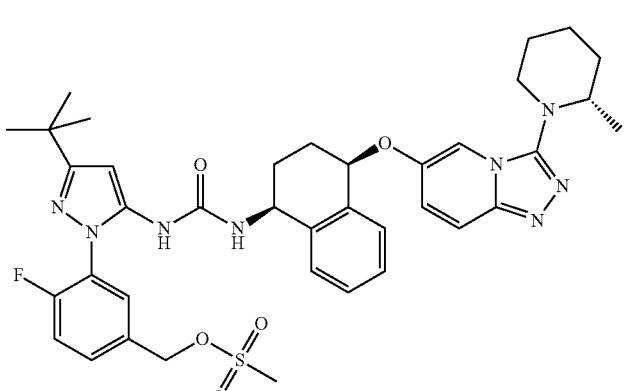<br>Methanesulfonic acid 3-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-4-fluoro-benzyl ester | HeB | (Method 3): Rt 3.87 min, m/z 685.5 [MH$^+$]. |

TABLE 2-continued

Mesylate Formation.

| Intermediate used | Structure of product | Intermediate No. | LCMS |
|---|---|---|---|
| IeB | Methanesulfonic acid 2-{3-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-4-fluoro-phenoxy}-ethyl ester | IfB | (Method 3): Rt 3.89 min, m/z 775.4 [MH+]. |
| IeC | Methanesulfonic acid 2-{3-[3-tert-butyl-5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-pyrazol-1-yl]-4-fluoro-phenoxy}-ethyl ester | IfC | (Method 3): Rt 4.10 min, m/z 789.3 [MH+]. |
| Example 82 | Methanesulfonic acid 5-(3-tert-butyl-5-{3-[(1S,4R)-4-(3-piperidin-1-yl-[1,2,4]triazolo[4,3-a]pyridin-6-yloxy)-1,2,3,4-tetrahydro-naphthalen-1-yl]-ureido}-pyrazol-1-yl)-2-chloro-benzyl ester | MeD | (Method 3): Rt 3.89 min, m/z 746.9 [MH+]. |

TABLE 2-continued

Mesylate Formation.

| Intermediate used | Structure of product | Intermediate No. | LCMS |
|---|---|---|---|
| Example 53 | 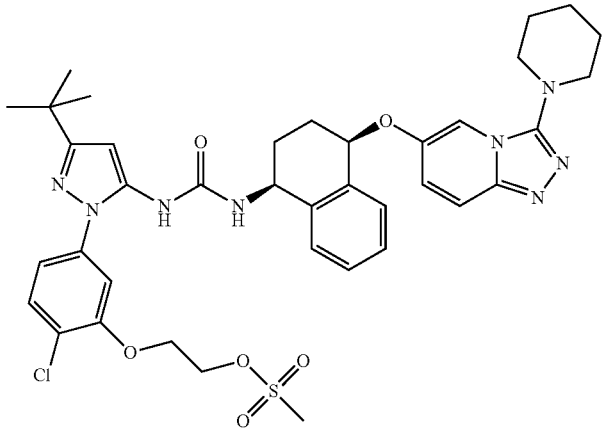<br><br>Methanesulfonic acid 2-[5-(3-tert-butyl-5-{3-[(1S,4R)-4-(3-piperidin-1-yl-[1,2,4]triazolo[4,3-a]pyridin-6-yloxy)-1,2,3,4-tetrahydro-naphthalen-1-yl]-ureido}-pyrazol-1-yl)-2-chloro-phenoxy]-ethyl ester | 53d | (Method 3): Rt 3.89 min, m/z 777.1/779.1 [MH$^+$]. |
| NcB | 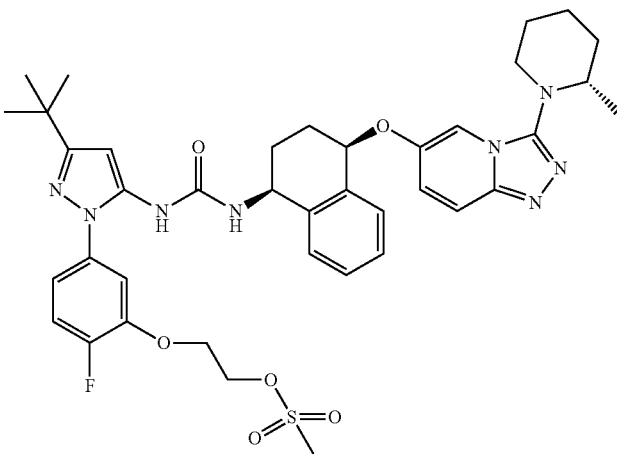<br><br>Mcihancsulfonic acid 2-{5-[3-tert-bulyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-2-fluoro-phenoxy}-ethyl ester | NdB | (Method 3): Rt 3.91 mins, m/z 775 [MH$^+$]. |

TABLE 2-continued

Mesylate Formation.

| Intermediate used | Structure of product | Intermediate No. | LCMS |
|---|---|---|---|
| NcC | Methanesulfonic acid 2-{5-[3-tert-butyl-5-(3-{(1S,4R)-4-[3-((2S,6R)-2,6-dimeihyl-piperidin-1-yl)-[1,2,4]triazolo[4,3-a]pyridin-6-yloxy]-1,2,3,4-tetrahydro-naphthalen-1-yl}-ureido)-pyrazol-1-yl]-2-fluoro-phenoxy}-ethyl ester | NdC | (Method 3): Rt 4.12 mins, m/z 789 [MH+]. |
| QcB | Methanesulfonic acid 2-{3-[3-tert-butyl-5-(3-{(1S,4R)-4-[3-((S-2-methyl-piperidin-1-yl)-[l,2,4]triazolo[4,3-a]pyridin-6-yloxy]-l,2,3,4-tetrahydro-naphthalen-1-yl}-ureido)-pyrazol-1-yl]-5-chloro-phenoxy}-ethyl ester | QdB | (Method 3): Rt 4.11 min, m/z 791 [MH+]. |
| RdD | Methanesulfonic acid 2-[5-(3-tert-butyl-5-{3-[(1S,4R)-4-(3-piperidin-1-yl-[1,2,4]triazolo[4,3-a]pyridin-6-yloxy)-l,2,3,4-tetrahydro-naphthalen-1-yl]-ureido}-pyrazol-1-yl)-2-chloro-phenyl]-ethyl ester | ReD | (Method 3): Rt 3.92 min, m/z 761 [MH+]. |

TABLE 2-continued

Mesylate Formation.

| Intermediate used | Structure of product | Intermediate No. | LCMS |
|---|---|---|---|
| SbD | Methanesulfonic acid 3-(3-tert-butyl-5-{3-[(1S,4R)-4-(3-piperidin-1-yl-[1,2,4]tiriazolo[4,3-a]pyridin-6-yloxy)-1,2,3,4-tetrahydro-naphthalen-1-yl]-ureido}-pyrazol-1-yl)-5-chloro-benzyl ester | ScD | (Method 3): Rt 3.96 min, m/z 747, 749 [MH$^+$]. |
| TeD | Methanesulfonic acid 2-[3-(3-tert-butyl-5-{3-[(1S,4R)-4-{3-piperidin-1-yl-[1,2,4]triazolo[4,3-a]pyridin-6-yloxy)-1,2,3,4-tetrahydro-naphthalen-1-yl]-ureido}-pyrazol-1-yl)-4-chloro-phenoxy]-ethyl ester | TfD | (Method 1): Rt 3.54 mins, m/z 777 [MH$^+$]. |
| UbC | Methanesulfonic acid 3-[3-tert-butyl-5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-pyrazol-1-yl]-5-fluoro-benzyl ester | UcC | (Method 1): Rt 3.96 mins, m/z 759 [MH$^+$]. |

TABLE 2-continued

Mesylate Formation.

| Intermediate used | Structure of product | Intermediate No. | LCMS |
|---|---|---|---|
| WdC | 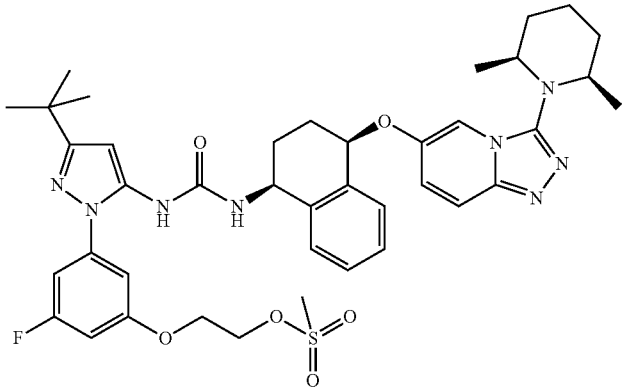<br>Methanesulfonic acid 2-{3-[3-tert-butyl-5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-pyrazol-1-yl]-5-fluoro-phenoxy}-ethyl ester | WeC | (Method 4): Rt 3.89 mins, m/z 789 [MH⁺]. |
| UbB | 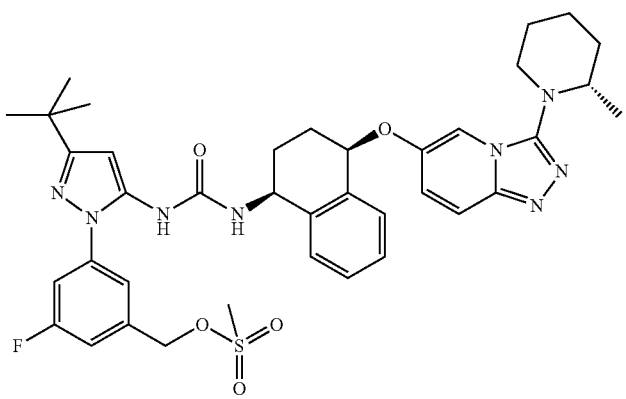<br>Methanesulfonic acid 3-[3-tert-butyl-5-(3-{(1S4R)-4-[3-((S-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-5-fluoro-benzyl ester | UcB | (Method 4): Rt 3.65 mins, m/z 745 [MH⁺]. |
| WdB | 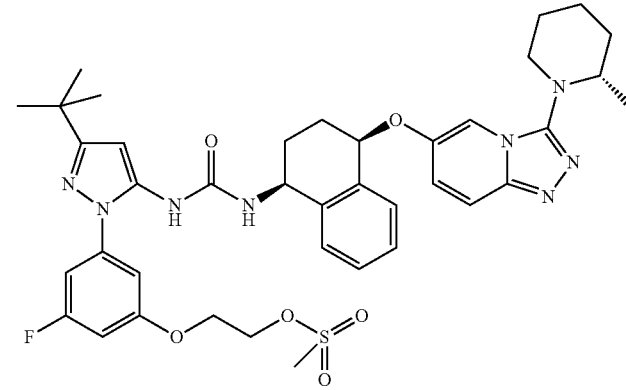<br>Methanesulfonic acid 2-{3-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-5-fluoro-phenoxy}-ethyl ester | WeB | (Method 4): Rt 3.65 mins, m/z 776 [MH⁺]. |

TABLE 2-continued

Mesylate Formation.

| Intermediate used | Structure of product | Intermediate No. | LCMS |
|---|---|---|---|
| XcB | Methanesulfonic acid 2-{5-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-2-cyano-phenoxy}-ethyl ester | XdB | (Method 4): Rt 3.58 mins, m/z 782 [MH$^+$]. |
| RdB | Methanesulfonic acid 2-{5-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-2-chloro-phenyl}-ethyl ester | ReB | (Method 3): Rt 4.06 mins, m/z 775/777 [MH$^+$]. |
| RdC | Methanesulfonic acid 2-{5-[3-tert-butyl-5-(3-{(1S,4R)-4-[3-((2S,6R)-2,6-dimethyl-piperidin-1-yl)-1,2,4]triazolo[4,3-a]pyridin-6-yloxy]-1,2,3,4-tetrahydro-naphthalen-1-yl}-ureido)-pyrazol-1-yl]-2-chloro-phenyl}-ethyl ester | ReC | (Method 3): Rt 4.28 mins, m/z 789/791 [MH$^+$]. |

TABLE 2-continued

Mesylate Formation.

| Intermediate used | Structure of product | Intermediate No. | LCMS |
|---|---|---|---|
| YdB | ethanesulfonic acid 2-{5-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-2-fluoro-phenyl}-ethyl ester | YeB | (Method 3): Rt: 3.94 mins, m/z 759 [MH$^+$]. |
| 53cE | Methanesulfonic acid 2-{5-[3-tert-butyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-pyrazol-1-yl]-2-chloro-phenoxy}-ethyl ester | 53dE | (Method 3): Rt 3.07 min, m/z 777 [MH$^+$]. |
| MdB | Methanesulfonic acid 5-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-2-chloro-benzyl ester | MeB | (Method 3): Rt 4.03 min, m/z 761 [MH$^+$]. |

TABLE 2-continued

Mesylate Formation.

| Intermediate used | Structure of product | Intermediate No. | LCMS |
|---|---|---|---|
| MdC | Methanesulfonic acid 5-[3-tert-butyl-5-(3-{(1S,4R)-4-[3-((2S,6R)-2,6-dimethyl-piperidin-1-yl)-[1,2,4]triazolo[4,3-a]pyridin-6-ylozy]-1,2,3,4-tetrahydro-naphthalen-1-yl}-yreido)-pyrazol-1-yl]-2-chloro-benzyl ester | MeC | (Method 3): Rt 4.22 min, m/z 775 [MH$^+$]. |
| ZbB | Methanesulfonic acid 5-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-2-fluoro-benzyl ester | ZcB | (Method 3): Rt 3.90 mins, m/z 745 [MH$^+$]. |

General Procedure for Table 3. Amine Displacement.

The compounds synthesised in Table 3 were prepared according to the following general procedure: the intermediate obtained in Table B and the corresponding amine were suspended in a suitable solvent (THF, MeOH) and heated (60-80° C.) for a suitable time until the reaction was complete (5-24 h). The reaction mixture was cooled, concentrated in vacuo and subjected to chromatographic purification methods described herein.

TABLE 3

Amine Displacement.

| Ex No. | Amine (equivalents used) | Intermediate | Example Structure | NMR (400 MHz) δ | LCMS |
|---|---|---|---|---|---|
| 1 | Pyrrolidine (3.0 eq.) | HeC | 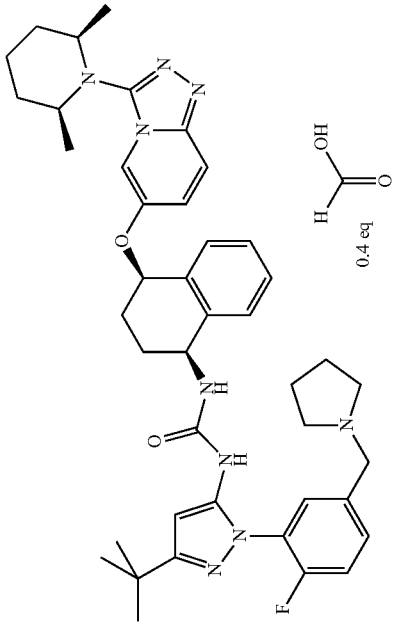<br>0.4 eq<br>1-[5-tert-Butyl-2-(2-fluoro-5-pyrrolidin-1-ylmethyl-phenyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt | (d₆-DMSO): 0.55 (3H, d, J = 6.3 Hz), 0.58 (3H, d, J = 6.3 Hz), 1.22 (9H, s), 1.33 (3H, m), 1.58-1.70 (6H, m), 1.72-1.84 (2H, m), 1.85-1.95 (1H, m), 1.96-2.07 (2H, m), 3.07-3.19 (3H, m), 3.27 (2H, m, obscured by water), 3.61 (2H, s), 4.72-4.81 (1H, m), 5.48 (1H, t, J = 4.3 Hz), 6.29 (1H, s), 6.93 (1H, d, J = 8.4 Hz), 7.13-7.17 (1H, dd, J = 2.2, 9.7 Hz), 7.17-7.24 (2H, m), 7.25-7.32 (2H, m), 7.33-7.39 (2H, m), 7.40-7.46 (1H, m), 7.59-7.65 (1H, m), 7.83 (1H, d, J = 1.3 Hz), 8.00 (1H, s), 8.10 (0.4H, s) | (Method 5): Rt 3.83 min, m/z 734.4 [MH⁺]. |

TABLE 3-continued

Amine Displacement.

| Ex No. | Amine (equivalents used) | Intermediate | Example Structure | NMR (400 MHz) δ | LCMS |
|---|---|---|---|---|---|
| 2 | 1-Methyl-piperazine (3.0 eq.) | HeC | 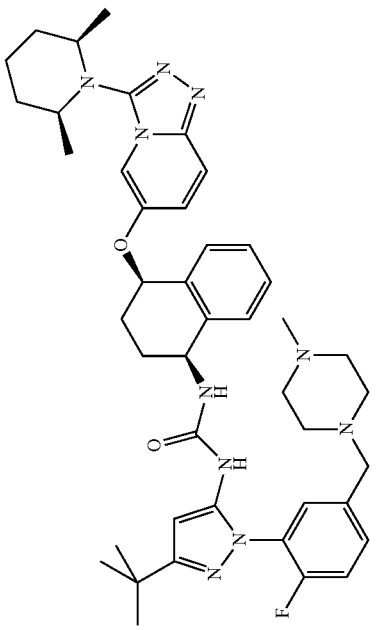<br>1-{5-tert-Butyl-2-[2-fluoro-5-(4-methyl-piperazin-1-ylmethyl)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}urea | (d$_6$-DMSO): 0.55 (3H, d, J = 6.3 Hz), 0.58 (3H, d, J = 6.3 Hz), 1.22 (9H, s), 1.32-1.57 (3H, s), 1.60-1.70 (2H, m), 1.71-1.84 (2H, m), 1.85-1.95 (1H, m), 1.96-2.05 (2H, m), 2.06 (3H, s), 2.24 (4H, bs), 2.34 (4H, bs), 3.06-3.20 (2H, m), 3.44 (2H, s), 4.72-4.81 (1H, m), 5.48 (1H, t, J = 4.3 Hz), 6.29 (1H, s), 6.91 (1H, d, J = 8.4 Hz), 7.12-7.17 (1H, dd, 2.2, 9.7 Hz), 7.17-7.24 (2H, m), 7.25-7.37 (4H, m), 7.37-7.43 (1h, m), 7.61-7.64 (1H, m), 7.84 (1H, d, J = 1.3 Hz), 7.99 (1H, s). | (Method 5): Rt 3.79 min, m/z 763.5 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 3 | Pyrrolidine (3.0 eq). | HeB | 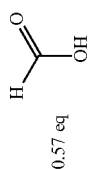<br>1-[5-tert-Butyl-2-(2-fluoro-5-pyrrolidin-1-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | (d$_6$-DMSO): 0.86 (3H, d, J = 6.2 Hz), 1.22 (9H, s), 1.42-1.51 (2H, m), 1.57-1.69 (6H, m), 1.70-1.84 (3H, m), 1.84-1.94 (1H, m), 1.95-2.08 (2H, m), 2.37-2.43 (4H, m), 2.80-2.91 (1H, m), 3.07-3.15 (2H, m), 3.56 (2H, s), 4.70-4.80 (1H, m), 5.47 (1H, t, J = 4.2 Hz), 6.29 (1H, s), 6.95 (1H, d, J = 8.7 Hz), 7.14 (1H, dd, J = 2.1, 9.9 Hz), 7.16-7.25 (2H, m), 7.25-7.29 (1H, m), 7.29-7.37 (3H, m), 7.38-7.45 (1H, m), 7.59 (1H, d, J = 9.7 Hz), 7.65 (1H, d, J = 1.6 Hz), 8.00 (1H, s), 8.16 (0.6H). | (Method 5): Rt 3.65 min, m/z 720.4 [MH$^+$]. |

0.57 eq

TABLE 3-continued

Amine Displacement.

| Ex No. | Amine (equivalents used) | Intermediate | Example Structure | NMR (400 MHz) δ | LCMS |
|---|---|---|---|---|---|
| 4 | 1-Methyl-piperazine (3.0 eq.) | HeB | 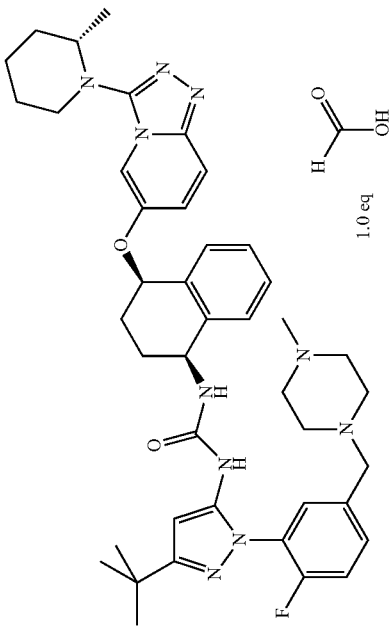<br>1-{5-tert-Butyl-2-[2-fluoro-5-(4-methyl-piperazin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}urea formate salt | (d$_6$-DMSO): 0.86 (3H, d, J = 6.4 1.22 (9H, s), 1.41-1.53 (2H, m), 1.55-1.68 (2H, m), 1.69-1.84 (3H, m), 1.85-1.93 (1H, m), 1.95-2.10 (3H, m), 2.06 (3H, s), 2.24 (4H, bs), 2.34 (4H, bs), 2.82-2.90 (1H, m), 3.07-3.15 (1H, m), 3.26 (3H, m, obscured by water), 3.44 (2H, s), 4.71-4.80 (1H, m), 5.47 (1H, t, J = 4.6 Hz), 6.29 (1H, s), 6.91 (1H, d, J = 8.5 Hz), 7.13 (1H, dd, J = 2.2, 10.1 Hz), 7.16-7.21 (1H, m), 7.21-7.25 (1H, m), 7.25-7.29 (1H, m), 7.29-7.37 (3H, m), 7.37-7.43 (1H, m), 7.56-7.61 (1H, m), 7.6 (1H, d, J = 1.4 Hz), 7.98 (1H, s). | (Method 5): Rt 3.62 min, m/z 749.4 [MH⁺]. |

TABLE 3-continued

Amine Displacement.

| Ex No. | Amine (equivalents used) | Intermediate | Example Structure | NMR (400 MHz) δ | LCMS |
|---|---|---|---|---|---|
| 5 | Dimethylamine, (2M solution in THF) | IIB | 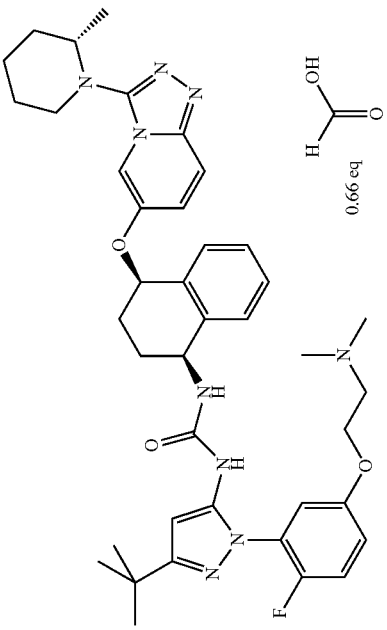<br>1-{5-tert-Butyl-2-[5-(2-dimethylamino-ethoxy)-2-fluoro-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | (d$_6$-DMSO): 0.86 (3H, d, J = 6.4 Hz), 1.22 (9H, s), 1.41-1.52 (2H, m), 1.56-1.68 (2H, m), 1.70-1.84 (3H, m), 1.85-1.94 (1H, m), 1.95-2.10 (2H, m), 2.14 (6H, s), 2.55 (2H, t, J = 5.8 Hz), 2.82-2.90 (1H, m), 3.08-3.15 (1H, m), 3.27 (1H, m, obscured by water), 4.02 (2H, t, J = 5.8 Hz), 4.72-4.81 (1H, m), 5.47 (1H, t, J = 4.2 Hz), 6.29 (1H, s), 6.97-7.02 (2H, m), 7.02-7.08 (1H, m), 7.14 (1H, dd, J = 2.2, 9.9 Hz), 7.18-7.25 (2H, m), 7.26-7.35 (3H, m), 7.59 (1H, d, J = 9.8 Hz), 7.65 (1H, d, J = 1.5 Hz), 8.01 (1H, s), 8.16 (0.66H, s) | (Method 5): Rt 3.65 min, m/z 724.4 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 6 | Dimethylamine, (2M solution in THF) | IfC | 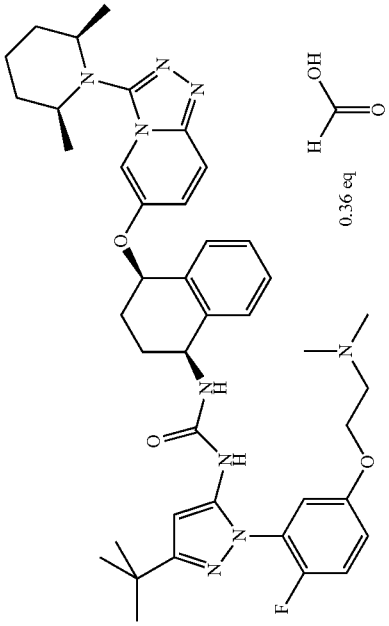<br>1-{5-tert-Butyl-2-[5-(2-dimethylamino-ethoxy)-2-fluoro-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt | (d₆-DMSO): 0.55 (3H, d, J = 6.3 Hz), 0.58 (3H, d, J = 6.3 Hz), 1.22 (9H, s), 1.33-1.57 (3H, m), 1.61-1.70 (2H, m), 1.72-1.85 (2H, m), 1.85-1.95 (1H, m), 1.98-2.06 (2H, m), 2.13 (6H, s), 2.55 (2H, t, J = 5.8 Hz), 3.08-3.19 (3H, m), 3.30 (2H, m, obscured by water), 4.02 (2H, t, J = 5.8 Hz), 4.73-4.82 (1H, m), 5.48 (1H, t, J = 4.4 Hz), 6.29 (1H, s), 6.97-7.08 (3H, m), 7.15 (1H, dd, J = 2.2, 9.9 Hz), 7.18-7.24 (2H, m), 7.25-7.34 (3H, m), 7.59-7.64 (1H, m), 7.84 (1H, d, J = 1.8 Hz), 8.03 (1H, s), 8.22 (0.37H, s). | (Method 5): Rt 3.82 min, m/z 738.4 [MH⁺]. |

TABLE 3-continued

Amine Displacement.

| Ex No. | Amine (equivalents used) | Intermediate | Example Structure | NMR (400 MHz) δ | LCMS |
|---|---|---|---|---|---|
| 7 | 1-Methyl-piperazine (3.5 eq.) | MeD | 1-{5-tert-Butyl-2-[4-chloro-3-(4-methyl-piperazin-1-ylmethyl)-phenyl]-2H-pyrazol-3-yl}-3-{(1S,4R)-4-(3-piperidin-1-yl-[1,2,4]triazolo[4,3-a]pyridin-6-yloxy)-1,2,3,4-tetrahydro-naphthalen-1-yl]-urea | (d$_6$-DMSO): 1.28 (9H, s), 1.57-1.66 (2H, m), 1.68-1.77 (4H, m), 1.81-1.96 (2H, m), 1.99-2.16 (5H, m), 2.21-2.50 (8H, m), 3.10-3.17 (4H, m), 3.57 (2H, br s), 4.76-4.84 (1H, m), 5.55 (1H, br t, J = 4.3 Hz), 6.33 (1H, s), 6.96 (1H, d, J = 8.4 Hz), 7.16 (1H, dd, J = 2.2, 10.0 Hz), 7.23-7.45 (5H, m), 7.55 (1H, d, J = 8.4 Hz), 7.58-7.63 (3H, m), 8.14 (1H, br s). | (Method 5): Rt 3.57 min, m/z 751.3 [MH$^+$]. |
| 8 | Morpholine (3.5 eq.) | MeD | 1-[5-tert-Butyl-2-(4-chloro-3-morpholin-4-ylmethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea | (d$_6$-DMSO): 1.28 (9H, s), 1.57-1.65 (2H, m), 1.68-1.76 (4H, m), 1.80-1.96 (2H, m), 1.99-2.16 (2H, m), 2.40-2.47 (4H, m), 3.10-3.17 (4H, m), 3.51-3.61 (6H, m), 4.76-4.84 (1H, m), 5.54 (1H, br t, J = 4.3 Hz), 6.33 (1H, s), 6.97 (1H, d, J 8.4), 7.16 (1H, dd, J = 2.0, 10.1 Hz), 7.21-7.46 (5H, m), 7.56 (1H, d, J = 8.5 Hz), 7.59-7.64 (3H, m), 8.14 (1H, br s). | (Method 5): Rt 3.58 min, m/z 738.3 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 9 | Dimethylamine (2M solution in THF) | 53d | 1-{5-tert-Butyl-2-[4-chloro-3-(2-dimethylamino-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea | ($d_6$-DMSO): 1.28 (9H, s), 1.57-1.66 (2H, m), 1.67-1.78 (4H, m), 1.79-1.97 (2H, m), 1.99-2.17 (2H, m), 2.19 (6H, s), 2.64 (2H, t, J = 5.7 Hz), 3.11-3.17 (4H, m), 4.16 (2H, t, J = 5.6 Hz), 4.76-4.85 (1H, m), 5.55 (1H, t, J = 4.3 Hz), 6.34 (1H, s), 7.05-7.18 (3H, m), 7.22-7.41 (5H, m), 7.54 (1H, d, J = 8.4 Hz), 7.59-7.65 (2H, m), 8.15 (1H, br s). | (Method 5): Rt 3.53 mins, m/z 726.3 [MH⁺]. |

TABLE 3-continued

Amine Displacement.

| Ex No. | Amine (equivalents used) | Intermediate | Example Structure | NMR (400 MHz) δ | LCMS |
|---|---|---|---|---|---|
| 10 | Diethylamine (3.0 eq) | 53d | 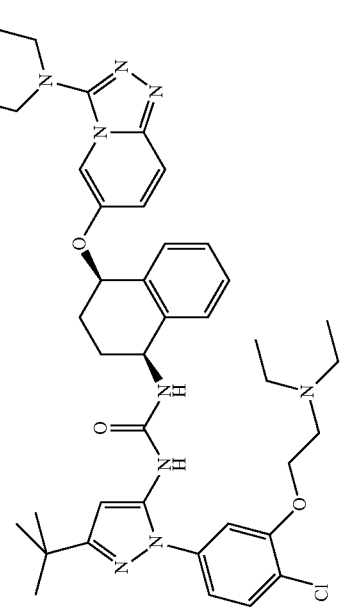<br>1-{5-tert-Butyl-2-[4-chloro-3-(2-diethylamino-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea | d$_6$-DMSO: 0.92 (6H, t, J = 7.2 Hz), 1.28 (9H, s), 1.57-1.66 (2H, m), 1.67-1.78 (4H, m), 1.79-1.97 (2H, m), 1.99-2.17 (2H, m), 2.51 (4H, q, under DMSO), 2.78 (2H, t, J = 5.8 Hz), 3.11-3.17 (4H, m), 4.11 (2H, t, J = 5.8 Hz), 4.77-4.85 (1H, m), 5.55 (1H, t, J = 4.3 Hz), 6.34 (1H, s), 7.04-7.18 (3H, m), 7.23-7.41 (5H, m), 7.54 (1H, d, J = 8.4 Hz), 7.59-7.64 (2H, m), 8.14 (1H, br s). | (Method 5): Rt 3.68 mins, m/z 754.4 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 11 | Piperidine (3.0 eq.) | 53d | 1-{5-tert-Butyl-2-[4-chloro-3-(2-piperidin-1-yl-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea | d₆-DMSO: 1.24-1.33 (1H, m), 1.37-1.46 (4H, m), 1.57-1.66 (2H, m), 1.68-1.78 (4H, m), 1.79-1.97 (2H, m), 1.99-2.17 (2H, m), 2.36-2.44 (4H, m), 2.62-2.70 (2H, m), 3.11-3.17 (4H, m), 4.17 (2H, t, J = 5.8 Hz), 4.76-4.85 (1H, m), 5.53 (1H, t, J = 4.3 Hz), 6.34 (1H, s), 7.07-7.18 (3H, m), 7.23-7.41 (5H, m), 7.53 (1H, d, J = 8.4 Hz), 7.59-7.64 (2H, m), 8.17 (1H, br s). | (Method 5): Rt 3.67 mins, m/z 766.6 [MH⁺]. |
| 12 | Pyrrolidine (3.0 eq.) | 53d | 1-{5-tert-Butyl-2-[4-chloro-3-(2-pyrrolidin-1-yl-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea | d₆-DMSO: 1.28 (9H, s), 1.57-1.66 (6H, m), 1.68-1.78 (4H, m), 1.80-1.97 (2H, m), 1.98-2.16 (2H, m), 2.46-2.55 (presumed 4H, m, under DMSO), 2.75-2.83 (2H, m), 3.11-3.17 (4H, m), 4.17 (2H, t, J = 5.8 Hz), 4.76-4.85 (1H, m), 5.55 (1H, t, J = 4.2 Hz), 6.34 (1H, s), 7.06-7.18 (3H, m), 7.22-7.41 (5H, m), 7.54 (1H, d, J = 8.5 Hz), 7.59-7.64 (2H, m), 8.15 (1H, br s). | (Method 5): Rt 3.62 mins, m/z 752.5 [MH⁺]. |

TABLE 3-continued

Amine Displacement.

| Ex No. | Amine (equivalents used) | Intermediate | Example Structure | NMR (400 MHz) δ | LCMS |
|---|---|---|---|---|---|
| 13 | Dimethylamine (2M solution in THF) | NdB | 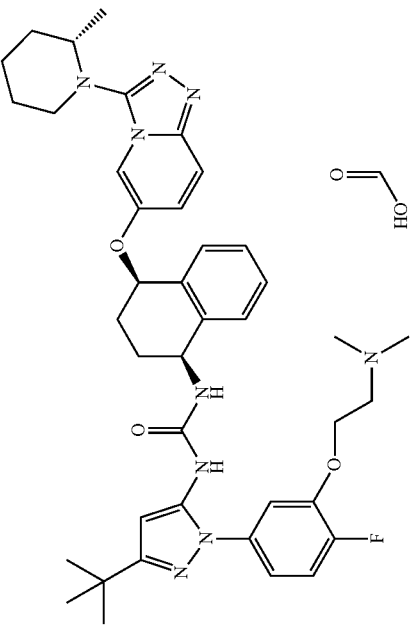<br>1-{5-tert-Butyl-2-[4-methyl-3-(2-morpholin-4-yl-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt | (d₆-DMSO): 0.91 (3H, d, J = 6.2 Hz), 1.27 (9H, s), 1.45-1.56 (2H, m), 1.62-1.72 (2H, m), 1.74-1.97 (4H, m), 2.00-2.18 (2H, m), 2.19 (6H, s), 2.64 (2H, t, J = 5.7 Hz), 2.87-2.95 (1H, m), 3.12-3.20 (1H, m, obscured by water), 3.27-3.35 (1H, m, obscured by water), 4.15 (2H, t, J = 5.6 Hz), 4.78-4.85 (1H, m), 5.52 (1H, t, J = 4.3 Hz), 6.33 (1H, s), 7.02-7.07 (1H, m), 7.09 (1H, d, J = 8.6 Hz), 7.18 (1H, dd, J = 9.7, 2.2 Hz), 7.24-7.39 (6H, m), 7.64 (1H, d, J = 9.6 Hz), 7.69 (1H, d, J = 1.7 Hz), 8.10 (1H, s), 8.17 (1H, s) | (Method 5): Rt 3.63 mins, m/z 724.4 [MH⁺]. |

TABLE 3-continued

Amine Displacement.

| Ex No. | Amine (equivalents used) | Intermediate | Example Structure | NMR (400 MHz) δ | LCMS |
|---|---|---|---|---|---|
| 14 | Dimethylamine (2M solution in THF) | NdC | 1-{5-tert-Butyl-2-[3-(2-dimethylamino-ethoxy)-4-fluoro-phenyl]-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt | (d₆-DMSO): 0.60 (3H, d, J = 6.2 Hz), 0.63 (3H, d, J = 6.2 Hz), 1.27 (9H, s), 1.38-1.58 (3H, m), 1.67-1.75 (2H, m), 1.77-1.98 (3H, m), 2.04-2.11 (2H, m), 2.18 (6H, s), 2.63 (2H, t, J = 5.9 Hz), 3.12-3.23 (2H, m, obscured by water), 4.15 (2H, t, J = 5.8 Hz), 4.78-4.86 (1H, m), 5.53 (1H, t, J = 4.1 Hz), 6.33 (1H, s), 7.02-7.07 (1H, m), 7.09 (1H, d, J = 8.6 Hz), 7.20 (1H, dd, J = 9.8, 2.3 Hz), 7.23-7.28 (2H, m), 7.29-7.37 (4H, m), 7.67 (1H, d, J = 10.0 Hz), 7.87 (1H, d, J = 2.0 Hz), 8.09 (1H, s), 8.17 (1H, s) | (Method 5): Rt 3.80 mins, m/z 738.5 [MH⁺]. |

TABLE 3-continued

Amine Displacement.

| Ex No. | Amine (equivalents used) | Intermediate | Example Structure | NMR (400 MHz) δ | LCMS |
|---|---|---|---|---|---|
| 15 | Dimethylamine (2M solution in THF) | Qdb | 1-{5-tert-Butyl-2-[3-chloro-5-(2-dimethylamino-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | (400 MHz, d$_6$-DMSO): 0.91 (3H, d, J = 6.3 Hz), 1.28 (9H, s), 1.45-1.56 (2H, m), 1.62-1.71 (2H, m), 1.75-1.85 (2H, m), 1.86-1.94 (1H, m), 2.00-2.08 (1H, m), 2.11-2.16 (1H, m), 2.19 (6H, s), 2.63 (2H, t, J = 5.7 Hz), 2.90 (1H, ddd, J = 12.2, 9.3, 3.8 Hz), 3.16 (1H, dt, J = 11.5, 4.5 Hz), 3.29-3.34 (1H, m), 4.12 (2H, t, J = 5.7 Hz), 4.81 (1H, m), 5.52 (1H, t, J = 4.2 Hz), 6.32 (1H, s), 7.06 (1H, t, J = 2.1 Hz), 7.10 (1H, t, J = 2.1 Hz), 7.14 (1H, d, J = 8.7 Hz), 7.18-7.21 (2H, m), 7.25-7.38 (4H, m), 7.64 (1H, dd, J = 0.8, 9.8 Hz), 7.69 (1H, d, J = 2.1), 8.16 (1H, s), 8.20 (1H, s). | (Method 5): Rt 3.80 min, m/z 740.5 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 16 | Morpholine (3.0 eq) | ReD | 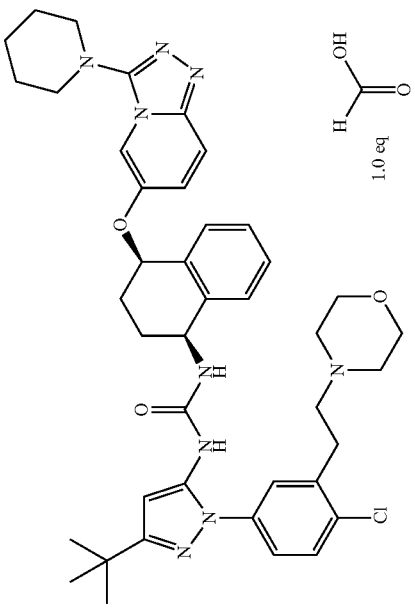<br>1-{5-tert-Butyl-2-[4-chloro-3-(2-morpholin-4-yl-ethyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt | (400 MHz, d$_6$-DMSO): 1.28 (9H, s), 1.58-1.64 (2H, m), 1.69-1.76 (4H, m), 1.81-1.95 (2H, m), 1.99-2.16 (2H, m), 2.41 (4H, t, J = 4.2 Hz), 2.52-2.55 (2H, m), 2.90 (2H, dd, J = 6.4, 9.1 Hz), 3.14 (4H, t, J = 5.2 Hz), 3.54 (4H, t, J = 4.5 Hz), 4.80 (1H, td, J = 8.5, 5.3 Hz), 5.54 (1H, t, J = 4.3 Hz), 6.33 (1H, s), 7.06 (1H, d, J = 8.5 Hz), 7.16 (1H, dd, J = 9.8, 2.2 Hz), 7.23-7.35 (3H, m), 7.37 (1H, d, J = 2.2 Hz), 7.40 (1H, d, J 2.6 Hz), 7.53 (1H, d, J = 8.6 Hz), 7.55 (1H, d, J = 2.5 Hz), 7.61 (1H, dd, J = 0.9, 8.0 Hz), 7.63 (1H, s), 8.14 (1H, s). | (Method 5): Rt 3.55 min, m/z 752.5 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 17 | Dimethylamine (2M solution in THF) | ReD | 1-{5-tert-Butyl-2-[4-chloro-3-(2-dimethylamino-ethyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]urea formate salt | (d₆-DMSO): 1.28 (9H, s), 1.58-1.65 (2H, m), 1.68-1.78 (4H, m), 1.81-1.95 (2H, m), 2.00-2.15 (2H, m), 2.17 (6H, s), 2.45-2.49 (2H, m), 2.86 (2H, dd, J = 8.8, 6.5 Hz), 3.14 (4H, t, J = 5.2 Hz), 4.80 (1H, td, J = 8.5, 5.6 Hz), 5.54 (1H, t, J = 4.3 Hz), 6.33 (1H, s), 7.06 (1H, d, J = 8.6 Hz), 7.16 (1H, dd, J = 2.0, 10.0 Hz), 7.24-7.40 (6H, m), 7.52 (1H, d, J = 1.8 Hz), 7.54 (1H, d, J = 4.3 Hz), 7.61 (1H, dd, J = 7.3, 0.9 Hz), 7.63 (1H, s), 8.14 (1H, s). | (Method 5): Rt 3.53 min, m/z 710.5 [MH⁺]. |
| 18 | Piperidine (3.0 eq) | ScD | 1-[5-tert-Butyl-2-(3-chloro-5-piperidin-1-ylmethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea | (d₆-DMSO): 1.28 (9H, s), 1.31-1.38 (2H, m), 1.42-1.51 (4H, m), 1.57-1.65 (2H, m), 1.67-1.77 (4H, m), 1.84-1.93 (2H, m), 1.97-2.08 (1H, m), 2.09-2.37 (1H, m), 2.26-2.38 (4H, m), 3.14 (4H, t, J = 5.2 Hz), 3.47 (2H, s), 4.76-4.85 (1H, m), 5.54 (1H, t, J = 4.0 Hz), 6.32 (1H, s), 7.05 (1H, d, J = 8.5 Hz), 7.16 (1H, dd, J = 2.0, 10.0 Hz), 7.24-7.34 (3H, m), 7.34-7.40 (2H, m), 7.41-7.43 (1H, m), 7.47 (1H, t, J = 2.0 Hz), 7.59-7.64 (2H, m), 8.18 (1H, s). | (Method 5): Rt 3.68 min, m/z 736, 738 [MH⁺]. |

TABLE 3-continued

Amine Displacement.

| Ex No. | Amine (equivalents used) | Intermediate | Example Structure | NMR (400 MHz) δ | LCMS |
|---|---|---|---|---|---|
| 19 | 1-methyl piperazine (3.0 eq.) | ScD | 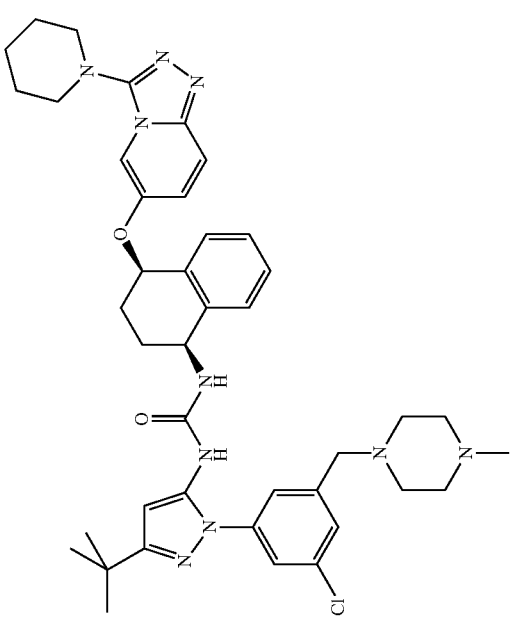  1-{5-tert-Butyl-2-[3-chloro-5-(4-methyl-piperazin-1-ylmethyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea | (d$_6$-DMSO): 1.28 (9H, s), 1.57-1.65 (2H, m), 1.68-1.78 )4H, m), 1.84-1.95 (2H, m), 1.97-2.07 (1H, m), 2.10 (3H, s), 2.09-2.18 (1H, m), 2.19-2.47 (7H, m), 3.14 (4H, t, J = 5.1 Hz), 3.32 (1H, m, obscured by water), 3.50 (2H, s), 4.80 (1H, dd, J = 6.4, 8.2 Hz), 5.54 (1H, t, J = 4.1 Hz), 6.32 (1H, s), 7.05 (1H, broad d, J = 8.3 Hz), 7.16 (1H, dd, J = 2.0, 10.0 Hz), 7.24-7.34 (3H, m), 7.34-7.40 (2H, m), 7.42 (1H, s), 7.46-7.51 (1H, m), 7.58-7.65 (2H, m), 8.19 (1H, s). | (Method 5): Rt 3.66 min, m/z 751, 753 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 20 | Dimethylamine (2M in MeOH) | TfD | 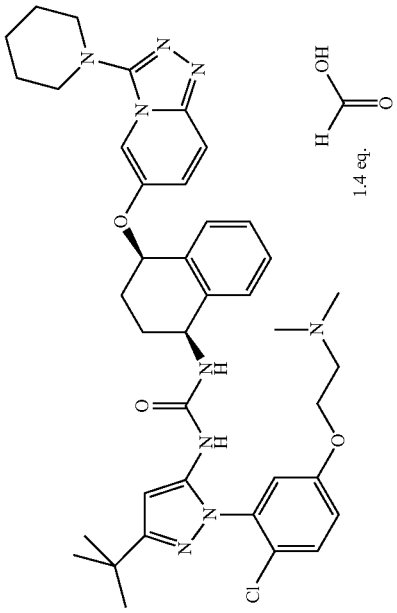<br>1-{5-tert-Butyl-2-[2-chloro-5-(2-dimethylamino-ethoxy)-phenyl]-2H-pyrazol-3-yl}-3-{(1S,4R)-4-(3-piperidin-1-yl-[1,2,4]triazolo[4,3-a]pyridin-6-yloxy)-1,2,3,4-tetrahydro-naphthalen-1-yl]-urea formate salt | (d$_6$-DMSO): 1.21 (9H, s), 1.54-1.60 (2H, m), 1.54-1.72 (4H, m), 1.74-1.84 (1H, m), 1.86-1.94 (1H, m), 1.96-2.08 (2H, m), 2.16 (6H, s), 2.59 (2H, t, J = 5.6 Hz), 3.09 (4H, t, J = 5.3 Hz), 4.05 (2H, t, J = 5.7 Hz), 4.77 (1H, td, J = 8.4, 5.5 Hz), 5.50 (1H, t, J = 4.5 Hz), 6.28 (1H, s), 6.95 (1H, d, J = 8.5 Hz), 7.05-7.12 (3H, m), 7.19-7.27 (3H, m), 7.33 (1H, dd, J = 7.6, 1.1 Hz), 7.49 (1H, d, J = 8.8 Hz), 7.56 (1H, d, J = 9.9 Hz), 7.58 (1H, d, J = 1.7 Hz), 7.89 (1H, s), 8.12 (1.4H, s). | (Method 5): Rt 3.59 mins, m/z 726 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 21 | Morpholine (3.0 eq.) | UcC | 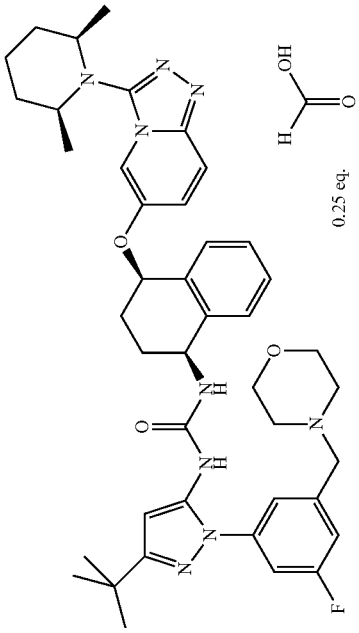<br>1-[5-tert-Butyl-2-(3-fluoro-5-morpholin-4-ylmethyl-phenyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt | (d$_6$-DMSO): 0.56 (3H, d, J = 6.2 Hz), 0.59 (3H, d, J = 6.2 Hz), 1.24 (9H, s), 1.36-1.56 (3H, m), 1.64-1.70 (2H, m), 1.73-1.80 (1H, m), 1.80-1.92 (2H, m), 1.97-2.10 (2H, m), 2.34 (4H, t, J = 4.3 Hz), 3.08-3.22 (2H, m), 3.48 (2H, s), 3.51 (4H, t, J = 4.5 Hz), 4.77 (1H, td, J = 8.4, 6.1 Hz), 5.48 (1H, t, J = 4.1 Hz), 6.29 (1H, s), 7.05 (1H, d, J = 8.6 Hz), 7.13 (1H, d, J = 9.5 Hz), 7.17 (1H, dd, J = 9.9, 2.2 Hz), 7.19-7.33 (6H, m), 7.62 (1H, d, J = 10.0 Hz), 7.84 (1H, d, J = 1.7 Hz), 8.13 (1H, s), 8.15 (0.25 H, br s). | (Method 5): Rt 3.86 mins, m/z 750 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 22 | 1-Methyl-piperazine (3.0. eq.) | UcC | 1-{5-tert-Butyl-2-[3-fluoro-5-(4-methyl-piperazin-1-ylmethyl)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt | (d₆-DMSO): 0.55 (3H, d, J = 6.1 Hz), 0.59 (3H, d, J = 6.1 Hz), 1.23 (9H, s), 1.35-1.56 (3H, m), 1.63-1.69 (2H, m), 1.73-1.80 (1H, m), 1.80-1.92 (2H, m), 1.95-2.10 (2H, m), 2.08 (3H, s), 2.22-2.42 (10H, br m), 3.10-3.22 (2H, m), 3.47 (3H, s), 4.77 (1H, td, J = 8.6, 5.9 Hz), 5.48 (1H, t, J = 4.2 Hz), 6.29 (1H, s), 7.05 (1H, d, J = 8.7 Hz), 7.10 (1H, d, J = 9.6 Hz), 7.17 (1H, dd, J = 9.8, 2.2 Hz), 7.19-7.28 (5H, m), 7.29-7.32 (1H, m), 7.62 (1H, d, J = 9.7 Hz), 7.84 (1H, d, J = 1.8 Hz), 8.14 (2.2H, s). | (Method 5): Rt 3.89 mins, m/z 763 [MH⁺]. |

TABLE 3-continued

Amine Displacement.

| Ex No. | Amine (equivalents used) | Intermediate | Example Structure | NMR (400 MHz) δ | LCMS |
|---|---|---|---|---|---|
| 23 | Dimethylamine (2M in MeOH) | WeC | 1-{5-tert-Butyl-2-[3-(2-dimethylamino-ethoxy)-5-fluoro-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt · 1.3 eq. HCOOH | (d₆-DMSO): 0.56 (3H, d, J = 6.3 Hz), 0.59 (3H, d, J = 6.3 Hz), 1.23 (9H, s), 1.35-1.57 (3H, m), 1.64-1.70 (2H, m), 1.72-1.80 (1H, m), 1.81-1.93 (2H, m), 1.95-2.10 (2H, m), 2.15 (6H, s), 2.58 (2H, t, J = 5.7 Hz), 3.10-3.20 (2H, m), 4.06 (2H, t, J = 5.7 Hz), 4.78 (1H, td, J = 8.8, 5.9 Hz), 5.49 (1H, t, J = 4.0 Hz), 6.29 (1H, s), 6.83 (1H, dt, J = 10.9, 2.2 Hz), 6.90-6.95 (2H, m), 7.11 (1H, d, J = 8.7 Hz), 7.17 (1H, dd, J = 9.8, 2.2 Hz), 7.20-7.33 (4H, m), 7.62 (1H, d, J = 9.8 Hz), 7.84 (1H, d, J = 1.9 Hz), 8.12 (1.3H, s), 8.14 (1H, s). | (Method 5): Rt 3.86 mins, m/z 738 [MH⁺]. |

TABLE 3-continued

Amine Displacement.

| Ex No. | Amine (equivalents used) | Intermediate | Example Structure | NMR (400 MHz) δ | LCMS |
|---|---|---|---|---|---|
| 24 | Morpholine (3.0 eq.) | UcB | 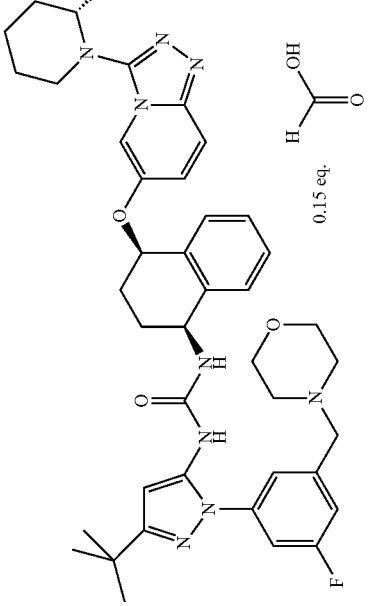<br>1-[5-tert-Butyl-2-(3-fluoro-5-morpholin-4-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | (d$_6$-DMSO): 0.86 (3H, d, J = 6.3 Hz), 1.24 (9H, s), 1.42-1.52 (2H, m), 1.58-1.68 (2H, m), 1.72-1.92 (4H, m), 1.96-2.05 (1H, m), 2.05-2.14 (1H, m), 2.34 (4H, t, J = 4.0 Hz), 2.86 (1H, ddd, J = 12.6, 9.0, 3.9 Hz), 3.12 (1H, dt, J = 11.7, 3.9 Hz), 1H, obscured by solvent, 3.48 (2H, s), 3.52 (4H, t, J = 4.4 Hz), 4.77 (1H, td, J = 8.3, 6.9 Hz), 5.47 (1H, t, J = 4.1 Hz), 6.29 (1H, s), 7.04 (1H, d, J = 8.6 Hz), 7.13 (1H, d, J = 9.2 Hz), 7.15 (1H, dd, J = 9.8, 2.1 Hz), 7.20-7.31 (5H, m), 7.31-7.34 (1H, d, J = 7.2 Hz), 7.60 (1H, d, J = 9.9 Hz), 7.65 (1H, d, J = 1.9 Hz), 8.12 (1H, s), 8.19 (0.15H, br s). | (Method 5): Rt 3.69 mins, m/z 736 [MH$^+$]. |

0.15 eq.

TABLE 3-continued

Amine Displacement.

| Ex No. | Amine (equivalents used) | Intermediate | Example Structure | NMR (400 MHz) δ | LCMS |
|---|---|---|---|---|---|
| 25 | N—Me-piperazine (3.0 eq.) | UcB | 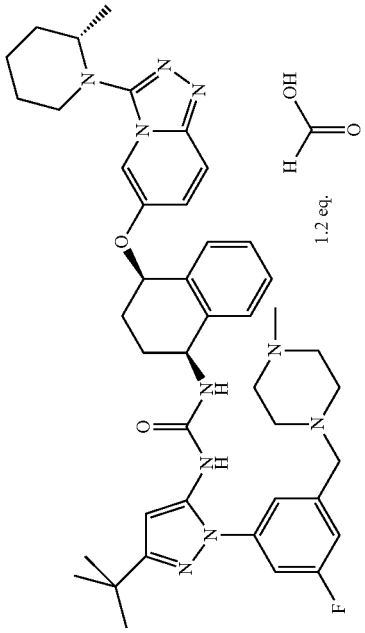 1-{5-tert-Butyl-2-[3-fluoro-5-(4-methyl-piperazin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | (d₆-DMSO): 0.86 (3H, d, J = 6.4 Hz), 1.24 (9H, s), 1.43-1.52 (2H, m), 1.58-1.68 (2H, m), 1.70-1.92 (4H, m), 1.96-2.04 (1H, m), 2.08 (3H, s), 2.08-2.13 (1H, m), 2.20-2.40 (10H, br m), 2.86 (1H, ddd, J = 12.6, 9.3, 4.0 Hz), 3.12 (1H, dt, J = 11.6, 4.1 Hz), 3.24-3.31 (1H, m), 3.48 (2H, s), 4.77 (1H, td, J = 8.3, 6.0 Hz), 5.47 (1H, t, J = 4.0 Hz), 6.29 (1H, s), 7.06 (1H, d, J = 8.6 Hz), 7.10 (1H, d, J = 9.3 Hz), 7.15 (1H, dd, J = 9.9, 2.1 Hz), 7.21-7.29 (5H, m), 7.31-7.35 (1H, m), 7.60 (1H, d, J = 9.7 Hz), 7.65 (1H, d, J = 1.9 Hz), 8.15 (1.2H, s), 8.16 (1H, s). | (Method 5): Rt 3.73 mins, m/z 749 [MH⁺]. |

TABLE 3-continued

Amine Displacement.

| Ex No. | Amine (equivalents used) | Intermediate | Example Structure | NMR (400 MHz) δ | LCMS |
|---|---|---|---|---|---|
| 26 | Dimethylamine (2M in MeOH) | WeB | 1-{5-tert-Butyl-2-[3-(2-dimethylamino-ethoxy)-5-fluoro-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | (d$_6$-DMSO): 0.86 (3H, d, J = 6.3 Hz), 1.23 (9H, s), 1.42-1.51 (2H, m), 1.58-1.68 (2H, m), 1.70-1.82 (2H, m), 1.82-1.92 (2H, m), 1.95-2.04 (1H, m), 2.08-2.14 (1H, m), 2.14 (6H, s), 2.58 (2H, t, J = 5.7 Hz), 2.86 (1H, ddd, J = 12.6, 9.3, 4.1 Hz), 3.12 (1H, dt, J = 11.9, 4.1 Hz), 3.24-3.31 (1H, m), 4.06 (2H, t, J = 5.7 Hz), 4.77 (1H, td, J = 8.2, 6.3 Hz), 5.47 (1H, t, J = 4.0 Hz), 6.29 (1H, s), 6.83 (1H, dt, J = 10.8, 2.2 Hz), 6.90-6.95 (2H, m), 7.13 (1H, d, J = 8.6 Hz), 7.16 (1H, dd, J = 9.9, 2.1 Hz), 7.20-7.26 (2H, m), 7.26-7.30 (1H, m), 7.30-7.34 (1H, m), 7.60 (1H, d, J = 9.8 Hz), 7.65 (1H, d, J = 1.9 Hz), 8.14 (1.2H, s), 8.18 (1H, s). | (Method 5): Rt 3.71 mins, m/z 724 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 27 | Dimethylamine (2M in MeOH) | XdB | 1-{5-tert-Butyl-2-[4-cyano-3-(2-dimethylamino-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt 0.4 eq. | (d$_6$-DMSO): 0.86 (3H, d, J = 6.3 Hz), 1.24 (9H, s), 1.42-1.52 (2H, m), 1.58-1.68 (2H, m), 1.70-1.82 (2H, m), 1.82-1.90 (2H, m), 1.94-2.04 (1H, m), 2.06-2.14 (1H, m), 2.14 (6H, s), 2.58-2.62 (2H, m), 2.86 (1H, ddd, J = 12.8, 9.0, 4.1 Hz), 3.12 (1H, dt, J = 12.0, 4.3 Hz), 3.24-3.30 (1H, m), 4.18 (2H, t, J = 5.7 Hz), 4.75 (1H, td, J = 8.5, 5.8 Hz), 5.47 (1H, t, J = 4.1 Hz), 6.33 (1H, s), 7.14 (1H, dd, J = 9.7, 2.1 Hz), 7.17-7.21 (2H, m), 7.22-7.30 (3H, m), 7.33 (1H, dd, J = 7.3, 1.6 Hz), 7.39 (1H, d, J = 1.8 Hz), 7.60 (1H, dd, J = 9.8, 0.7 Hz), 7.65 (1H, d, J = 1.9 Hz), 7.79 (1H, d, J = 16.3 Hz), 8.23 (0.4H, s), 8.38 (1H, s). | (Method 5): Rt 3.72 mins, m/z 731 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 28 | [1,4]-Oxazepane (3.0 eq.) | Intermediate 53d | 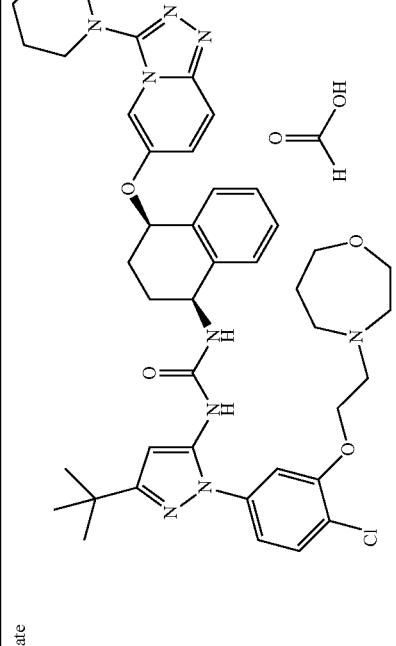<br>1-{5-tert-Butyl-2-[4-chloro-3-(2-[1,4]oxazepan-4-yl-ethoxy)-phenyl]-2H-pyrazol-3-yl}-3-{(1S,4R)-4-(3-piperidin-1-yl-[1,2,4]triazolo[4,3-a]pyridin-6-yloxy)-1,2,3,4-tetrahydro-naphthalen-1-yl]-urea formate salt | (d$_6$-DMSO): 1.28 (9H, s), 1.57-1.65 (2H, m), 1.67-1.77 (6H, m), 1.79-1.97 (2H, m), 1.98-2.17 (2H, m), 2.69-2.75 (4H, m), 2.87-2.92 (2H, m), 3.14 (4H, t, J = 5.2 Hz, obscured by water), 3.52-3.56 (2H, m, obscured by water), 3.60 (2H, t, J = 6.0 Hz, obscured by water), 4.17 (2H, t, J = 5.7 Hz), 4.76-4.85 (1H, m), 5.55 (1H, t, J = 4.1 Hz), 6.34 (1H, s), 7.06-7.12 (2H, m), 7.15 (1H, dd, J = 10.1, 2.0 Hz), 7.22-7.36 (4H, m), 7.39 (1H, dd, J = 7.4, 1.7 Hz), 7.54 (1H, d, J = 8.6 Hz), 7.59-7.64 (2H, m), 8.14-8.19 (2H, m). | (Method 5): Rt 3.60 mins, m/z 782.4 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 29 | 8-Oxa-3-aza-bicyclo[3.2.1]octane (3.0 eq.) | Intermediate 53d | 1-(5-tert-Butyl-2-{4-chloro-3-[2-(3-oxa-8-aza-bicyclo[3.2.1]oct-8-yl)-ethoxy]-phenyl}-2H-pyrazol-3-yl)-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt  0.6 eq. | (d$_6$-DMSO): 1.28 (9H, s), 1.57-1.78 (8H, m), 1.79-1.96 (4H, m), 1.98-2.17 (2H, m), 2.62 (2H, t, J = 6.0 Hz), 3.10-3.17 (6H, m, obscured by water), ~3.33 (2H, completely obscured by water), 3.45-3.50 (2H, m, obscured by water), 4.17 (2H, t, J = 5.8 Hz), 4.77-4.85 (1H, m), 5.55 (1H, t, J = 4.2 Hz), 6.34 (1H, s), 7.07-7.17 (3H, m), 7.22-7.41 (5H, m), 7.54 (1H, d, J = 8.5 Hz), 7.60-7.64 (2H, m), 8.18 (1H, s), 8.21 (0.6H, s). | (Method 5): Rt 3.63 mins, m/z 794.6 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 30 | Dimethylamine (2M solution in THF) | ReB | 1-{5-tert-Butyl-2-[4-chloro-3-(2-dimethylamino-ethyl)-phenyl]-2H-pyrazol-3-yl}-3-((1S,4R)-4-[3-((S)-2-methyl-piperidin-1-yl)-[1,2,4]triazolo[4,3-a]pyridin-6-yloxy]-1,2,3,4-tetrahydro-naphthalen-1-yl]-urea formate salt (1.8 eq.) | (d$_6$-DMSO): 0.91 (3H, d, J = 6.2 Hz), 1.28 (9H, s), 1.46-1.56 (2H, m), 1.62-1.73 (2H, m), 1.74-1.98 (4H, m), 1.99-2.17 (2H, m), 2.21 (6H, s), 2.50-2.56 (2H, m, obscured by solvent), 2.85-2.95 (3H, m), 3.12-3.20 (1H, m, obscured by water), 3.27-3.36 (1H, m, obscured by water), 4.76-4.85 (1H, m), 5.51 (1H, t, J = 4.2 Hz), 6.33 (1H, s), 7.08 (1H, d, J = 8.5 Hz), 7.19 (1H, dd, J = 10.0, 2.0 Hz), 7.23-7.42 (5H, m), 7.52-7.56 (2H, m), 7.64 (1H, d, J = 9.8 Hz), 7.69 (1H, d, J = 1.9 Hz), 8.16 (1H, s), 8.17 (1.8H, s). | (Method 5): Rt 3.70 mins, m/z 724.5 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 31 | Dimethylamine (2M solution in THF) | ReC | 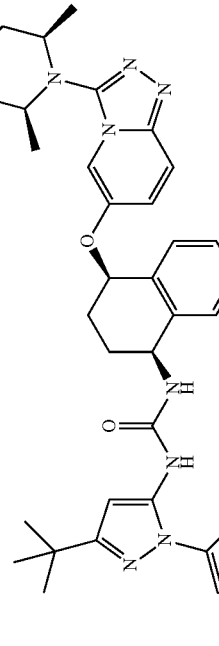<br>1-{5-tert-Butyl-2-[4-chloro-3-(2-dimethylaminoethyl)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt | (d$_6$-DMSO): 0.60 (3H, d, J = 6.1 Hz), 0.63 (3H, d, J = 6.1 Hz), 1.28 (9H, s), 1.38-1.61 (3H, m), 1.66-1.75 (2H, m), 1.76-1.98 (3H, m), 2.02-2.12 (2H, m), 2.18 (6H, s), 2.87 (2H, br, t, J = 7.8 Hz), 3.12-3.24 (4H, m, obscured by water), 4.77-4.85 (1H, m), 5.52 (1H, t, J = 4.2 Hz), 6.33 (1H, s), 7.07 (1H, d, J = 8.7 Hz), 7.18-7.41 (6H, m), 7.51-7.55 (2H, m), 7.67 (1H, d, J = 10.1 Hz), 7.88 (1H, d, J = 2.4 Hz), 8.14 (1H, s), 8.18 (0.9H, s). | (Method 5): Rt 3.87 mins, m/z 738.4 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 32 | Morpholine (3.0 eq.) | ReC | 1-{5-tert-Butyl-2-[4-chloro-3-(2-morpholin-4-yl-ethyl)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt | (d$_6$-DMSO): 0.60 (3H, d, J = 6.1 Hz), 0.64 (3H, d, J = 6.1 Hz), 1.28 (9H, s), 1.38-1.61 (3H, m), 1.66-1.75 (2H, m), 1.76-1.97 (3H, m), 2.01-2.13 (2H, m), 2.38-2.44 (4H, m), 2.50-2.56 (2H, m, obscured by solvent), 2.86-2.93 (2H, m), 3.12-3.23 (2H, m, obscured by water), 3.54 (4H, t, J = 4.5 Hz), 4.76-4.85 (1H, m), 5.52 (1H, t, J = 4.2 Hz), 6.33 (1H, s), 7.07 (1H, d, J = 8.4 Hz), 7.18-7.42 (6H, m), 7.51-7.57 (2H, m), 7.66 (1H, d, J = 10.0 Hz), 7.88 (1H, d, J = 2.1 Hz), 8.15 (1H, s), 8.22 (0.4H, s). | (Method 5): Rt 3.88 mins, m/z 780.4 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 33 | 1-Methyl piperazine (3.0 eq.) | ReC | 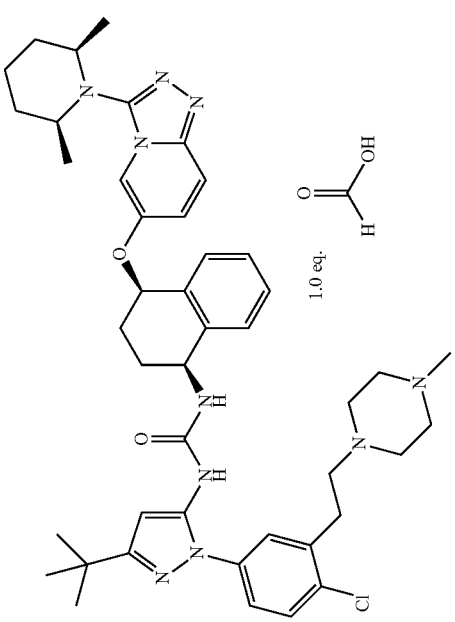 1-(5-tert-Butyl-2-{4-chloro-3-[2-(4-methyl-piperazin-1-yl)-ethyl]-phenyl}-2H-pyrazol-3-yl)-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt | (d$_6$-DMSO): 0.60 (3H, d, J = 6.1 Hz), 0.63 (3H, d, J = 6.1 Hz), 1.28 (9H, s), 1.37-1.62 (3H, m), 1.67-1.75 (2H, m), 1.77-1.98 (3H, m), 2.02-2.11 (2H, m), 2.12 (3H, s), 2.20-2.36 (4H, m), 2.37-2.48 (4H, m), 2.84-2.91 (2H, m), 3.12-3.23 (4H, m, obscured by water), 4.77-4.85 (1H, m), 5.53 (1H, t, J = 4.3 Hz), 6.32 (1H, s), 7.07 (1H, d, J = 8.6 Hz), 7.17-7.41 (6H, m), 7.51-7.56 (2H, m), 7.66 (1H, d, J = 9.9 Hz), 7.88 (1H, d, J = 2.1 Hz), 8.14 (1H, s), 8.18 (1H, s). | (Method 5): Rt 3.84 mins, m/z 793.4 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 34 | 4-Methoxy-piperidine (3.0 eq.) | YeB | 1-(5-tert-Butyl-2-{4-fluoro-3-[2-(4-methoxy-piperidin-1-yl)-ethyl]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt; 1.5 eq. formic acid | (d$_6$-DMSO): 0.91 (3H, d, J = 6.2 Hz), 1.27 (9H, s), 1.32-1.43 (2H, m), 1.44-1.56 (2H, m), 1.60-1.72 (2H, m), 1.72-1.97 (6H, m), 1.99-2.17 (4H, m), 2.50-2.56 (2H, m, obscured by solvent), 2.68-2.76 (2H, m), 2.76-2.83 (2H, m), 2.86-2.95 (1H, m), 3.07-3.17 (2H, m), 3.18 (3H, s), 3.27-3.36 (1H, m, obscured by water), 4.76-4.86 (1H, m), 5.52 (1H, t, J = 4.1 Hz), 6.31 (1H, s), 7.06 (1H, dd, J = 8.6 Hz), 7.19 (1H, dd, J = 9.8, 2.1 Hz), 7.24-7.40 (6H, m), 7.47 (1H, dd, J = 6.9, 2.7 Hz), 7.64 (1H, d, J = 9.8 Hz), 7.69 (1H, d, J = 1.6 Hz), 8.08 (1H, s), 8.17 (1.5H, s). | (Method 5): Rt 3.70 mins, m/z 778.6 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 35 | Azetidine (3.0 eq.) | YeB | 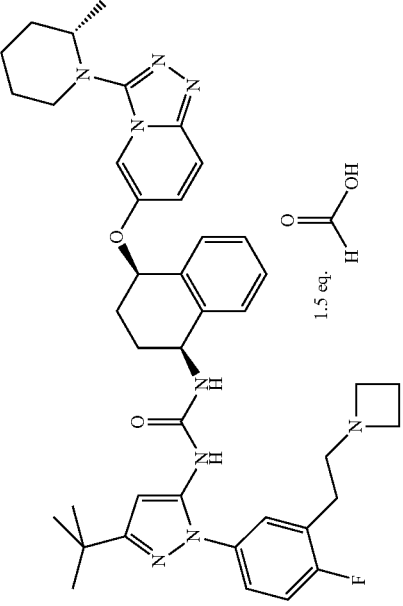<br>1-{2-[3-(2-Azetidin-1-yl-ethyl)-4-fluoro-phenyl]-5-tert-butyl-2H-pyrazol-3-yl}-3-{(1S,4R)-4-[3-(S)-2-methyl-piperidin-1-yl)-[1,2,4]triazolo[4,3-a]pyridin-6-yloxy]-1,2,3,4-tetrahydro-naphthalen-1-yl}-urea formate salt | (d₆-DMSO): 0.91 (3H, d, J = 6.1 Hz), 1.27 (9H, s), 1.46-1.56 (2H, m), 1.61-1.73 (2H, m), 1.75-1.87 (2H, m), 1.88-1.97 (4H, m), 1.99-2.17 (2H, m), 2.63 (4H, s), 2.86-2.94 (1H, m), 3.15 (4H, t, J = 7.0 Hz), 3.12-3.19 (1H, m), 3.27-3.35 (1H, m, obscured by water), 4.77-4.85 (1H, m), 5.51 (1H, t, J = 4.2 Hz), 6.32 (1H, s), 7.10 (1H, d, J = 8.5 Hz), 7.19 (1H, dd, J = 9.9, 2.2 Hz), 7.23-7.40 (6H, m), 7.43 (1H, dd, J = 6.8, 2.8 Hz), 7.64 (1H, d, J = 10.1 Hz), 7.69 (1H, d, J = 1.7 Hz), 8.13 (1H, s), 8.19 (1.5H, s). | (Method 5): Rt 3.67 mins, m/z 720.5 [MH⁺]. |

TABLE 3-continued

Amine Displacement.

| Ex No. | Amine (equivalents used) | Intermediate | Example Structure | NMR (400 MHz) δ | LCMS |
|---|---|---|---|---|---|
| 36 | Azetidin-3-yl-dimethyl-amine (3.0 eq.) | YeB | 1-(5-tert-Butyl-2-{3-[2-(3-dimethylamino-azetidin-1-yl)-ethyl]-4-fluoro-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | (d$_6$-DMSO): 0.91 (3H, d, J = 6.0 Hz), 1.27 (9H, s), 1.45-1.56 (2H, m), 1.61-1.72 (2H, m), 1.74-1.94 (4H, m), 1.96 (6H, s), 1.98-2.18 (2H, m), 2.64 (4H, s), 2.68-2.80 (3H, m), 2.86-2.95 (1H, m), 3.12-3.20 (1H, m), 3.27-3.35 (1H, m), 3.38 (2H, t, J = 5.4 Hz), 4.77-4.86 (1H, m), 5.52 (1H, t, J = 4.2 Hz), 6.31 (1H, s), 7.07 (1H, d, J = 8.7 Hz), 7.19 (1H, dd, J = 10.0, 2.1 Hz), 7.23-7.39 (6H, m), 7.43 (1H, dd, J = 6.8, 2.6 Hz), 7.64 (1H, d, J = 9.6 Hz), 7.69 (1H, d, J = 2.0 Hz), 8.09 (1H, s), 8.17 (1.7H, s). | (Method 5): Rt 3.34 mins, m/z 763.6 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 37 | Dimethylamine (2M solution in THF) | YeB | 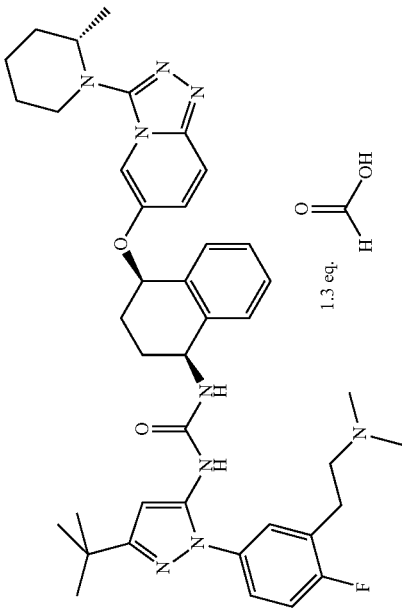<br>1.3 eq.<br>1-{5-tert-Butyl-2-[3-(2-dimethylamino-ethyl)-4-fluoro-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | (d$_6$-DMSO): 0.91 (3H, d, J = 6.1 Hz), 1.28 (9H, s), 1.45-1.56 (2H, m), 1.61-1.72 (2H, m), 1.74-1.98 (4H, m), 1.99-2.16 (2H, m), 2.18 (6H, s), 2.51-2.55 (2H, m, obscured by solvent), 2.79 (2H, t, J = 5.7 Hz), 2.86-2.95 (1H, m), 3.12-3.19 (1H, m, obscured by water), 3.27-3.36 (1H, m, obscured by water), 4.77-4.86 (1H, m), 5.51 (1H, t, J = 4.3 Hz), 6.32 (1H, s), 7.08 (1H, d, J = 8.5 Hz), 7.19 (1H, dd, J = 9.9, 2.1 Hz), 7.24-7.39 (6H, m), 7.46 (1H, dd, J = 6.7, 2.5 Hz), 7.64 (1H, d, J = 10.1 Hz), 7.69 (1H, d, J = 1.6 Hz), 8.10 (1H, s), 8.18 (1.3H, s). | (Method 5): Rt: 3.60 min, m/z 708.5 [MH]. |

TABLE 3-continued

Amine Displacement.

| Ex No. | Amine (equivalents used) | Intermediate | Example Structure | NMR (400 MHz) δ | LCMS |
|---|---|---|---|---|---|
| 38 | Dimethylamine (2M solution in THF) | Intermediate 53dE | 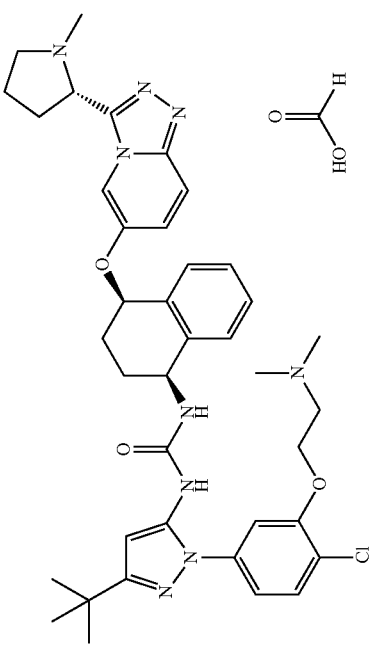<br>1-{5-tert-Butyl-2-[4-chloro-3-(2-dimethylamino-ethoxy)-phenyl]-2H-pyrazol-3-yl}-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea formate salt | (d₆-DMSO): 1.28 (9H, s), 1.81-2.26 (9H, m), 2.13 (3H, s), 2.19 (6H, s), 2.32-2.39 (1H, m), 2.63 (2H, t, J = 5.7 Hz), 3.11-3.16 (1H, m), 3.99 (1H, t, J = 8.2 Hz), 4.15 (2H, t, J = 5.7 Hz), 4.81 (1H, td, J = 8.6, 5.6 Hz), 5.39 (1H, t, J = 4.3 Hz), 6.34 (1H, s), 7.08 (1H, t, J = 2.4 Hz), 7.11 (1H, t, J = 2.4 Hz), 7.24-7.41 (6H, m), 7.54 (1H, d, J = 8.5 Hz), 7.76 (1H, d, J = 9.9 Hz), 8.14 (1H, s), 8.25 (1H, d, J = 2.1 Hz). | (Method 5): Rt 2.80 min, m/z 726.5 [MH⁺]. |

TABLE 3-continued

Amine Displacement.

| Ex No. | Amine (equivalents used) | Intermediate | Example Structure | NMR (400 MHz) δ | LCMS |
|---|---|---|---|---|---|
| 39 | Morpholine (3.0 eq.) | Intermediate 77c | 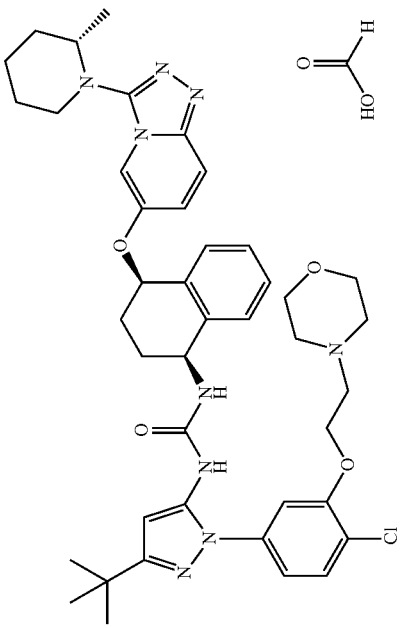<br>1-{5-tert-Butyl-2-[4-chloro-3-(2-morpholin-4-yl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | (d$_6$-DMSO): 0.91 (3H, d, J = 6.3 Hz), 1.28 (9H, s), 1.43-1.57 (2H, m), 1.63-1.73 (2H, m), 1.75-1.96 (4H, m), 2.01-2.17 (2H, m), 2.45 (4H, t, J = 4.5 Hz), 2.65-2.75 (2H, m), 2.91 (1H, ddd, J = 12.2, 9.3, 4.2 Hz), 3.16 (1H, dt, J = 12.2, 4.2 Hz), 3.27-3.33 (1H, m), 3.51 (4H, t, J = 4.6 Hz), 4.20 (2H, t, J = 5.7 Hz), 4.81 (1H, td, J = 8.6, 5.5 Hz), 5.52 (1H, t, J = 4.3 Hz), 6.34 (1H, s), 7.07 (1H, d, J = 8.7 Hz), 7.10 (1H, dd, J = 8.6, 2.4 Hz), 7.18 (1H, dd, J = 9.8, 2.2 Hz), 7.23-7.38 (5H, m), 7.54 (1H, d, J = 8.5 Hz), 7.61 (1H, dd, J = 9.8, 0.8 Hz), 7.70 (1H, d, J = 2.1 Hz), 8.13 (1H, s). | (Method 5): Rt 3.72 min, m/z 782.6 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 40 | Pyrrolidine (3.0 eq.) | MeB | 1-[5-tert-Butyl-2-(4-chloro-3-pyrrolidin-1-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | (d$_6$-DMSO): 0.91 (3H, d, J = 6.3 Hz), 1.28 (9H, s), 1.43-1.56 (2H, m), 1.63-1.72 (6H, m), 1.76-1.96 (4H, m), 2.00-2.16 (2H, m), 2.53 (4H, d, J = 7.9 Hz), 2.90 (1H, ddd, J = 12.3, 8.9, 4.1 Hz), 3.16 (1H, dt, J = 12.3, 4.0 Hz), 3.29-3.34 (1H, m), 3.71 (2H, s), 4.80 (1H, td, J = 8.5, 5.5 Hz), 5.51 (1H, t, J = 4.3 Hz), 6.32 (1H, s), 6.99 (1H, d, J = 8.5 Hz), 7.19 (1H, dd, J = 9.8, 2.2 Hz), 7.23-7.32 (3H, m), 7.36 (1H, td, J = 7.5, 1.6 Hz), 7.42 (1H, dd, J = 8.5, 2.6 Hz), 7.54 (1H, d, J = 8.5 Hz), 7.60 (1H, d, J = 2.6 Hz), 7.64 (1H, dd, J = 9.9, 0.8 Hz), 7.68 (1H, dd, J = 2.1, 0.9 Hz), 8.14 (1H, s), 8.16 (1.4H, s). | (Method 5): Rt 3.70 min, m/z 736.5 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 41 | Morpholine (3.0 eq.) | MeB | 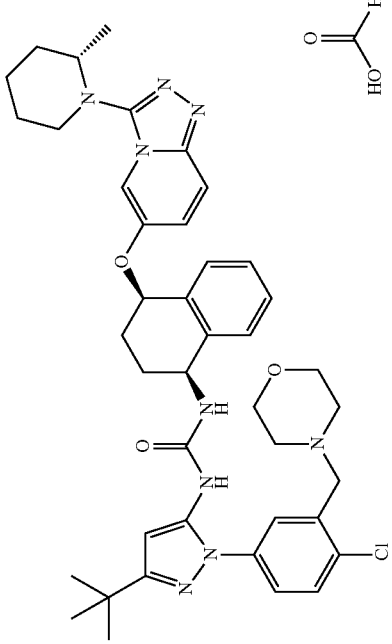<br>1-[5-tert-Butyl-2-(4-chloro-3-morpholin-4-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | (d$_6$-DMSO): 0.91 (3H, d, J = 6.3 Hz), 1.28 (9H, s), 1.47-1.55 (2H, m), 1.63-1.71 (2H, m), 1.75-1.96 (4H, m), 2.00-2.16 (2H, m), 2.44 (4H, t, J = 4.2 Hz), 2.92-2.90 (1H, ddd, J = 12.3, 9.2, 4.1 Hz), 3.16 (1H, dt, J = 12.1, 4.1 Hz), 3.29-3.34 (1H, m), 3.55 (4H, t, J = 4.5 Hz), 3.59 (2H, s), 4.80 (1H, td, J = 8.6, 5.6 Hz), 5.51 (1H, t, J = 4.3 Hz), 6.33 (1H, s), 7.00 (1H, d, J = 8.5 Hz), 7.19 (1H, dd, J = 9.8, 2.1 Hz), 7.22-7.32 (3H, m), 7.35 (1H, td, J = 7.4, 1.6 Hz), 7.44 (1H, dd, J = 8.6, 2.6 Hz), 7.56 (1H, d, J = 8.5 Hz), 7.62-7.65 (2H, m), 7.69 (1H, dd, J = 2.1, 0.9 Hz), 8.17 (1H, s), 8.17 (1H, s). | (Method 5): Rt 3.74 min, m/z 752.5 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 42 | N-methyl piperazine (3.0 eq.) | MeB | 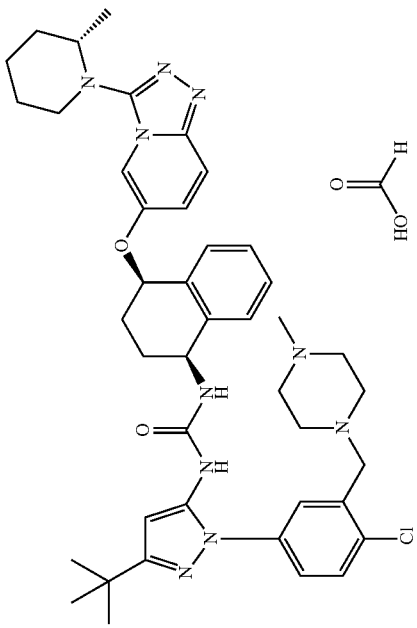  1-{5-tert-Butyl-2-[4-chloro-3-(4-methyl-piperazin-1-ylmethyl)-2H-pyrazol-3-yl]}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | (d$_6$-DMSO): 0.91 (3H, d, J = 6.3 Hz), 1.28 (9H, s), 1.45-1.56 (2H, m), 1.62-1.71 (2H, m), 1.76-1.97 (4H, m), 2.00-2.16 (2H, m), 2.12 (3H, s), 2.32 (4H, br s), 2.46 (4H, br s), 2.90 (1H, ddd, J = 12.2, 9.2, 4.2 Hz), 3.16 (1H, dt, J = 12.2, 4.2 Hz), 3.29-3.34 (1H, m), 3.58 (2H, s), 4.81 (1H, td, J = 8.5, 5.6 Hz), 5.51 (1H, t, J = 4.3 Hz), 6.33 (1H, s), 6.99 (1H, d, J = 8.5 Hz), 7.19 (1H, dd, J = 9.8, 2.2 Hz), 7.25 (1H, d, J = 7.6 Hz), 7.28 (1H, dd, J = 7.3, 1.7 Hz), 7.31 (1H, dd, J = 7.4, 1.8 Hz), 7.36 (1H, td, J = 7.5, 1.6 Hz), 7.43 (1H, dd, J = 8.6, 2.6 Hz), 7.55 (1H, d, J = 8.5 Hz), 7.60 (1H, d, J = 2.6 Hz), 7.64 (1H, dd, J = 9.8, 0.8 Hz), 7.69 (1H, dd, J = 2.1, 0.9 Hz), 8.16 (1H, s), 8.17 (1.5H, br s). | (Method 5): Rt 3.76 min, m/z 765.6 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 43 | Morpholine (3.0 eq.) | MeC | 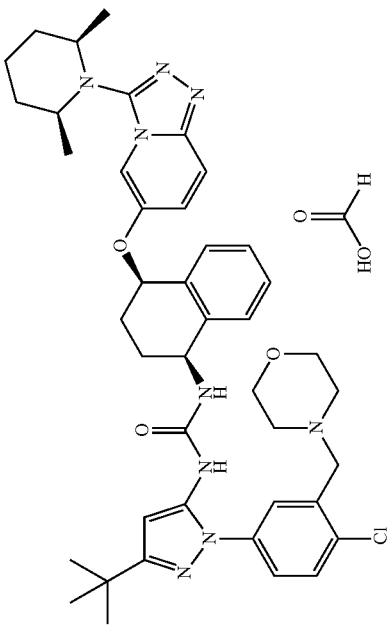<br>1-[5-tert-Butyl-2-{4-chloro-3-morpholin-4-ylmethyl-phenyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt | (d$_6$-DMSO): 0.60 (3H, d, J = 6.2 Hz), 0.63 (3H, d, J = 6.2 Hz), 1.28 (9H, s), 1.39-1.60 (3H, m), 1.68-1.74 (2H, m), 1.77-1.97 (3H, m), 2.02-2.12 (2H, m), 2.44 (4H, t, J = 4.2 Hz), 3.13-3.23 (2H, m), 3.55 (4H, t, J = 4.5 Hz), 3.59 (2H, s), 4.81 (1H, td, J = 8.6, 5.5 Hz), 5.52 (1H, t, J = 4.3 Hz), 6.33 (1H, s), 7.00 (1H, d, J = 8.5 Hz), 7.21 (1H, dd, J = 9.9, 2.1 Hz), 7.24-7.35 (4H, m), 7.44 (1H, dd, J = 8.5, 2.6 Hz), 7.56 (1H, d, J = 8.5 Hz), 7.63 (1H, d, J = 2.6 Hz), 7.67 (1H, d, J = 9.8 Hz), 7.88 (1H, d, J = 2.1 Hz), 8.17 (2H, s). | (Method 5): Rt 3.93 min, m/z 766.6 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 44 | N-methyl piperazine (3.0 eq.) | MeC | 1-{5-tert-Butyl-2-[4-chloro-3-(4-methyl-piperazin-1-ylmethyl)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt (1.5 eq.) | (d$_6$-DMSO): 0.60 (3H, d, J = 6.2 Hz), 0.63 (3H, d, J = 6.2 Hz), 1.28 (9H, s), 1.25-1.60 (3H, m), 1.68-1.73 (2H, m), 1.77-1.97 (3H, m), 2.02-2.12 (2H, m), 2.12 (3H, s), 2.32 (4H, br s), 2.46 (4H, br s), 3.13-3.23 (2H, m), 3.57 (2H, s), 4.81 (1H, td, J = 8.6, 5.5 Hz), 5.53 (1H, t, J = 4.3 Hz), 6.33 (1H, s), 7.01 (1H, d, J = 8.5 Hz), 7.21 (1H, dd, J = 9.8, 2.2 Hz), 7.24-7.36 (4H, m), 7.43 (1H, dd, J = 8.5, 2.6 Hz), 7.55 (1H, d, J = 8.5 Hz), 7.60 (1H, d, J = 2.6 Hz), 7.67 (1H, d, J = 9.8 Hz), 7.88 (1H, d, J = 2.1 Hz), 8.18 (1.5H, s), 8.19 (1H, s). | (Method 5): Rt 3.92 min, m/z 779.6 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 45 | Pyrrolidine (3.0 eq.) | ZcB | 1-[5-tert-Butyl-2-(4-fluoro-3-pyrrolidin-1-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | (d₆-DMSO): 0.90 (3H, d, J = 6.2 Hz), 1.27 (9H, s), 1.50 (2H, m), 1.66 (6H, m), 1.74-2.16 (7H, m), 2.47 (m, signal overlapped with solvent peak), 2.90 (1H, m), 3.16 (m, signal overlapped with solvent peak), 3.65 (2H, s), 4.80 (1H, m), 5.51 (1H, t, J = 4.2 Hz), 6.31 (1H, s), 7.03 (1H, d, J = 8.6 Hz), 7.19 (1H, dd, J = 10.0, 2.1 Hz), 7.22-7.39 (5H, m), 7.42 (1H, m), 7.50 (1H, dd, J = 6.7, 2.9 Hz), 7.64 (1H, d, J = 10.1 Hz), 7.68 (1H, m), 8.11 (1H, s), 8.21 (1H, s). | (Method 5): Rt 3.63 mins, m/z 720 [MH⁺]. |

TABLE 3-continued

Amine Displacement.

| Ex No. | Amine (equivalents used) | Intermediate | Example Structure | NMR (400 MHz) δ | LCMS |
|---|---|---|---|---|---|
| 46 | 1-Methyl piperazine (3.0 eq.) | ZcB | 1-{5-tert-Butyl-2-[4-fluoro-3-(4-methyl-piperazin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | (d$_6$-DMSO): 0.91 (3H, d, J = 6.6 Hz), 1.27 (9H, s), 1.50 (2H, m), 1.66 (2H, m), 1.74-2.15 (6H, m), 2.09 (3H, s), 2.28 (4H, m), 2.42 (4H, m), 2.90 (1H, m), 3.16 (m, signal overlapped with solvent peak), 3.54 (s, signal overlapped with solvent peak), 4.81 (1H, m), 5.51 (1H, t, J = 4.4 Hz), 6.31 (1H, s), 7.02 (1H, d, J = 8.4 Hz), 7.19 (1H, dd, J = 9.7, 2.2 Hz), 7.23-7.39 (5H, m), 7.43 (1H, m), 7.48 (1H, dd, J = 6.7, 2.7 Hz), 7.64 (1H, d, J = 9.7 Hz), 7.68 (1H, d, J = 1.8 Hz), 8.13 (1H, s), 8.21 (1H, s). | (Method 5): Rt 3.64 mins, m/z 749 [MH$^+$]. |

TABLE 3-continued

Amine Displacement.

| Ex No. | Amine (equivalents used) | Intermediate | Example Structure | NMR (400 MHz) δ | LCMS |
|---|---|---|---|---|---|
| 47 | Morpholine (3.0 eq.) | ZcB | 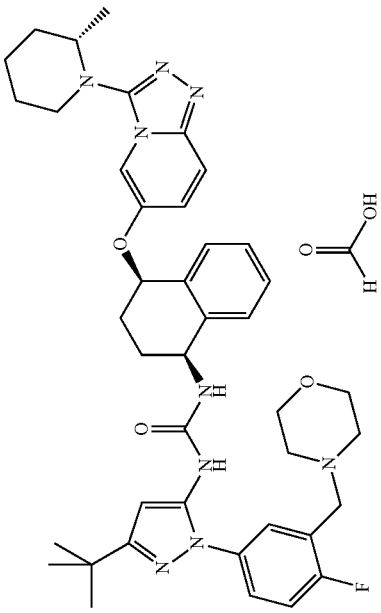

1-[5-tert-Butyl-2-(4-fluoro-3-morpholin-4-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | (d$_6$-DMSO): 0.91 (3H, d, J = 6.2 Hz), 1.27 (9H, s), 1.50 (2H, m), 1.66 (2H, m), 1.74-1.96 (4H, m), 1.99-2.17 (2H, m), 2.40 (4H, m), 2.90 (1H, m), 3.16 (1H, m), 3.50-3.57 (6H, m), 4.80 (1H, m), 5.51 (1H, t, J = 4.1 Hz), 6.31 (1H, s), 7.04 (1H, d, J = 8.6 Hz), 7.19 (1H, dd, J = 9.7, 2.1 Hz), 7.22-7.38 (5H, m), 7.44 (1H, m), 7.51 (1H, dd, J = 6.4, 2.6 Hz), 7.64 (1H, d, J = 9.7 Hz), 7.69 (1H, d, J = 1.6 Hz)), 8.14 (1H, s), 8.40 (0.2H, s). | (Method 5): Rt 3.62 mins, m/z 736 [MH$^+$]. |

Example 48

1-[5-tert-Butyl-2-(4-chloro-3-hydroxy-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea

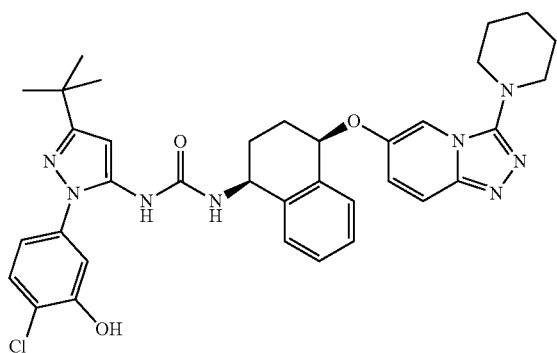 [SMILES: CC(C)(C)c1cc(NC(=O)N[C@H]2CC[C@@H](Oc3ccc4nnc(N5CCCCC5)n4c3)c3ccccc32)n(-c2ccc(Cl)c(O)c2)n1]

a. 1-[5-tert-Butyl-2-(4-chloro-3-triisopropylsilanyloxy-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea (Intermediate 48a)

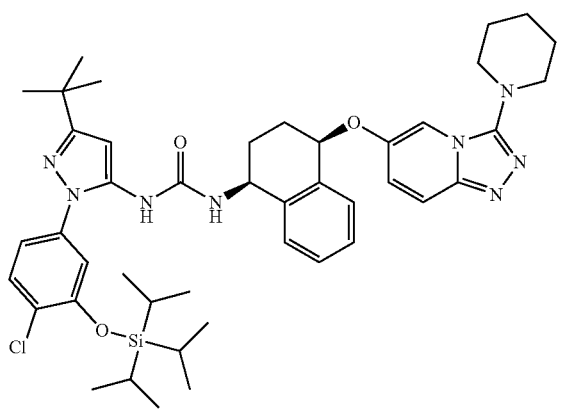 [SMILES: CC(C)[Si](Oc1cc(-n2nc(C(C)(C)C)cc2NC(=O)N[C@H]2CC[C@@H](Oc3ccc4nnc(N5CCCCC5)n4c3)c3ccccc32)ccc1Cl)(C(C)C)C(C)C]

A solution of [5-tert-butyl-2-(4-chloro-3-triisopropylsilanyloxy-phenyl)-2H-pyrazol-3-yl]-carbamic acid 2,2,2-trichloro-ethyl ester (WO2011/154734A1, which is incorporated herein by reference; 190 mg, 0.32 mmol), Intermediate D (105 mg, 0.289 mmol) and DIPEA (0.075 mL, 0.43 mmol) in dioxane (4 mL) was stirred at 60° C. for 18 h. The cooled solution was concentrated in vacuo, redissolved in EtOAc (20 mL), then washed with water (10 mL), brine (10 mL), dried (Na$_2$SO$_4$), filtered and concentrated in vacuo. FCC, using 2% MeOH in EtOAc, gave the title compound (202 mg, 86%). LCMS (Method 3): Rt 5.63 mins, m/z 811 [MH$^+$].

b. 1-[5-tert-Butyl-2-(4-chloro-3-hydroxy-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea. (Example 48)

To a solution of Intermediate 48a (198 mg, 0.24 mmol) in THF (4 mL) was added TBAF (1M in THF, 0.29 mL, 0.29 mmol) and the red solution was stirred at RT for 15 min. The solution was concentrated in vacuo, suspended in water (10 mL) and extracted with EtOAc (2×10 mL). The combined organics were washed with brine (10 mL), dried (Na$_2$SO$_4$), filtered and concentrated in vacuo. FCC, using 4-8% MeOH in DCM, gave the title compound (124 mg, 78%). LCMS (Method 5): Rt 4.50 min, m/z 655 [MH$^+$]. $^1$H NMR (400 MHz, d$_6$-DMSO): 1.27 (9H, s), 1.60-1.63 (2H, m), 1.70-1.75 (4H, m), 1.84-1.96 (2H, m), 1.99-2.13 (2H, m), 3.14 (4H, t, J=5.2 Hz), 4.82 (1H, m), 5.55 (1H, t, J 4.4), 6.33 (1H, s), 6.94 (1H, dd, J=8.5, 2.4 Hz), 7.08 (1H, d, J=8.5 Hz), 7.12 (1H, d, J=2.4 Hz), 7.16 (1H, dd, J=9.8, 2.2 Hz), 7.27-7.39 (4H, m), 7.43 (1H, d, J=8.5 Hz), 7.60-7.63 (2H, m), 8.13 (1H, s), 10.59 (1H, br s).

Example 49

1-[5-tert-Butyl-2-(3-chloro-4-hydroxy-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea

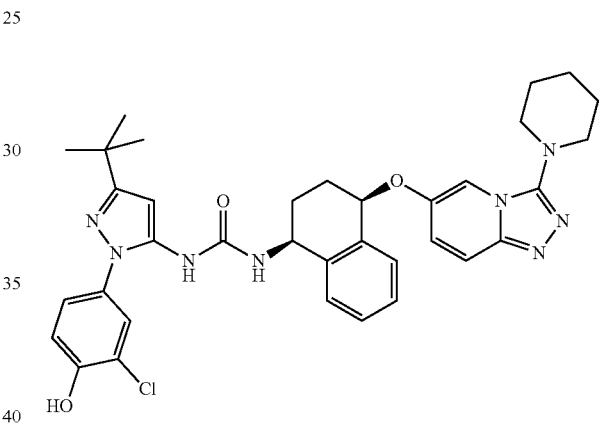

a. 1-[5-tert-Butyl-2-(3-chloro-4-triisopropylsilanyloxy-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea (Intermediate 49a)

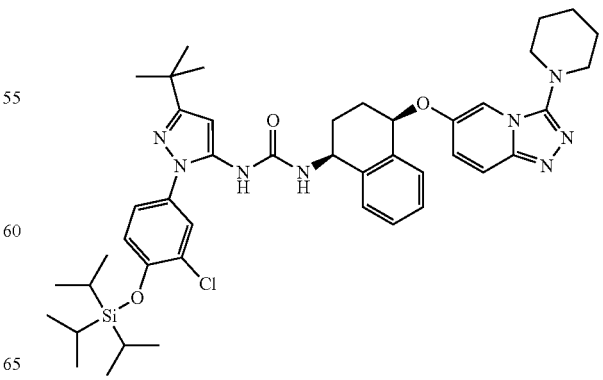

A solution of [5-tert-Butyl-2-(3-chloro-4-triisopropylsilanyloxy-phenyl)-2H-pyrazol-3-yl]-carbamic acid 2,2,2-trichloroethyl ester (WO2011/154734A, which is incorporated herein by reference; 157 mg, 0.26 mmol), Intermediate D (91.0 mg, 0.25 mmol) and DIPEA (0.054 mL, 0.31 mmol) in dioxane (4 mL) was stirred at 60° C. for 18 h, and at 100° C. for 1 h. The cooled solution was concentrated in vacuo, suspended in water (4 mL) and extracted with DCM (2×4 mL). The combined organics were passed through a hydrophobic frit and concentrated in vacuo. FCC, using 0-4% [2M NH₃ in MeOH] in DCM, gave a solid (153 mg, 75%). LCMS (Method 3): Rt 5.53 min, m/z 811 [MH⁺].

b. 1-[5-tert-Butyl-2-(3-chloro-4-hydroxy-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea. (Example 49)

A solution of Intermediate 49a (152 mg, 0.19 mmol) and TBAF (1M in THF, 0.225 mL, 0.225 mmol) in THF (4 mL) was stirred at RT for 10 min. The solution was concentrated in vacuo, suspended in water (5 mL) and extracted with EtOAc (2×5 mL). The combined organics were washed with brine (5 mL), dried (Na₂SO₄), filtered and concentrated in vacuo. FCC, using 5-15% [2M NH₃ in MeOH] in DCM, gave a solid. Further purification by HPLC (XBridge C18 column, 25-75% MeCN in H₂O, 0.1% NH₄OH) gave the title compound (42.9 mg, 35%). LCMS (Method 5): Rt 4.46 min, m/z 655 [MH⁺]. NMR (400 MHz, d₆-DMSO): 1.26 (9H, s), 1.60-1.66 (2H, m), 1.69-1.76 (4H, m), 1.82-1.96 (2H, m), 1.99-2.07 (1H, m), 2.09-2.16 (1H, m), 3.14 (4H, t, J=5.2 Hz), 4.78-4.84 (1H, m), 5.54 (1H, t, J=4.3 Hz), 6.28 (1H, s), 7.05 (2H, d, J=8.6 Hz), 7.16 (1H, dd, J=2.2, 9.8 Hz), 7.29-7.27 (4H, m), 7.38 (1H, d, J=7.6 Hz), 7.43 (1H, d, J=2.5 Hz), 7.61 (1H, dd, J=0.7, 11.9 Hz), 7.62 (1H, s), 8.00 (1H, s), 10.46 (1H, br s).

Example 50

1-[5-tert-Butyl-2-(3-chloro-4-hydroxy-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea

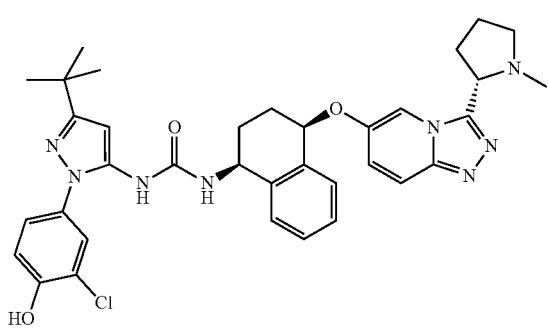 [SMILES: CN1CCC[C@H]1c1nnc2ccc(O[C@@H]3CC[C@H](NC(=O)Nc4cc(C(C)(C)C)nn4-c4ccc(O)c(Cl)c4)c4ccccc43)cn12]

a. 1-[5-tert-Butyl-2-(3-chloro-4-triisopropylsilanyloxy-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea (Intermediate 50a)

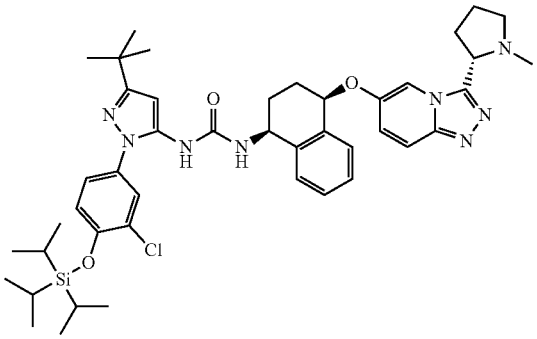 [SMILES: CC(C)[Si](Oc1ccc(-n2nc(C(C)(C)C)cc2NC(=O)N[C@H]2CC[C@@H](Oc3ccc4nnc([C@@H]5CCCN5C)n4c3)c3ccccc32)cc1Cl)(C(C)C)C(C)C]

A mixture of Intermediate E (145 mg, 0.40 mmol) and [5-tert-butyl-2-(3-chloro-4-triisopropylsilanyloxy-phenyl)-2H-pyrazol-3-yl]-carbamic acid 2,2,2-trichloro-ethyl ester (WO2011/154734A1, which is incorporated herein by reference, 251 mg, 0.420 mmol) in 1,4-dioxane (4 mL) and DIPEA (110 μL, 0.63 mmol) was stirred at 90° C. for 5.5 h. The cooled mixture was concentrated in vacuo. The residue was purified by FCC, using 0-12% MeOH in DCM, to give the title compound (288 mg, 89%). LCMS (Method 3): Rt 3.85 min, m/z 811 [MH⁺].

b. 1-[5-tert-Butyl-2-(3-chloro-4-hydroxy-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea (Example 50)

A solution of Intermediate 50a (280 mg, 0.345 mmol) and TBAF (1M in THF, 0.41 mL, 0.41 mmol) in THF (3 mL) was stirred at RT for 0.5 h. Water was added and the mixture extracted with DCM (3×15 mL). The combined organics were concentrated in vacuo. The residue was purified by FCC, using 0-14% MeOH in DCM, to give the title compound (154 mg, 68%). LCMS (Method 5): Rt 3.52 min, m/z 655.2 [MH⁺]. ¹H NMR (400 MHz, d₆-DMSO): 1.26 (9H, s), 1.82-2.26 (11H, m), 2.31-2.39 (1H, m), 3.10-3.16 (1H, m), 3.99 (1H, d, J=8.2 Hz), 4.77-4.85 (1H, m), 5.35-5.42 (1H, m), 6.28 (1H, s), 7.03-7.10 (2H, m), 7.22-7.38 (6H, m), 7.43 (1H, d, J=2.5 Hz), 7.75 (1H, dd, J=9.9 Hz), 7.99 (1H, s), 8.24 (1H, br d), 10.56 (1H, v br).

Example 51

1-[5-tert-Butyl-2-(4-chloro-3-hydroxy-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea

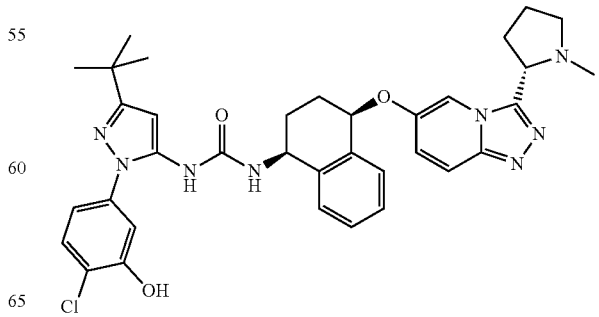

The title compound (193 mg, 76%) was prepared starting from Intermediate E (155 mg, 0.427 mmol) and [5-tert-butyl-2-(4-chloro-3-triisopropylsilanyloxy-phenyl)-2H-pyrazol-3-yl]-carbamic acid 2,2,2-trichloro-ethyl ester (WO2011/154734A1, which is incorporated herein by reference, 260 mg, 0.436 mmol), using analogous procedures to those described in Example 50. LCMS (Method 5): Rt 3.54 min, m/z 655.2 [MH+]. ¹H NMR (400 MHz, d₆-DMSO): 1.27 (9H, s), 1.82-2.26 (11H, m), 2.31-2.39 (1H, m), 3.10-3.17 (1H, m), 3.99 (1H, d, J=8.1 Hz), 4.78-4.86 (1H, m), 5.37-5.42 (1H, m), 6.33 (1H, s), 6.89-6.95 (1H, br d), 7.07-7.12 (2H, m), 7.24-7.38 (5H, m), 7.42 (1H, d, J=8.4 Hz), 7.75 (1H, dd, J=9.8 Hz), 8.12 (1H, s), 8.25 (1H, br d), 10.64 (1H, v br).

Example 52

1-[5-tert-Butyl-2-(3-chloro-4-hydroxy-phenyl)-2H-pyrazol-3-yl]-3-{(1S,4R)-4-[3-(4-hydroxymethyl-piperidin-1-yl)-[1,2,4]triazolo[4,3-a]pyridin-6-yloxy]-1,2,3,4-tetrahydronaphthalen-1-yl}-urea

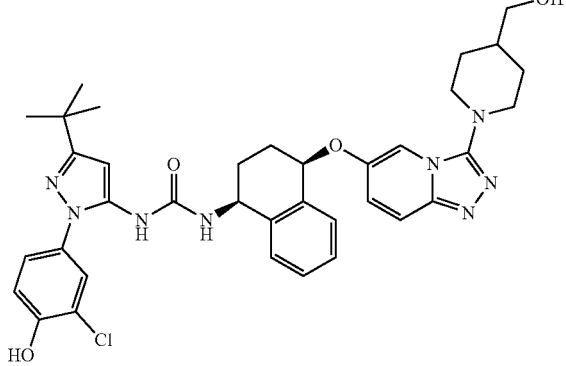

A solution of Intermediate G (153 mg, 0.28 mmol) and [5-tert-butyl-2-(3-chloro-4-triisopropylsilanyloxy-phenyl)-2H-pyrazol-3-yl]-carbamic acid 2,2,2-trichloro-ethyl ester (WO2011/154734A1, which is incorporated herein by reference, 167 mg, 0.28 mmol) in 1,4-dioxane (4 mL) and DIPEA (87 μL, 0.50 mmol) was stirred at 95° C. for 4 h. The cooled mixture was concentrated in vacuo. The residue was purified by FCC, using 0-7.5% MeOH in DCM, to give 1-[5-tert-butyl-2-(3-chloro-4-triisopropylsilanyloxy-phenyl)-2H-pyrazol-3-yl]-3-{(1S,4R)-4-[3-(4-triisopropylsilanyloxymethyl-piperidin-1-yl)-[1,2,4]triazolo[4,3-a]pyridin-6-yloxy]-1,2,3,4-tetrahydro-naphthalen-1-yl}-urea (193 mg). This was dissolved in THF (3 mL) and treated with TBAF (1M in THF, 0.47 mL, 0.47 mmol). The solution was stirred at RT for 1.75 h, then diluted with water and extracted with DCM (3×20 mL). The combined organics were dried and concentrated in vacuo. The residue was purified by FCC, using 0-25% [2M NH₃ in MeOH] in DCM, to give the product. This was further purified by HPLC (C18 X-select column, 30-98% MeCN in H₂O, 0.1% HCO₂H) to give the title compound (72 mg, 56%). LCMS (Method 5): Rt 3.99 min, m/z 685 [MH+]. ¹H NMR (400 MHz, d₆-DMSO): 1.26 (9H, s), 1.38-1.52 (2H, m), 1.55-1.66 (1H, m), 1.73-1.96 (4H, m), 1.98-2.17 (2H, m), 2.85-2.97 (2H, m), 3.3-3.5 (4H, m, under water signal), 4.52 (1H, br s), 4.77-4.85 (1H, m), 5.55 (1H, br t, J=4.4 Hz), 6.28 (1H, s), 7.05 (1H, s), 7.08 (1H, s), 7.15 (1H, dd, J=2.0, 9.8 Hz), 7.23-7.40 (5H, m), 7.44 (1H, d, J=2.5 Hz), 7.61 (1H, d, J=9.9 Hz), 7.64 (1H, br d, J=1.5 Hz), 8.02 (1H, br s), 10.55 (1H, br s).

Example 53

1-{5-tert-Butyl-2-[4-chloro-3-(2-hydroxy-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea

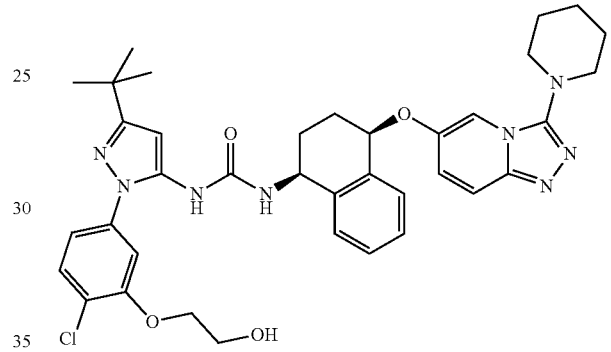

a. 5-tert-Butyl-2-{4-chloro-3-[2-(tetrahydro-pyran-2-yloxy)-ethoxy]-phenyl}-2H-pyrazol-3-ylamine (Intermediate 53a)

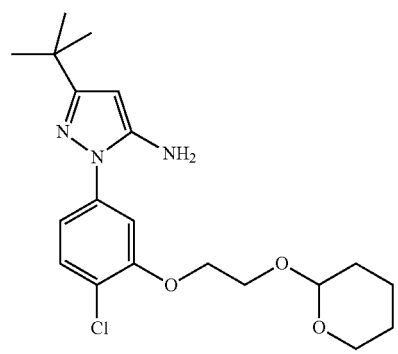 [SMILES: CC(C)(C)c1cc(N)n(-c2ccc(Cl)c(OCCOC3CCCCO3)c2)n1]

To a solution of 5-(5-Amino-3-tert-butyl-pyrazol-1-yl)-2-chloro-phenol (WO2011/154734A1, which is incorporated herein by reference, 340 mg, 1.28 mmol), 2-(tetrahydro-pyran-2-yloxy)-ethanol (0.26 mL, 1.92 mmol) and Ph₃P (671 mg, 2.56 mmol) in dry THF (10 mL) was added diethylazodicarboxylate (0.41 mL, 2.56 mmol) and the mixture stirred for 10 min. Water (4 drops) was added and the mixture concentrated in vacuo. The residue was purified by FCC, using 0-50% EtOAc in cyclohexane, to give the title compound (450 mg, 89%). LCMS (Method 3): Rt 3.73 min, m/z 394 [MH$^+$].

b. (5-tert-Butyl-2-{4-chloro-3-[2-(tetrahydro-pyran-2-yloxy)-ethoxy]-phenyl}-2H-pyrazol-3-yl)-carbamic acid 2,2,2-trichloro-ethyl ester (Intermediate 53b)

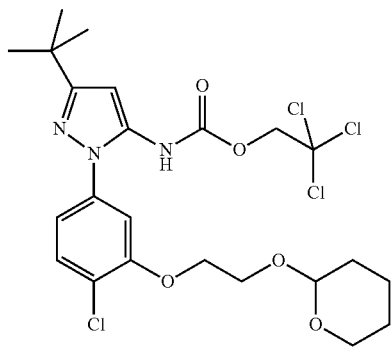 [SMILES: CC(C)(C)c1cc(NC(=O)OCC(Cl)(Cl)Cl)n(-c2ccc(Cl)c(OCCOC3CCCCO3)c2)n1]

To a solution of Intermediate 53a (445 mg, 1.13 mmol) in EtOAc (4 mL) and 1N sodium hydroxide solution (2.40 mL, 2.40 mmol) was added 2,2,2-trichloroethyl chloroformate (165 µL, 1.20 mmol), and the mixture stirred vigorously at RT for 1.5 h. The aqueous layer was extracted with EtOAc (2×10 mL), and then the combined organics dried and concentrated in vacuo. The residue was purified by FCC, using 0-30% EtOAc in cyclohexane, to give the title compound (650 mg, 100%). LCMS (Method 3): Rt 4.90 min, m/z 568, 570, 572 [MH$^+$].

c. 1-(5-tert-Butyl-2-{4-chloro-3-[2-(tetrahydro-pyran-2-yloxy)-ethoxy]-phenyl}-2H-pyrazol-3-yl)-3-[(1S,4R)-4-(3-piperidin-1-yl-[1,2,4]triazolo[4,3-a]pyridin-6-yloxy)-1,2,3,4-tetrahydro-naphthalen-1-yl]-urea (Intermediate 53c)

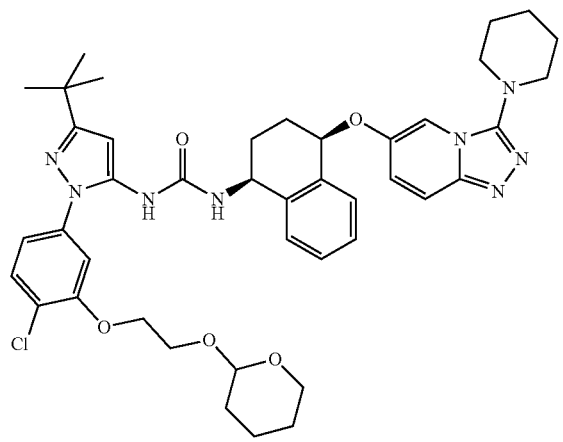 [SMILES: CC(C)(C)c1cc(NC(=O)N[C@H]2CC[C@@H](Oc3ccc4nnc(N5CCCCC5)n4c3)c3ccccc32)n(-c2ccc(Cl)c(OCCOC3CCCCO3)c2)n1]

A solution of Intermediate D (408 mg, 1.12 mmol) and Intermediate 53b (640 mg, 1.12 mmol) in 1,4-dioxane (4 mL) and DIPEA (300 µL, 1.70 mmol) was stirred at 70° C. for 16 h. The mixture was cooled, then water added and the mixture extracted with DCM (4×10 mL). The combined organics were dried and concentrated in vacuo. The residue was purified by FCC, using 0-10% MeOH in DCM, to give the title compound (836 mg, 95%). LCMS (Method 3): Rt 4.27 min, m/z 783 [MH$^+$].

d. 1-{5-tert-Butyl-2-[4-chloro-3-(2-hydroxy-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea (Example 53)

A solution of Intermediate 53c (830 mg, 1.06 mmol) and pyridinium p-toluenesulphonate (799 mg, 3.18 mmol) in methanol (7 mL) was stirred at 40-45° C. for 18.5 h. The cooled mixture was concentrated in vacuo, diluted with sat. sodium hydrogen carbonate solution and extracted with DCM (3×15 mL). The combined organics were dried and concentrated in vacuo. The residue was purified by FCC, using 0-12% MeOH in DCM, to give the product as a solid (613 mg, 83%). An aliquot (50 mg) was further purified by HPLC (XBridge C18 column, 30-90% MeCN in H$_2$O, 0.1% NH$_4$OH) to give the title compound (38 mg). LCMS (Method 5): Rt 4.42 min, m/z 699.5 [MH$^+$]. $^1$H NMR (400 MHz, d$_6$-DMSO): 1.28 (9H, s), 1.57-1.65 (2H, m), 1.68-1.77 (4H, m), 1.80-1.97 (2H, m), 1.98-2.17 (2H, m), 3.11-3.17 (4H, m), 3.74 (2H, q, J=5.0 Hz), 4.12 (2H, t, J=5.0 Hz), 4.76-4.85 (1H, m), 4.90 (1H, t, J=5.1 Hz), 5.54 (1H, t, J=4.3 Hz), 6.34 (1H, s), 7.05-7.11 (2H, m), 7.16 (1H, dd, J=2.0, 9.9 Hz), 7.21-7.41 (5H, m), 7.54 (1H, d, J=8.5 Hz), 7.59-7.65 (2H, m), 8.14 (1H, br s).

Example 54

1-[5-tert-Butyl-2-(3-hydroxy-5-methyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea

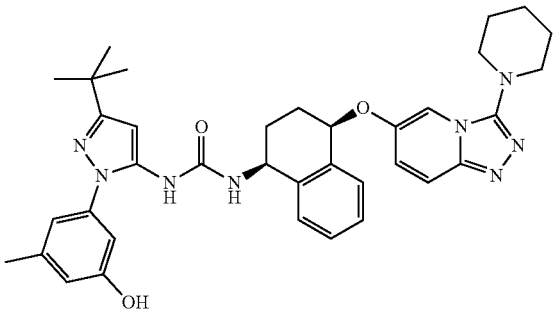 [SMILES: Cc1cc(O)cc(-n2nc(C(C)(C)C)cc2NC(=O)N[C@H]2CC[C@@H](Oc3ccc4nnc(N5CCCCC5)n4c3)c3ccccc32)c1]

a. 3-(5-Amino-3-tert-butyl-pyrazol-1-yl)-5-methyl-phenol (Intermediate 54a)

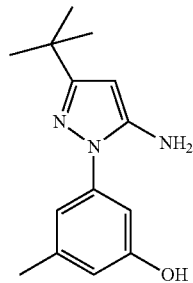 [SMILES: Cc1cc(O)cc(-n2nc(C(C)(C)C)cc2N)c1]

5-tert-Butyl-2H-pyrazol-3-ylamine (1.11 g, 8.00 mmol), potassium carbonate (2.32 g, 16.8 mmol), copper (I) iodide (0.076 g, 0.40 mmol), and 3-bromo-5-methylphenol (1.80 g, 9.60 mmol) were weighed into a large microwave vial. This was then purged with argon then trans-N,N-dimethylcyclohexane-1,2-diamine (0.25 mL, 1.60 mmol) added. To this mixture was then added degassed toluene (8 mL). The mixture was then purged with argon again, the vial sealed, and heated for 1 h at 140° C. in the microwave, then a further 4 h at 135° C. The mixture was cooled, diluted with ethyl acetate and passed through a pad of celite/silica, washing with more ethyl acetate. The dark solution was concentrated in vacuo. The residue was purified by FCC, using 0-40% DCM in EtOAc, to give the title compound (966 mg, 49%). $^1$H NMR (300 MHz, CDCl$_3$): 1.32 (9H, s), 2.24 (3H, s), 3.82 (2H, br s), 5.49 (1H, s), 6.45-6.52 (1H, m), 6.65-6.71 (1H, m), 6.85-6.91 (1H, m).

b. 5-tert-Butyl-2-(3-methyl-5-triisopropylsilanyloxy-phenyl)-2H-pyrazol-3-ylamine (Intermediate 54b)

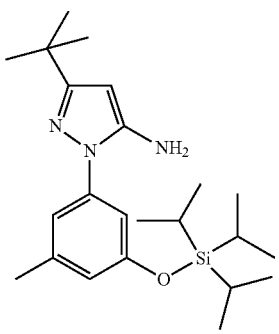 [SMILES: Cc1cc(O[Si](C(C)C)(C(C)C)C(C)C)cc(-n2nc(C(C)(C)C)cc2N)c1]

To a solution of Intermediate 54a (430 mg, 1.75 mmol) in DCM (10 mL) and triethylamine (0.36 mL, 2.63 mmol) was added triisopropylsilyltrifluoromethanesulphonate (0.52 mL, 1.93 mmol). Mixture stirred for 1 h at RT, diluted with DCM, washed with sat. sodium hydrogen carbonate solution then brine, dried, and concentrated in vacuo. The residue was purified by FCC, using 0-25% EtOAc in cyclohexane, to give impure title compound (740 mg), contaminated with the ~25% bis-silyl impurity. $^1$H NMR (300 MHz, CDCl$_3$): inter alia 1.03-1.15 (18H, m), 1.18-1.35 (12H, m), 2.32 (3H, s), 3.74 (2H, br s), 5.49 (1H, s), 6.60-6.66 (1H, m), 6.85-6.89 (1H, m), 6.95-7.00 (1H, m).

c. [5-tert-Butyl-2-(3-methyl-5-triisopropylsilanyloxy-phenyl)-2H-pyrazol-3-yl]-carbamic acid 2,2,2-trichloro-ethyl ester (Intermediate 54c)

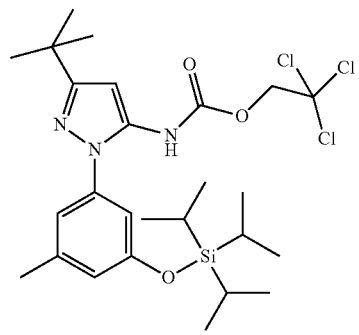 [SMILES: Cc1cc(O[Si](C(C)C)(C(C)C)C(C)C)cc(-n2nc(C(C)(C)C)cc2NC(=O)OCC(Cl)(Cl)Cl)c1]

To a solution of Intermediate 54b (0.73 g, assumed 1.70 mmol) in ethyl acetate (8 mL) was added 1N sodium hydroxide solution (4.5 mL, 4.50 mmol). Stirred for 5 min then 2,2,2-trichloroethyl chloroformate (275 μL, 2.00 mmol) was added and the mixture stirred vigorously at RT for 3.5 h. Diluted with EtOAc, washed with water and brine, dried, and concentrated in vacuo. The residue was purified by FCC, using 0-15% EtOAc in cyclohexane, to give the still impure title compound (1.01 g). NMR (300 MHz, CDCl$_3$): inter alia 1.02-1.15 (18H, m), 1.18-1.38 (12H, m), 2.34 (3H, s), 4.82 (2H, s), 6.43 (1H, s), 6.69-6.77 (2H, m), 6.84-6.96 (2H, m).

d. 1-[5-tert-Butyl-2-(3-methyl-5-triisopropylsilanyloxy-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea (Intermediate 54d)

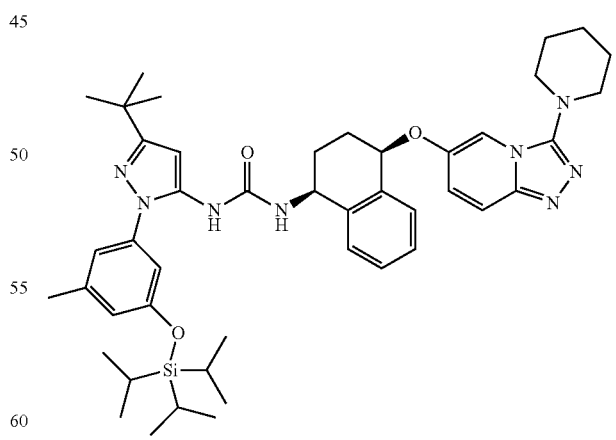

A solution of Intermediate D (170 mg, 0.468 mmol) and Intermediate 54c (386 mg, 0.47 mmol) in 1,4-dioxane (4 mL) and DIPEA (122 μL, 0.70 mmol) was stirred at 95° C. for 3 h. The mixture was cooled and concentrated in vacuo. The residue was purified by FCC, using 0-10% MeOH in DCM, to give the title compound (306 mg, 83%). LCMS (Method 3): Rt 5.57 min, m/z 791.2 [MH+].

e. 1-[5-tert-Butyl-2-(3-hydroxy-5-methyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea (Example 54)

To a solution of Intermediate 54d (300 mg, 0.38 mmol) in THF (4 mL) was added a solution of tetrabutylammonium fluoride in THF (1M, 0.49 mL, 0.49 mmol). Stirred at RT for 0.5 h, then diluted with water and extracted with DCM (5×20 mL). The combined organics were dried and concentrated in vacuo. The residue was purified by FCC, using 0-10% MeOH in DCM, to give the impure product as a solid (210 mg). This was further purified by HPLC (XBridge C18 column, 40-85% MeCN in H$_2$O, 0.1% NH$_4$OH) to give the title compound (73 mg, 30%). LCMS (Method 5): Rt 4.44 min, m/z 635.3 [MH+]. $^1$H NMR (400 MHz, d$_6$-DMSO): 1.26 (9H, s), 1.57-1.65 (2H, m), 1.68-1.77 (4H, m), 1.81-1.98 (2H, m), 1.99-2.18 (2H, m), 2.27 (3H, s), 3.10-3.18 (4H, m), 4.79-4.88 (1H, m), 5.55 (1H, t, J=4.3 Hz), 6.31 (1H, s), 6.59-6.64 (1H, m), 6.67-6.71 (1H, m), 6.71-6.74 (1H, m), 7.09-7.19 (2H, m), 7.25-7.41 (4H, m), 7.58-7.65 (2H, m), 8.06 (1H, br s), 9.65 (1H, br s).

Examples 55, 56, and 57 a. 4-Iodo-2-[2-(tetrahydro-pyran-2-yloxy)-ethoxy]-benzoic acid methyl ester (Intermediate 55a)

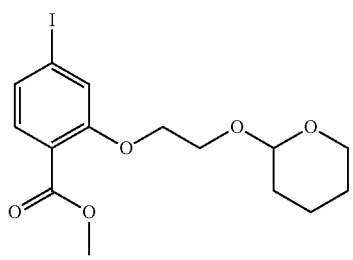 [SMILES: COC(=O)c1ccc(I)cc1OCCOC1CCCCO1]

To a solution of 4-Iodo-methyl salicylate (2.00 g, 7.20 mmol) and triphenylphosphine (3.77 g, 14.4 mmol) in THF (20 mL), under Argon atmosphere, was added 2-(tetrahydro-pyran-2-yloxy)-ethanol (1.54 mL, 10.8 mmol) followed by dropwise addition of DEAD (2.84 mL, 14.4 mmol). The reaction was stirred at RT overnight. The reaction mixture was partitioned between water (50 mL) and EtOAc (50 mL). The organic phase was washed with brine and dried over Na$_2$SO$_4$ and evaporated under reduced pressure. The residue was purified by FCC, eluting with 0-20% EtOAc in DCM, to give the title compound as a colourless oil (2.64 g, 90%). $^1$H NMR (300 MHz, CDCl$_3$): 1.48-1.67 (4H, m), 1.68-1.90 (2H, m), 3.5-3.59 (1H, m), 3.75-3.94 (5H, m), 3.96-4.13 (1H, m), 4.14-4.27 (2H, m), 4.75 (1H, t), 7.33 (1H, dd, J=8.23, 1.45 Hz), 7.40 (1H, d, J=1.5 Hz), 7.47 (1H, d, J=8.3 Hz).

b. 4-(5-Amino-3-tert-butyl-pyrazol-1-yl)-2-[2-(tetrahydro-pyran-2-yloxy)-ethoxy]-benzoic acid methyl ester (Intermediate 55b)

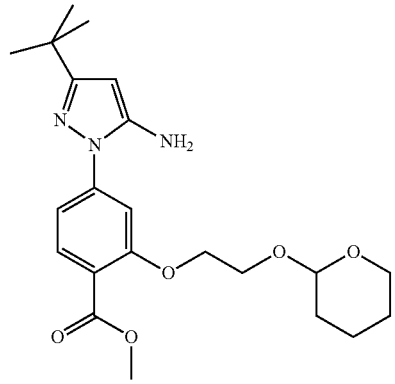 [SMILES: COC(=O)c1ccc(-n2nc(C(C)(C)C)cc2N)cc1OCCOC1CCCCO1]

A solution of Intermediate 55a (2.64 g, 6.50 mmol), 3-tert-butyl-1H-pyrazole-5-amine (997 mg, 7.1 mmol) and trans-N,N'-dimethylcyclohexane-diamine (185 mg, 0.33 mmol) was formed in toluene (25 mL). Potassium carbonate (1.9 g, 13.7 mmol) was added and the mixture degassed by bubbling nitrogen through it. Copper(I) iodide (64.0 mg, 1.30 mmol) was added and the mixture was refluxed at 110° C. for 24 h. The solvent was evaporated under reduce pressure and the residue was partitioned between EtOAc/Water and extracted with EtOAc. The combined organics were dried over Na$_2$SO$_4$, filtered and evaporated. Purification by FCC eluting with a gradient of 0-50% EtOAc in cyclohexane gave the title compound (1.72 g, 64%). LCMS (Method 3): Rt 3.69 min, m/z 418 [MH+].

c. {4-(5-Amino-3-tert-butyl-pyrazol-1-yl)-2-[2-(tetrahydro-pyran-2-yloxy)-ethoxy]-phenyl}-methanol (Intermediate 55c)

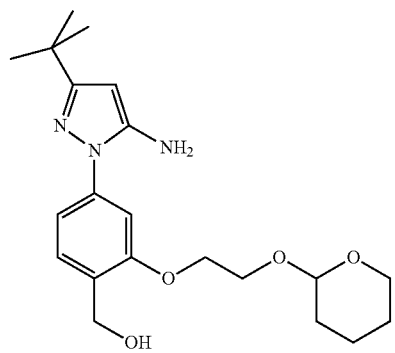 [SMILES: CC(C)(C)c1cc(N)n(-c2ccc(CO)c(OCCOC3CCCCO3)c2)n1]

A solution of Intermediate 55b (1.72 g, 4.12 mmol) in THF (30 mL) was treated with LiAlH$_4$ (2M in THF, 2.5 mL, 4.94 mmol) [CARE: gas evolution]. The reaction mixture was left to stir at RT for 5 h. The reaction was quenched slowly with water and the product was extracted with EtOAc. The organic phase was separated, washed with brine, dried over Na$_2$SO$_4$, and evaporated under reduced pressure to give the title compound (1.57 g, 95%). LCMS (Method 3): Rt 2.80 min, m/z 390 [MH+].

d. 5-tert-Butyl-2-{3-[2-(tetrahydro-pyran-2-yloxy)-ethoxy]-4-triisopropylsilanyloxy-methyl-phenyl}-2H-pyrazol-3-ylamine (Intermediate 55d)

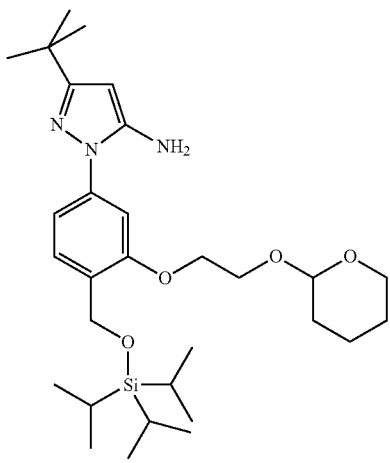 [SMILES: CC(C)[Si](OCc1ccc(-n2nc(C(C)(C)C)cc2N)cc1OCCOC1CCCCO1)(C(C)C)C(C)C]

A solution of Intermediate 55c (1.57 g, 4.03 mmol) and imidazole (581 mg, 8.06 mmol) in THF (80 mL) was treated with chlorotriisopropylsilane (1.37 mL, 6.04 mmol). The reaction mixture was refluxed for 24 h. The reaction was evaporated under reduced pressure and the residue was partitioned between water and EtOAc. The organic phase was separated, washed with brine, dried over Na₂SO₄, and evaporated under reduced pressure. The product was purified by FCC, eluting with 0-40% EtOAc in cyclohexane, to give the title compound (2.3 g, 95%). LCMS (Method 3): Rt 5.53 min., m/z 546 [MH+].

e. 5-tert-Butyl-2-{3-[2-(tetrahydro-pyran-2-yloxy)-ethoxy]-4-triisopropylsilanyloxymethyl-phenyl}-2H-pyrazol-3-ylamine (Intermediate 55e)

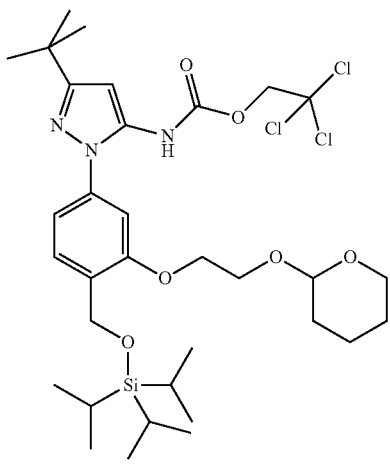 [SMILES: CC(C)[Si](OCc1ccc(-n2nc(C(C)(C)C)cc2NC(=O)OCC(Cl)(Cl)Cl)cc1OCCOC1CCCCO1)(C(C)C)C(C)C]

To a solution of Intermediate 55d (2.30 g, 4.21 mmol) in EtOAc (20 mL) was added NaOH 1N (8 mL, 7.94 mmol) followed by 2,2,2-trichloroethylchloroformate (637 µL, 4.63 mmol). The reaction was stirred for 2 h at RT and then partitioned between EtOAc and water. The aqueous layer was then extracted with EtOAc (3×60 mL). The combined organic layers were washed with brine, dried (Na₂SO₄), filtered and evaporated in vacuo. The residue was purified by FCC, using 0-30% EtOAc in cyclohexane, to give the title compound (1.57 g, 40%). ¹H NMR (300 MHz, CDCl₃): 1.05-1.13 (18H, m), 1.14-1.26 (3H, m), 1.45-1.67 (4H, m), 1.68-1.87 (2H, m), 3.47-3.59 (1H, m), 3.74-3.82 (1H, m), 3.83-3.93 (1H, m), 3.99-4.11 (1H, m), 4.11-4.22 (3H, m), 4.71 (1H, t, J=3.2 Hz), 4.81 (2H, s), 4.88 (2H, s), 6.44 (1H, bs), 6.96 (1H, d, J=1.63 Hz), 7.03 (1H, dd, J=7.97, 1.74 Hz), 7.67 (1H, d, J=7.97 Hz).

f. 1-{5-tert-Butyl-2-[3-(2-hydroxy-ethoxy)-4-triisopropylsilanyloxymethyl-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl]-urea (Intermediate 55eB)

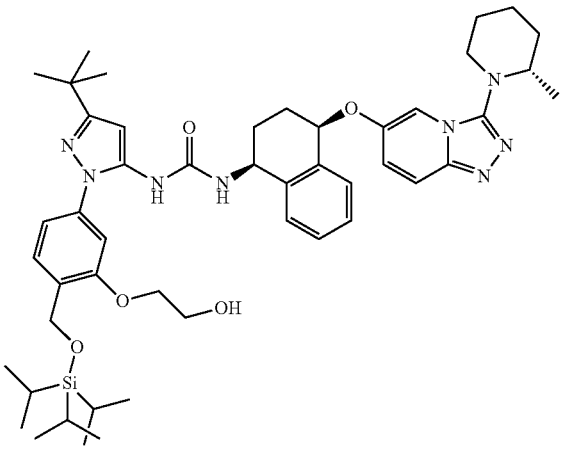 [SMILES: CC(C)[Si](OCc1ccc(-n2nc(C(C)(C)C)cc2NC(=O)N[C@H]2CC[C@@H](Oc3ccc4nnc(N5CCCC[C@@H]5C)n4c3)c3ccccc32)cc1OCCO)(C(C)C)C(C)C]

A solution of Intermediate 55e (343 mg, 0.48 mmol), Intermediate B (180 mg, 0.48 mmol) and DIPEA (118 µL, 0.71 mmol) in 1,4-dioxane (5 mL) was stirred at 60° C. overnight. After cooling, the mixture was partitioned between EtOAc and water. The aqueous layer was then extracted with EtOAc (3×10 mL). The combined organic layers were washed with brine, dried (Na₂SO₄), filtered and evaporated in vacuo to give a gum (505 mg, 95%) that was used without further purification in the next step. TLC [DCM/MeOH (19:1); Rf=0.5]. A solution of the above product (505 mg, 0.50 mmol) in MeOH (25 mL) was treated with pyridinium p-toluene sulfonate (400 mg, 1.60 mmol) and the resulting mixture was heated at 45° C. overnight. The volatiles were removed under reduced pressure and the residue was taken up in DCM (40 mL) and washed with water (10 mL). The organic phase was separated using a phase separating cartridge and the organic layer was evaporated in vacuo. The product was purified by FCC, eluting with 0-10% MeOH in DCM, to give the title compound (260 mg, 57%). LCMS (Method 3): Rt 5.21 min, m/z 865,866 [MH+].

g. Methanesulfonic acid 2-{5-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-2-triisopropylsilanyloxymethyl-phenoxy}-ethyl ester (Intermediate 55fB)

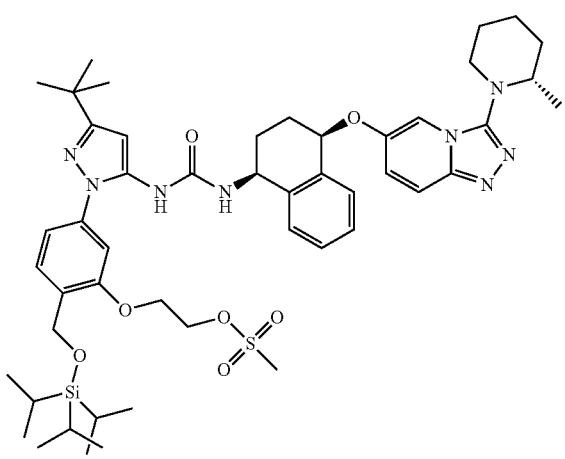 [SMILES: CC(C)[Si](OCc1ccc(-n2nc(C(C)(C)C)cc2NC(=O)N[C@H]2CC[C@@H](Oc3ccc4nnc(N5CCCC[C@@H]5C)n4c3)c3ccccc32)cc1OCCOS(C)(=O)=O)(C(C)C)C(C)C]

A mixture of Intermediate 55eB (26.0 mg, 0.30 mmol), methanesulfonyl chloride (70.0 μL, 0.90 mmol) and DIPEA (208 μL, 1.20 mmol) in DCM (8 mL) was stirred at RT for 1 h. The reaction mixture was partitioned between DCM and water. The organic layer was washed with brine, separated through a phase separating cartridge and concentrated in vacuo to afford the title compound (275 mg, 97%). LCMS (Method 3): Rt 5.23 min, m/z 943 [MH+].

h. 1-{5-tert-Butyl-2-[3-(2-dimethylamino-ethoxy)-4-triisopropylsilanyloxymethyl-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 55gB)

A mixture of Intermediate 55fB (100 mg, 0.11 mmol) and dimethylamine (2.0M in THF, 0.80 mL, 1.60 mmol) in THF (3 mL) was stirred at 60° C. for 18 h in a sealed vial. The volatiles were concentrated in vacuo and the residue was used in the next step without further purification (94 mg, 100%). LCMS (Method 3): Rt 3.75 min, m/z 893 [MH+].

i. General TBAF Deprotection Procedure.

A solution of the silyl protected alcohol (e.g. Intermediate 55gB, 0.10 mmol) in THF (2 mL) was treated with tetrabutyl ammonium fluoride (1M in THF, 0.50 mmol) and the resulting mixture was heated at 50° C. for 24 h. The volatiles were evaporated under reduced pressure and the residue was partitioned between saturated solution of NaHCO$_3$ (10 mL) and DCM (20 mL). The product was extracted in DCM and the organic phase was separated with a phase separating cartridge and evaporated under reduced pressure. The product was purified by HPLC (Gemini C18, 20-35% MeCN in H$_2$O, 0.1% HCO$_2$H, 18 ml/min.) and freeze dried to afford the title compound (40-50%).

Table 4 summarises the examples prepared using analogous procedures described in step (h), using Intermediate 55fB with the appropriate amine, and step (i).

TABLE 4

| Ex. No. | Amine used | Example Structure | NMR (400 MHz) δ | LCMS |
|---|---|---|---|---|
| 55 | Dimethyl-amine | 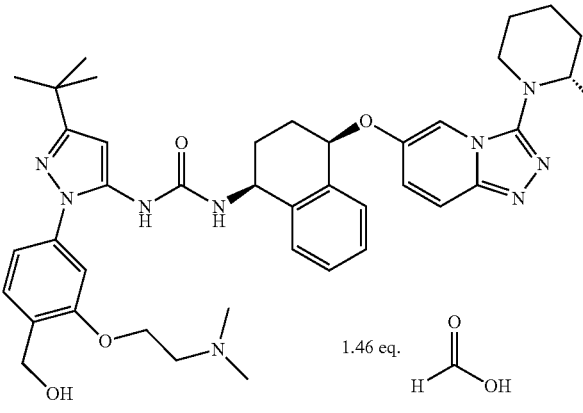<br>1-{5-tert-Butyl-2-[3-(2-dimethylamino-ethoxy)-4-hydroxymethyl-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | (CDCl$_3$): 0.9 (3H, d, J = 6.59 Hz), 1.27 (9H, s), 1.45-1.56 (2H, m), 1.62-1.71 (2H, m), 1.74-1.87 (2H, m), 1.88-2.15 (4H, m), 2.19 (6H, s), 2.62 (2H, t, J = 5.5 Hz), 2.85-2.95 (2H, m), 3.11-3.19 (2H, m), 4.09 (2H, t, J = 5.6 Hz), 4.53 (2H, s), 4.78-4.86 (1H, m), 5.51 (1H, t, J = 3.9), 6.33 (1H, s), 7.04-7.08 (2H, d), 7.09-7.14 (1H, d, J = 8.0 Hz), 7.16-7.20 (1H, dd, J = 2.1, 10.0 Hz), 7.26-7.3 (2H, d, J = 7.1 Hz), 7.30-7.33 (1H, dd), 7.34-7.38 (1H, dd), 7.45-7.49 (1H, d, J = 7.7 Hz), 7.61-7.66 (1H, d, J = 9.9 Hz), 7.69 (1H, d, J = 1.7 Hz), 8.11 (1H, s), 8.2 (1.46H, s). | (Method 5): Rt 3.55 min., m/z 736.5 [MH$^+$]. |
| 56 | Pyrrolidine | 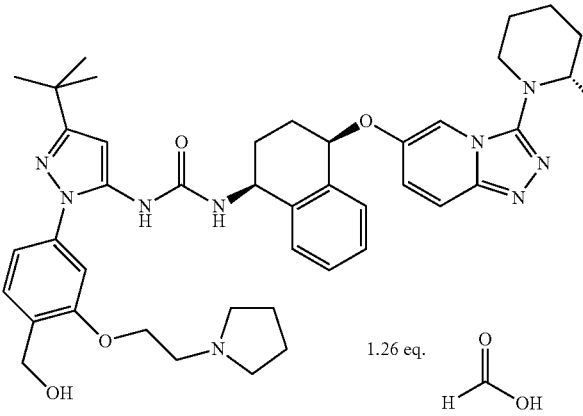<br>1-{5-tert-Butyl-2-[4-hydroxymethyl-3-(2-pyrrolidin-1-yl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | (CDCl$_3$): 0.9 (3H, d, J = 6.6 Hz), 1.27 (9H, s), 1.45-1.56 (2H, m), 1.58-1.71 (5H, m), 1.73-1.94 (4H, m), 2.0-2.18 (2H, m), 2.75-2.81 (2H, t, J = 6.0 Hz), 2.84-2.96 (2H, m), 3.11-3.19 (6H, m), 4.11 (2H, t, J = 5.5 Hz), 4.53 (2H, s), 4.76-4.86 (1H, q), 5.51 (1H, t, J = 3.9 Hz), 6.33 (1H, s), 7.03-7.08 (2H, d), 7.09-7.14 (1H, d, J 32 8.0 Hz), 7.15-7.21 (1H, dd, J = 2.1, 10.0 Hz), 7.26-7.3 (2H, d, J = 7.1 Hz), 7.30-7.34 (1H, dd), 7.34-7.38 (1H, dd), 7.45-7.50 (1H, d, J = 7.7 Hz), 7.61-7.67 (1H, d, J = 9.9 Hz), 7.69 (1H, d, J = 1.7 Hz), 8.10 (1H, s), 8.19 (1.26H, s). | (Method 5): Rt 3.60 min, m/z 762 [MH$^+$]. |

TABLE 4-continued

| Ex. No. | Amine used | Example Structure | NMR (400 MHz) δ | LCMS |
|---|---|---|---|---|
| 57 | 1-Methyl-piperazine | 1-(5-tert-Butyl-2-{4-hydroxymethyl-3-[2-(4-methyl-piperazin-1-yl)-ethoxy]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | (CDCl₃): 0.9 (3H, d, J = 6.6 Hz), 1.28 (9H, s), 1.45-1.62 (4H, m), 1.62-1.71 (2H, m), 1.76-1.87 (3H, m), 1.89-1.99 (1H, m), 2.0-2.15 (2H, m), 2.19 (3H, s), 2.36-2.46 (3H, bs), 2.7 (2H, t, J = 5.48 Hz), 2.85-2.96 (1H, m), 3.12-3.19 (4H, m), 3.39-3.42 (2H, m), 4.11 (2H, t, J = 5.6 Hz), 4.53 (2H, s), 4.78-4.86 (1H, m), 5.51 (1H, t, J = 3.86 Hz), 6.33 (1H, s), 7.03-7.13 (3H, dd), 7.15-7.21 (1H, dd, J = 2.1, 10.0 Hz), 7.24-7.3 (2H, d, J = 7.1 Hz), 7.30-7.33 (1H, dd), 7.34-7.39 (1H, dd), 7.45-7.50 (1H, d, J = 7.7 Hz), 7.61-7.66 (1H, d, J = 9.9 Hz), 7.69 (1H, d, J = 1.7 Hz), 8.09 (1H, s), 8.13 (1H, s). | (Method 5): Rt 3.50 min, m/z 791 [MH⁺]. |

Examples 58, 59, and 60 a. 1-{5-tert-Butyl-2-[3-(2-hydroxy-ethoxy)-4-triisopropylsilanyloxymethyl-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl]-urea (Intermediate 55eC)

A solution of Intermediate 55e (710 mg, 2.17 mmol), Intermediate C (385 mg, 2.17 mmol) and DIPEA (250 μL, 3.25 mmol) in 1,4-dioxane (10 mL) was stirred at 60° C. overnight. After cooling, the mixture was partitioned between EtOAc and water. The aqueous layer was then extracted with EtOAc (3×10 mL). The combined organic layers were washed with brine, dried (Na₂SO₄), filtered and evaporated in vacuo to give a gum (1.25 g, quantitative) that was used without further purification in the next step. TLC [DCM/MeOH (9:1) Rf=0.4]. A solution of the above product (1.25 g, 1.30 mmol) in MeOH (30 mL) was treated with pyridinium p-toluenesulfonate (978 mg, 3.90 mmol) and the resulting mixture was heated at 45° C. overnight. The volatiles were removed under reduced pressure and the residue was taken up in DCM (80 mL) and washed with water (20 mL). The organic phase was separated using a phase separating cartridge and the organic layer was evaporated in vacuo. The product was purified by FCC, eluting with 0-10% MeOH in DCM, to give the title compound (430 mg, 40%). LCMS (Method 3): Rt 5.41 min, m/z 879,880 [MH⁺].

b Methanesulfonic acid 2-{5-[3-tert-butyl-5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-pyrazol-1-yl]-2-triisopropylsilanyloxy methyl-phenoxy}-ethyl ester (Intermediate 55fC)

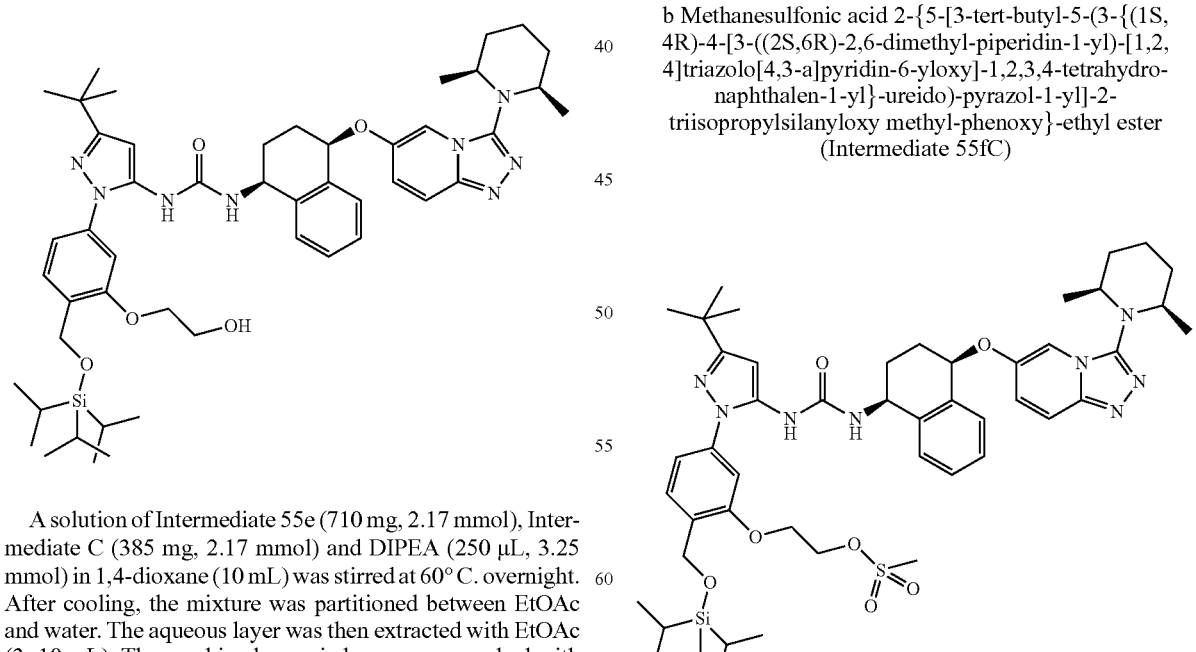

A mixture of Intermediate 55eC (430 mg, 0.49 mmol), methanesulfonyl chloride (114 μL, 1.47 mmol) and DIPEA (236 μL, 1.96 mmol) in DCM (10 mL) was stirred at RT for 1 h. The reaction mixture was partitioned between DCM and water. The organic layer was washed with brine, separated through a phase separating cartridge and concentrated in vacuo to afford the title compound (470 mg, quantitative). LCMS (Method 3): Rt 5.41 min, m/z 958 [MH⁺].

c. 1-{5-tert-Butyl-2-[3-(2-dimethylamino-ethoxy)-4-triisopropylsilanyloxymethyl-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea (Intermediate 55gC)

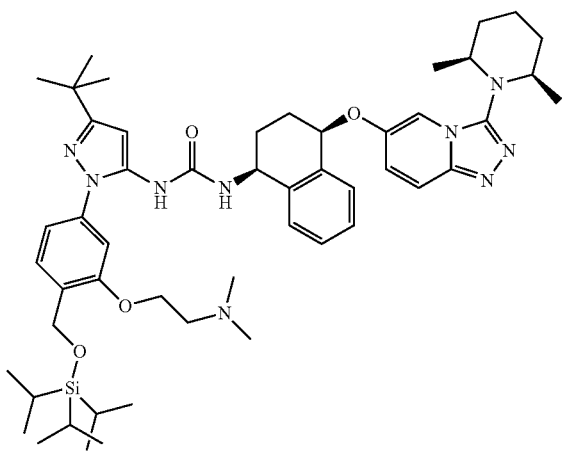 [SMILES: CC(C)[Si](OCc1ccc(-n2nc(C(C)(C)C)cc2NC(=O)N[C@H]2CC[C@@H](Oc3ccc4nnc(N5[C@H](C)CCC[C@@H]5C)n4c3)c3ccccc32)cc1OCCN(C)C)(C(C)C)C(C)C]

A mixture of Intermediate 55fC (157 mg, 0.16 mmol) and dimethylamine (2.0M in THF, 1.23 mL, 2.46 mmol) in THF (3 mL) was stirred at 40° C. for 72 h in a sealed vial. The volatiles were concentrated in vacuo and the residue was used in the next step without further purification (149 mg, 100%). LCMS (Method 3): Rt 3.58 min, m/z 906.7 [MH⁺].

d. General TBAF Deprotection Procedure

A solution of the silyl protected alcohol (e.g. Intermediate 55gC, 0.10 mmol) in THF (2 mL) was treated with tetrabutyl ammonium fluoride (1M in THF, 0.50 mmol) and the resulting mixture was heated at 50° C. for 24 h. The volatiles were evaporated under reduced pressure and the residue was partitioned between saturated solution of $NaHCO_3$ (10 mL) and DCM (20 mL). The product was extracted in DCM and the organic phase was separated with a phase separating cartridge and evaporated under reduced pressure. The product was purified by HPLC (Gemini C18, 20-35% MeCN in $H_2O$, 0.1% $HCO_2H$, 18 ml/min.) and freeze dried to afford the title compound (40-50%).

Table 5 summarises the examples prepared, using analogous procedures as described in step (c), using Intermediate 55fC with the appropriate amine, and step (d).

TABLE 5

| Ex. No. | Amine | Example Structure | NMR (400 MHz) δ | LCMS |
|---|---|---|---|---|
| 58 | Dimethyl-amine | 1-{5-tert-Butyl-2-[3-(2-dimethylamino-ethoxy)-4-hydroxymethyl-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea | (CDCl3): 0.61 (6H, dd, J = 10.88, J = 6.78 Hz), 1.27 (9H, s), 1.37-1.58 (3H, m), 1.67-1.74 (3H, m), 1.76-1.89 (2H, m), 1.91-1.98 (1H, m), 2.04-2.11 (1H, m), 2.18 (6H, s), 2.61 (2H, t, J = 6.0 Hz), 3.13-3.22 (2H, m), 4.10 (2H, t, J = 5.5 Hz), 4.53 (2H, s), 4.79-4.86 (1H, q), 5.52 (1H, t, J = 3.9 Hz), 6.33 (1H, s), 7.04-7.08 (2H, m), 7.10 (1H, d, J = 8.0 Hz), 7.19 (1H, dd, J = 9.5, J = .2.33 Hz), 7.23-7.30 (2H, m), 7.30-7.36 (2H, m), 7.47 (1H, d, J = 8.67 Hz), 7.65 (1H, s), 7.67 (1H, m), 7.87 (1H, d, J = 1.99 Hz), 8.07 (1H, s), 8.16 (0.1H, s) | (Method 5): Rt min., m/z [MH⁺]. |

TABLE 5-continued

| Ex. No. | Amine | Example Structure | NMR (400 MHz) δ | LCMS |
|---|---|---|---|---|
| 59 | Pyrrolidine | 1-{5-tert-Butyl-2-[4-hydroxymethyl-3-(2-pyrrolidin-1-yl-ethoxy)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl]urea formate salt | (CDCl3): 0.61 (6H, dd, J = 10.88, J = 6.78 Hz), 1.27 (9H, s), 1.40-1.58 (3H, m), 1.60-1.65 (4H, m), 1.67-1.74 (3H, m), 1.76-1.89 (2H, m), 1.91-1.98 (1H, m), 2.0-2.11 (2H, m), 2.79 (2H, t, J = 6.0 Hz), 3.12-3.22 (5H, m), 4.11 (2H, t, J = 5.5 Hz), 4.53 (2H, s), 4.79-4.86 (1H, q), 5.52 (1H, t, J = 3.9 Hz), 5.75 (1H, s), 6.33 (1H, s), 7.04-7.08 (2H, m), 7.10 (1H, d, J = 8.0 Hz), 7.19 (1H, dd, J = 9.5, J = .2.33 Hz), 7.23-7.30 (2H, m), 7.30-7.36 (2H, m), 7.47 (1H, d, J = 8.67 Hz), 7.67 (1H, d, J = 9.9 Hz), 7.87 (1H, d, J = 1.99 Hz), 8.09 (1H, s), 8.16 (0.4H, s) | (Method 5): Rt 5 mins, m/z [MH+]. |
| 60 | 1-Methyl piperazine | 1-(5-tert-Butyl-2-{4-hydroxymethyl-3-[2-(4-methyl-piperazin-1-yl)-ethoxy]-phenyl}-2H-pyrazol-3-yl)-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt | (CDCl3): 0.61 (6H, dd, J = 10.88, J = 6.78 Hz), 1.27 (9H, s), 1.38-1.58 (3H, m), 1.67-1.74 (2H, m), 1.76-1.89 (2H, m), 1.91-1.98 (1H, m), 2.04-2.07 (2H, m), 2.08 (3H, s), 2.20-2.30 (3H, bs), 2.37-2.47 (3H, bs), 2.66 (2H, t, J = 6.0 Hz), 3.12-3.22 (4H, m), 4.11 (2H, t, J = 5.5 Hz), 4.53 (2H, s), 4.79-4.86 (1H, q), 5.53 (1H, t, J = 3.9 Hz), 5.75 (1H, s), 6.33 (1H, s), 7.04-7.08 (2H, m), 7.10 (1H, d, J = 8.0 Hz), 7.19 (1H, dd, J = 9.5, J = .2.33 Hz), 7.23-7.30 (2H, m), 7.30-7.36 (2H, m), 7.47 (1H, d, J = 8.67 Hz), 7.67 (1H, d, J = 9.9 Hz), 7.88 (1H, d, J = 1.99 Hz), 8.09 (1H, s), 8.16 (0.4H, s) | (Method 5): Rt 5 mins, m/z [MH+]. |

Example 61

1-{5-tert-Butyl-2-[4-hydroxy-3-(4-methyl-piperazin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

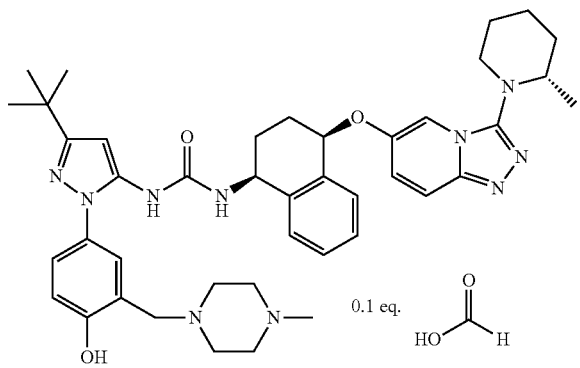 [SMILES: C[C@H]1CCCCN1c1nnc2ccc(O[C@@H]3CC[C@H](NC(=O)Nc4cc(C(C)(C)C)nn4-c4ccc(O)c(CN5CCN(C)CC5)c4)c4ccccc43)cn12 ; O=CO]

a. 5-Iodo-2-triisopropylsilanyloxy-benzoic acid methyl ester (Intermediate 61a)

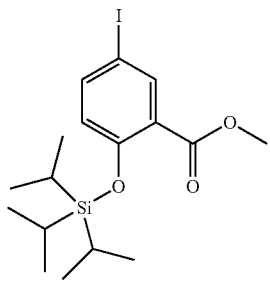 [SMILES: COC(=O)c1cc(I)ccc1O[Si](C(C)C)(C(C)C)C(C)C]

A solution of methyl 5-iodosalicylate (2.00 g, 7.20 mmol) in DMF (20 mL) was treated with imidazole (1.22 g, 18.0 mmol) then chlorotriisopropylsilane (1.85 mL, 8.60 mmol). The mixture was stirred at RT for 18 h. The mixture was evaporated in vacuo and the residue was partitioned between EtOAc and water. The aqueous layer was then extracted with EtOAc (2×). The combined organic layers were washed with a 10% aqueous citric acid solution, 1N aqueous NaOH solution and brine, dried (Na$_2$SO$_4$), filtered and evaporated in vacuo. The residue was purified by FCC, using 0-10% EtOAc in cyclohexane, to give the title compound as a colorless oil (2.88 g, 92%). LCMS (Method 3): Rt 5.72 min, m/z 435 [MH$^+$].

b. (5-Iodo-2-triisopropylsilanyloxy-phenyl)-methanol (Intermediate 61b)

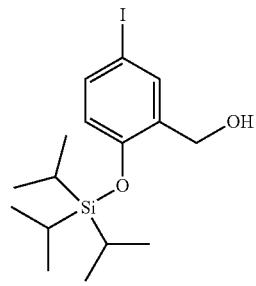 [SMILES: CC(C)[Si](Oc1ccc(I)cc1CO)(C(C)C)C(C)C]

A solution of Intermediate 61a (2.88 g, 6.60 mmol) in DCM (50 mL) at 0° C. under N$_2$ was treated dropwise with diisobutyl aluminium hydride (1.0M in THF, 16.6 mL, 16.6 mmol) and the mixture was stirred at RT overnight. The mixture was cooled to 0° C., then treated dropwise with another portion of diisobutyl aluminium hydride (1.0M in THF, 8.3 mL, 8.30 mmol) and stirred at RT for 1 h. The mixture was cooled to 0° C. and quenched by dropwise addition of water to give a gel that was partitioned between EtOAc/ether and brine/water/aqueous potassium sodium tartrate solution. The insoluble salts were filtered off and the phases separated. The aqueous phase was extracted with EtOAc (2×) and the combined organic layers were washed with a 10% aqueous citric acid solution, saturated sodium bicarbonate solution and brine, dried (Na$_2$SO$_4$), filtered and evaporated in vacuo. The residue was pre-adsorbed onto diatomaceous earth and purified by FCC, using 0-15% EtOAc in cyclohexane, to give the title compound as a colorless oil (1.04 g, 39%). LCMS (Method 3): Rt 5.29 min, m/z 405 [MH$^+$].

c. [5-(5-Amino-3-tert-butyl-pyrazol-1-yl)-2-triisopropylsilanyloxy-phenyl]-methanol (Intermediate 61c)

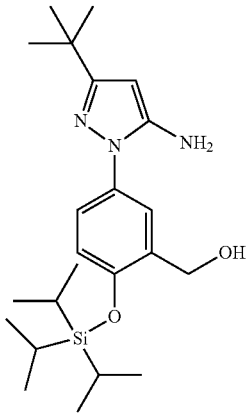 [SMILES: CC(C)[Si](Oc1ccc(-n2nc(C(C)(C)C)cc2N)cc1CO)(C(C)C)C(C)C]

3-(Tert-butyl)-1H-pyrazol-5-amine (0.32 g, 2.30 mmol) was treated with a solution of Intermediate 61b (1.04 g, 2.60 mmol) in toluene (4 mL) then potassium carbonate (0.68 g, 4.90 mmol), (1S,2S)—N,N'-bis-methyl-1,2-cyclohexane-diamine (0.07 g, 0.47 mmol) and copper (I) iodide (0.022 g, 0.11 mmol) were added. The mixture was degassed then heated at 150° C. for 1 h using microwave irradiation. Another portion of copper (I) iodide (0.022 g, 0.11 mmol) was added and the reaction mixture heated at 150° C. for a further 1 h using microwave irradiation. The mixture was diluted with EtOAc and water and the phases separated. The aqueous layer was then extracted with EtOAc (2×). The combined organic layers were washed with brine, dried (Na$_2$SO$_4$), filtered and evaporated in vacuo. The organic layer was evaporated in vacuo. The residue was purified by FCC, using 0-15% EtOAc in DCM, to give the title compound (0.14 g, 15%). LCMS (Method 3): Rt 3.87 min, m/z 418 [MH⁺].

d. [5-tert-Butyl-2-(3-hydroxymethyl-4-triisopropylsilanyloxy-phenyl)-2H-pyrazol-3-yl]-carbamic acid 2,2,2-trichloro-ethyl ester (Intermediate 61d)

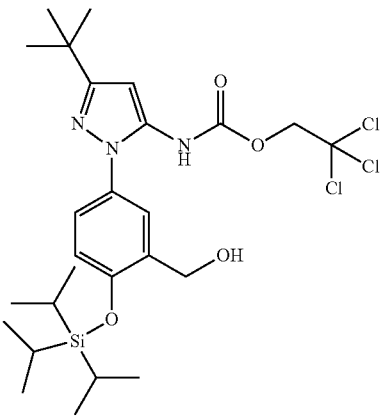 [SMILES: CC(C)[Si](Oc1ccc(-n2nc(C(C)(C)C)cc2NC(=O)OCC(Cl)(Cl)Cl)cc1CO)(C(C)C)C(C)C]

To a solution of Intermediate 61c (0.15 g, 0.36 mmol) in EtOAc (1.8 mL) was added 1N aqueous NaOH solution (0.6 mL, 0.60 mmol) followed by 2,2,2-trichloroethylchloroformate (54.0 µL, 0.40 mmol). The reaction was stirred at RT overnight then treated with another portion of 1N aqueous NaOH solution (0.3 mL, 0.30 mmol) followed by 2,2,2-trichloroethylchloroformate (27.0 µL, 0.20 mmol). After stirring for another 4 h, the mixture was diluted with EtOAc and water. The aqueous layer was then extracted with EtOAc (2×). The combined organic layers were washed with brine, dried (Na₂SO₄), filtered and evaporated in vacuo. The residue was purified by FCC, using 0-25% EtOAc in cyclohexane, to give the title compound (176 mg, 84%). LCMS (Method 3): Rt 5.35 min, m/z 592, 594 [MH⁺].

e. 1-[5-tert-Butyl-2-(3-hydroxymethyl-4-triisopropylsilanyloxy-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 61e)

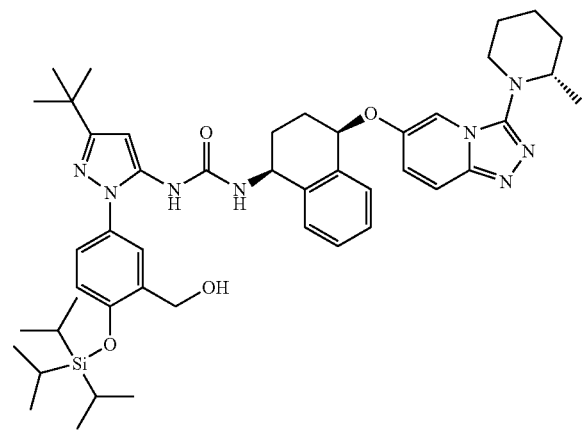 [SMILES: CC(C)[Si](Oc1ccc(-n2nc(C(C)(C)C)cc2NC(=O)N[C@H]2CC[C@@H](Oc3ccc4nnc(N5CCCC[C@@H]5C)n4c3)c3ccccc32)cc1CO)(C(C)C)C(C)C]

A solution of Intermediate 61d (173 mg, 0.29 mmol), Intermediate B (100 mg, 0.27 mmol) and DIPEA (58 µL, 0.33 mmol) in 1,4-dioxane (2.9 mL) was stirred at 70° C. for 42 h. The mixture was evaporated in vacuo and the residue was partitioned between DCM and water. The aqueous layer was then extracted with DCM (2×). The combined organic layers were washed with brine, dried (Na₂SO4), filtered and evaporated in vacuo. The residue was purified by FCC, using 0-5% MeOH in DCM, to give the title compound as a cream colored glass (127 mg, 58%). LCMS (Method 3): Rt 4.97 min, m/z 821 [MH⁺].

f. 1-[5-tert-Butyl-2-(3-chloromethyl-4-triisopropylsilanyloxy-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 61f)

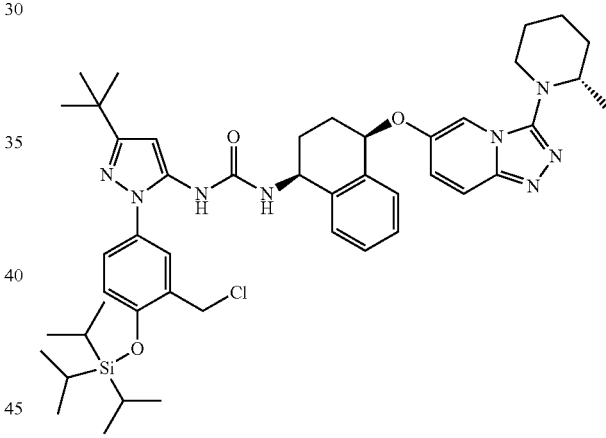

A solution of Intermediate 61e (124 mg, 0.15 mmol) in DCM (1.5 mL) at 0° C. was treated with DIPEA (79 µL, 0.45 mmol) then methanesulfonyl chloride (23 µL, 0.30 mmol) and the mixture was stirred at RT for 1 h. The mixture was cooled to 0° C. and treated with another portion of DIPEA (40 µL, 0.23 mmol) and methanesulfonyl chloride (12 µL, 0.15 mmol) and stirred at RT for 30 min. The mixture was diluted with DCM and a saturated aqueous sodium bicarbonate solution. The layers were separated and the aqueous layer was then extracted with DCM (2×). The combined organic layers were washed with water, a saturated aqueous sodium bicarbonate solution and brine, dried (Na₂SO4), filtered and evaporated in vacuo. The residue was purified by FCC, using 0-4% MeOH in DCM, to give the title compound (34 mg, 27%). LCMS (Method 3): Rt 5.56 min, m/z 839 [MH⁺].

g. 1-{(5-tert-Butyl-2-[3-(4-methyl-piperazin-1-ylmethyl)-4-triisopropylsilanyloxy-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 61g)

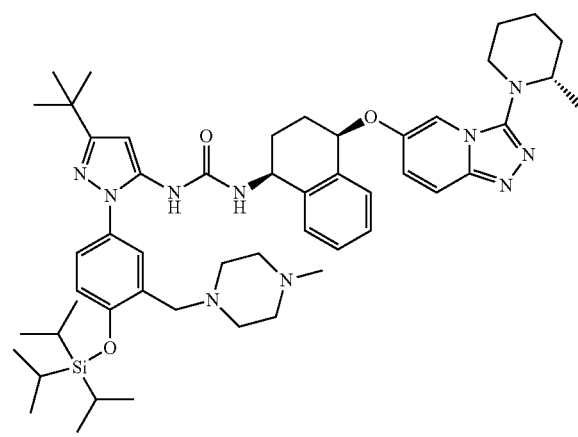 [SMILES: CC(C)[Si](Oc1ccc(-n2nc(C(C)(C)C)cc2NC(=O)N[C@H]2CC[C@@H](Oc3ccc4nnc(N5CCCC[C@@H]5C)n4c3)c3ccccc32)cc1CN1CCN(C)CC1)(C(C)C)C(C)C]

A solution of Intermediate 61f (31.0 mg, 0.04 mmol) in THF (0.4 mL) was treated with 1-methyl-piperazine (41 µL, 0.37 mmol) and the mixture was heated to 50° C. for 64 h. The mixture was evaporated in vacuo and the residue was partitioned between DCM and water. The aqueous layer was then extracted with DCM (2×). The combined organic layers were washed with water (2×), dried (Na$_2$SO4), filtered and evaporated in vacuo. The residue was purified by FCC, using 0-5% [2M NH$_3$ in MeOH] in DCM, to give the title compound as a colorless glass (18 mg, 55%). LCMS (Method 3): Rt 3.64 min, m/z 903.7 [MH⁺].

h. 1-{5-tert-Butyl-2-[4-hydroxy-3-(4-methyl-piperazin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt (Example 61)

A solution of Intermediate 61g (18 mg, 0.02 mmol) in THF (0.10 mL) was treated with tetrabutylammonium fluoride (1M in THF, 0.10 mL, 0.10 mmol) and the mixture was heated to 50° C. for 2 h. The mixture was diluted with DCM and a saturated aqueous sodium bicarbonate solution. The layers were separated and the aqueous layer was then extracted with DCM (2×). The combined organic layers were washed with brine, dried (Na$_2$SO4), filtered and evaporated in vacuo. The residue was purified by HPLC (Method 6; 5-95% MeCN in H$_2$O, 0.1% HCO$_2$H over 25 mins) to give the title compound (5 mg, 33%). LCMS (Method 5): Rt 3.52 min, m/z 747.6 [MH⁺]. ¹H NMR (400 MHz, d$_6$-DMSO): 0.91 (3H, d, J=6.4 Hz), 1.26 (9H, s), 1.44-1.56 (2H, m), 1.61-1.73 (2H, m), 1.74-1.98 (4H, m), 1.99-2.12 (2H, m), 2.13 (3H, s), 2.25-2.37 (3H, m), 2.37-2.49 (5H, m, obscured by DMSO), 2.86-2.95 (1H, m), 3.12-3.19 (1H, m, obscured by water), 3.20-3.44 (1H obscured by water), 3.64 (2H, s), 4.77-4.86 (1H, m), 5.51 (1H, t, J=4.4 Hz), 6.28 (1H, s), 6.81-6.85 (1H, m), 7.05 (1H, d, J=8.6 Hz), 7.15-7.21 (3H, m), 7.24-7.30 (2H, m), 7.30-7.39 (2H, m), 7.63 (1H, d, J=10.2 Hz), 7.69 (1H, d, J=1.7 Hz), 7.95 (1H, s), 8.36 (0.1H, s).

Example 62

1-[5-tert-Butyl-2-(3-chloro-5-hydroxy-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea

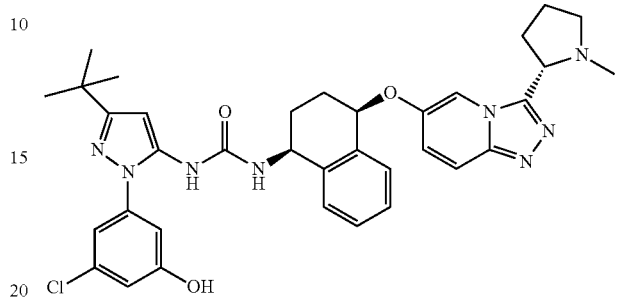

a. 3-Bromo-5-chloro-phenol (Intermediate 62a)

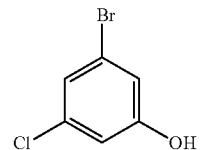

A flask containing (1,5-cyclooctadiene)(methoxy)-iridium (I) dimer (84 mg, 0.13 mmol), 4,4'-di-tert butyl-2-2'-dipyridyl (69 mg, 0.26 mmol) and bis(pinacolato)diboron (1.29 g, 5.11 mmol) was purged with Ar, then hexanes (26 mL) and 1-bromo-3-chlorobenzene (1 mL, 8.51 mmol) were added sequentially. The solution was stirred at RT for 18 h. The reaction mixture was concentrated in vacuo, re-dissolved in acetone (26 mL), then oxone (5.23 g, 8.51 mmol) in water (26 mL) added [Caution: exotherm observed]. After 10 min, the reaction mixture was diluted with DCM. The layers separated, and the aqueous layer extracted with DCM. The combined organics were washed with brine, dried and concentrated in vacuo to give the title compound (1.43 g, 81%). LCMS (Method 3): Rt 3.74 min, m/z 205, 207 [M-H⁺].

b. 3-(5-Amino-3-tert-butyl-pyrazol-1-yl)-5-chloro-phenol (Intermediate 62b)

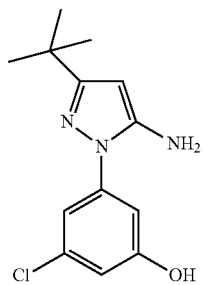 [SMILES: CC(C)(C)c1cc(N)n(-c2cc(O)cc(Cl)c2)n1]

A microwave vial containing 3-tert butyl-1h-pyrazol-5-amine (559 mg, 4.02 mmol), Intermediate 62a (1.00 g, 4.82 mmol), copper(I) iodide (38 mg, 0.20 mmol) and potassium carbonate (1.16 g, 8.44 mmol) was repeatedly purged with argon. Trans-N,N'-dimethylcyclohexane-1,2-diamine (126 µL, 0.80 mmol) was added and the mixture was re-purged with argon. Degassed toluene (4 mL) was added and the resulting suspension was stirred and heated at 110° C. for 24 h. The cooled suspension was passed through Celite pad and diluted with water and extracted with EtOAc. The combined organics were dried and concentrated in vacuo. The residue was purified by FCC, using 0-50% EtOAc in cyclohexane, to give the title compound (620 mg, 62%). LCMS (Method 3): Rt 3.13 min, m/z 266 [MH+].

c. 5-tert-Butyl-2-[3-(tert-butyl-dimethyl-silanyloxy)-5-chloro-phenyl]-2H-pyrazol-3-ylamine (Intermediate 62c)

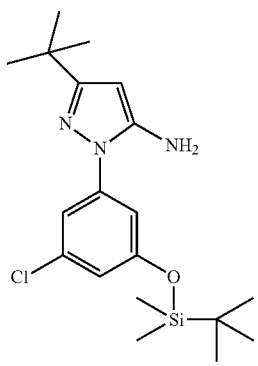 [SMILES: CC(C)(C)c1cc(N)n(-c2cc(Cl)cc(O[Si](C)(C)C(C)(C)C)c2)n1]

A solution of Intermediate 62b (615 mg, 2.31 mmol) and imidazole (189 mg, 2.78 mmol) in DMF (4.5 mL) was added tert-butyl dimethylchlorosilane (384 mg, 2.55 mmol). The solution was stirred for 2 h then added tert-butyl dimethylchlorosilane (192 mg, 1.28 mmol). After 1.5 h, the solution was diluted with water and extracted with EtOAc. The combined organics were dried and concentrated in vacuo to give the title compound (831 mg, 94%). LCMS (Method 3): Rt 5.21 min, m/z 380 [MH+].

d. {5-tert-Butyl-2-[3-(tert-butyl-dimethyl-silanyloxy)-5-chloro-phenyl]-2H-pyrazol-3-yl}-carbamic acid 2,2,2-trichloro-ethyl ester (Intermediate 62d)

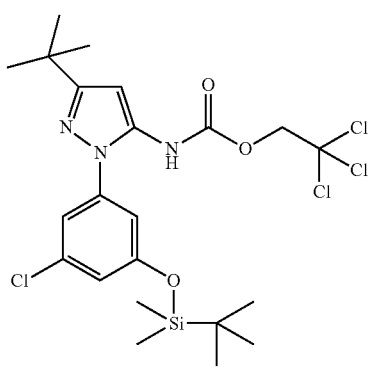 [SMILES: CC(C)(C)c1cc(NC(=O)OCC(Cl)(Cl)Cl)n(-c2cc(Cl)cc(O[Si](C)(C)C(C)(C)C)c2)n1]

To a bi-phasic mixture of Intermediate 62c (807 mg, 2.12 mmol) in EtOAc (7.5 mL) and 1N NaOH solution (1.38 ml, 1.38 mmol) at 0° C. was added 2,2,2-trichloroethyl chloroformate (0.35 mL, 2.54 mmol) and the mixture stirred for 5 h. The layers were separated and the organic layer was washed with brine, dried and concentrated in vacuo to give the title compound (1.27 g, 99%). LCMS (Method 3): Rt 5.66 min, m/z 553, 555, 557 [MH+].

e. 1-{5-tert-Butyl-2-[3-(tert-butyl-dimethyl-silanyloxy)-5-chloro-phenyl]-2H-pyrazol-3-yl}-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea (Intermediate 62e)

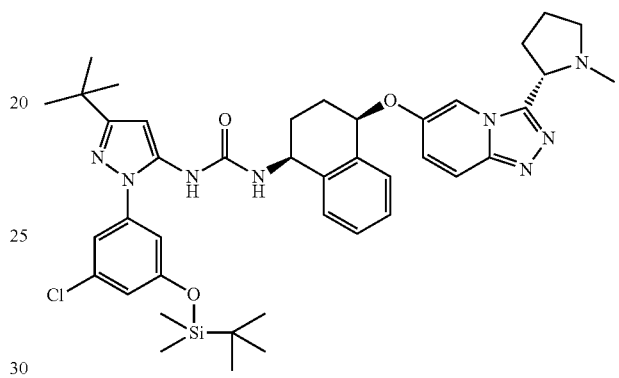

A solution of Intermediate 62d (193 mg, 0.35 mmol) and Intermediate E (115 mg, 0.32 mmol) and DIPEA (166 µL, 0.94 mmol) in THF (3.5 mL) was stirred at reflux for 24 h. The cooled reaction mixture was diluted with water and extracted with DCM. The combined organics were dried and concentrated in vacuo to give the title compound (265 mg, 99%). LCMS (Method 3): Rt 3.82 min, m/z 769 [MH+].

f. 1-[5-tert-Butyl-2-(3-chloro-5-hydroxy-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea (Example 62f)

A solution of Intermediate 62e (265 mg, 0.32 mmol) and TBAF (1M in THF, 0.38 mL, 0.38 mmol) in THF (3 mL) was stirred at RT for 1.3 h, then diluted with water and extracted with DCM. The combined organics were dried and concentrated in vacuo. The residue was purified by FCC, using 0-10% [2M NH$_3$ in MeOH] in DCM, to give the impure product. This residue was purified further by HPLC (XBridge C18 column, 35-98% MeCN in H$_2$O, 0.1% NH$_4$OH) to give the product. This residue purified further by HPLC (XBridge C18 column, 20-98% MeCN in H$_2$O, 0.1% NH$_4$OH) to give the title compound (63 mg, 30%). LCMS (Method 5): Rt 3.61 min, m/z 655 [MH+]. $^1$H NMR (400 MHz, d$_6$-DMSO): 1.27 (9H, s), 1.93-2.12 (5H, m), 2.13 (3H, s), 2.14-2.25 (3H, m), 2.34-2.37 (1H, m), 3.12-3.15 (1H, m), 3.99 (1H, t, J=8.2 Hz), 4.80-4.83 (1H, m), 5.39 (1H, t, J=4.2 Hz), 6.31 (1H, s), 6.78

(1H, s), 6.89 (1H, s), 6.96 (1H, s), 7.15 (1H, d, J=8.6 Hz), 7.29-7.41 (5H, m), 7.75 (1H, dd, J=9.9, 0.8 Hz), 8.14 (1H, s), 8.25 (1H, d, J=2.1 Hz).

Example 63

1-[5-tert-Butyl-2-(3-chloro-5-hydroxy-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea

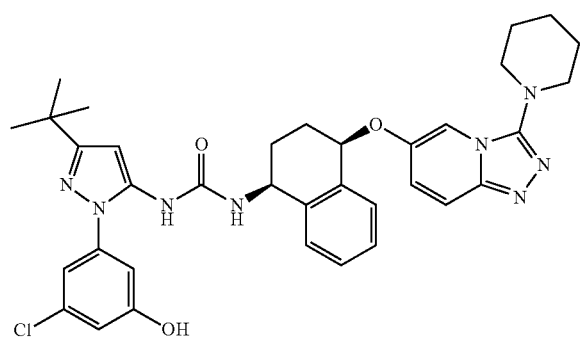 [SMILES: CC(C)(C)c1cc(NC(=O)N[C@H]2CC[C@@H](Oc3ccc4nnc(N5CCCCC5)n4c3)c3ccccc32)n(-c2cc(O)cc(Cl)c2)n1]

The title compound (118 mg, 54%) was prepared in an analogous fashion using the procedures described in Example 62 (steps (e) and (f)) using Intermediate 62d and Intermediate D. LCMS (Method 5): Rt 4.65 min, m/z 655 [MH+]. ¹H NMR (400 MHz, d₆-DMSO): 1.27 (9H, s), 1.60-1.63 (2H, m), 1.71-1.75 (4H, m), 1.89-1.95 (2H, m), 2.01-2.05 (1H, m), 2.13-2.17 (1H, m), 3.14 (4H, t, J=5.2 Hz), 4.80-4.83 (1H, m), 5.54 (1H, t, J=4.2 Hz), 6.31 (1H, s), 6.80 (1H, t, J=2.0 Hz), 6.93 (1H, t, J=2.0 Hz), 7.01 (1H, t, J=1.8 Hz), 7.14-7.21 (2H, m), 7.31-7.43 (4H, m), 7.61-7.64 (2H, m), 8.16 (1H, s).

Example 64

1-[5-tert-Butyl-2-(4-chloro-3-hydroxy-phenyl)-2H-pyrazol-3-yl]-3-[(1S,4R)-4-(3-[1,4]oxazepan-4-yl-[1,2,4]triazolo[4,3-a]pyridin-6-yloxy)-1,2,3,4-tetrahydro-naphthalen-1-yl]-urea

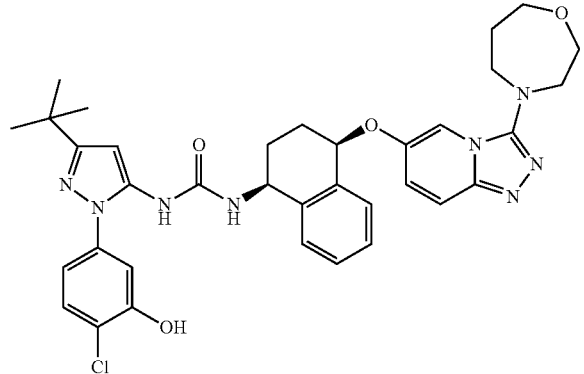 [SMILES: CC(C)(C)c1cc(NC(=O)N[C@H]2CC[C@@H](Oc3ccc4nnc(N5CCCOCC5)n4c3)c3ccccc32)n(-c2ccc(Cl)c(O)c2)n1]

a. 1-[5-tert-Butyl-2-(4-chloro-3-triisopropylsilanyloxy-phenyl)-2H-pyrazol-3-yl]-3-[(1S,4R)-4-(3-[1,4]oxazepan-4-yl-[1,2,4]triazolo[4,3-a]pyridin-6-yloxy)-1,2,3,4-tetrahydro-naphthalen-1-yl]-urea (Intermediate 64a)

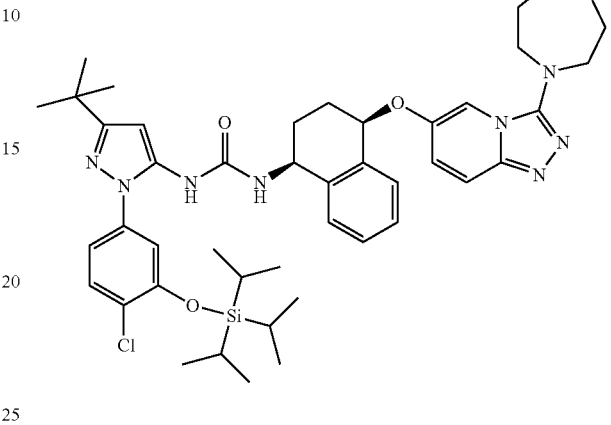

A solution of Intermediate F (112 mg, 0.29 mmol), 5-tert-butyl-2-(3-chloro-4-triisopropylsilanyloxy-phenyl)-2H-pyrazol-3-yl]-carbamic acid 2,2,2-trichloro-ethyl ester (WO2011/154734A1, which is incorporated herein by reference in it is entirety, 194 mg, 0.32 mmol) and DIPEA (155 µL, 0.89 mmol) in THF (3 mL) was stirred at reflux for 18 h. The cooled reaction mixture was diluted with water and extracted with DCM. The combined organics were dried and concentrated in vacuo to give the title compound (243 mg, 99%). LCMS (Method 3): Rt 5.24 min, m/z 827 [MH+].

b. 1-[5-tert-Butyl-2-(4-chloro-3-hydroxy-phenyl)-2H-pyrazol-3-yl]-3-[(1S,4R)-4-(3-[1,4]oxazepan-4-yl-[1,2,4]triazolo[4,3-a]pyridin-6-yloxy)-1,2,3,4-tetrahydro-naphthalen-1-yl]-urea (Example 64)

A solution of Intermediate 64a (243 mg, 0.29 mmol) and TBAF (1M in THF, 1.3 mL, 1.33 mmol) in THF (3 mL) was stirred at RT for 1 h, then diluted with water and extracted with DCM (3×20 mL). The combined organics were dried and concentrated in vacuo. The residue was purified by FCC, using 0-5% [2M NH₃ in MeOH] in DCM, to give the product. This was further purified by HPLC (XBridge C18 column, 25-98% MeCN in H₂O, 0.1% NH₄OH) to give the title compound (58 mg, 29%). LCMS (Method 5): Rt 4.10 min, m/z 671 [MH+]. ¹H NMR (400 MHz, d₆-DMSO): 1.27 (9H, s), 1.84-2.13 (6H, m), 3.46-3.50 (4H, m), 3.81-3.92 (4H, m), 4.81-4.85 (1H, m), 5.52 (1H, t, J=4.4 Hz), 6.33 (1H, s), 6.94 (1H, dd, J=8.5, 2.4 Hz), 7.08 (1H, d, J=8.4 Hz), 7.12-7.19 (2H, m), 7.31-7.43 (4H, m), 7.43 (1H, d, J=8.5 Hz), 7.60-7.62 (2H, m), 8.12 (1H, s).

Example 65

1-[5-tert-Butyl-2-(4-chloro-3-piperidin-1-ylmethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea

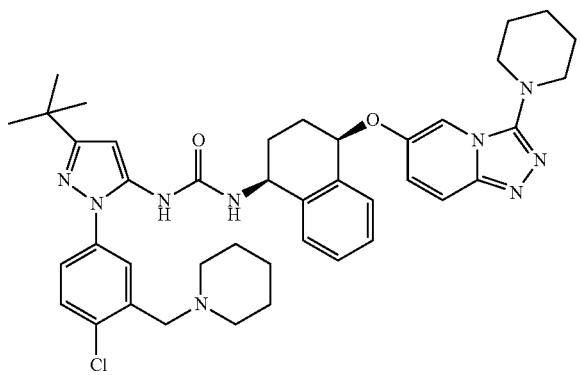 [SMILES: CC(C)(C)c1cc(NC(=O)N[C@H]2CC[C@@H](Oc3ccc4nnc(N5CCCCC5)n4c3)c3ccccc32)n(-c2ccc(Cl)c(CN3CCCCC3)c2)n1]

To a solution of Example 82 (530 mg, 0.79 mmol) and Et₃N (328 µL, 2.37 mmol) in DCM (7 mL) at 0° C. was added mesyl chloride (95 µL, 0.95 mmol), and the mixture stirred for 0.5 h. The solution was washed with water, dried, and concentrated in vacuo to give methanesulfonic acid 5-(3-tert-butyl-5-{3-[(1S,4R)-4-(3-piperidin-1-yl-[1,2,4]triazolo[4,3-a]pyridin-6-yloxy)-1,2,3,4-tetrahydro-naphthalen-1-yl]-ureido}-pyrazol-1-yl)-2-chloro-benzyl ester (390 mg). A portion of this (150 mg, 0.20 mmol) was dissolved in THF (2 mL) and DIPEA (70 µL, 0.40 mmol) then piperidine (60 µL, 0.60 mmol) added and the solution stirred and heated at reflux for 35 min. Water was added and the mixture extracted with DCM. The combined organics were dried and concentrated in vacuo. The residue was purified by HPLC (XBridge C18 column, 30-98% MeCN in H₂O, 0.1% NH₄OH, 20 min gradient, 18 mL/min) to give the title compound (44 mg, 29%). LCMS (Method 5): Rt 3.59 min, m/z 736 [MH⁺]. ¹H NMR (400 MHz, d₆-DMSO): 1.28 (9H, s), 1.33-1.37 (2H, m), 1.44-1.49 (4H, m), 1.60-1.64 (2H, m), 1.69-1.76 (4H, m), 1.87-1.93 (2H, m), 2.03-2.09 (2H, m), 2.40 (4H, t, J=4.8 Hz), 3.14 (4H, t, J=5.2 Hz), 3.53 (2H, s), 4.79-4.82 (1H, m), 5.54 (1H, t, J=4.4 Hz), 6.33 (1H, s), 6.97 (1H, d, J=8.5 Hz), 7.15 (1H, dd, J=2.0, 10.0 Hz), 7.29-7.35 (3H, m), 7.39-7.43 (2H, m), 7.54 (1H, d, J=8.5 Hz), 7.60-7.63 (3H, m), 8.16 (1H, s).

Example 66

1-[5-tert-Butyl-2-(4-chloro-3-pyrrolidin-1-ylmethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea

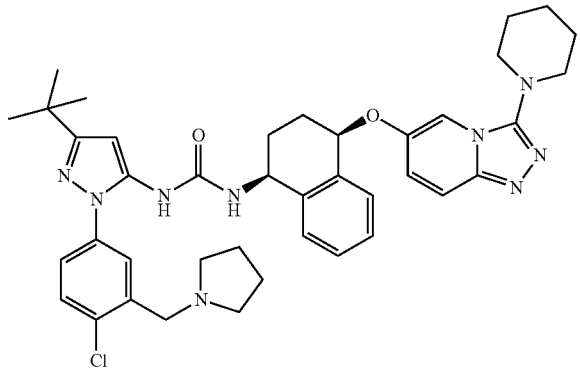 [SMILES: CC(C)(C)c1cc(NC(=O)N[C@H]2CC[C@@H](Oc3ccc4nnc(N5CCCCC5)n4c3)c3ccccc32)n(-c2ccc(Cl)c(CN3CCCC3)c2)n1]

The title compound (45 mg, 31%) was prepared in an analogous fashion using procedure described for Example 65 using pyrrolidine. LCMS (Method 5): Rt 3.53 min, m/z 722 [MH⁺]. ¹H NMR (400 MHz, d₆-DMSO): 1.28 (9H, s), 1.60-1.64 (2H, m), 1.67-1.76 (12H, m), 1.81-1.91 (2H, m), 2.02-2.09 (2H, m), 3.14 (4H, t, J=5.2 Hz), 3.71 (2H, s), 4.77-4.81 (1H, m), 5.54 (1H, t, J=4.3 Hz), 6.32 (1H, s), 6.98 (1H, d, J=8.5 Hz), 7.16 (1H, dd, J=2.0, 10.0 Hz), 7.33-7.45 (5H, m), 7.57-7.63 (4H, m), 8.13 (1H, s).

Example 67

1-{5-tert-Butyl-2-[1-(2-dimethylamino-ethyl)-2-oxo-1,2-dihydro-pyridin-4-yl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}urea formate salt

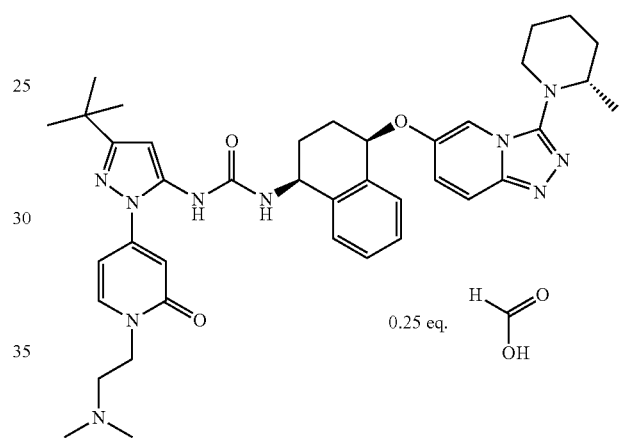

a. 4-Fluoro-2-[2-(tetrahydro-pyran-2-yloxy)-ethoxy]-pyridine (Intermediate 67a)

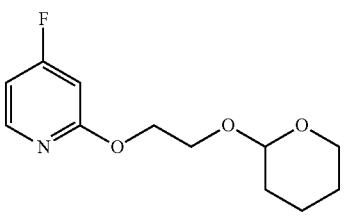 [SMILES: Fc1ccnc(OCCOC2CCCCO2)c1]

2-(Tetrahydro-2H-pyran-2-yl-oxy)ethanol (731 mg, 679 µL, 5.00 mmol) was suspended in anhydrous THF and NaH (60% dispersion in mineral oil, 240 mg, 6.0 mmol) was added portionwise, resulting in evolution of gas and the reaction stirred at room temp. After 15 min, a solution of 2,4-difluoropyridine (690 mg, 6.00 mmol) in anhydrous THF (2 mL) was slowly added. After stirring for 2 h, the reaction was partitioned between H₂O and EtOAc. The organic layer was separated, and the aqueous extracted again with EtOAc. The combined organics were dried over MgSO₄, concentrated in vacuo and subjected to FCC, eluting with 0-30% EtOAc/ cyclohexane, to afford the title compound as a colourless oil (633 mg, 43%). LCMS (Method 3) Rt 3.57 min, m/z 264.2 [M+Na].

b. {2-[2-(Tetrahydro-pyran-2-yloxy)-ethoxy]-pyridin-4-yl}-hydrazine (Intermediate 67b)

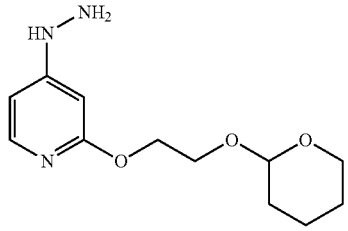 [SMILES: NNc1ccnc(OCCOC2CCCCO2)c1]

Intermediate 67a (633 mg, 2.62 mmol) was suspended in EtOH (5 mL) and hydrazine hydrate (50-60%, 5 mL) in a microwave vial fitted with a stirrer bar and sealed with a crimped septum, and heated to 80° C. for 18 h. The reaction was cooled, and partitioned between H₂O and EtOAc. The organic layer was separated, and the aqueous extracted again with EtOAc. The combined organics were dried over MgSO₄, and concentrated in vacuo to afford the title compound as a colorless oil (593 mg, 89%). LCMS (Method 3) Rt 0.41 and 1.71 min, m/z 276.2 [M+Na].

c. 2-[4-(5-Amino-3-tert-butyl-pyrazol-1-yl)-pyridin-2-yloxy]-ethanol (Intermediate 67c)

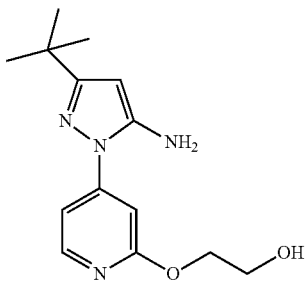 [SMILES: CC(C)(C)c1cc(N)n(-c2ccnc(OCCO)c2)n1]

4,4-Dimethyl-3-oxopentanenitrile (293 mg, 2.34 mmol) and Intermediate 67b (593 mg, 2.34 mmol) were suspended in MeOH (10 mL) and a few drops of concentrated HCl added and the reaction heated to reflux for 72 h. The reaction was cooled, concentrated in vacuo and partitioned between H₂O and EtOAc. The organic layer was separated, and the aqueous extracted again with EtOAc. The combined organics were dried over MgSO₄ and subjected to FCC, eluting with 10-50% EtOAc/cyclohexane to afford the title compound after crystallisation (139 mg, 21%). LCMS (Method 3) Rt 2.77 min, m/z 277.3 [MH⁺].

d. {5-tert-Butyl-2-[2-(2-hydroxy-ethoxy)-pyridin-4-yl]-2H-pyrazol-3-yl}-carbamic acid 2,2,2-trichloro-ethyl ester (Intermediate 67d)

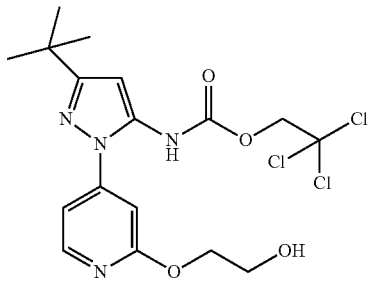 [SMILES: CC(C)(C)c1cc(NC(=O)OCC(Cl)(Cl)Cl)n(-c2ccnc(OCCO)c2)n1]

To a stirred solution of Intermediate 67c (139 mg, 0.50 mmol) in EtOAc (5 mL) and 1M NaOH solution (1.26 mL, 1.26 mmol) was added 2,2,2-trichloroethyl chloroformate (117 mg, 76 μL, 0.55 mmol) and the reaction was stirred at RT. After 1 h, a further 1.1 eq of 2,2,2-trichloroethyl chloroformate was added, stirred for an additional 1 h, then a further 2.2 eq. of 2,2,2-trichloroethyl chloroformate added. After stirring for an additional 2 h, the reaction was partitioned between H₂O and EtOAc. The organic layer was separated, and the aqueous layer extracted with EtOAc. The combined organics were dried over MgSO₄, concentrated in vacuo and subjected to FCC, eluting with 0-50% EtOAc/cyclohexane, and triturated with Et₂O to afford the title compound (74 mg, 33%). LCMS (Method 3) Rt 3.93 min, 451.1, 453 [MH⁺].

e. 1-{5-tert-Butyl-2-[2-(2-hydroxy-ethoxy)-pyridin-4-yl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 67e)

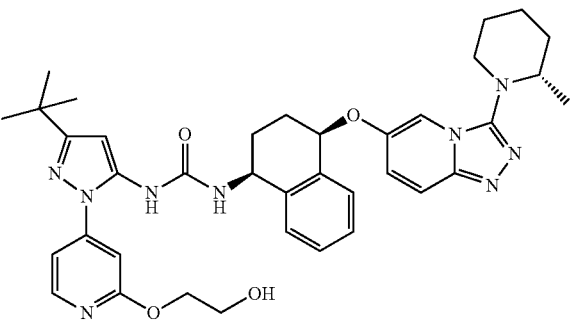 [SMILES: C[C@H]1CCCCN1c1nnc2ccc(O[C@@H]3CC[C@H](NC(=O)Nc4cc(C(C)(C)C)nn4-c4ccnc(OCCO)c4)c4ccccc43)cn12]

Intermediate 67d (74 mg, 0.16 mmol) and Intermediate B (62 mg, 0.16 mmol) were suspended in 1,4-dioxane (5 mL) and DIPEA (32 mg, 42 μL, 0.25 mmol) added and the reaction heated to 60° C. for 18 h. The reaction was cooled, concentrated in vacuo and subjected to FCC, eluting with 0-5% 2M NH₃ in MeOH/DCM, to afford the title compound (92 mg, 83%). LCMS (Method 3) Rt 3.51 min, 680.4 [MH⁺].

f. 1-{5-tert-Butyl-2-[1-(2-dimethylamino-ethyl)-2-oxo-1,2-dihydro-pyridin-4-yl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}urea formate salt (Example 67)

Intermediate 67e (86 mg, 0.13 mmol) and DIPEA (49 mg, 65 µL) were suspended in DCM (5 mL) and methanesulfonyl chloride (19 mg, 13 µL, 0.16 mmol) was added, and the reaction was stirred at room temp. After 30 min, H$_2$O (5 mL) and DCM (5 mL) was added, stirred, and passed through a phase separator cartridge and the organics concentrated in vacuo. The resulting residue was then suspended in dimethylamine solution (2M in THF, 2.5 mL) in a microwave vial, sealed with a crimped septum and stirred at 60° C. The reaction was then cooled, concentrated in vacuo, subjected to FCC, eluting with 0-7% 2M NH$_3$ in MeOH/DCM, then purified further by HPLC (Gemini C18, 10-98% MeCN in H$_2$O, 0.1% HCO$_2$H, 20 min gradient, 18 mL/min) and the combined fractions freeze dried to afford the title compound (22 mg, 24%). LCMS (Method 5): Rt 3.55 min, m/z 707.4 [MH$^+$]. $^1$H NMR (400 MHz, d$_6$-DMSO): 0.91 (3H, d, J=6.2 Hz), 1.27 (9H, s), 1.46-1.54 (2H, m), 1.61-1.73 (2H, m), 1.75-1.87 (2H, m), 1.89-1.97 (2H, m), 1.99-2.10 (1H, m), 2.17 (6H, s), 2.15-2.22 (2H, m), 2.87-2.95 (1H, m), 3.13-3.20 (1H, dt, J=12.0, 4.5 Hz), 3.32 (2H, m, obscured by water), 3.98 (2H, t, J=6.2 Hz), 4.83 (1H, q, J=7.9 Hz), 5.53 (1H, t, J=4.1 Hz), 6.37 (1H, s), 6.54-6.56 (1H, m), 6.57-6.61 (1H, dd, J=7.4, 2.4 Hz), 7.18-7.23 (1H, dd, J=2.3, 9.9 Hz), 7.24-7.32 (2H, m), 7.35-7.40 (3H, m), 7.64 (1H, dd, J=0.8, 9.8 Hz), 7.70-7.72 (1H, m), 7.73 (1H, d, J=7.5 Hz), 8.22 (0.25H, s), 8.35 (1H, s).

Example 68

1-{5-tert-Butyl-2-[4-chloro-3-(piperidin-4-yloxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea

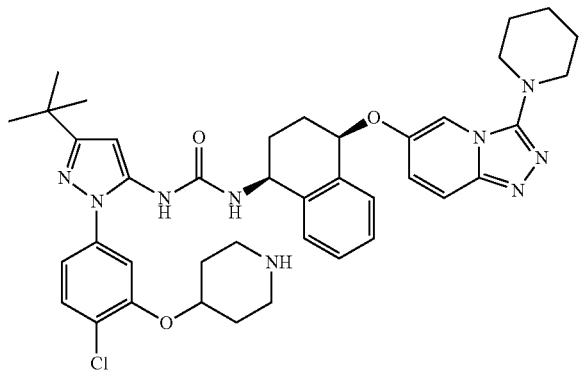 [SMILES: CC(C)(C)c1cc(NC(=O)N[C@H]2CC[C@@H](Oc3ccc4nnc(N5CCCCC5)n4c3)c3ccccc32)n(-c2ccc(Cl)c(OC3CCNCC3)c2)n1]

To a solution of Intermediate VeD (910 mg, 1.03 mmol) in THF (10 mL) was added dropwise tetrabutylammonium fluoride solution (1M in THF, 1.55 mL, 1.55 mmol) and the reaction stirred at RT. After stirring for 2.5 h, the reaction was refluxed for another 2 h, then cooled and partitioned between H$_2$O and DCM, and passed through a phase separator cartridge. The organics were concentrated in vacuo, and subjected to FCC, eluting with 0-20% 2 M NH$_3$ in MeOH. The crude product (55 mg) obtained after FCC was purified further by HPLC (XBridge C18 column, 30-98% MeCN in H$_2$O, 0.1% NH$_4$OH, 20 min gradient, 18 mL/min) to afford the title compound (32 mg, 58%). LCMS (Method 5): Rt 3.61 min, m/z 738, 740 [MH$^+$]. $^1$H NMR (400 MHz, d$_6$-DMSO): 1.28 (9H, s), 1.45-1.56 (2H, s), 1.57-1.66 (2H, m), 1.67-1.78 (4H, m), 1.81-1.96 (4H, m), 1.97-2.18 (2H, m), 2.53 (2H, m, obscured by solvent), 2.85-2.95 (2H, m), 3.14 (4H, t, J=5.3 Hz), 4.45 (1H, septet, J=4.2 Hz), 4.76-4.85 (1H, m), 5.55 (1H, t, J=4.3 Hz), 6.33 (1H, s), 7.02-7.10 (2H, m), 7.15 (1H, dd, J=2.2, 9.9 Hz), 7.22-7.35 (4H, m), 7.36-7.41 (1H, m), 7.54 (1H, d, J=8.6 Hz), 7.58-7.64 (2H, m), 8.14 (1H, s).

Example 69

1-{5-tert-Butyl-2-[4-chloro-3-(1-methyl-piperidin-4-yloxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea

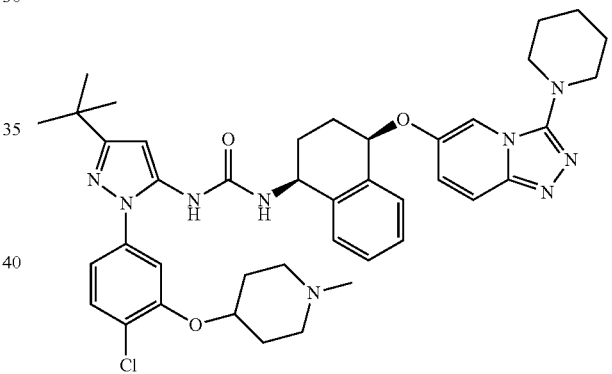

To a stirred solution of Example 68 (605 mg, 0.82 mmol) in DCM (8 mL) was added formaldehyde solution (37 wt % in H$_2$O, 610 µL, 8.19 mmol), followed by acetic acid (47 µL, 0.82 mmol), and then sodium triacetoxyborohydride (347 mg, 1.64 mmol) and the reaction stirred at RT under a N$_2$ atmosphere. After 3 h, the reaction was partitioned between H$_2$O and DCM, and passed through a phase separator cartridge. The organics were concentrated in vacuo and subjected to FCC, eluting with 0-7.5% 2M NH$_3$ in MeOH/DCM, and the product purified further by HPLC (XBridge C18 column, 45-85% MeCN in H$_2$O, 0.1% NH$_4$OH, 20 min gradient, 18 mL/min) to afford the title compound (331 mg, 54%). LCMS (Method 5): Rt 3.61 min, m/z 752, 754 [MH$^+$]. $^1$H NMR (400 MHz, d$_6$-DMSO): 1.27 (9H, s), 1.58-1.65 (2H, m), 1.65-1.77 (6H, m), 1.80-1.97 (4H, m), 2.11 (3H, s), 2.12-2.23 (4H, m), 3.14 (4H, t, J=5.1 Hz), 4.45-4.55 (1H, m), 4.76-4.83 (1H, m), 5.55 (1H, t, J=4.3 Hz), 6.33 (1H, s), 7.04 (1H, broad d, J=8.4 Hz), 7.08 (1H, dd, J=2.3, 8.6 Hz), 7.15

(1H, dd, J=2.2, 9.7 Hz), 7.22-7.36 (4H, m), 7.36-7.41 (1H, m), 7.52-7.56 (1H, m), 7.59-7.65 (2H, m), 8.13 (1H, s).

Example 70

1-{5-tert-Butyl-2-[4-chloro-3-((R)-piperidin-3-yloxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea

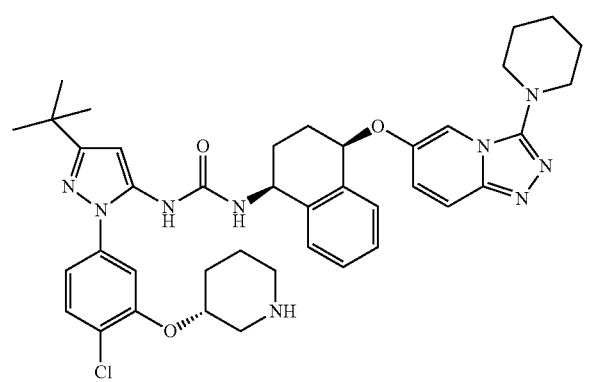 [SMILES: CC(C)(C)c1cc(NC(=O)N[C@H]2CC[C@@H](Oc3ccc4nnc(N5CCCCC5)n4c3)c3ccccc32)n(-c2ccc(Cl)c(O[C@@H]3CCCNC3)c2)n1]

The title compound was prepared in an analogous fashion to the procedures described for Example 68, starting from (S)-1-boc-3-hydroxypiperidine. LCMS (Method 5): Rt 3.62 min, m/z 738, 740 [MH$^+$]. NMR (400 MHz, d$_6$-DMSO): 1.28 (9H, s), 1.33-1.44 (1H, m), 1.49-1.68 (4H, m), 1.69-1.78-(4H, m), 1.80-1.96 (2H, m), 1.97-2.08 (2H, m), 2.08-2.17 (1H, m), 2.47 (1H, m, obscured by solvent), 2.55 (1H, m, obscured by solvent), 2.71 (1H, dt, J=4.4, 12.4 Hz), 3.03-3.11 (1H, m), 3.14 (4H, t, J=5.2 Hz), 4.33 (1H, septet, J=4.0 Hz), 4.76-4.84 (1H, m), 5.54 (1H, t, J=4.1 Hz), 6.33 (1H, s), 7.05 (1H, broad d, J=8.8 Hz), 7.08 (1H, dd, J=2.3, 8.4 Hz), 7.15 (1H, dd, J=2.2, 9.7 Hz), 7.23-7.36 (4H, m), 7.36-7.40 (1H, m), 7.54 (1H, d, J=8.8 Hz), 7.59-7.64 (2H, m), 8.14 (1H, s), no NH signal observed.

Example 71

1-{5-tert-Butyl-2-[4-chloro-3-((S)-piperidin-3-yloxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea

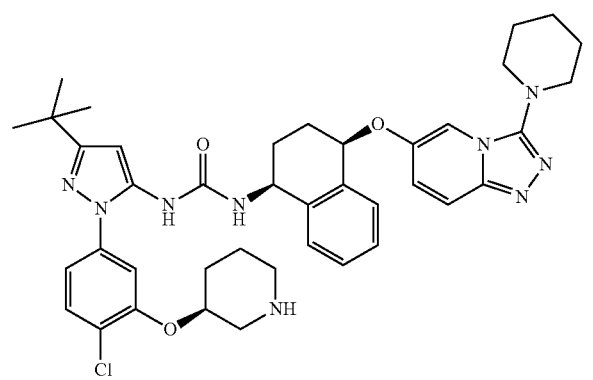 [SMILES: CC(C)(C)c1cc(NC(=O)N[C@H]2CC[C@@H](Oc3ccc4nnc(N5CCCCC5)n4c3)c3ccccc32)n(-c2ccc(Cl)c(O[C@H]3CCCNC3)c2)n1]

The title compound was prepared in an analogous fashion to the procedures described for Example 68, starting from (R)-1-boc-3-hydroxypiperidine. LCMS (Method 5): Rt 3.63 min, m/z 738, 740 [MH$^+$]. $^1$H NMR (400 MHz, d$_6$-DMSO): 1.28 (9H, s), 1.33-1.44 (1H, m), 1.49-1.68 (4H, m), 1.69-1.78-(4H, m), 1.80-1.96 (2H, m), 1.97-2.08 (2H, m), 2.08-2.17 (1H, m), 2.47 (1H, m, obscured by solvent), 2.55 (1H, m, obscured by solvent), 2.71 (1H, dt, J=4.4, 12.4 Hz), 3.03-3.11 (1H, m), 3.14 (4H, t, J=5.2 Hz), 4.33 (1H, septet, J=4.0 Hz), 4.76-4.84 (1H, m), 5.54 (1H, t, J=4.1 Hz), 6.33 (1H, s), 7.05 (1H, broad d, J=8.8 Hz), 7.08 (1H, dd, J=2.3, 8.4 Hz), 7.15 (1H, dd, J=2.2, 9.7 Hz), 7.23-7.36 (4H, m), 7.36-7.40 (1H, m), 7.54 (1H, d, J=8.8 Hz), 7.59-7.64 (2H, m), 8.14 (1H, s), no NH signal observed.

Example 72

1-{5-tert-Butyl-2-[4-chloro-3-((R)-1-methyl-piperidin-3-yloxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea

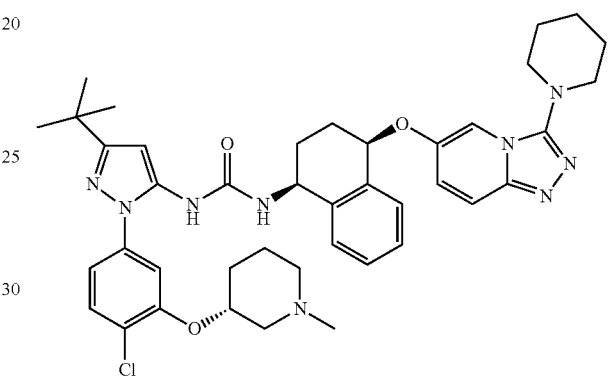

The title compound was prepared in an analogous fashion to the procedures described for Example 69 starting from Example 70. LCMS (Method 5): Rt 3.64 min, m/z 752, 754 [MH$^+$]. $^1$H NMR (400 MHz, d$_6$-DMSO): 1.28 (9H, s), 1.32-1.56 (2H, m), 1.57-1.65 (2H, m), 1.66-1.77 (5H, m), 1.80-2.08 (5H, m), 2.08-2.16 (2H, m), 2.14 (3H, s), 2.78-2.87 (1H, m), 3.14 (4H, t, J=5.4 Hz), 4.46 (1H, septet, J=4.2 Hz), 4.77-4.85 (1H, m), 5.54 (1H, t, J=4.2 Hz), 6.34 (1H, s), 7.05 (1H, broad d, J=8.6 Hz), 7.10 (1H, dd, J=2.2, 8.4 Hz), 7.15 (1H, dd, J=2.1, 10.0 Hz), 7.22-7.35 (4H, m), 7.36-7.40 (1H, m), 7.52-7.56 (1H, m), 7.59-7.64 (2H, m), 8.15 (1H, s).

Example 73

1-{5-tert-Butyl-2-[4-chloro-3-((S)-1-methyl-piperidin-3-yloxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea

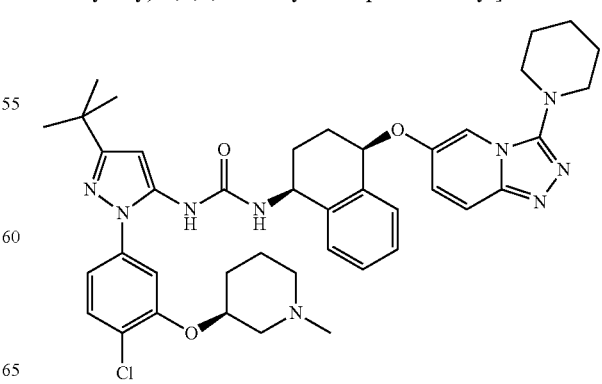

The title compound was prepared in an analogous fashion to the procedures described for Example 69 starting from Example 71. LCMS (Method 5): Rt 3.59 min, m/z 752, 754 [MH$^+$]. $^1$H NMR (400 MHz, d$_6$-DMSO): 1.28 (9H, s), 1.32-1.56 (2H, m), 1.57-1.65 (2H, m), 1.66-1.77 (5H, m), 1.80-2.08 (5H, m), 2.08-2.16 (2H, m), 2.14 (3H, s), 2.78-2.87 (1H, m), 3.14 (4H, t, J=5.4 Hz), 4.46 (1H, septet, J=4.2 Hz), 4.77-4.85 (1H, m), 5.54 (1H, t, J=4.2 Hz), 6.34 (1H, s), 7.05 (1H, broad d, J=8.6 Hz), 7.10 (1H, dd, J=2.2, 8.4 Hz), 7.15 (1H, dd, J=2.1, 10.0 Hz), 7.22-7.35 (4H, m), 7.36-7.40 (1H, m), 7.52-7.56 (1H, m), 7.59-7.64 (2H, m), 8.15 (1H, s).

Example 74

1-[3-tert-Butyl-1'-(2-dimethylamino-ethyl)-3'-hydroxymethyl-1'H-[1,4]bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

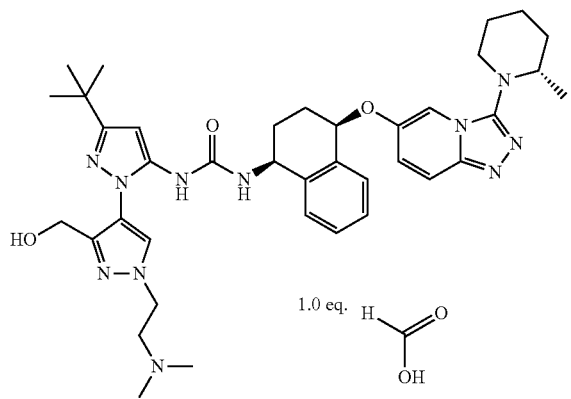 [SMILES: C[C@H]1CCCCN1c1nnc2ccc(O[C@@H]3CC[C@H](NC(=O)Nc4cc(C(C)(C)C)nn4-c4cn(CCN(C)C)nc4CO)c4ccccc43)cn12 ; O=CO]

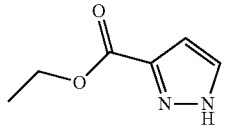

a. 1H-Pyrazole-3-carboxylic acid ethyl ester (Intermediate 74a)

A solution of ethyl propiolate (10.0 g, 0.10 mol) in THF (67 mL) was treated dropwise with (trimethylsilyl)diazomethane (51 mL, 0.10 mol) maintaining the temperature between 20-30° C. with ice bath cooling. The mixture was stirred at RT for 4 h then treated cautiously with water (250 mL) with cooling in an ice bath. The organics were evaporated in vacuo and the resulting precipitate was collected by filtration, washed with water and dried at RT in vacuo to give the title compound (13.5 g, 94%). LCMS (Method 3): Rt 2.22 min, m/z 141 [MH$^+$].

b. 4-Iodo-1H-pyrazole-3-carboxylic acid ethyl ester (Intermediate 74b)

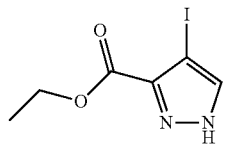

A suspension of Intermediate 74a (5.00 g, 35.7 mmol) in acetonitrile (90 mL) was treated with iodine (9.10 g, 35.7 mmol) then ceric ammonium nitrate (19.6 g, 35.7 mmol) and the mixture was stirred at RT overnight. Another portion of iodine (2.28 g, 9.0 mmol) was added and the mixture was stirred for a further 24 h then treated with ice-cold aqueous sodium hydrogensulphite solution (5%, 100 mL). The mixture was filtered through Celite rinsing with EtOAc and water. The phases were separated and the aqueous phase was extracted with EtOAc (2×). The combined organic layers were washed with water and brine, dried (Na$_2$SO4), filtered and evaporated in vacuo. The resulting solid was triturated with ether/cyclohexane, filtered off, washed with cyclohexane and dried at 50° C. in vacuo to give the title compound (3.70 g, 39%). LCMS (Method 3): Rt 2.88 min, m/z 267 [MH$^+$] (weak).

c. 4-Iodo-1-[2-(tetrahydro-pyran-2-yloxy)-ethyl]-1H-pyrazole-3-carboxylic acid ethyl ester (Intermediate 74c)

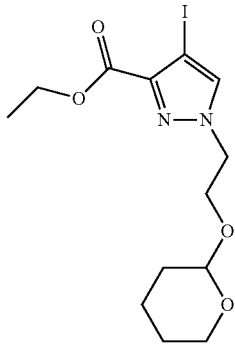 [SMILES: CCOC(=O)c1nn(CCOC2CCCCO2)cc1I]

A suspension of Intermediate 74b (2.72 g, 10.2 mmol) in acetonitrile (27 mL) was treated with caesium carbonate (5.0 g, 15.3 mmol) then 2-(2-bromoethoxy)tetrahydro-2H-pyran (1.70 mL, 11.2 mmol) and the mixture was stirred at 60° C. for 3.5 h. The mixture was evaporated in vacuo and the residue was partitioned between EtOAc and water. The aqueous layer was then extracted with EtOAc (2×). The combined organic layers were washed with saturated aqueous sodium bicarbonate solution and brine, dried (Na$_2$SO4), filtered and evaporated in vacuo. The residue was purified by FCC, using 0-50% EtOAc in cyclohexane, isolating the lower running spot to give the title compound as a colourless glass (1.57 g, 39%). LCMS (Method 3): Rt 3.67 min, m/z 417 [M+Na$^+$].

d. {4-Iodo-1-[2-(tetrahydro-pyran-2-yloxy)-ethyl]-1H-pyrazol-3-yl}-methanol (Intermediate 74d)

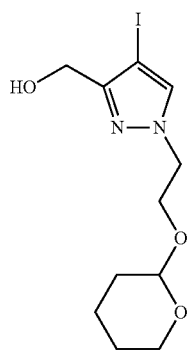 [SMILES: OCc1nn(CCOC2CCCCO2)cc1I]

A solution of Intermediate 74c (1.22 g, 3.09 mmol) in dry THF (12 mL) was treated with lithium borohydride (0.10 g, 4.64 mmol) and the mixture was stirred at 60° C. for 5 h then stood at RT overnight. The mixture was stirred at 60° C. for a further 5 h then cautiously quenched with water and diluted with EtOAc and water. The phases were separated and the aqueous layer was extracted with EtOAc (2×). The combined organic layers were washed with saturated aqueous sodium bicarbonate solution and brine, dried ($Na_2SO_4$), filtered and evaporated in vacuo. The residue was purified by FCC, using 0-100% EtOAc in cyclohexane, to give the title compound as a colorless oil (0.68 g, 62%). LCMS (Method 3): Rt 2.89 min, m/z 375 [M+Na$^+$].

e. {5-Amino-3-tert-butyl-1'-[2-(tetrahydro-pyran-2-yloxy)-ethyl]-1'H-[1,4]bipyrazolyl-3'-yl}-methanol (Intermediate 74e)

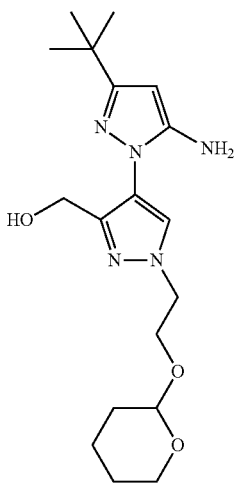 [SMILES: CC(C)(C)c1cc(N)n(-c2cn(CCOC3CCCCO3)nc2CO)n1]

A solution of Intermediate 74d (0.51 g, 1.45 mmol) in xylene (2.4 mL) was treated with 3-(tert-butyl)-1H-pyrazol-5-amine (0.18 g, 1.32 mmol) then potassium carbonate (0.38 g, 2.76 mmol), trans-N,N'-Dimethyl-1,2-cyclohexanediamine (0.037 g, 0.26 mmol) and copper (I) iodide (0.013 g, 0.066 mmol) were added. The mixture was degassed then heated at 150° C. for 4 h using microwave irradiation. Another portion of copper (I) iodide (0.006 g, 0.03 mmol) was added and the reaction mixture heated at 150° C. for a further 2 h using microwave irradiation. The mixture was diluted with water (1 mL), conc. aqueous ammonium hydroxide (1 mL) and EtOAc (1 mL) and the phases separated. The aqueous layer was then extracted with EtOAc (2×). The combined organic layers were washed with water and brine, dried ($Na_2SO_4$), filtered and evaporated in vacuo. The residue was purified by FCC, using 0-5% MeOH in DCM to give the title compound as a dark green gum (0.30 g, 63%). LCMS (Method 3): Rt 2.46 min, m/z 364 [MH$^+$].

f. 3-tert-Butyl-1'-[2-(tetrahydro-pyran-2-yloxy)-ethyl]-3'-triisopropylsilanyloxymethyl-1'H-[1,4'] bipyrazolyl-5-ylamine (Intermediate 74f)

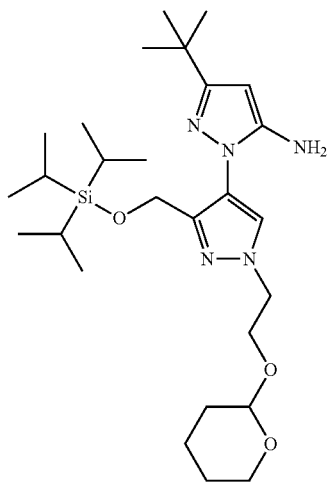 [SMILES: CC(C)[Si](OCc1nn(CCOC2CCCCO2)cc1-n1nc(C(C)(C)C)cc1N)(C(C)C)C(C)C]

A solution of Intermediate 74e (0.39 g, 1.10 mmol) in DMF (3.9 mL) was treated with imidazole (0.18 g, 2.7 mmol) then chlorotriisopropylsilane (0.28 mL, 1.3 mmol) and the mixture was stirred at RT for 22 h. The mixture was evaporated in vacuo and the residue was partitioned between EtOAc and water. The aqueous layer was then extracted with EtOAc (2×). The combined organic layers were washed with saturated aqueous sodium bicarbonate solution and brine, dried ($Na_2SO_4$), filtered and evaporated in vacuo. The residue was purified by FCC, using 0-4% MeOH in DCM, to give the title compound (0.44 g, 79%). LCMS (Method 3): Rt 4.20 min, m/z 520 [MH$^+$].

g. {3-tert-Butyl-1'-[2-(tetrahydro-pyran-2-yloxy)-ethyl]-3'-triisopropylsilanyloxymethyl-1'H-[1,4]bipyrazolyl-5-yl}-carbamic acid 2,2,2-trichloro-ethyl ester (Intermediate 74g)

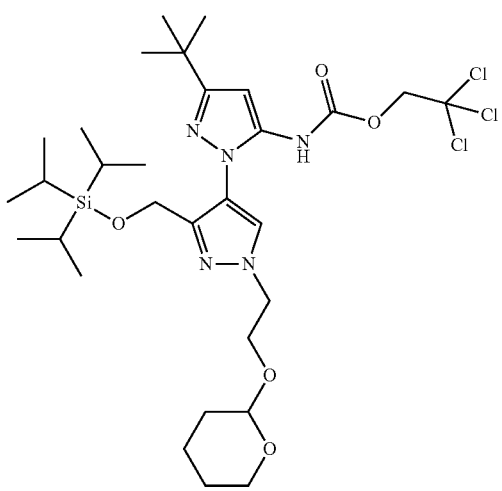 [SMILES: CC(C)[Si](OCc1nn(CCOC2CCCCO2)cc1-n1nc(C(C)(C)C)cc1NC(=O)OCC(Cl)(Cl)Cl)(C(C)C)C(C)C]

To a solution of Intermediate 74f (0.44 g, 0.85 mmol) in EtOAc (5 mL) was added 1N aqueous NaOH solution (1.7 mL, 1.7 mmol) followed by 2,2,2-trichloroethylchloroformate (0.13 mL, 0.93 mmol). The reaction was stirred at RT for 4 h then treated with another portion of 2,2,2-trichloroethylchloroformate (35 µL, 0.25 mmol) and stirred over the weekend. The reaction was treated with another portion of 2,2,2-trichloroethylchloroformate (35 µL, 0.25 mmol) and stirred for 1 h then diluted with EtOAc and water and the layers were separated. The aqueous layer was then extracted with EtOAc (2×). The combined organic layers were washed with saturated aqueous sodium bicarbonate solution, and brine, dried (Na₂SO₄), filtered and evaporated in vacuo. The residue was purified by FCC, using 0-4% MeOH in DCM, to give the title compound (0.47 g, 80%). ¹H NMR (300 MHz, CDCl₃): 0.96 (18H, d, J=6.8 Hz), 1.01-1.17 (3H, m), 1.25 (9H, s), 1.38-1.51 (4H, m), 1.54-1.75 (2H, m), 3.36-3.45 (1H, m), 3.58-3.68 (1H, m), 3.68-3.77 (1H, m), 3.97-4.07 (1H, m), 4.24 (2H, t, J=4.7 Hz), 4.51 (1H, t, J=3.2 Hz), 4.59 (2H, s), 4.69-4.73 (2H, m), 6.26 (1H, s), 7.63 (1H, s), 7.74 (1H, s).

h. 1-{3-tert-Butyl-1'-[2-(tetrahydro-pyran-2-yloxy)-ethyl]-3'-triisopropylsilanyloxymethyl-1'H-[1,4]bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 74h)

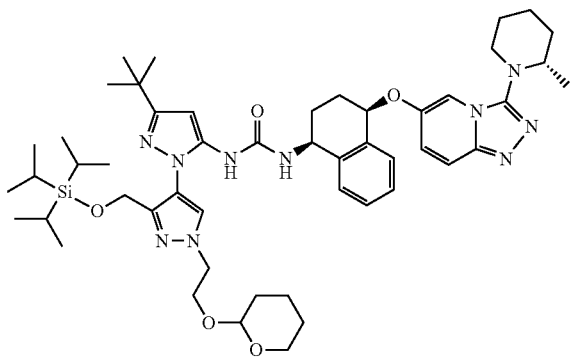 [SMILES: CC(C)[Si](OCc1nn(CCOC2CCCCO2)cc1-n1nc(C(C)(C)C)cc1NC(=O)N[C@H]1CC[C@@H](Oc2ccc3nnc(N4CCCC[C@@H]4C)n3c2)c2ccccc21)(C(C)C)C(C)C]

Intermediate B (0.23 g, 0.61 mmol) was treated with a solution of Intermediate 74g (0.47 g, 0.68 mmol) in 1,4-dioxane (3.4 mL) then DIPEA (0.13 mL, 0.74 mmol) was added. The mixture was stirred at 70° C. overnight. The mixture was evaporated in vacuo and the residue was partitioned between DCM and water. The aqueous layer was then extracted with DCM (2×). The combined organic layers were washed with brine, dried (Na₂SO4), filtered and evaporated in vacuo. The residue was purified by FCC, using 0-7% MeOH in DCM, to give the title compound (0.34 g, 60%). LCMS (Method 3): Rt 5.48 min, m/z 923.7 [MH⁺].

i. 1-[3-tert-Butyl-1'-(2-hydroxy-ethyl)-3'-triisopropylsilanyloxymethyl-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 74i)

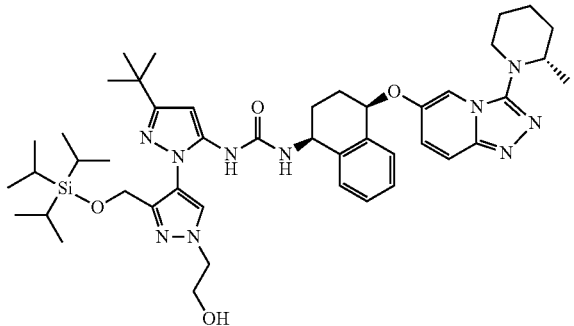 [SMILES: CC(C)[Si](OCc1nn(CCO)cc1-n1nc(C(C)(C)C)cc1NC(=O)N[C@H]1CC[C@@H](Oc2ccc3nnc(N4CCCC[C@@H]4C)n3c2)c2ccccc21)(C(C)C)C(C)C]

A solution of Intermediate 74h (0.34 g, 0.37 mmol) in MeOH (3.7 mL) was treated with pyridinium p-toluenesulfonate (0.28 g, 1.1 mmol) and the mixture was stirred at 45° C. for 24 h. The mixture was evaporated in vacuo and the residue was partitioned between DCM and a saturated aqueous sodium bicarbonate solution. The aqueous layer was then extracted with DCM (2×). The combined organic layers were washed with water, a saturated aqueous sodium bicarbonate solution and brine, dried (Na₂SO4), filtered and evaporated in vacuo. The residue was purified by FCC, using 0-8% MeOH in DCM, to give the title compound as a golden glass (142 mg, 46%). LCMS (Method 3): Rt 4.81 min, m/z 839.6 [MH⁺].

j. Methanesulfonic acid 2-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-3'-triisopropylsilanyloxymethyl-[1,4']bipyrazol-1'-yl]-ethyl ester (Intermediate 74j)

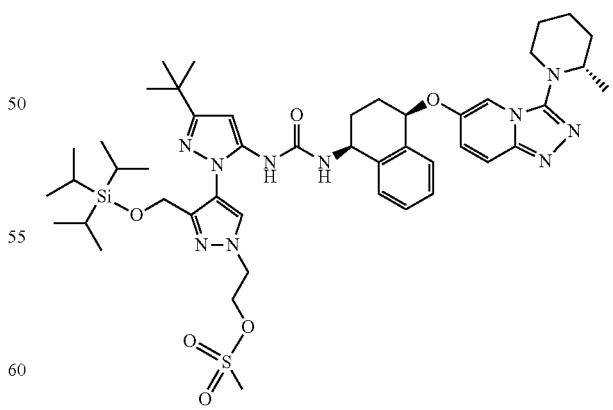

A solution of Intermediate 74i (134 mg, 0.16 mmol) in DCM (1.6 mL) was treated with DIPEA (83 µL, 0.48 mmol) then cooled to 0° C. Methanesulfonyl chloride was added and the mixture was stirred at 0° C. for 5 min then at RT for 1 h.

The mixture was diluted with DCM and a saturated aqueous sodium bicarbonate solution and the phases were separated. The aqueous layer was then extracted with DCM (2×). The combined organic layers were washed with a saturated aqueous sodium bicarbonate solution and brine, dried (Na$_2$SO4), filtered and evaporated in vacuo. The residue was purified by FCC, using 0-8% MeOH in DCM, to give the title compound (107 mg, 73%). LCMS (Method 3): Rt 5.06 min, m/z 917.4 [MH$^+$].

k. 1-[3-tert-Butyl-1'-(2-dimethylamino-ethyl)-3'-triisopropylsilanyloxymethyl-1'H-[1,4]bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 74k)

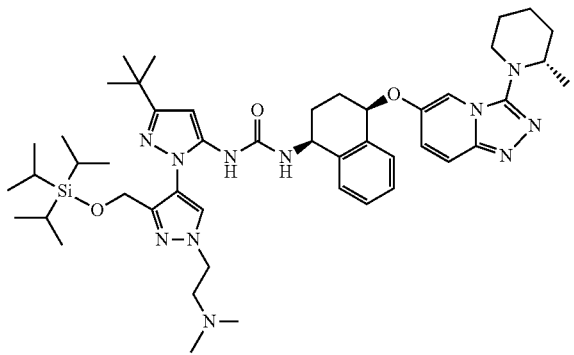 [SMILES: CC(C)[Si](OCc1nn(CCN(C)C)cc1-n1nc(C(C)(C)C)cc1NC(=O)N[C@H]1CC[C@@H](Oc2ccc3nnc(N4CCCC[C@@H]4C)n3c2)c2ccccc21)(C(C)C)C(C)C]

A solution of Intermediate 74j (104 mg, 0.11 mmol) in THF (0.5 mL) was treated with dimethylamine (2M in THF, 0.57 mL, 1.1 mmol) and the mixture was stirred at RT over the weekend. The mixture was evaporated in vacuo and the residue was partitioned between DCM and water. The aqueous layer was then extracted with DCM (2×). The combined organic layers were washed with brine, dried (Na$_2$SO4), filtered and evaporated in vacuo. The residue was purified by FCC, using 0-7% [2M NH$_3$ in MeOH] in DCM, to give the title compound (79 mg, 81%). LCMS (Method 3): Rt 3.46 min, m/z 866.6 [MH$^+$].

l. 1-[3-tert-Butyl-1'-(2-dimethylamino-ethyl)-3'-hydroxymethyl-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt (Example 74)

A solution of Intermediate 74k (76 mg, 0.088 mmol) in THF (0.44 mL) was treated with tetrabutylammonium fluoride (1M in THF, 0.44 mL, 0.44 mmol) and the mixture was heated to 50° C. for 5 h. The mixture was evaporated in vacuo and the residue was partitioned between DCM and a saturated aqueous sodium bicarbonate solution. The layers were separated and the aqueous layer was then extracted with DCM (2×). The combined organic layers were washed with brine, dried (Na$_2$SO4), filtered and evaporated in vacuo. The residue was purified by FCC, using 0-9% [2M NH$_3$ in MeOH] in DCM. Further purification by HPLC in 3 portions (Method 6, 30-60% MeCN in H$_2$O, 0.1% HCO$_2$H over 25 min) gave a colourless glass that was triturated with ether. The solid was collected by filtration, washed with ether and dried at 50° C. in vacuo to give the title compound (20 mg, 32%). LCMS (Method 5): Rt 3.47 min, m/z 710.5 [MH$^+$]. $^1$H NMR (400 MHz, d$_6$-DMSO): 0.91 (3H, d, J=6.3 Hz), 1.25 (9H, s), 1.44-1.57 (2H, m), 1.61-1.74 (2H, m), 1.74-1.92 (3H, m), 1.92-2.02 (1H, m), 2.01-2.16 (2H, m), 2.18 (6H, s), 2.68 (2H, t, J=6.8 Hz), 2.87-2.95 (1H, m), 3.16 (1H, dt, J=12.0, 4.1 Hz, partially obscured by water), 3.27-3.36 (1H, m, obscured by water), 4.16 (2H, t, J=7.0 Hz), 4.31 (2H, s), 4.80-4.88 (1H, m), 4.92-5.11 (0.3H, br s), 5.53 (1H, t, J=4.3 Hz), 6.30 (1H, s), 7.14-7.22 (2H, m), 7.25-7.40 (4H, m), 7.64 (1H, d, J=10.0 Hz), 7.70 (1H, d, J=1.6 Hz), 8.00 (1H, s), 8.07 (1H, s), 8.19 (1H, s).

Example 75

1-{5-tert-Butyl-2-[4-chloro-3-(2-hydroxy-propoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea

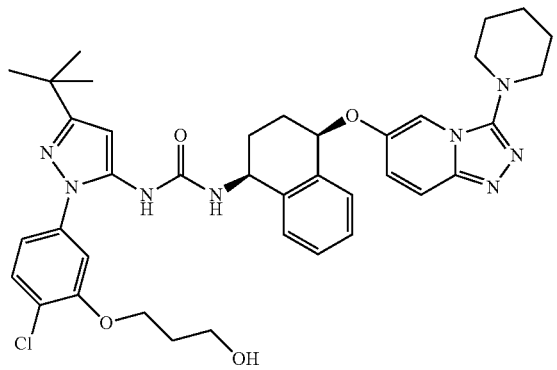 [SMILES: CC(C)(C)c1cc(NC(=O)N[C@H]2CC[C@@H](Oc3ccc4nnc(N5CCCCC5)n4c3)c3ccccc32)n(-c2ccc(Cl)c(OCCCO)c2)n1]

a. 5-tert-Butyl-2-{4-chloro-3-[3-(tetrahydro-pyran-2-yloxy)-propoxy]-phenyl}-2H-pyrazol-3-ylamine (Intermediate 75a)

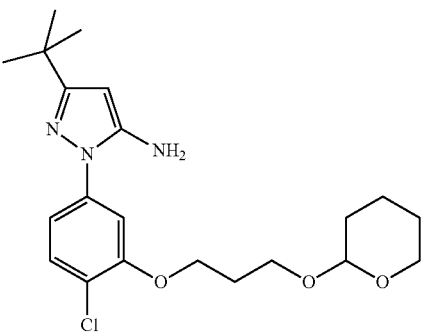 [SMILES: CC(C)(C)c1cc(N)n(-c2ccc(Cl)c(OCCCOC3CCCCO3)c2)n1]

To a solution of 5-(5-amino-3-tert-butyl-pyrazol-1-yl)-2-chloro-phenol (WO20111154734A1, which is incorporated herein by reference in it is entirety; 500 mg, 1.88 mmol), and Ph₃P (986 mg, 3.76 mmol) in dry THF (10 mL) was added 3-(tetrahydro-pyran-2-yloxy)-propan-1-ol (Can. J. Chem. Vol. 73, 1195, pp 1682, which is incorporated herein by reference in it is entirety; 452 mg, 2.82 mmol). The resulting mixture was cooled to 0° C. using an ice bath and diethylazodicarboxylate (0.69 mL, 3.76 mmol) was added to the chilled mixture which was allowed to warm up to RT. The volatiles were removed under reduced pressure. The residue was purified by FCC, using 0-50% EtOAc in cyclohexane, to give the title compound (739 mg, 96%). LCMS (Method 1): Rt 3.63 min, m/z 408 [MH⁺].

b. (5-tert-Butyl-2-{4-chloro-3-[3-(tetrahydro-pyran-2-yloxy)-propoxy]-phenyl}-2H-pyrazol-3-yl)-carbamic acid-2,2,2-trichloro-ethyl ester (Intermediate 75b)

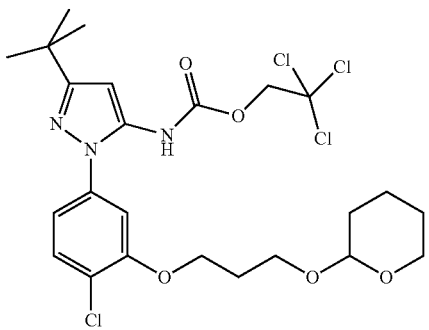 [SMILES: CC(C)(C)c1cc(NC(=O)OCC(Cl)(Cl)Cl)n(-c2ccc(Cl)c(OCCCOC3CCCCO3)c2)n1]

To a solution of Intermediate 75a (739 mg, 1.811 mmol) in EtOAc (9 mL) and 1N sodium hydroxide solution (4.5 mL, 4.53 mmol) was added 2,2,2-trichloroethyl chloroformate (341 μL, 2.54 mmol), and the mixture stirred vigorously at RT for 1 h. The aqueous layer was extracted with EtOAc (2×20 mL), and then the combined organics dried and concentrated in vacuo. The residue was purified by FCC, using 0-10% MeOH in DCM, to give the title compound (743 mg, 70%). LCMS (Method 4): Rt 4.69 min, m/z 582, 584, 586 [MH⁺].

c. 1-(5-tert-Butyl-2-{4-chloro-3-[3-(tetrahydro-pyran-2-yloxy)-propoxy]-phenyl}-2H-pyrazol-3-yl)-3-[(1S,4R)-4-(3-piperidin-1-yl-[1,2,4]triazolo[4,3-a]pyridin-6-yloxy)-1,2,3,4-tetrahydro-naphthalen-1-yl]-urea (Intermediate 75c)

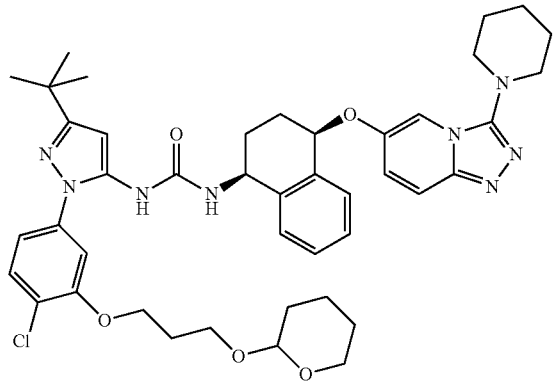 [SMILES: CC(C)(C)c1cc(NC(=O)N[C@H]2CC[C@@H](Oc3ccc4nnc(N5CCCCC5)n4c3)c3ccccc32)n(-c2ccc(Cl)c(OCCCOC3CCCCO3)c2)n1]

A solution of Intermediate D (153 mg, 0.421 mmol) and Intermediate 75b (265 mg, 0.454 mmol) in DMF (5 mL) and DIPEA (147 μL, 0.84 mmol) was stirred at 100° C. for 5 h. The mixture was cooled, then water added and the mixture extracted with EtOAc (50 mL). The combined organics were dried and concentrated in vacuo. The residue was purified by FCC, using 0-10% MeOH in DCM, to give the title compound (836 mg, 95%). LCMS (Method 4): Rt 4.04 min, m/z 797 [MH⁺].

d. 1-{5-tert-Butyl-2-[4-chloro-3-(2-hydroxy-propoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea (Example 75)

A solution of Intermediate 75c (247 mg, 0.31 mmol) and pyridinium p-toluenesulphonate (233 mg, 0.93 mmol) in methanol (14 mL) was stirred at 40-45° C. for 18.5 h. The cooled mixture was concentrated in vacuo, diluted with sat. sodium hydrogen carbonate solution and extracted with DCM (3×15 mL). The combined organics were dried and concentrated in vacuo. The residue was purified by FCC, using 0-12% MeOH in DCM, to give the product (199.7 mg, 99%). Part of this (50 mg) was further purified by HPLC (XBridge C18 column, 30-90% MeCN in H₂O, 0.1% NH₄OH) to give the title compound (35 mg). LCMS (Method 5): Rt 4.53 min, m/z 713.4 [MH⁺]. ¹H NMR (400 MHz, d₆-DMSO): 1.28 (9H, s), 1.57-1.65 (2H, m), 1.68-1.77 (4H, m), 1.80-1.94 (4H, m), 1.97-2.17 (2H, m), 3.07-3.17 (4H, m), 3.48-3.64 (2H, q, J=6.2 Hz), 4.09-4-20 (2H, t, J=6.52 Hz), 4.48-4.58 (1H, t, J=5.7), 4.76-4.84 (1H, m), 5.54 (1H, t, J=4.3 Hz), 6.34 (1H, s), 7.05-7.11 (2H, m), 7.16 (1H, dd, J=2.0, 9.9 Hz), 7.21-7.41 (5H, m), 7.54 (1H, d, J=8.5 Hz), 7.59-7.65 (2H, m), 8.14 (1H, br s).

Example 76

1-{5-tert-Butyl-2-[4-chloro-3-(3-morpholin-4-yl-propoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea (Example 76)

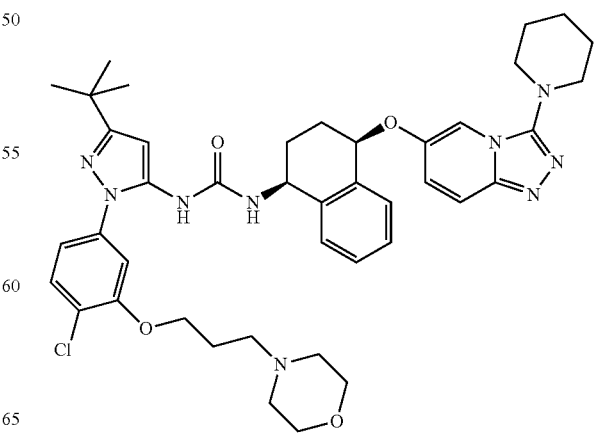

a. Methanesulfonic acid 3-[5-(3-tert-butyl-5-{3-[(1S, 4R)-4-(3-piperidin-1-yl-[1,2,4]triazolo[4,3-a]pyridin-6-yloxy)-1,2,3,4-tetrahydro-naphthalen-1-yl]-ureido}-pyrazol-1-yl)-2-chloro-phenoxy]-propyl ester (Intermediate 76a)

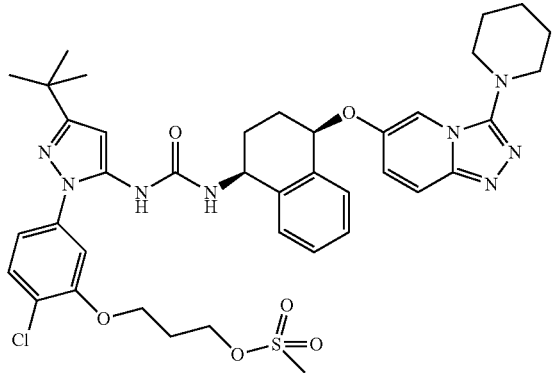 [SMILES: CC(C)(C)c1cc(NC(=O)N[C@H]2CC[C@@H](Oc3ccc4nnc(N5CCCCC5)n4c3)c3ccccc32)n(-c2ccc(Cl)c(OCCCOS(C)(=O)=O)c2)n1]

A mixture of Example 75 (193 mg, 0.27 mmol), methanesulfonyl chloride (63 μL, 0.81 mmol) and DIPEA (200 μL, 1.08 mmol) in DCM (10 mL) was stirred at RT for 1 h. The volatiles were evaporated under reduced pressure to afford the title compound (214 mg, Quantitative). LCMS (Method 4): Rt 3.57 min, m/z 791 [MH$^+$].

b. 1-{5-tert-Butyl-2-[4-chloro-3-(3-morpholin-4-yl-propoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea (Example 76)

A solution of Intermediate 76a (214 mg, 0.27 mmol) and DIPEA (95 μL, 0.54 mmol) in THF (5 mL) was treated with morpholine (47 μL, 0.54 mmol). The mixture was stirred at 50° C. for 18 h in a sealed vial. The volatiles were concentrated in vacuo and the product was purified by MDAP purification (Method 7) to give the title compound (72 mg, 34%). LCMS (Method 5): Rt 3.60 min, m/z 782.6 [MH$^+$].$^+$]. $^1$H NMR (400 MHz, d$_6$-DMSO): 1.28 (9H, s), 1.57-1.65 (2H, m), 1.68-1.77 (4H, m), 1.80-1.94 (4H, m), 1.99-2.17 (2H, m), 2.24-2.32 (3H, bs), 2.36-2.42 (2H, t, J=6.9), 3.11-3.17 (4H, m), 3.48-3.52 (4H, m), 4.09-4.15 (2H, t, J=6.52 Hz), 4.76-4.84 (1H, m), 5.54 (1H, t, J=4.3 Hz), 6.34 (1H, s), 7.03-7.11 (2H, m), 7.16 (1H, dd, J=2.0, 9.9 Hz), 7.21-7.41 (5H, m), 7.54 (1H, d, J=8.5 Hz), 7.59-7.65 (2H, m), 8.14 (1H, br s).

Example 77

1-{5-tert-Butyl-2-[4-chloro-3-(2-dimethylamino-ethoxy)-phenyl]-2H-pyrazol-3-yl}-3-{1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

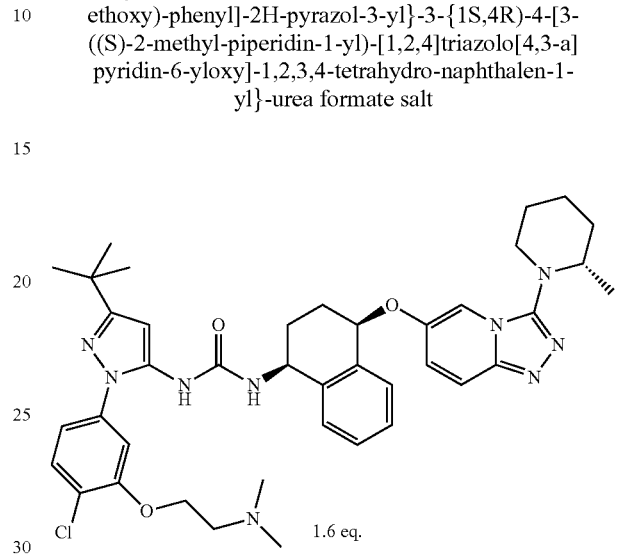

1.6 eq.

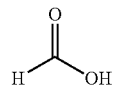

a. 1-(5-tert-Butyl-2-{4-chloro-3-[2-(tetrahydro-pyran-2-yloxy)-ethoxy]-phenyl}-2H-pyrazol-3-yl)-{3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 77a)

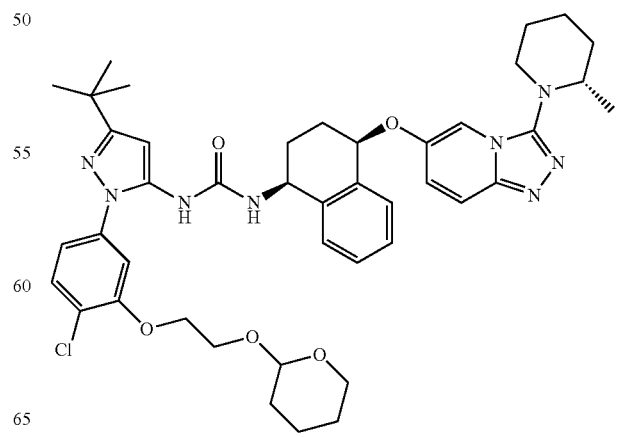

A mixture of Intermediate 53b (150 mg, 0.26 mmol), and Intermediate B (99 mg, 0.26 mmol) and DIPEA (69 μL, 0.40 mmol) in dioxane (1 mL) was heated at 70° C. for 18 h. The mixture was cooled, diluted with DCM (5 mL) and washed with water (2×5 mL). The organic layer was passed through a phase separator and concentrated in vacuo. The residue was purified by FCC, using 0-10% MeOH in DCM, to afford the title compound (154 mg, 73%). LCMS (Method 3): Rt: 4.41 min, m/z 797 [MH$^+$].

b. 1-{5-tert-Butyl-2-[4-chloro-3-(2-hydroxy-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 77b)

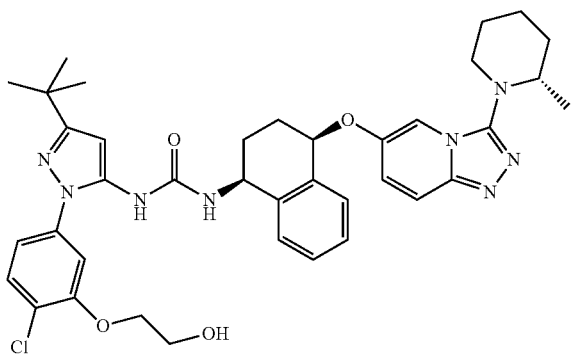 [SMILES: C[C@H]1CCCCN1c1nnc2ccc(O[C@@H]3CC[C@H](NC(=O)Nc4cc(C(C)(C)C)nn4-c4ccc(Cl)c(OCCO)c4)c4ccccc43)cn12]

A mixture of Intermediate 77a (150 mg, 0.19 mmol) and pyridinium p-toluene sulfonate (140 mg, 0.56 mmol) in MeOH (1.5 mL) was heated at 45° C. for 18 h. The mixture was cooled, diluted with DCM (4 mL) and washed with saturated aqueous NaHCO$_3$ solution (2×4 mL). The organic layer was passed through a phase separator and concentrated in vacuo. The residue was purified by FCC, using 0-10% MeOH:DCM to afford the title compound (92 mg, 69%). LCMS (Method 3): Rt: 3.81 min, m/z 713 [MH$^+$].

c. Methanesulfonic acid 2-{5-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-2-chloro-phenoxy}-ethyl ester (Intermediate 77c)

d. 1-{5-tert-Butyl-2-[4-chloro-3-(2-dimethylamino-ethoxy)-phenyl]-2H-pyrazol-3-yl}-3-{1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt (Example 77)

A mixture of Intermediate 77b (90 mg, 0.13 mmol), methanesulfonyl chloride (12 μL, 0.15 mmol) and DIPEA (66 μL, 0.38 mmol) in DCM (2 mL) was stirred at RT for 1 h. A further drop of methanesulfonyl chloride was added and the mixture continued to stir at RT for 30 min. The reaction mixture was diluted with DCM (2 mL) and washed with water (2×4 mL). The organic layer was passed through a phase separator and concentrated in vacuo to afford Intermediate 77c (LCMS (Method 3): Rt: 4.01 min, m/z 791,793 [MH$^+$]). This residue (94 mg) was dissolved in THF (2 mL) and treated with dimethylamine solution (2M in THF, 1.5 mL, 3.00 mmol). The reaction mixture was heated at 60° C., in a sealed tube for 18 h. The mixture was concentrated in vacuo and the residue was purified by FCC, using 0-12% 2M NH$_3$ in MeOH in DCM, to afford a solid. This was purified by MDAP to afford the title compound (50 mg, 54%). LCMS (Method 5): Rt: 3.71 min, m/z 740.5 [MH$^+$]. NMR (400 MHz, d$_6$-DMSO): 0.91 (3H, d, J=6.3 Hz), 1.28 (9H, s), 1.45-1.56 (2H, m), 1.61-1.74 (2H, m), 1.74-1.98 (4H, m), 1.98-2.18 (2H, m), 2.22 (6H, s), 2.67 (2H, t, J=5.7 Hz), 2.85-2.95 (1H, m, obscured by water), 3.13-3.20 (1H, m, obscured by water), 3.28-3.36 (1H, m, obscured by water), 4.17 (2H, t, J=5.7 Hz), 4.77-4.85 (1H, m), 5.52 (1H, t, J=4.1 Hz), 6.34 (1H, s), 7.07-7.13 (2H, m), 7.19 (1H, dd, J=9.7, 2.1 Hz), 7.23-7.40 (5H, m), 7.54 (1H, d, J=8.5 Hz), 7.64 (1H, d, J=9.9 Hz), 7.69 (1H, d, J=2.1 Hz), 8.16 (2.6H, s).

Example 78

1-{5-tert-Butyl-2-[4-chloro-3-(2-dimethylamino-ethoxy)-phenyl]-2H-pyrazol-3-yl}-3-{(1S,4R)-4-[3-((S)-2-methyl-pyrrolidin-1-yl)-[1,2,4]triazolo[4,3-a]pyridin-6-yloxy]-1,2,3,4-tetrahydro-naphthalen-1-yl}-urea formate salt

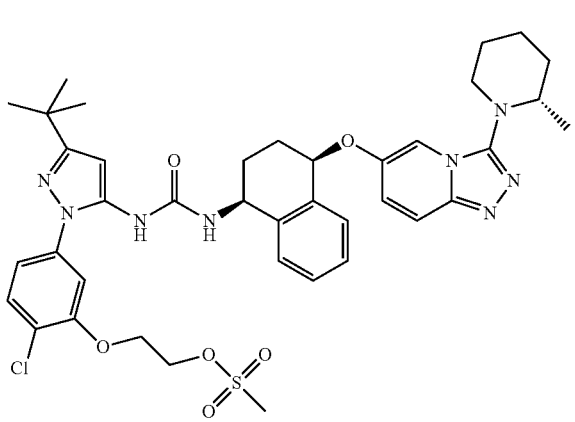 [SMILES: C[C@H]1CCCCN1c1nnc2ccc(O[C@@H]3CC[C@H](NC(=O)Nc4cc(C(C)(C)C)nn4-c4ccc(Cl)c(OCCOS(C)(=O)=O)c4)c4ccccc43)cn12]

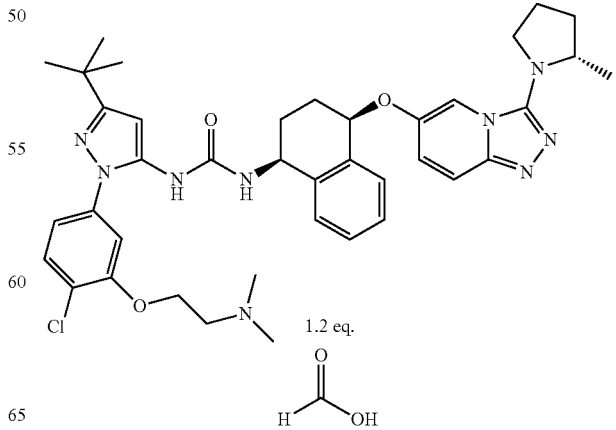

1.2 eq.

a. 6-Fluoro-3-((S)-2-methyl-pyrrolidin-1-yl)-[1,2,4]triazolo[4,3-a]pyridine (Intermediate 78a)

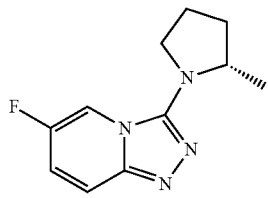 [SMILES: C[C@H]1CCCN1c1nnc2ccc(F)cn12]

A mixture of Intermediate Fb (576 mg, 3.36 mmol) and (S)-2-methylpyrrolidine (1.00 g, 11.8 mmol) in DMA (10 mL) was subjected to microwave irradiation, at 175° C. for 2 h. The reaction mixture was concentrated in vacuo and the residue purified by FCC, using 0-15% MeOH in EtOAc, to afford the title compound, which crystallised on standing (357 mg, 48%). LCMS (Method 3): Rt: 2.35 min, m/z 221 [MH⁺].

b. (1S,4R)-4-[3-((S)-2-Methyl-pyrrolidin-1-yl)-[1,2,4]triazolo[4,3-a]pyridin-6-yloxy]-1,2,3,4-tetrahydro-naphthalen-1-ylamine (Intermediate 78b)

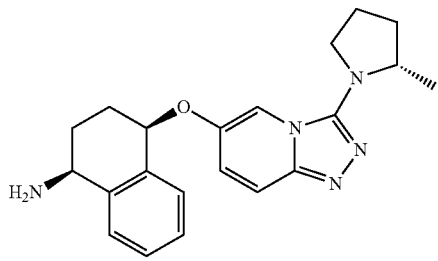 [SMILES: C[C@H]1CCCN1c1nnc2ccc(O[C@@H]3CC[C@H](N)c4ccccc43)cn12]

Intermediate A (318 mg, 1.95 mmol) was dissolved in DMF (1 mL) and sodium hydride (60% dispersion in oil, 125 mg, 3.25 mmol) was added portionwise. The mixture was stirred at RT for 10 min. A solution of Intermediate 78a (357 mg, 1.62 mmol) in DMF (1 mL) was added and the reaction mixture was heated at 60° C. for 1.5 h. The mixture was cooled to RT and partitioned between EtOAc (10 mL) and water (10 mL). The organic layer was dried (MgSO₄), filtered and concentrated in vacuo. The residue was purified by FCC, using 0-10% [2M NH₃ in MeOH] in DCM, to afford the title compound as an orange gum (226 mg, 38%). LCMS (Method 3): Rt 0.42, 2.06 min, m/z 364 [MH⁺].

c. 1-(5-tert-Butyl-2-{4-chloro-3-[2-(tetrahydro-pyran-2-yloxy)-ethoxy]-phenyl}-2H-pyrazol-3-yl)-3-{(1S,4R)-4-[3-((S)-2-methyl-pyrrolidin-1-yl)-[1,2,4]triazolo[4,3-a]pyridin-6-yloxy]-1,2,3,4-tetrahydro-naphthalen-1-yl}-urea (Intermediate 78c)

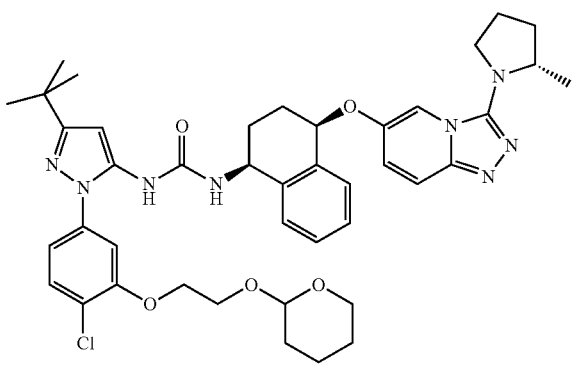 [SMILES: C[C@H]1CCCN1c1nnc2ccc(O[C@@H]3CC[C@H](NC(=O)Nc4cc(C(C)(C)C)nn4-c4ccc(Cl)c(OCCOC5CCCCO5)c4)c4ccccc43)cn12]

A solution of Intermediate 53b (238 mg, 0.41 mmol), Intermediate 78b (220 mg, 0.61 mmol) and DIPEA (158 μL, 0.91 mmol) in dioxane (2.5 mL) was heated at 60° C. for 18 h. The reaction mixture was cooled and diluted with DCM (5 mL). The organic layer was washed with water (2×5 mL), passed through a phase separator and concentrated in vacuo. The residue was purified by FCC, using 0-10% [2M NH₃ in MeOH] in DCM, to afford the title compound (62 mg, 19%). LCMS (Method 3): Rt: 4.00 min, m/z 783/785 [MH⁺].

d. 1-{5-tert-Butyl-2-[4-chloro-3-(2-hydroxy-ethoxy)-phenyl]-2H-pyrazol-3-yl}-3-{(1S,4R)-4-[3-((S)-2-methyl-pyrrolidin-1-yl)-[1,2,4]triazolo[4,3-a]pyridin-6-yloxy]-1,2,3,4-tetrahydro-naphthalen-1-yl}-urea (Intermediate 78d)

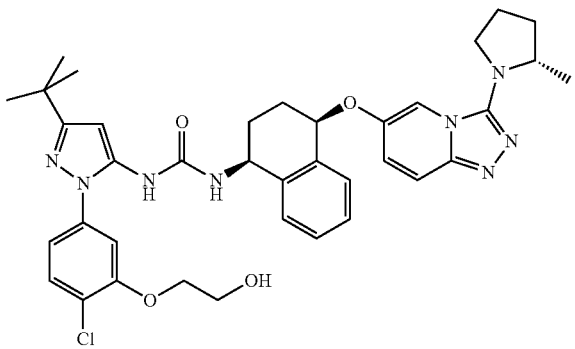 [SMILES: C[C@H]1CCCN1c1nnc2ccc(O[C@@H]3CC[C@H](NC(=O)Nc4cc(C(C)(C)C)nn4-c4ccc(Cl)c(OCCO)c4)c4ccccc43)cn12]

A solution of Intermediate 78c (60.0 mg, 0.08 mmol) and pyridinium p-toluene sulphonate (58.0 mg, 0.23 mmol) in MeOH (1 mL) was heated at 45° C. for 18 h. The reaction mixture was cooled and diluted with DCM (5 mL). This was washed with sat. aq. NaHCO₃ (2×5 mL). The organic layer was passed through a phase separator and concentrated in vacuo. The residue was purified by FCC, using 0-10% MeOH in DCM, to afford the title compound (42 mg, 78%). LCMS (Method 3): Rt: 3.47 min, m/z 699/701 [MH⁺].

e. Methanesulfonic acid 2-{5-[3-tert-butyl-5-(3-{(1S, 4R)-4-[3-((S)-2-methyl-pyrrolidin-1-yl)-[1,2,4]triazolo[4,3-a]pyridin-6-yloxy]-1,2,3,4-tetrahydro-naphthalen-1-yl}-ureido)-pyrazol-1-yl]-2-chloro-phenoxy}-ethyl ester (Intermediate 78e)

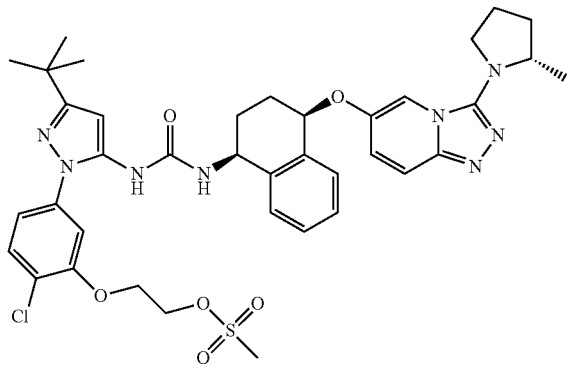

Methanesulfonyl chloride (5.80 μL, 0.074 mmol) was added to a solution of Intermediate 78d (40 mg, 0.057 mmol) and DIPEA (30 μL, 0.17 mmol) in DCM (1 mL) and the reaction mixture was stirred at RT for 1 h. The mixture was diluted with DCM (2 mL) and washed with water (2×2 mL). The organic layer was passed through a phase separator and concentrated in vacuo to afford the title compound (44 mg, 100%). LCMS (Method 3): Rt: 3.68 min, m/z 777/779 [MH⁺].

f. 1-{5-tert-Butyl-2-[4-chloro-3-(2-dimethylamino-ethoxy)-phenyl]-2H-pyrazol-3-yl}-3-{(1S,4R)-4-[3-((S)-2-methyl-pyrrolidin-1-yl)-[1,2,4]triazolo[4,3-a]pyridin-6-yloxy]-1,2,3,4-tetrahydro-naphthalen-1-yl}-urea formate salt (Example 78)

A solution of Intermediate 78e (44 mg, 0.057 mmol) and dimethylamine (2M in THF, 0.57 mL, 1.14 mmol) in THF (1 mL) was heated at 60° C. for 18 h. The reaction mixture was cooled to RT and the solvent was removed under a stream of air, to leave a residue which was purified by MDAP (Method 7), to afford the title compound (16 mg, 38%). LCMS (Method 5): Rt: 3.42 min, m/z 726.5 [MH⁺]. ¹H NMR (400 MHz, d₆-DMSO): 1.10 (3H, d, J=6.2 Hz), 1.28 (9H, s), 1.54-1.65 (1H, m), 1.78-1.95 (3H, m), 1.95-2.08 (2H, m), 2.08-2.19 (2H, m), 2.21 (6H, s), 2.65 (2H, t, J=5.6 Hz), 3.09-3.16 (1H, m, obscured by water), 3.80-3.89 (1H, m), 4.06-4.14 (1H, m), 4.16 (2H, t, J=5.6 Hz), 4.75-4.84 (1H, m), 5.52 (1H, t, J=4.0 Hz), 6.34 (1H, s), 7.04-7.13 (3H, m), 7.22-7.39 (5H, m), 7.52-7.58 (2H, m), 7.79 (1H, d, J=1.9 Hz), 8.15-8.19 (2.2H, m).

Example 79

1-{5-tert-Butyl-2-[4-chloro-3-(2-dimethylamino-ethoxy)-phenyl]-2H-pyrazol-3-yl}-3-{(1S,4R)-4-[3-((R)-2-methyl-pyrrolidin-1-yl)-[1,2,4]triazolo[4,3-a]pyridin-6-yloxy]-1,2,3,4-tetrahydro-naphthalen-1-yl}-urea formate salt

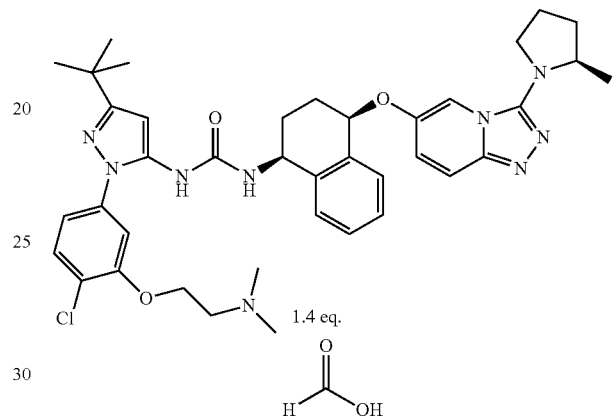

The title compound was prepared in an analogous fashion to the procedures described for Example 78, using (R)-2-methylpyrrolidine. LCMS (Method 5): Rt: 3.42 min, m/z 726.5 [MH⁺]. ¹H NMR (400 MHz, d₆-DMSO): 1.10 (3H, d, J=6.2 Hz), 1.28 (9H, s), 1.54-1.65 (1H, m), 1.79-2.11 (6H, m), 2.12-2.21 (1H, m), 2.22 (6H, s), 2.67 (2H, t, J=5.6 Hz), 3.10-3.18 (1H, m, obscured by water), 3.83-3.91 (1H, m), 4.03-4.13 (1H, m), 4.17 (2H, t, J=5.6 Hz), 4.76-4.85 (1H, m), 5.52 (1H, t, J=4.3 Hz), 6.34 (1H, s), 7.06 (1H, dd, J=9.8, 2.1 Hz), 7.08-7.13 (2H, m), 7.22-7.35 (4H, m), 7.39 (1H, dd, J=7.4, 1.6 Hz), 7.52-7.58 (2H, m), 7.78 (1H, d, J=1.7 Hz), 8.16 (2.4H, s).

Examples 80-87

General Procedure for Table 6

Urea Formation

The compounds synthesised in Table 6 were prepared according to the following general procedure: A mixture of Intermediate LHS (1.0 eq), Intermediate RHS (1.0 eq) and DIPEA (1.2-1.5 eq.) in a suitable solvent (for example 1,4-dioxane, 2-methyltetrahydrofuran or THF) was heated (60-80° C.) for a suitable time until the reaction was complete (e.g. 5-24 h). The reaction mixture was cooled, concentrated in vacuo and subjected to chromatographic purification methods described herein.

TABLE 6

Examples 80-87.

| Ex. No. | Intermediate used (LHS) | Intermediate used (RHS) | Example Structure | NMR (δ) | LCMS |
|---|---|---|---|---|---|
| 80 | Jb | E | 1-[5-tert-Butyl-2-(3,4-dimethyl-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea | (400 MHz, d$_6$-DMSO): 1.27 (9H, s), 1.83-2.23, (8H, m), 2.13 (3H, s), 2.27 (6H, s), 2.35 (1H, q, J = 8.6 Hz), 3.13 (1H, m), 3.99 (1H, t, J = 8.2), 4.83 (1H, td, J = 8.6, 5.5 Hz), 5.39 (1H, t, J = 4.3 Hz), 6.31 (1H, s), 7.09 (1H, d, J = 8.6 Hz), 7.18 (1 H, dd, J = 2.2, 8.1), 7.31-7.29 (7 H, m), 7.75 (1H, dd, J 0.8, 9.9 Hz), 8.00 (1H, s), 8.24 (1H, d, J = 2.1 Hz). | (Method 5): Rt 3.80 min, m/z 633 [MH$^+$]. |
| 81 | K | E | 1-[5-tert-Butyl-2-(2,5-dimethyl-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea | (400 MHz, d$_6$-DMSO): 1.26 (9H, s), 1.78-2.10 (7H, m), 1.94 (3H, s), 2.12 (3H, s), 2.20 (1H, m), 2.32 (3H, s), 2.35 (1H, q, J = 8.9 Hz), 3.12 (1H, m), 3.98 (1H, t, J = 8.2 Hz), 4.82 (1H, td, J = 5.4, 8.5 Hz), 5.38 (1H, t, J = 4.5 Hz), 6.31 (1H, s), 7.04 (1H, d, .1 = 8.50 Hz), 7.12 (1H, s), 7.21-7.36 (7H, m), 7.74 (1H, dd, J = 0.8, 9.9 Hz), 7.81 (1H, s), 8.23 (1H, d, J = 2.1 Hz). | (Method 5): Rt 3.77 min, m/z 633 [MH$^+$]. |
| 82 | Md | D | 1-[5-tert-Butyl-2-(4-chloro-3-hydroxymethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea | (400 MHz, d$_6$-DMSO): 1.28 (9H, s), 1.58-1.65 (2H, m), 1.68-1.77 (4H, m), 1.81-1.96 (2H, m), 1.98-2.17 (2H, m), 3.11-3.16 (4H, m), 4.60 (2H, br s), 4.76-4.84 (1H, m), 5.49-5.59 (2H, m), 6.33 (1H, s), 7.06 (1H, d, J = 8.6 Hz), 7.16 (1H, dd, J = 9.8, 2.1 Hz), 7.24-7.44 (5H, m), 7.52 (1H, d, J = 8.6 Hz), 7.59-7.64 (2H, m), 7.68 (1H, d, J = 2.5 Hz), 8.18 (1H, br s). | (Method 5): Rt 4.46 min, m/z 669.2 [MH$^+$]. |

TABLE 6-continued

Examples 80-87.

| Ex. No. | Intermediate used (LHS) | Intermediate used (RHS) | Example Structure | NMR (δ) | LCMS |
|---|---|---|---|---|---|
| 83 | L | E | 1-[5-tert-Butyl-2-(2,4-dimethyl-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea | (400 MHz, d₆-DMSO): 1.25 (9H, s), 1.82-1.87 (3H, m), 1.94 (3H, s), 1.99-2.03 (2H, m), 2.06-2.11 (2H, m), 2.12 (3H, s), 2.18-2.22 (1H, m), 2.34-2.38 (4H, m), 3.11-3.13 (1H, m), 3.98 (1H, t, J 8.2), 4.79-4.82 (1H, m), 5.38 (1H, t, J = 4.5 Hz), 6.30 (1H, s), 7.04 (1H, d, J 8.5), 7.23-7.35 (8H, m), 7.74-7.77 (2H, m), 8.22 (1H, dd, J = 0.9, 2.2 Hz). | (Method 5): Rt 3.74 min, m/z 633 [MH⁺]. |
| 84 | Ob | E | 1-{5-tert-Butyl-2-[4-chloro-3-(2-morpholin-4-yl-ethoxy)-phenyl]-2H-pyrazol-3-yl}-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea | (400 MHz, d₆-DMSO): 1.23 (9H, s), 1.83-2.08 (6H, m), 2.09 (3H, s), 2.10-2.19 (2H, m), 2.30-2.32 (1H, m), 2.40 (4H, t, J = 4.4 Hz), 2.66 (2H, td, J = 2.5, 5.7 Hz), 3.08-3.10 (1H, m), 3.46 (4H, t, J = 4.6 Hz), 3.95 (1H, t, J = 8.2 Hz), 4.15 (2H, t, J = 5.7 Hz), 4.75-4.78 (1H, m), 5.35 (1H, t, J = 4.2 Hz), 6.30 (1H, s), 7.06 (2H, dd, J = 2.4, 8.5 Hz), 7.25-7.37 (6H, m), 7.50 (1H, d, J = 8.5 Hz), 7.71 (1H, dd, J = 0.8, 9.9 Hz), 8.10 (1H, s), 8.21 (1H, d, J = 2.1 Hz). | (Method 5): Rt 2.81 min, m/z 768 [MH⁺] |

TABLE 6-continued

Examples 80-87.

| Ex. No. | Intermediate used (LHS) | Intermediate used (RHS) | Example Structure | NMR (δ) | LCMS |
|---|---|---|---|---|---|
| 85 | Ob | D | 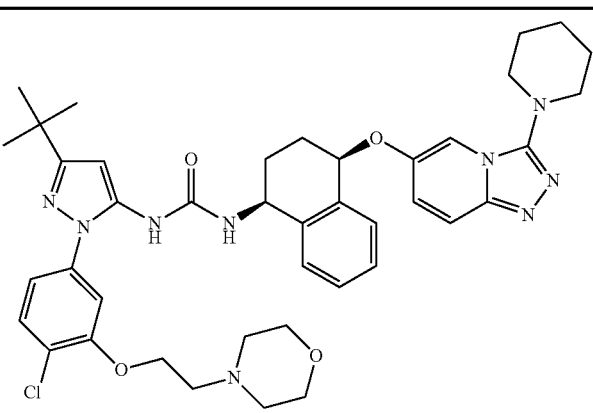<br>1-{5-tert-Butyl-2-[4-chloro-3-(2-morpholin-4-yl-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea | (400 MHz, d$_6$-DMSO): 1.27 (9H, s), 1.60-1.64 (2H, m), 1.70-1.76 (4H, m), 1.80-1.96 (2H, m), 1.98-2.15 (2H, m), 2.43-2.46 (4H, m), 2.66-2.74 (2H, m), 3.14 (4H, t, J = 5.2 Hz), 3.50 (4H, t, J = 4.6), 4.19 (2H, t, J = 5.7 Hz), 4.80 (1H, t, J = 5.5, 8.6 Hz), 5.54 (1H, t, J = 4.3 Hz), 6.34 (1H, s), 7.06-7.16 (3H, m), 7.22-7.33 (4H, m), 7.37-7.39 (1H, m), 7.53 (1H, d, J = 8.5 Hz), 7.61 (1H, dd, J = 0.9, 7.6 Hz), 7.63 (1H, s), 8.14 (1H, s). | (Method 5): Rt 3.64 min, m/z 768 [MH$^+$]. |
| 86 | Pd | D | 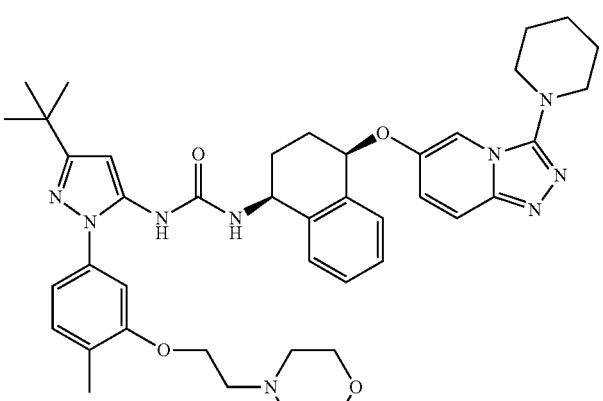<br>1-{5-tert-Butyl-2-[4-methyl-3-(2-morpholin-4-yl-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea | (400 MHz, d$_6$-DMSO): 1.23 (9H, s), 1.54-1.60 (2H, m), 1.64-1.72 (4H, m), 1.75-1.95 (2H, m), 1.95-2.10 (2H, m), 2.15 (3H, s), 2.40 (4H, t, J = 4.5 Hz), 2.65 (2H, t, J = 5.7 Hz), 3.10 (4H, t, J = 5.3 Hz), 3.47 (4H, t, J = 4.7 Hz), 4.07 (2H, t, J = 5.7 Hz), 4.77 (1H, m), 5.50 (1H, t, J = 4.3 Hz), 6.28 (1H, s), 6.91 (1H, dd, J = 2.0, 7.9 Hz), 7.01 (1H, d, J = 2.0 Hz), 7.05 (1H, d, J = 8.6 Hz), 7.10 (1H, m), 7.19-7.30 (4H, m), 7.34 (1H, d, J = 7.4 Hz), 7.56 (1H, d, J = 8.0 Hz), 7.58 (1H, s), 8.02 (1H, s). | (Method 5): Rt 3.70 min, m/z 748.4 [MH$^+$]. |
| 87 | Sb | D | 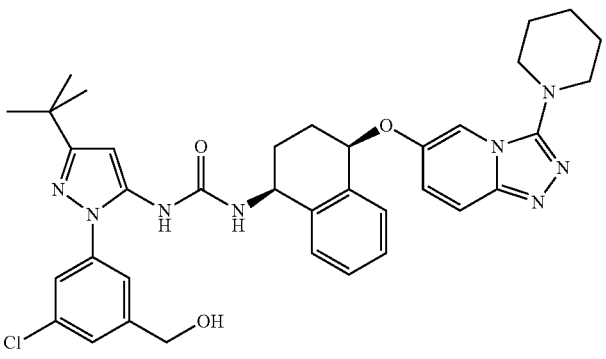<br>1-[5-tert-Butyl-2-(3-chloro-5-hydroxymethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea | (400 MHz, d$_6$-DMSO): 1.28 (9H, s), 1.57-1.66 (2H, m), 1.67-1.79 (4H, m), 1.84-1.95 (2H, m), 1.98-2.08 (1H, m), 2.10-2.19 (1H, m), 3.14 (4H, t, J = 5.4 Hz), 4.57 (2H, d, J = 4.9 Hz), 4.75-4.85 (1H, m), 5.45 (1H, t, J = 5.5 Hz), 5.54 (1H, t, J = 4.2 Hz), 6.32 (1H, s), 7.09 (1H, d, J = 8.6 Hz), 7.17 (1H, dd, J = 2.2, 9.6 Hz), 7.24-7.31 (2H, m), 7.31-7.40 (3H, m), 7.43-7.49 (2H, m), 7.58-7.64 (2H, m), 8.16 (1H, s). | (Method 5): Rt 4.53 min, m/z 669, 671 [MH$^+$]. |

Biological Assays.
P38alpha Enzyme Inhibition Assay.

The inhibitory activity of compounds was determined using an Alphascreen® (Perkin Elmer) based kinase activity assay. Kinase reactions consisted of 25 mM HEPES pH 7.5, 10 mM $MgCl_2$, 100 µM $Na_3VO_4$, 2 mM DTT, 0.05 mg/ml Tween 20, 100 pM p38alpha (Invitrogen, PV3304), 1% DMSO and 0.3 µg/ml ATF-2 fusion protein (New England Biolabs, 9224). Compounds were incubated under these conditions for 2 hours, at 25° C., prior to the initiation of the kinase activity by the addition of the 250 µM ATP. Reaction volumes were 20 uL. After 1 hr at 25° C. reactions were stopped by the adding 10 uL of 25 mM HEPES pH 7.5 containing 62.5 mM EDTA, 0.05% Triton X-100, 10% BSA and 0.83 ng/uL anti-phospho-ATF2 antibody (Abcam, ab28812). Detection was performed by measuring luminescence following the addition of Alphascreen Donor beads (Perkin Elmer 6765300) and Protein A Alphascreen Acceptor beads (Perkin Elmer 6760137), both at a final concentration of 20 ug/ml. $IC_{50}$ values were determined from concentration-response curves.

All the compounds of the invention have a p38☐ binding potency less than 10 nM.

LPS-Stimulated PBMC TNFα Release Assay.

Peripheral Blood Mononuclear Cells (PBMCs) were isolated from healthy human volunteer blood using a standard density gradient centrifugation technique. Citrated blood was placed onto Histopaque™ and centrifuged. The PBMCs were removed from the density gradient interface and washed in phosphate buffered saline (PBS). The PBMCs were suspended in RPMI 1640 medium (without serum), dispensed into a 96-well plate and incubated at 37° C. for 3 h in a humidified incubator. After incubation, the medium was replaced (with medium containing 1% foetal bovine serum) and the plate incubated at 37° C., for 1 h, in the presence of test compound or the appropriate vehicle. LPS (10 ng/ml), or an appropriate vehicle control, was then added to the cells and the plate returned to the incubator for 18 h. Cell-free supernatants were removed and assayed for TNFα levels using an ELISA kit from R&D Systems.

A dose response curve to each test compound was performed and the effect of compound in each experiment was expressed as a percentage inhibition of the control TNFα release. Dose response curves were plotted and compound potency ($IC_{50}$) was determined. Compounds were tested in at least three separate experiments.

All the compounds of the invention show p38 ☐ potencies ($IC_{50}$ values) lower than 10 nM.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I) or a pharmaceutically acceptable salt thereof:

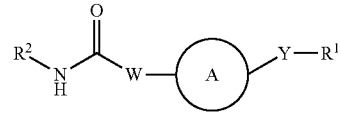

wherein
W is N substituted with —H;
Y is —O—;
$R^1$ is a group (IIc):

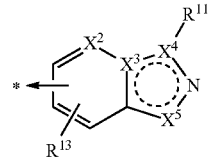

$X^2$, $X^3$, $X^4$ and $X^5$ are each independently a carbon atom, a nitrogen atom, a group —(CH)— or a group —NH—; such that each combination thereof forms an aromatic ring system;

$R^{11}$ is linked to $X^4$ and is selected from the group consisting of —$NR^AR^B$; —$N(R^C)(C_2$-$C_6$alkylene)-$NR^AR^B$; —$N(R^C)(C_3$-$C_7$cycloalkylene)-$NR^AR^B$; —($C_1$-$C_6$alkylene)-$NR^AR^B$; —($C_3$-$C_7$cycloalkylene)-$NR^AR^B$; and ($C_3$-$C_7$)heterocycloalkyl, wherein said ($C_3$-$C_7$)heterocycloalkyl may be optionally substituted with one, two, or three $C_1$-$C_6$ alkyl groups;

$R^A$ and $R^B$ are at each occurrence independently —H, $C_1$-$C_6$ alkyl or $C_3$-$C_7$ cycloalkyl, said $C_1$-$C_6$ alkyl and $C_3$-$C_7$ cycloalkyl being optionally substituted by a group $C_1$-$C_3$ alkyl $C_3$-$C_7$cycloalkyl, —$OR^D$, —CN or halo; alternatively, $R^A$ and $R^B$, may form together with the nitrogen atom to which they are attached an azetidine or a 4-11-membered saturated heterocyclic monocyclic or bicyclic ring system which is optionally substituted by one or more groups —$OR^D$, —CN, halo, $C_1$-$C_6$ alkyl, ($C_1$-$C_6$)hydroxyalkyl or $C_3$-$C_7$ cycloalkyl, said $C_1$-$C_6$ alkyl and $C_3$-$C_7$ cycloalkyl being optionally substituted by a group $C_1$-$C_3$ alkyl, $C_3$-$C_7$cycloalkyl, —$OR^D$, —CN or halo; and which 4-11-membered saturated heterocyclic monocyclic or bicyclic ring optionally contains a further heteroatom which is oxygen or nitrogen, said nitrogen atom optionally substituted by $C_1$-$C_6$ alkyl or $C_3$-$C_6$ cycloalkyl, wherein any of said $C_1$-$C_6$ alkyl or $C_3$-$C_6$ cycloalkyl may be optionally substituted by a group $C_1$-$C_6$ alkyl, $C_3$-$C_7$ cycloalkyl, —$OR^D$, —CN, or halo; or $R^A$ and $R^B$ may be linked to one carbon atom of the —($C_1$-$C_6$alkylene)-, —($C_2$-$C_6$alkylene)- or —($C_3$-$C_7$cycloalkylene)- portion of the group linked to the nitrogen to which they are connected to form a saturated cycle of up to 6 ring atoms;

$R^C$ is at each occurrence independently —H, $C_1$-$C_6$ alkyl, ($C_1$-$C_4$)hydroxyalkyl or $C_3$-$C_6$ cycloalkyl, said $C_1$-$C_6$ alkyl and $C_3$-$C_6$ cycloalkyl being optionally substituted by a group $C_1$-$C_3$ alkyl, —$OR^D$, —CN or halo;
alternatively $R^C$ may be linked to one carbon atom of the —($C_2$-$C_6$alkylene)- or —($C_3$-$C_7$cycloalkylene)- portion of the group linked to the nitrogen to which they are connected to form a saturated cycle of up to 6 ring atoms $R^D$ is at each occurrence independently —H, —$CH_3$ or —$C_2H_5$;

$R^{13}$ is —H, $C_1$-$C_6$ alkyl, or halogen;

A is a divalent cycloalkylene radical having 6 ring atoms; said cycloalkylene ring being attached to W and Y and fused to a phenyl ring;

$R^2$ is a radical of formula (IIIb):

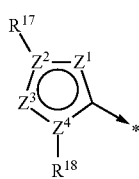

(IIIb)

wherein $R^{17}$ is a group of general formula (IV)

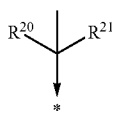

(IV)

wherein $R^{20}$ is —$CH_3$;

$R^{21}$ is —$CH_3$;

$R^{18}$ is selected from the group consisting of aryl and heteroaryl, wherein any of said aryl or heteroaryl is substituted by two or more groups independently selected from the group consisting of —CN, —OH, =O, halo, $C_1$-$C_6$ alkyl, —O—($C_1$-$C_6$alkyl), —($C_1$-$C_6$alkylene)-$NR^HR^J$, and —O—($C_2$-$C_6$alkylene)-$NR^HR^J$, wherein any of said $C_1$-$C_6$alkyl portion in the above listed groups may be optionally substituted by a group, —$OR^L$;

$R^H$ and $R^J$ are each $C_1$-$C_6$ alkyl; alternatively, $R^H$ and $R^J$ may form together with the nitrogen atom to which they are attached a 4-11-membered saturated monocyclic or bicyclic heterocyclic ring system which is optionally substituted by one or more groups —$OR^M$ or $NR^OR^P$; and which 4-11-membered saturated monocyclic or bicyclic heterocyclic ring optionally contains a further heteroatom which is oxygen or nitrogen, said nitrogen atom optionally substituted by $C_1$-$C_6$ alkyl;

$R^L$ is —H;

$R^M$ is at each occurrence independently —H or $C_1$-$C_6$ alkyl;

$R^O$ and $R^P$ are each $C_1$-$C_6$ alkyl;

$z^1$ is CH, $z^2$ is C, $z^3$ and $z^4$ are N.

2. A compound or pharmaceutically acceptable salt according to claim 1, wherein $R^A$ and $R^B$ form together with the nitrogen atom to which they are attached an azetidine or a 4-11-membered saturated heterocyclic monocyclic or bicyclic ring system which is optionally substituted by one or more groups —$OR^D$, —CN, halo, $C_1$-$C_6$ alkyl, ($C_1$-$C_6$)hydroxyalkyl or $C_3$-$C_7$ cycloalkyl, said $C_1$-$C_6$ alkyl and $C_3$-$C_7$ cycloalkyl being optionally substituted by a group $C_1$-$C_3$ alkyl, $C_3$-$C_7$cycloalkyl, —$OR^D$, —CN or halo; and which 4-11-membered saturated heterocyclic monocyclic or bicyclic ring optionally contains a further heteroatom which is oxygen or nitrogen, said nitrogen atom optionally substituted by $C_1$-$C_6$ alkyl or $C_3$-$C_6$ cycloalkyl, wherein any of said $C_1$-$C_6$ alkyl or $C_3$-$C_6$ cycloalkyl may be optionally substituted by a group $C_1$-$C_6$ alkyl, $C_3$-$C_7$ cycloalkyl, —$OR^D$, —CN, or halo; or $R^A$ and $R^B$ may be linked to one carbon atom of the —($C_1$-$C_6$alkylene)-, —($C_2$-$C_6$alkylene)- or —($C_3$-$C_7$cycloalkylene)- portion of the group linked to the nitrogen to which they are connected to form a saturated cycle of up to 6 ring atoms.

3. A compound or pharmaceutically acceptable salt according to claim 1, wherein A is group

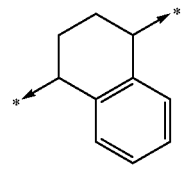

$R^1$ is a group of formula (IIca) which is connected to the group Y through the carbon adjacent to $X^2$

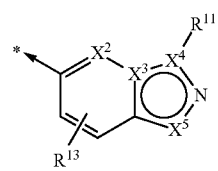

(IIca)

$X^4$ is a carbon atom, $X^5$ is a nitrogen atom, $X^3$ is a nitrogen atom and $X^2$ is a group —CH—, and $R^{13}$ is —H;

$R^{11}$ is a group:

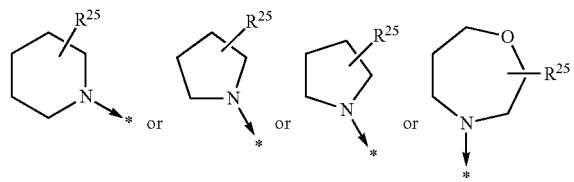

wherein $R^{25}$ is optionally present and represents one, two or three substituents independently selected from the group consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$;

$z^1$=—CH—, $z^2$=C, $z^3$ and $z^4$ are N $R^{18}$ is aryl substituted by two or more groups independently selected from the group consisting of —CN, —OH, halo, $C_1$-$C_6$alkyl, —O—($C_1$-$C_6$alkyl), ($C_1$-$C_6$alkylene)-$NR^HR^J$, and —O—($C_2$-$C_6$alkylene)-$NR^HR^J$, wherein any of said $C_1$-$C_6$alkyl, —($C_1$-$C_6$alkylene)-, and —($C_2$-$C_6$alkylene)- portion may be optionally substituted by a group $OR^L$ or halo;

$R^H$ and $R^J$ are independently —H or $C_1$-$C_6$ alkyl; or $R^H$ and $R^J$ may form together with the nitrogen atom to which they are attached a 4-11-membered saturated monocyclic or bicyclic heterocyclic ring system which 4-11-membered saturated monocyclic or bicyclic heterocyclic ring optionally contain a further heteroatom which is oxygen or nitrogen; and $R^M$ is —H.

4. A compound or pharmaceutically acceptable salt according to claim 1, wherein A is group

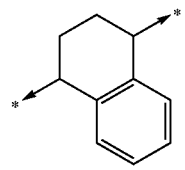

$R^1$ is a group of formula (IIca) which is connected to the group Y through the carbon adjacent to $X^2$

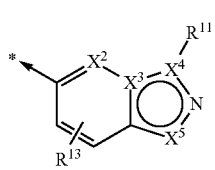

(IIca)

wherein $X^4$ is a carbon atom, $X^5$ is a nitrogen atom, $X^3$ is a nitrogen atom and $X^2$ is a group —CH—, and $R^{13}$ is —H;

$R^{11}$ is a group

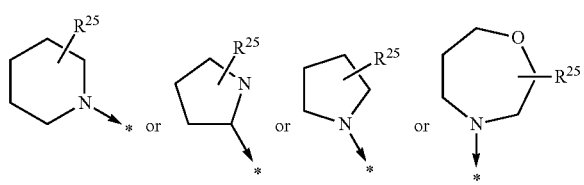

wherein $R^{25}$ is optionally present and represents one, two or three substituents independently selected from the group consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$;

wherein $z^1$=—CH—, $z^2$=C, $z^3$ and $z^4$ are N $R^{20}$ and $R^{21}$ are —$CH_3$;

$R^{18}$ is a phenyl substituted by two or more groups independently selected from the group consisting of —OH, halo, $C_1$-$C_6$alkyl, —O—($C_2$-$C_6$alkylene)-$NR^HR^J$ and —($C_1$-$C_6$alkylene)-$NR^HR^J$, wherein any of such $C_1$-$C_6$alkyl, —($C_1$-$C_6$alkylene)- and —($C_2$-$C_6$alkylene)- portion may be optionally substituted by a group $OR^L$;

$R^H$ and $R^J$ are independently —H or $C_1$-$C_6$ alkyl, said $C_1$-$C_6$ alkyl; or $R^H$ and $R^J$ may form together with the nitrogen atom to which they are attached a 4-11-membered saturated monocyclic or bicyclic heterocyclic ring system which 4-11-membered saturated monocyclic or bicyclic heterocyclic ring optionally contain a further heteroatom which is oxygen or nitrogen; and $R^M$ is —H.

5. A compound or pharmaceutically acceptable salt according to claim 1, wherein A is group

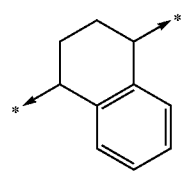

$R^1$ is a group of formula (IIca) which is connected to the group Y through the carbon adjacent to $X_2$

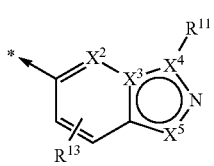

(IIca)

$X^4$ is a carbon atom, $X^5$ is a nitrogen atom, $X^3$ is a nitrogen atom and $X^2$ is a group —CH—, and $R^{13}$ is —H;

$R^{11}$ is a group

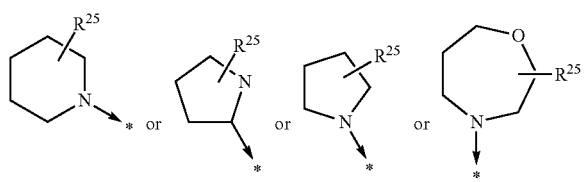

wherein $R^{25}$ is optionally present and represents one two or three substituents independently selected from the group consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$;

$z^1$=—CH—, $z^2$=C, $z^3$ and $z^4$ are N $R^{18}$ is a 5 or 6-membered heteroaryl which is substituted by two or more groups independently selected from the group consisting of $C_1$-$C_6$alkyl, and —($C_1$-$C_6$alkylene)-$NR^HR^J$, wherein any of said $C_1$-$C_6$alkyl and —($C_1$-$C_6$alkylene)- portion in the above listed groups may be optionally substituted by a group $OR^L$.

6. A compound or pharmaceutically acceptable salt according to claim 1, wherein A is group

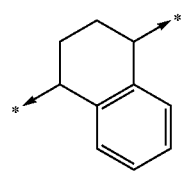

$R^1$ is a group of formula (IIca) which is connected to the group Y through the carbon adjacent to $X_2$

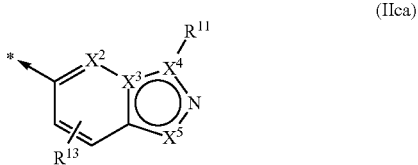

(IIca)

X⁴ is a carbon atom, X⁵ is a nitrogen atom, X³ is a nitrogen atom and X² is a group —CH—, and R¹³ is —H;
R¹¹ is a group

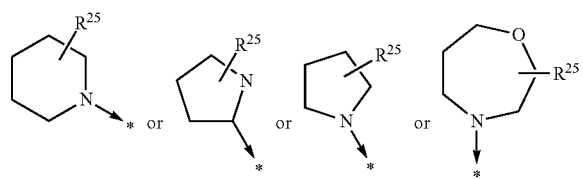

wherein R²⁵ is optionally present and represents one two or three substituents independently selected from the group consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group R¹¹ to the rest of the molecule via X⁴;
z¹=—CH—, z²=C, z³ and z⁴ are N; and
R¹⁸ is a heterocycloalkyl substituted by two or more groups independently selected from the group consisting of =O, $C_1$-$C_6$alkyl, and —($C_1$-$C_6$alkylene)-NR$^H$R$^J$, wherein any of said $C_1$-$C_6$alkyl and —($C_1$-$C_6$alkylene)- portion in the above listed groups may be optionally substituted by a group OR$^L$.

7. A compound or pharmaceutically acceptable salt thereof, which is selected from the group consisting of 1-[5-tert-butyl-2-(2-fluoro-5-pyrrolidin-1-ylmethyl-phenyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[2-fluoro-5-(4-methyl-piperazin-1-ylmethyl)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}urea;

1-[5-tert-butyl-2-(2-fluoro-5-pyrrolidin-1-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[2-fluoro-5-(4-methyl-piperazin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl urea formate salt;

1-{5-tert-butyl-2-[5-(2-dimethylamino-ethoxy)-2-fluoro-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[5-(2-dimethylamino-ethoxy)-2-fluoro-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[4-chloro-3-(4-methyl-piperazin-1-ylmethyl)-phenyl]-2H-pyrazol-3-yl}-3-(1S,4R)-4-(3-piperidin-1-yl-[1,2,4]triazolo[4,3-a]pyridin-6-yloxy)-1,2,3,4-tetrahydro-naphthalen-1-yl]-urea;

1-[5-tert-butyl-2-(4-chloro-3-morpholin-4-ylmethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-butyl-2-[4-chloro-3-(2-dimethylamino-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-butyl-2-[4-chloro-3-(2-diethylamino-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-butyl-2-[4-chloro-3-(2-piperidin-1-yl-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-butyl-2-[4-chloro-3-(2-pyrrolidin-1-yl-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-butyl-2-[4-methyl-3-(2-morpholin-4-yl-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt;

1-{5-tert-butyl-2-[3-(2-dimethylamino-ethoxy)-4-fluoro-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[3-chloro-5-(2-dimethylamino-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[4-chloro-3-(2-morpholin-4-yl-ethyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt;

1-{5-tert-butyl-2-[4-chloro-3-(2-dimethylamino-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt;

1-[5-tert-butyl-2-(3-chloro-5-piperidin-1-ylmethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-butyl-2-[3-chloro-5-(4-methyl-piperazin-1-ylmethyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-butyl-2-[2-chloro-5-(2-dimethylamino-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt;

1-[5-tert-butyl-2-(3-fluoro-5-morpholin-4-ylmethyl-phenyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[3-fluoro-5-(4-methyl-piperazin-1-ylmethyl)-phenyl]-2H-pyrazol-3-yl}-3-{(1S,4R)-4-[3-

((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[3-(2-dimethylamino-ethoxy)-5-fluoro-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-[5-tert-butyl-2-(3-fluoro-5-morpholin-4-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[3-fluoro-5-(4-methyl-piperazin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[3-(2-dimethylamino-ethoxy)-5-fluoro-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[4-cyano-3-(2-dimethylamino-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[4-chloro-3-(2-[1,4]oxazepan-4-yl-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt;

1-(5-tert-butyl-2-{4-chloro-3-[2-(3-oxa-8-aza-bicyclo[3.2.1]oct-8-yl)-ethoxy]-phenyl}-2H-pyrazol-3-yl)-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt;

1-{5-tert-butyl-2-[4-chloro-3-(2-dimethylamino-ethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[4-chloro-3-(2-dimethylamino-ethyl)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[4-chloro-3-(2-morpholin-4-yl-ethyl)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-(5-tert-butyl-2-{4-chloro-3-[2-(4-methyl-piperazin-1-yl)-ethyl]-phenyl}-2H-pyrazol-3-yl)-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-(5-tert-butyl-2-{4-fluoro-3-[2-(4-methoxy-piperidin-1-yl)-ethyl]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{2-[3-(2-azetidin-1-yl-ethyl)-4-fluoro-phenyl]-5-tert-butyl-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-(5-tert-butyl-2-{3-[2-(3-dimethylamino-azetidin-1-yl)-ethyl]-4-fluoro-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[3-(2-dimethylamino-ethyl)-4-fluoro-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[4-chloro-3-(2-dimethylamino-ethoxy)-phenyl]-2H-pyrazol-3-yl}-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea formate salt;

1-{5-tert-butyl-2-[4-chloro-3-(2-morpholin-4-yl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[5-tert-butyl-2-(4-chloro-3-pyrrolidin-1-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[5-tert-butyl-2-(4-chloro-3-morpholin-4-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[4-chloro-3-(4-methyl-piperazin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[5-tert-butyl-2-(4-chloro-3-morpholin-4-ylmethyl-phenyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[4-chloro-3-(4-methyl-piperazin-1-ylmethyl)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-[5-tert-butyl-2-(4-fluoro-3-pyrrolidin-1-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[4-fluoro-3-(4-methyl-piperazin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[5-tert-butyl-2-(4-fluoro-3-morpholin-4-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[5-tert-butyl-2-(4-chloro-3-hydroxy-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[5-tert-butyl-2-(3-chloro-4-hydroxy-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[5-tert-butyl-2-(3-chloro-4-hydroxy-phenyl)-2H-pyrazol-3-yl]-3-{(1S,4R)-4-[3-((S)-1-methyl-pyrrolidin-2- yl)-[1,2,4]triazolo[4,3-a]pyridin-6-yloxy]-1,2,3,4-tetrahydro-naphthalen-1-yl}-urea;

1-[5-tert-butyl-2-(4-chloro-3-hydroxy-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-[5-tert-butyl-2-(3-chloro-4-hydroxy-phenyl)-2H-pyrazol-3-yl]-3-{(1S,4R)-4-[3-(4-hydroxymethyl-piperidin-1-yl)-[1,2,4]triazolo[4,3-a]pyridin-6-yloxy]-1,2,3,4-tetrahydronaphthalen-1-yl}-urea;

1-{5-tert-butyl-2-[4-chloro-3-(2-hydroxy-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[5-tert-butyl-2-(3-hydroxy-5-methyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-butyl-2-[3-(2-dimethylamino-ethoxy)-4-hydroxymethyl-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[4-hydroxymethyl-3-(2-pyrrolidin-1-yl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl]-urea formate salt;

1-(5-tert-butyl-2-{4-hydroxymethyl-3-[2-(4-methyl-piperazin-1-yl)-ethoxy]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[3-(2-dimethylamino-ethoxy)-4-hydroxymethyl-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea;

1-{5-tert-butyl-2-[4-hydroxymethyl-3-(2-pyrrolidin-1-yl-ethoxy)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl]-urea formate salt;

1-(5-tert-butyl-2-{4-hydroxymethyl-3-[2-(4-methyl-piperazin-1-yl)-ethoxy]-phenyl}-2H-pyrazol-3-yl)-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[4-hydroxy-3-(4-methyl-piperazin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[5-tert-butyl-2-(3-chloro-5-hydroxy-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-[5-tert-butyl-2-(3-chloro-5-hydroxy-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[5-tert-butyl-2-(4-chloro-3-hydroxy-phenyl)-2H-pyrazol-3-yl]-3-[(1S,4R)-4-(3-[1,4]oxazepan-4-yl-[1,2,4]triazolo[4,3-a]pyridin-6-yloxy)-1,2,3,4-tetrahydro-naphthalen-1-yl]-urea;

1-[5-tert-butyl-2-(4-chloro-3-piperidin-1-ylmethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[5-tert-butyl-2-(4-chloro-3-pyrrolidin-1-ylmethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-butyl-2-[1-(2-dimethylamino-ethyl)-2-oxo-1,2-dihydro-pyridin-4-yl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}urea formate salt;

1-{5-tert-butyl-2-[4-chloro-3-(piperidin-4-yloxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-butyl-2-[4-chloro-3-(1-methyl-piperidin-4-yloxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-butyl-2-[4-chloro-3-((R)-piperidin-3-yloxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-butyl-2-[4-chloro-3-((S)-piperidin-3-yloxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-butyl-2-[4-chloro-3-((R)-1-methyl-piperidin-3-yloxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]urea;

1-{5-tert-butyl-2-[4-chloro-3-((S)-1-methyl-piperidin-3-yloxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[3-tert-butyl-1'-(2-dimethylamino-ethyl)-3'-hydroxymethyl-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[4-chloro-3-(2-hydroxy-propoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-butyl-2-[4-chloro-3-(3-morpholin-4-yl-propoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-butyl-2-[4-chloro-3-(3-morpholin-4-yl-propoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-butyl-2-[4-chloro-3-(2-dimethylamino-ethoxy)-phenyl]-2H-pyrazol-3-yl}-3-{1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[4-chloro-3-(2-dimethylamino-ethoxy)-phenyl]-2H-pyrazol-3-yl}-3-{1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[4-chloro-3-(2-dimethylamino-ethoxy)-phenyl]-2H-pyrazol-3-yl}-3-{(1S,4R)-4-[3-((S)-2-methyl-pyrrolidin-1-yl)-[1,2,4]triazolo[4,3-a]pyridin-6-yloxy]-1,2,3,4-tetrahydro-naphthalen-1-yl}-urea formate salt;

1-{5-tert-butyl-2-[4-chloro-3-(2-dimethylamino-ethoxy)-phenyl]-2H-pyrazol-3-yl}-3-{(1S,4R)-4-[3-((R)-2-methyl-pyrrolidin-1-yl)-[1,2,4]triazolo[4,3-a]pyridin-6-yloxy]-1,2,3,4-tetrahydro-naphthalen-1-yl}-urea formate salt;

1-[5-tert-butyl-2-(3,4-dimethyl-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-[5-tert-butyl-2-(2,5-dimethyl-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-[5-tert-butyl-2-(4-chloro-3-hydroxymethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[5-tert-butyl-2-(2,4-dimethyl-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-{5-tert-butyl-2-[4-chloro-3-(2-morpholin-4-yl-ethoxy)-phenyl]-2H-pyrazol-3-yl}-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-{5-tert-butyl-2-[4-chloro-3-(2-morpholin-4-yl-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-butyl-2-[4-methyl-3-(2-morpholin-4-yl-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[5-tert-butyl-2-(3-chloro-5-hydroxymethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[3-tert-butyl-1'-(2-dimethylamino-ethyl)-4'-hydroxymethyl-1'H-[1,3']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea; and 1-[5-tert-butyl-2-(3,5-dimethyl-isoxazol-4-yl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea or pharmaceutically acceptable salt thereof.

8. A pharmaceutical composition, comprising a compound or pharmaceutically acceptable salt as claimed in claim 1 and one or more pharmaceutically acceptable carriers.

9. A pharmaceutical composition, comprising a compound or pharmaceutically acceptable salt as claimed in claim 7 and one or more pharmaceutically acceptable carriers.

\* \* \* \* \*